United States Patent
Beigelman et al.

(10) Patent No.: US 9,758,544 B2
(45) Date of Patent: Sep. 12, 2017

(54) SUBSTITUTED NUCLEOSIDES, NUCLEOTIDES AND ANALOGS THEREOF

(71) Applicant: ALIOS BIOPHARMA, INC., South San Francisco, CA (US)

(72) Inventors: Leonid Beigelman, San Mateo, CA (US); David Bernard Smith, San Mateo, CA (US); Guangyi Wang, Carlsbad, CA (US); Natalia Dyatkina, Mountain View, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

(21) Appl. No.: 14/970,896

(22) Filed: Dec. 16, 2015

(65) Prior Publication Data

US 2016/0176911 A1 Jun. 23, 2016

Related U.S. Application Data

(60) Provisional application No. 62/094,458, filed on Dec. 19, 2014.

(51) Int. Cl.

| | | |
|---|---|---|
| *A01N 43/04* | (2006.01) | |
| *A61K 31/70* | (2006.01) | |
| *C07H 19/10* | (2006.01) | |
| *A61K 31/7072* | (2006.01) | |
| *A61K 31/708* | (2006.01) | |
| *A61K 45/06* | (2006.01) | |
| *C07H 19/20* | (2006.01) | |
| *C12N 7/00* | (2006.01) | |
| *C12N 9/12* | (2006.01) | |
| *A61K 31/7076* | (2006.01) | |
| *C07H 19/06* | (2006.01) | |
| *C07H 19/11* | (2006.01) | |
| *C07H 19/16* | (2006.01) | |
| *C07H 19/213* | (2006.01) | |
| *A61K 31/706* | (2006.01) | |
| *A61K 31/7064* | (2006.01) | |

(52) U.S. Cl.
CPC .......... *C07H 19/10* (2013.01); *A61K 31/708* (2013.01); *A61K 31/7072* (2013.01); *A61K 31/7076* (2013.01); *A61K 45/06* (2013.01); *C07H 19/06* (2013.01); *C07H 19/11* (2013.01); *C07H 19/16* (2013.01); *C07H 19/20* (2013.01); *C07H 19/213* (2013.01); *C12N 7/00* (2013.01); *C12N 9/127* (2013.01); *A61K 31/706* (2013.01); *A61K 31/7064* (2013.01); *C12N 2770/24261* (2013.01); *C12Y 207/07048* (2013.01)

(58) Field of Classification Search
None
See application file for complete search history.

(56) References Cited

U.S. PATENT DOCUMENTS

| | | | |
|---|---|---|---|
| 5,432,272 | A | 7/1995 | Benner et al. |
| 7,125,855 | B2 | 10/2006 | Bhat et al. |
| 9,108,999 | B2 * | 8/2015 | Zhang .................... C07H 19/06 |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2012/0165286 | A1 | 6/2012 | Beigelman et al. |
| 2013/0164261 | A1 | 6/2013 | Wang et al. |
| 2013/0165400 | A1 | 6/2013 | Beigelman et al. |
| 2013/0252920 | A1 | 9/2013 | Blatt et al. |
| 2013/0253181 | A1 | 9/2013 | Serebryany et al. |
| 2013/0281687 | A1 | 10/2013 | Serebryany et al. |
| 2014/0179627 | A1 | 6/2014 | Beigelman et al. |
| 2014/0179910 | A1 | 6/2014 | Beigelman et al. |
| 2014/0303108 | A1 | 10/2014 | Beigelman et al. |
| 2014/0303113 | A1 | 10/2014 | Krop et al. |
| 2014/0309164 | A1 * | 10/2014 | Deshpande ........... C07F 9/2429 514/4.3 |
| 2015/0011497 | A1 | 1/2015 | Beigelman et al. |
| 2015/0038451 | A1 | 2/2015 | Smith et al. |
| 2015/0051167 | A1 | 2/2015 | Wang et al. |
| 2015/0105341 | A1 | 4/2015 | Beigelman et al. |
| 2015/0141363 | A1 | 5/2015 | Wang et al. |
| 2015/0175647 | A1 | 6/2015 | Kuldipkumar et al. |
| 2015/0183819 | A1 | 7/2015 | Beigelman et al. |
| 2015/0315228 | A1 | 11/2015 | Beigelman et al. |
| 2015/0366887 | A1 | 12/2015 | Blatt et al. |
| 2015/0366888 | A1 | 12/2015 | Blatt et al. |
| 2015/0368286 | A1 | 12/2015 | Serebryany et al. |
| 2016/0016987 | A1 | 1/2016 | Beigelman et al. |
| 2016/0022724 | A1 | 1/2016 | Chanda et al. |
| 2016/0024136 | A1 | 1/2016 | Beigelman et al. |
| 2016/0039858 | A1 | 2/2016 | Beigelman et al. |
| 2016/0039861 | A1 | 2/2016 | Smith et al. |
| 2016/0115190 | A1 | 4/2016 | Serebryany et al. |
| 2016/0176910 | A1 | 6/2016 | Wang et al. |
| 2016/0264610 | A1 | 9/2016 | Beigelman et al. |
| 2016/0318967 | A1 | 11/2016 | Dyatkina et al. |
| 2016/0318969 | A1 | 11/2016 | Kuldipkumar et al. |
| 2016/0331770 | A1 | 11/2016 | Beigelman et al. |

FOREIGN PATENT DOCUMENTS

| | | |
|---|---|---|
| WO | WO 2010/108140 | 9/2010 |
| WO | WO 2012/142085 | 10/2012 |
| WO | WO 2013/092481 | 6/2013 |
| WO | WO 2013/142124 | 9/2013 |
| WO | WO 2013/142159 | 9/2013 |

(Continued)

OTHER PUBLICATIONS

International Search Report and Written Opinion mailed Apr. 1, 2016 for PCT Application No. PCT/US2015/065981, filed Dec. 16, 2015.

(Continued)

*Primary Examiner* — Patrick Lewis
(74) *Attorney, Agent, or Firm* — Knobbe, Martens, Olson & Bear, LLP

(57) ABSTRACT

Disclosed herein are nucleotide analogs, methods of synthesizing nucleotide analogs and methods of treating diseases and/or conditions such as a HCV infection with one or more nucleotide analogs.

54 Claims, 63 Drawing Sheets

(56) References Cited

FOREIGN PATENT DOCUMENTS

| | | |
|---|---|---|
| WO | WO 2013/142525 | 9/2013 |
| WO | WO 2014/099941 | 6/2014 |
| WO | WO 2014/100498 | 6/2014 |
| WO | WO 2014/100505 | 6/2014 |
| WO | WO 2014/134251 | 9/2014 |
| WO | WO 2014/164533 | 10/2014 |
| WO | WO 2014/186637 | 11/2014 |
| WO | WO 2014/209979 | 12/2014 |
| WO | WO 2014/209983 | 12/2014 |
| WO | WO 2015/054465 | 4/2015 |
| WO | WO 2016/022464 | 2/2016 |

OTHER PUBLICATIONS

Greene, et al., Protective Groups in Organic Synthesis, 3. Ed., John Wiley & Sons, (1999) Cover & Contents pages.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
McOmie, J. F. W., Protective Groups in Organic Chemistry, Plenum Press, 1973. Cover & Contents pages only.
Arnold et al., "Sensitivity of mitochondrial transcription and resistance of RNA polymerase II dependent nuclear transcription to antiviral ribonucleosides." PLoS Pathogens (2012) 8(11):e1003030.
Nelson et al., "Balapiravir plus peginterferon alfa-2a (40KD)/ribavirin in a randomized trial of hepatitis C genotype 1 patients" Annals of Hepatology (2012), 11(1), 15-31.

* cited by examiner

Figure 1: HCV Protease Inhibitors

Figure 1 (cont.): HCV Protease Inhibitors
| # | Name | Structure |
|---|---|---|
| 1009 | GS-9451 | 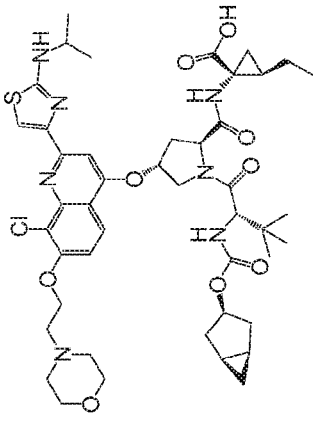 |
| 1010 | IDX-320 | 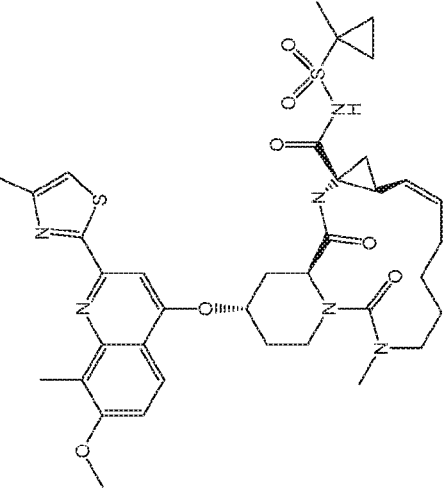 |
| # | Name | Structure |
|---|---|---|
| 1006 | BMS-650032<br>BM032<br>Asunaprevir | 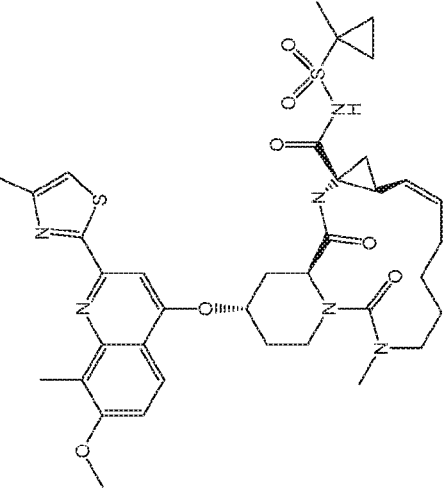 |
| 1007 | Boceprevir<br>SCH 503034 | 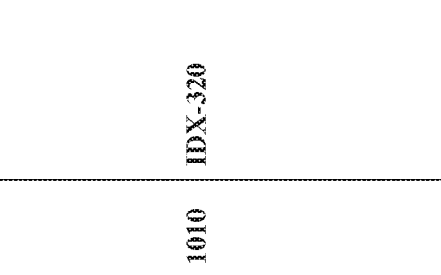 |
| 1008 | GS-9256 | |

Figure 1 (cont.): HCV Protease Inhibitors
| # | Name | Structure |
|---|------|-----------|
| 1013 | TMC-435<br>TMC-435350 | 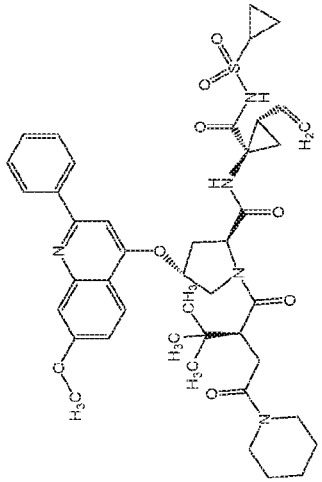 |
| 1014 | Danoprevir<br>ITMN-191<br>RG7227<br>RO5190591 | 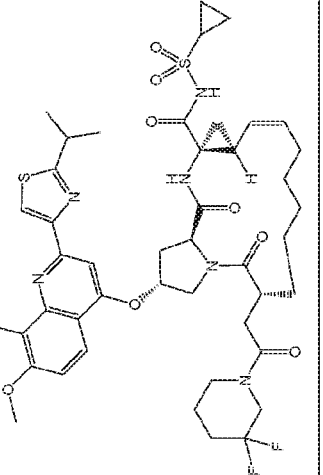 |
| 1011 | Sovaprevir<br>ACH-1625 | 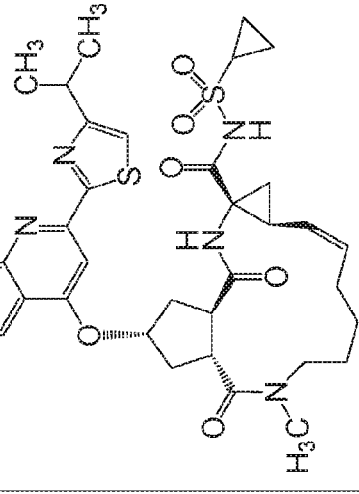 |
| 1012 | Deldeprevir<br>ACH-2684 | 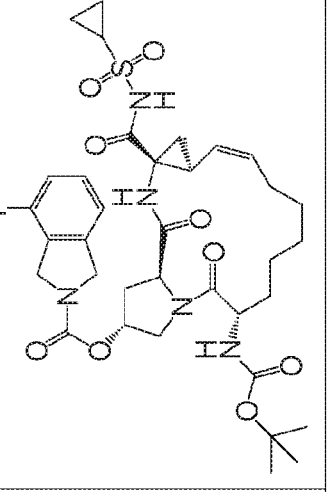 |

Figure 1 (cont.): HCV Protease Inhibitors
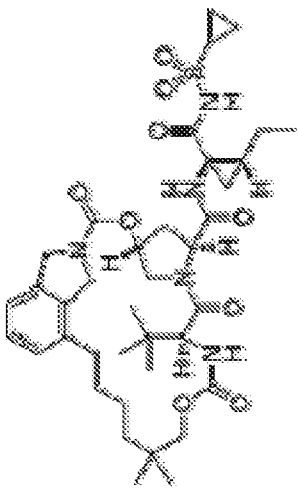
| # | Name | Structure |
|---|---|---|
| 1015 | MK-7009 Vaniprevir | 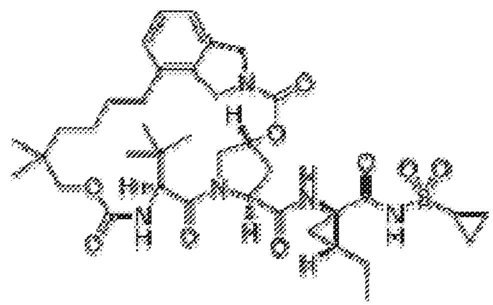 |
| 1016 | PHX1766 | |

Figure 2: HCV Polymerase Inhibitors – Nucleosides, Nucleotides and Analogs Thereof
| # | Name | Structure |
|---|---|---|
| 2001 | RG7128 Mericitabine | |
| 2002 | PSI-7851 | |
| 2003 | PSI-7977 GS-7977, Sofosbuvir | |
| 2004 | PSI-352938 GS-938 | 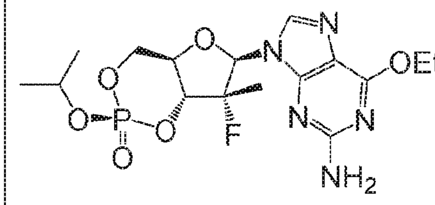 |
| 2005 | 4'-azidouridine and its prodrugs | 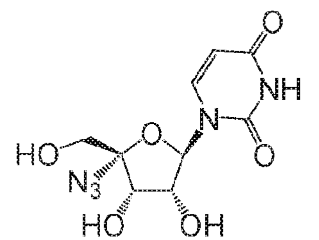 |
| 2006 | PSI-661 | |
| 2007 | GS-6620 | 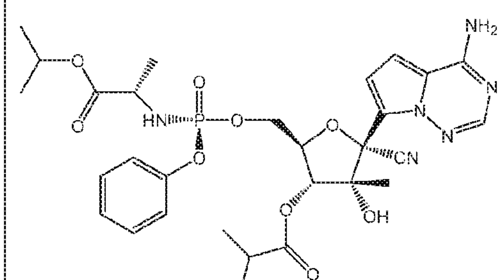 |
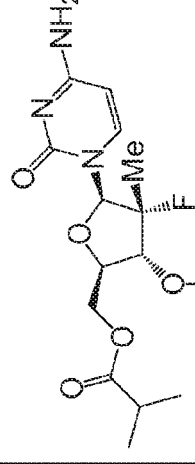

Figure 2 (cont.): HCV Polymerase Inhibitors – Nucleosides, Nucleotides and Analogs Thereof

| # | Name | Structure |
|---|---|---|
| 2008 | TMC649128 | |
| 2009 | NM283 | (structure shown: cytosine base with 2'-methyl, 2'-OH, 3'-O-valinyl, 5'-OH ribose) |
| 2010 | BCX5191 | |
| 2011 | IDX19368 | |
| 2012 | IDX19370 | |

Figure 3: HCV Polymerase Inhibitors – Non-Nucleosides

| # | Name | Structure |
|---|---|---|
| 3004 | HCV-796 | 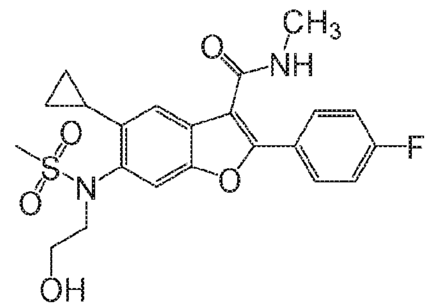 |
| 3005 | BI-207127 | |
| 3006 | GS-9190 | 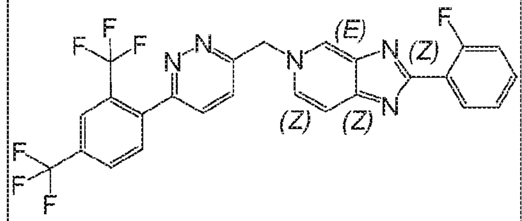 |
| 3007 | Filibuvir PF-00868554 | 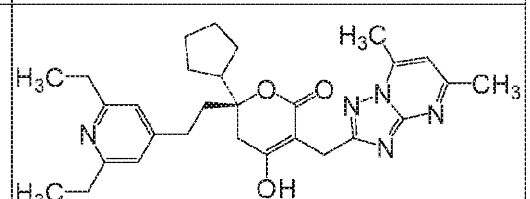 |

| # | Name | Structure |
|---|---|---|
| 3001 | ABT-333 | |
| 3002 | ANA-598 Setrobuvir | |
| 3003 | VX-222 S1480 VCH-222 | |

Figure 3 (cont.): HCV Polymerase Inhibitors – Non-Nucleosides

| # | Name | Structure |
|---|---|---|
| 3008 | VX-497 | 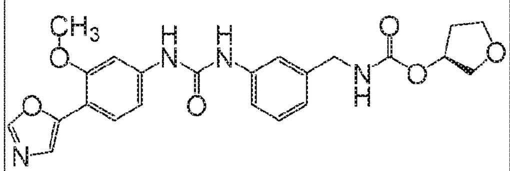 |
| 3009 | ABT-072 | |
| 3010 | MK-3281 | 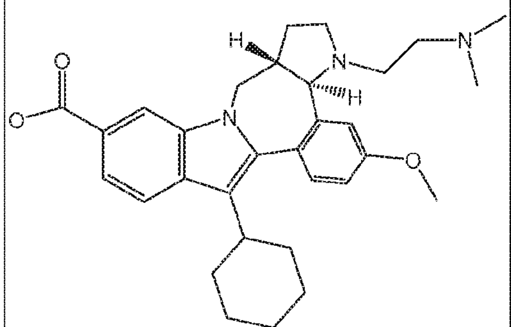 |
| 3011 | TMC647055 | 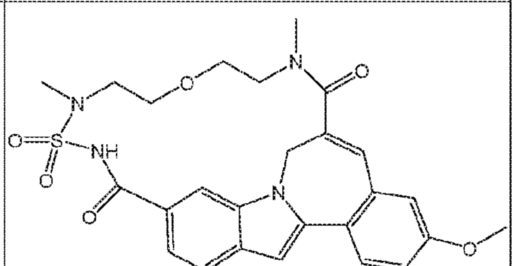 |

| # | Name | Structure |
|---|---|---|
| 3012 | BMS-791325 | |
| 3013 | PPI-383 | |
| 3014 | GS9669 | |

Figure 4: NS5A Inhibitors

| # | Name | Structure |
|---|---|---|
| 4001 | BMS-790052<br>BMS052<br>S1482<br>Daclatasvir | 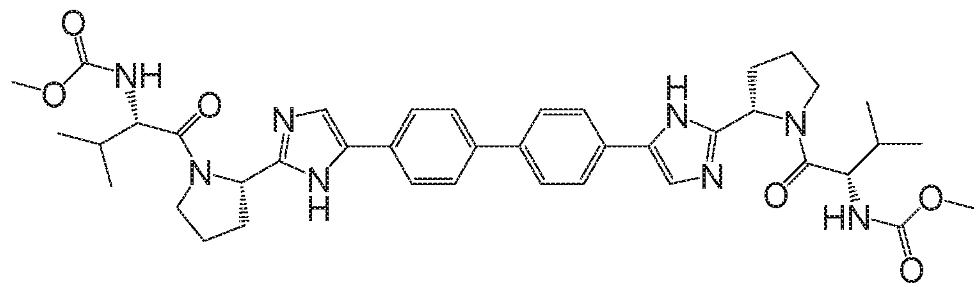 |
| 4002 | PPI-461 | |
| 4003 | ACH-2928 | |
| 4004 | Ledipasvir<br>GS-5885 | 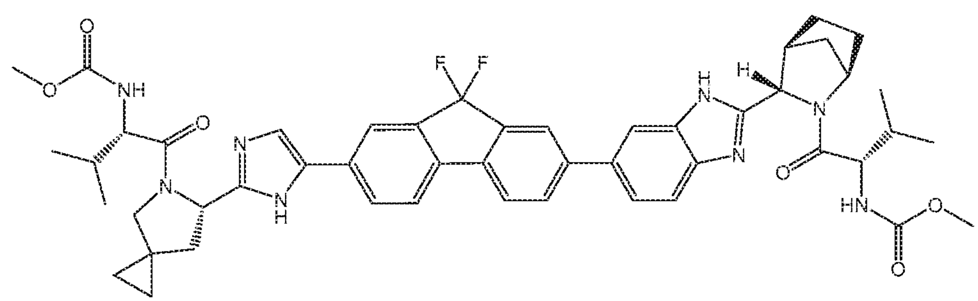 |
| 4005 | BMS-824393 | |

Figure 4 (cont.): NS5A inhibitors

| # | Name | Structure |
|---|---|---|
| 4006 | Onbitasvir ABT 267 | 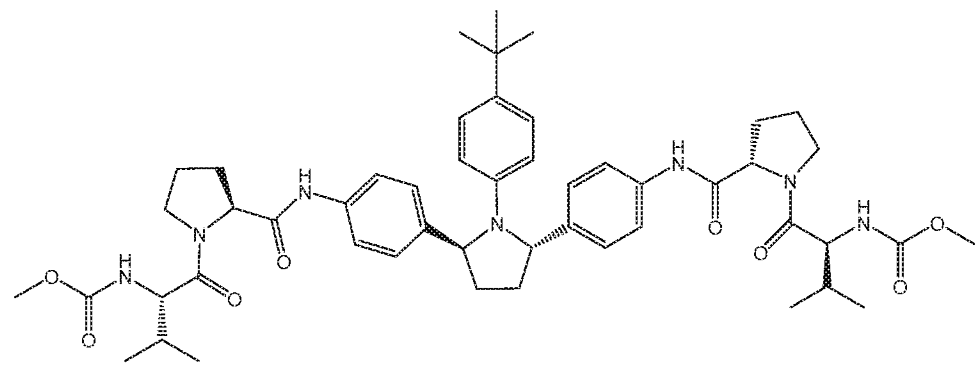 |
| 4007 | ACH-3102 | |
| 4008 | AZD-7295 | |
| 4009 | Samatasvir IDX719 | 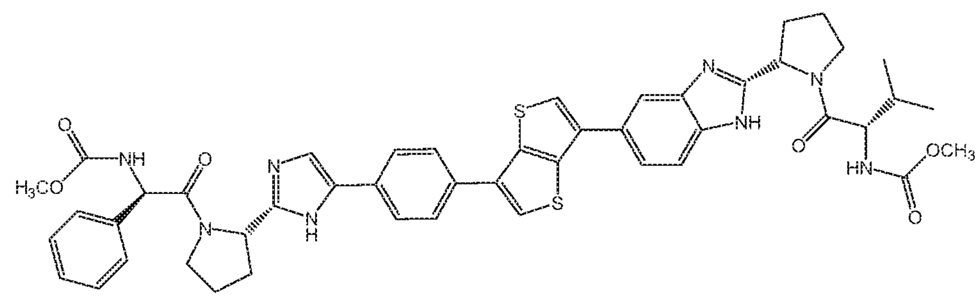 |
| 4010 | PPI-668 | |

Figure 4 (cont.): NS5A inhibitors

| # | Name | Structure |
|---|------|-----------|
| 4011 | Elbasvir MK8742 | 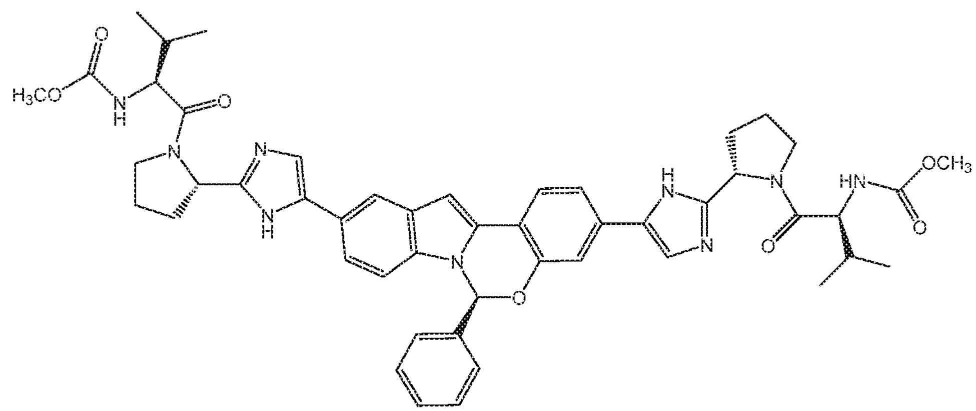 |
| 4012 | GSK805 | 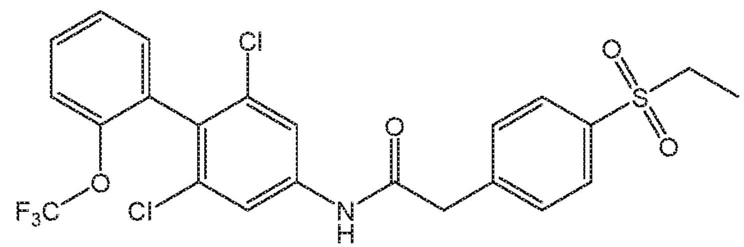 |

Figure 5: Other Antivirals and Ribavirin

| # | Name | Structure |
|---|---|---|
| 5001 | Debio-025 Alisporivir | 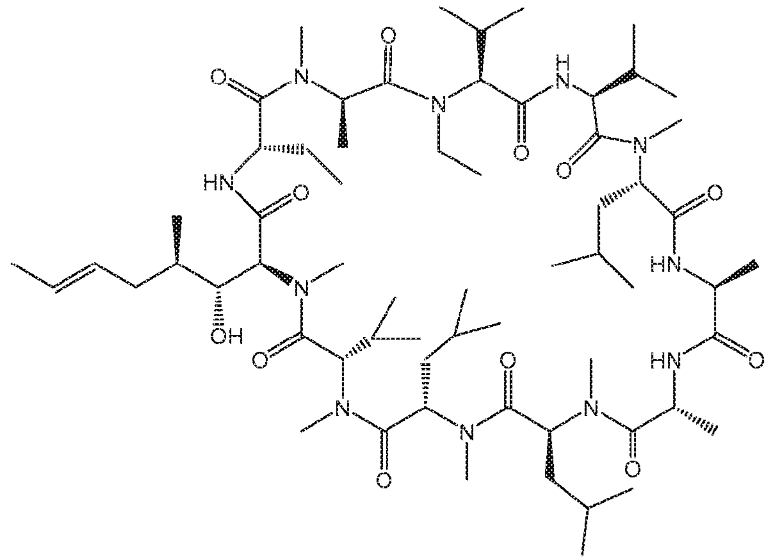 |
| 5002 | Clemizole | 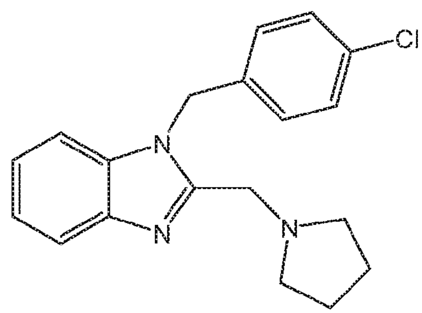 |

Figure 5 (cont.): Other Antivirals and Ribavirin

| # | Name | Structure |
|---|------|-----------|
| 5003 | ITX 5061 | 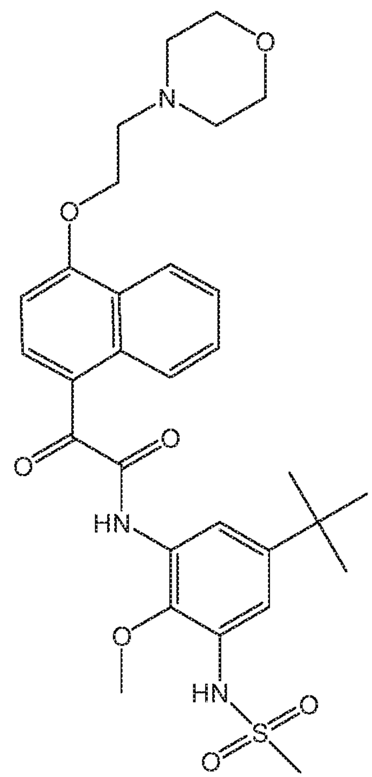 |

Figure 5 (cont.): Other Antivirals and Ribavirin
| # | Name | Structure |
|---|---|---|
| 5004 | BIT225 | 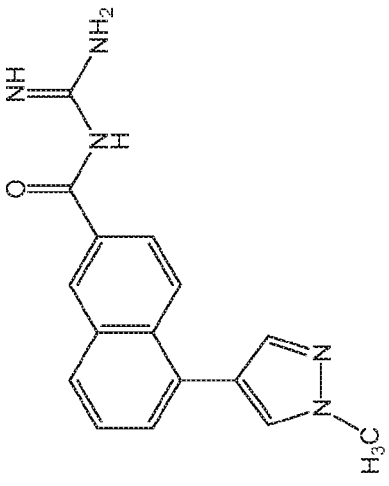 |
| 5005 | NIM811 | 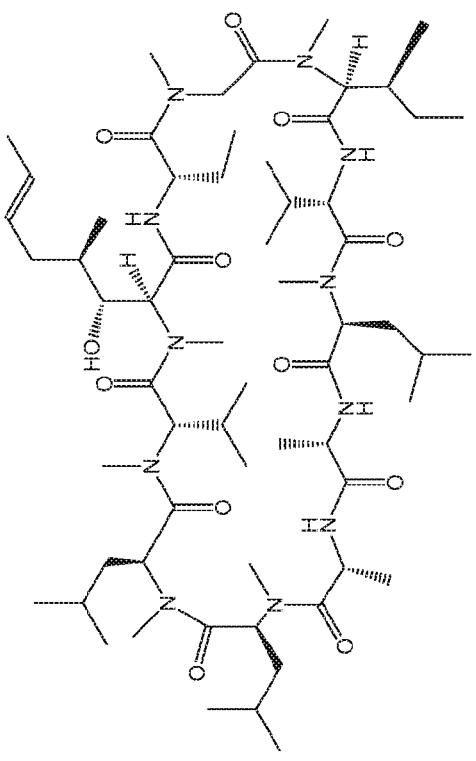 |

Figure 5 (cont.): Other Antivirals and Ribavirin
| # | Name | Structure |
|---|---|---|
| 5006 | SCY-635 | 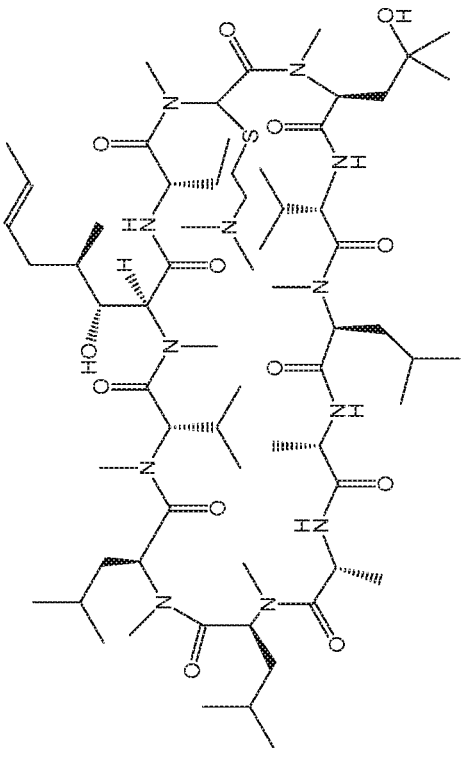 |
| 5007 | Nitazoxanide | 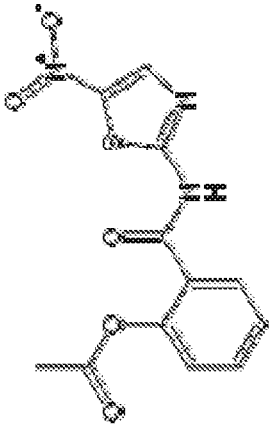 |
| 5008 | Miravirsen | |

Figure 5 (cont.): Other Antivirals and Ribavirin

| # | Name | Structure |
|---|---|---|
| 5009 | Celgosivir | 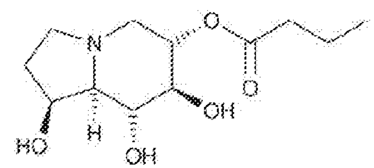 |
| 5010 | GS9620 | 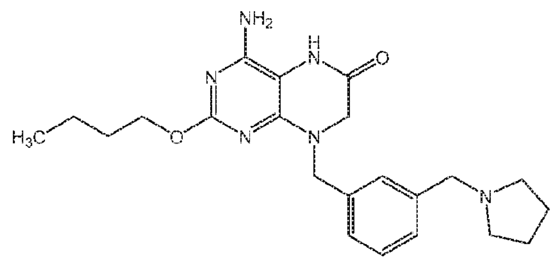 |
| 5011 | Ribavirin | 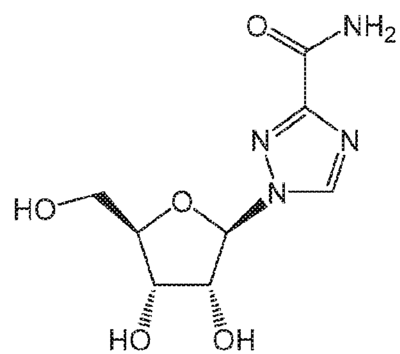 |

Figure 6: Compounds of Formula (CC) and alpha-thiotriphosphates thereof

| # | Structure |
|---|---|
| 6000 | (structure with $R^{CC2}O$, $R^{CC1}$, $R^{CC3a}$, $R^{CC3b}$, $B^{CC1}$, $R^{CC4}$, $R^{CC5}$, $R^{CC6}$, $R^{CC7}$, $R^{CC8}$, $R^{CC9}$ substituents on a thiophosphate ribose scaffold) |
| 6001 | (uracil nucleoside with 2'-C-methyl, 3'-OH, 4'-OH, naphthyl thiophosphoramidate with alanine isopropyl ester) |
| 6002 | (uracil nucleoside with 2'-C-methyl, 3'-OH, 4'-OH, phenyl thiophosphoramidate with alanine isopropyl ester) |
| 6003 | (uracil nucleoside with 2'-C-methyl, 3'-OH, 4'-OH, phenyl thiophosphoramidate with alanine isopropyl ester) |
| 6004 | (uracil nucleoside with 2'-C-methyl, 3'-OH, 4'-OH, phenyl thiophosphoramidate with alanine isopropyl ester) |

Figure 6 (cont.): Compounds of Formula (CC) and alpha-thiotriphosphates thereof

| # | Structure |
|---|---|
| 6007 | (structure) |
| 6008 | (structure) |
| 6005 | (structure) |
| 6006 | (structure) |

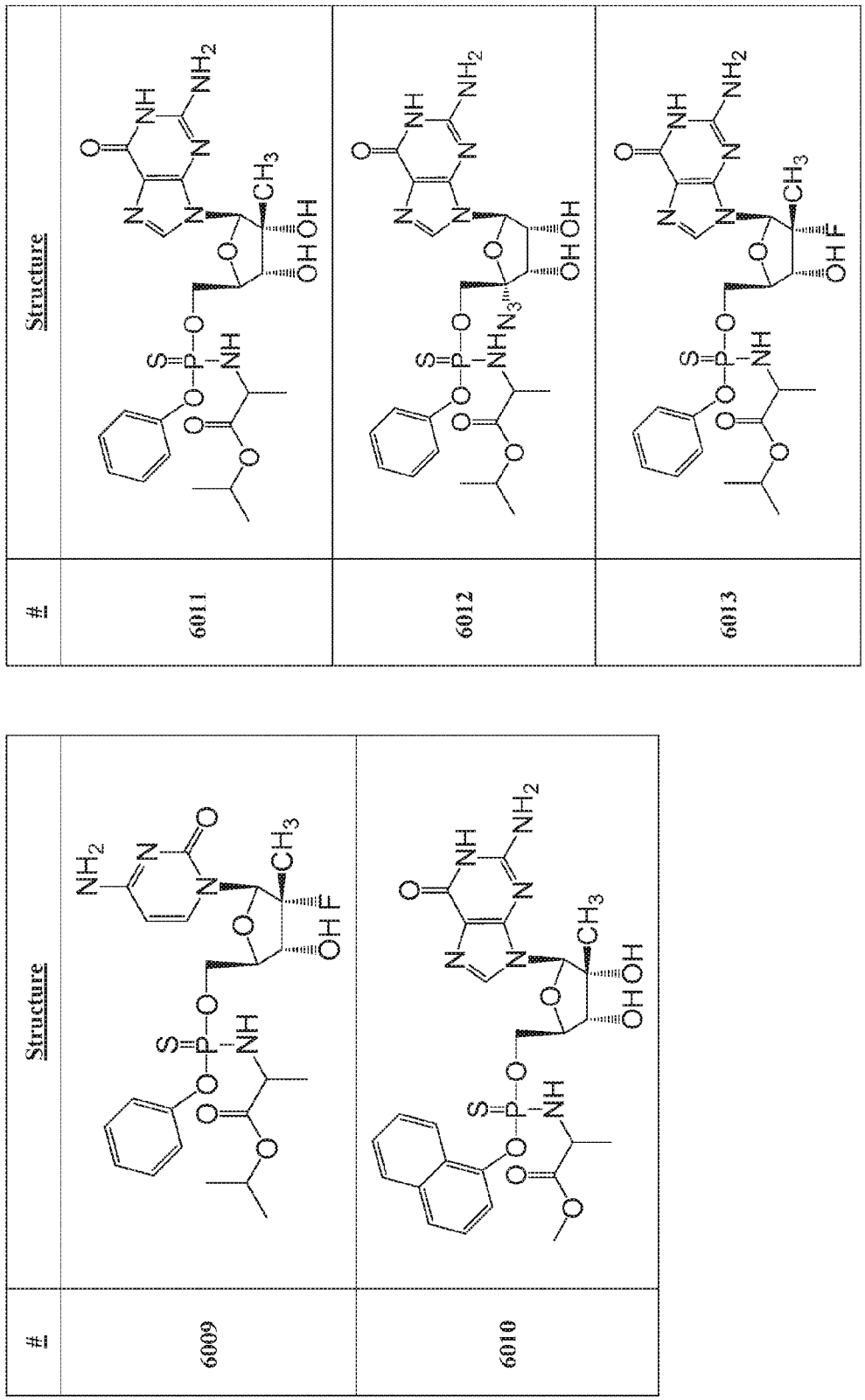
Figure 6 (cont.): Compounds of Formula (CC) and alpha-thiotriphosphates thereof Figure 6 (cont.): Compounds of Formula (CC) and alpha-thiotriphosphates thereof
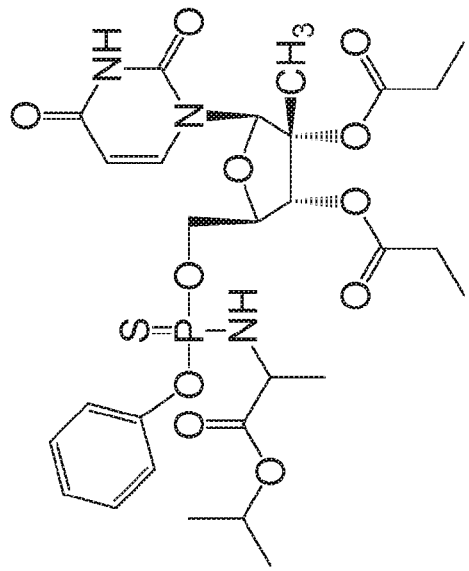
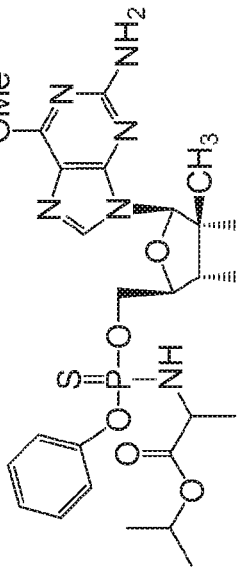
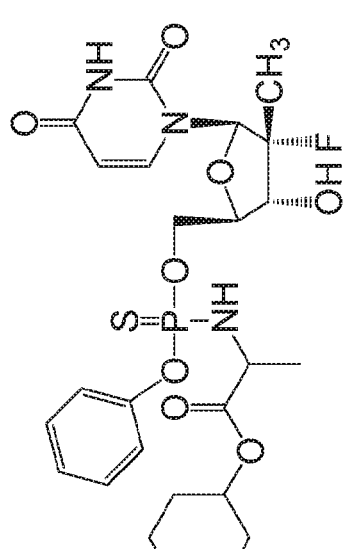
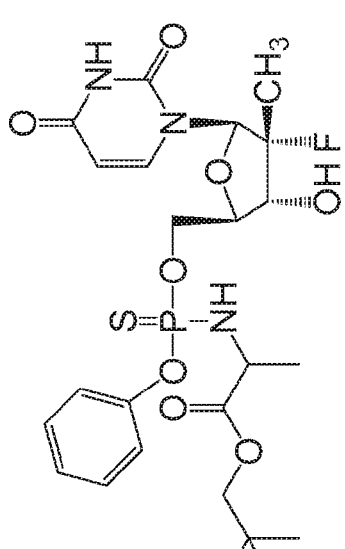

Figure 6 (cont.): Compounds of Formula (CC) and alpha-thiotriphosphates thereof

Figure 6 (cont.): Compounds of Formula (CC) and alpha-thiotriphosphates thereof Figure 6 (cont.): Compounds of Formula (CC) and alpha-thiotriphosphates thereof Figure 6 (cont.): Compounds of Formula (CC) and alpha-thiotriphosphates thereof
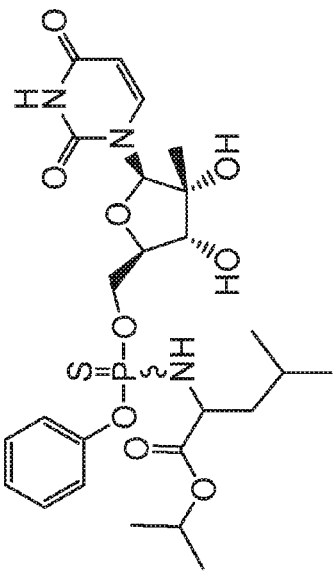

Figure 6 (cont.): Compounds of Formula (CC) and alpha-thiotriphosphates thereof

Figure 6 (cont.): Compounds of Formula (CC) and alpha-thiotriphosphates thereof
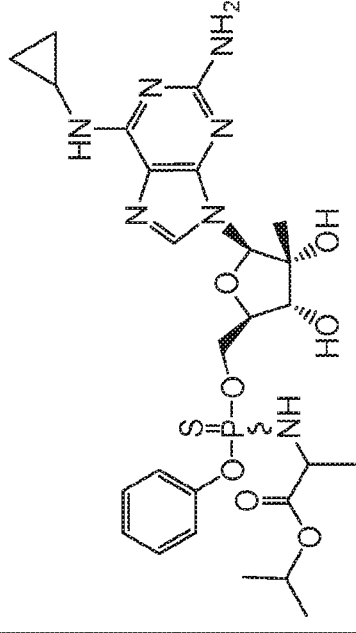
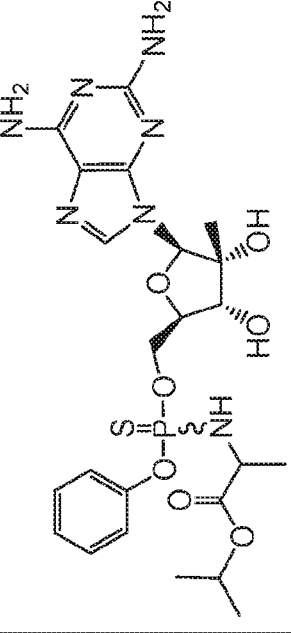
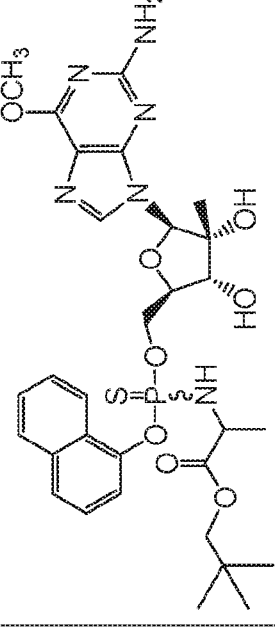
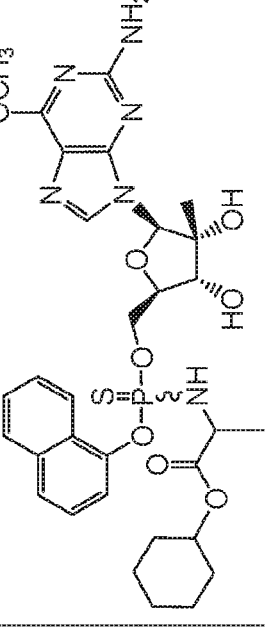

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6060 | 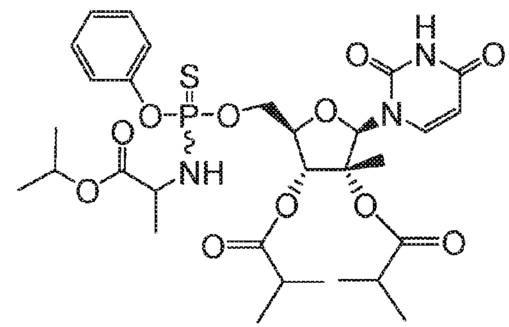 |
| 6061 | 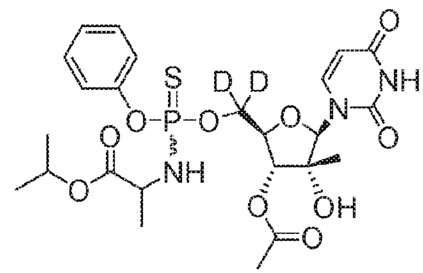 |
| 6062 | 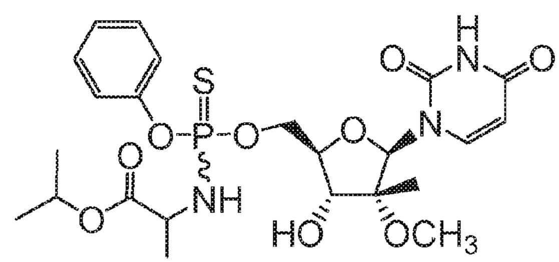 |

| # | Structure |
|---|---|
| 6058 | 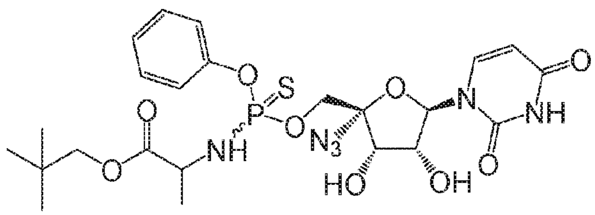 |
| 6059 | 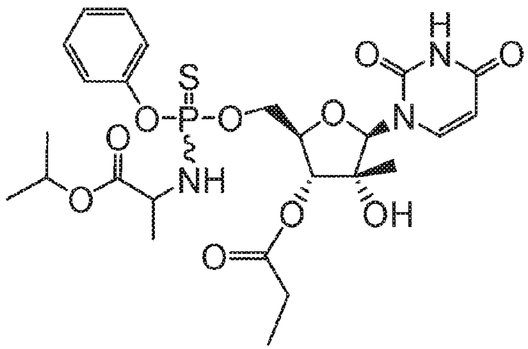 |

Figure 6 (cont.): Compounds of Formula (CC) and alpha-thiotriphosphates thereof

Figure 6 (cont.): Compounds of Formula (CC) and alpha-thiotriphosphates thereof
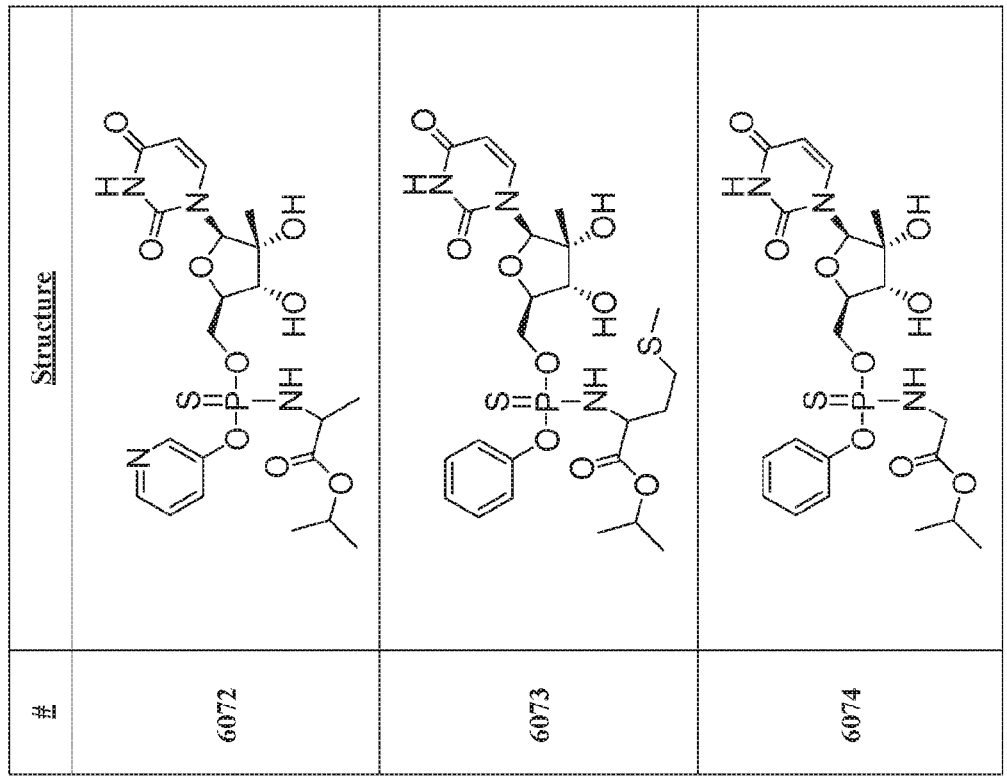
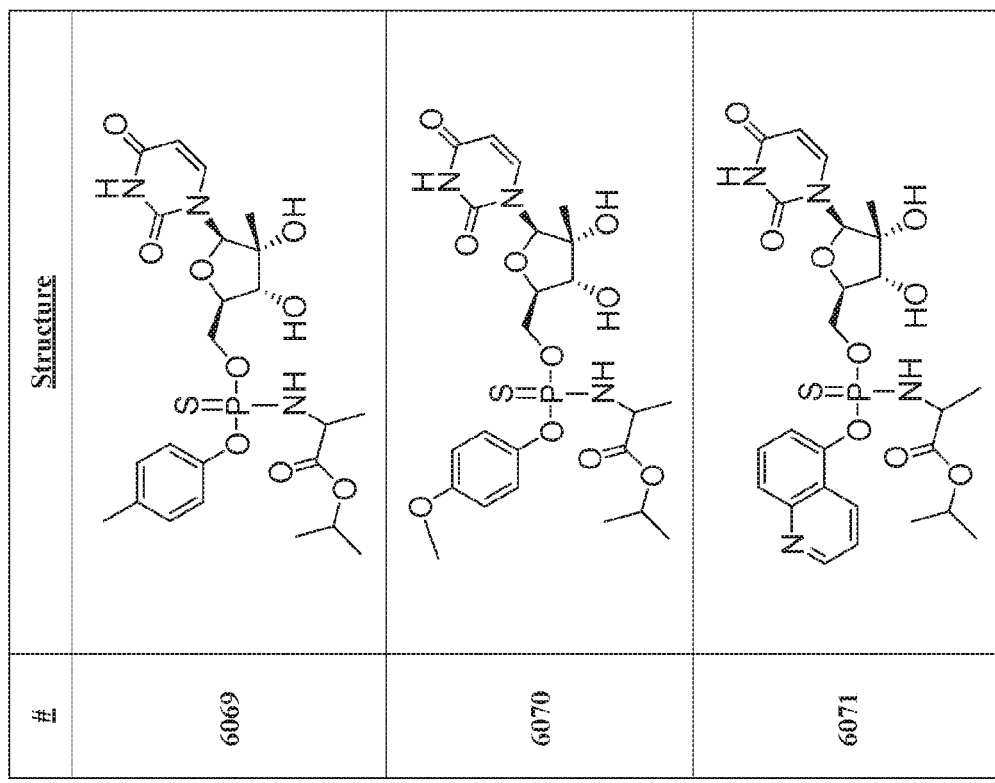

Figure 6 (cont.): Compounds of Formula (CC) and alpha-thiotriphosphates thereof
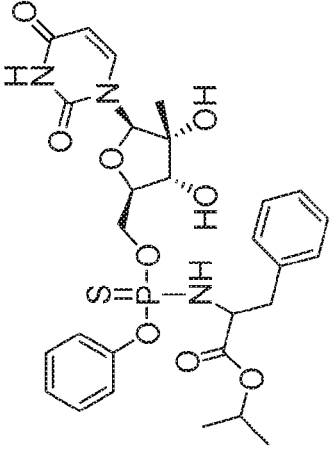
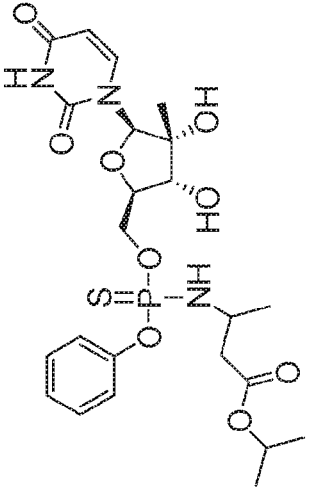
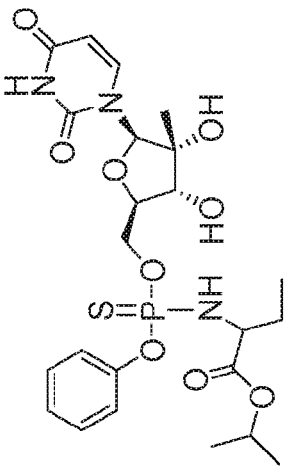
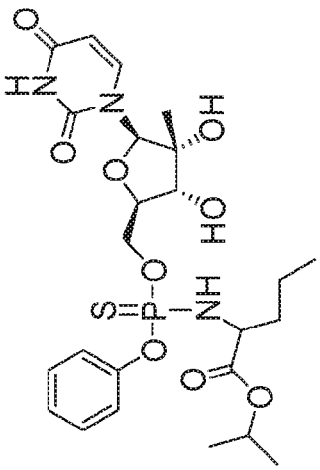

Figure 7: Compounds of Formula (AA)

| # | Structure |
|---|---|
| 7000 | (structure with B1AA, R1AA, R2AA, R3AA, R4AA, R5AA substituents on a thiophosphate sugar) |
| 7001 | (uridine 2'-C-ethynyl-2'-OH nucleoside with 5'-phenyl(isopropoxyalaninyl)thiophosphoramidate) |
| 7002 | (uridine 2'-C-vinyl-2'-OH nucleoside with 5'-phenyl(isopropoxyalaninyl)thiophosphoramidate) |
| 7003 | (uridine 2'-C-ethyl-2'-OH nucleoside with 5'-phenyl(isopropoxyalaninyl)thiophosphoramidate) |

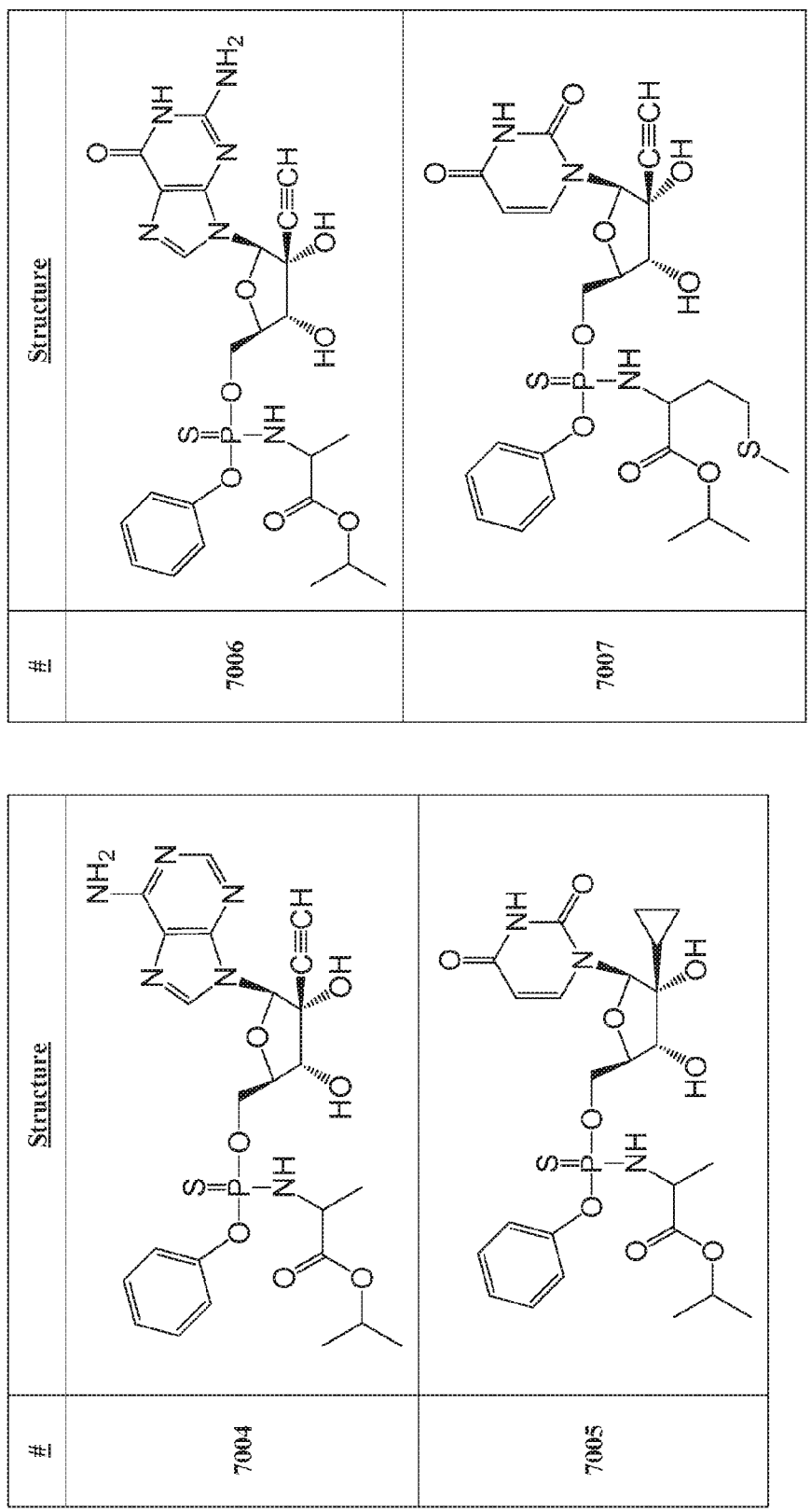
Figure 7 (cont.): Compounds of Formula (AA)

Figure 7 (cont.): Compounds of Formula (AA)
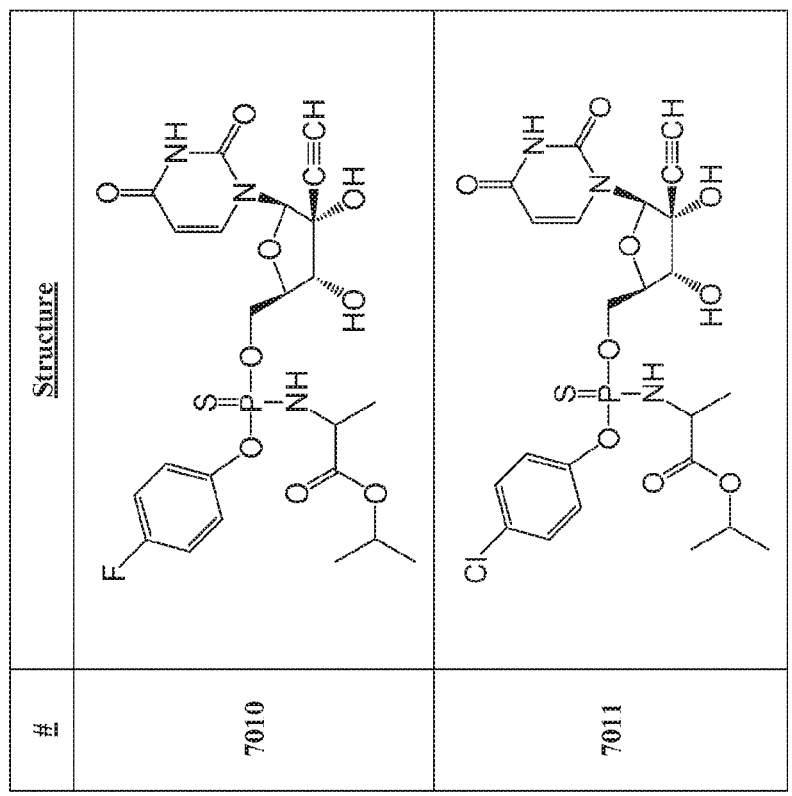
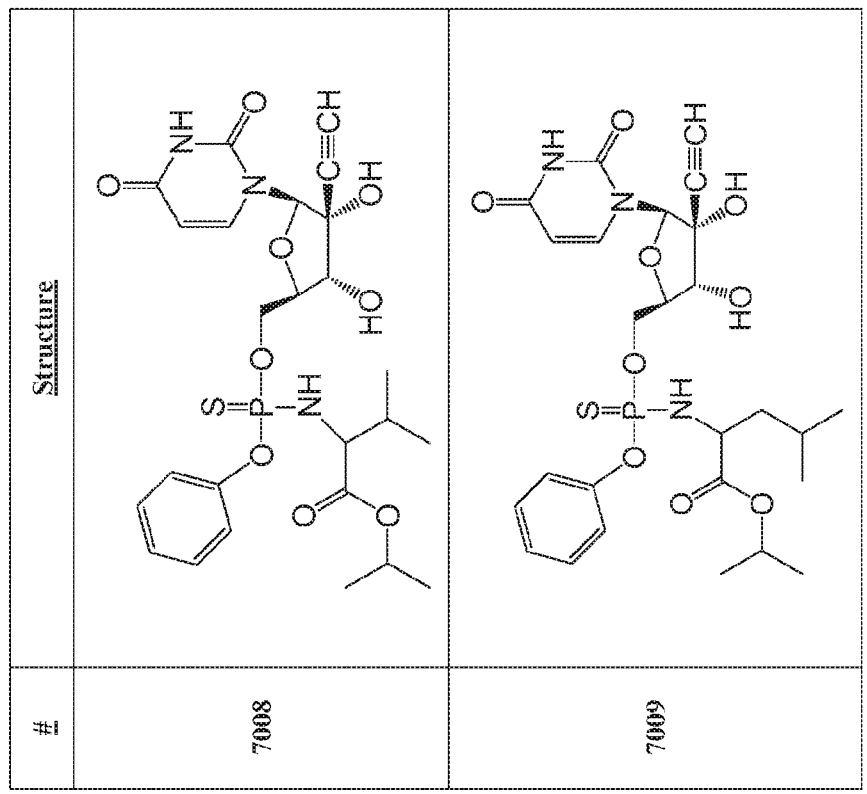

Figure 7 (cont.): Compounds of Formula (AA)

| # | Structure |
|---|---|
| 7014 | (structure of uridine analog with 4'-propynyl-CH3, 3'-OH, 5'-O-phosphorothioate with phenoxy and isopropyl alaninate) |
| 7015 | (structure of uridine analog with 4'-ethynyl, 3'-OH, 5'-O-phosphorothioate with phenoxy and isopropyl alaninate) |

| # | Structure |
|---|---|
| 7012 | (structure of uridine analog with 4'-ethynyl, 3'-OH, 5'-O-phosphorothioate with 3-chloro-4-fluorophenoxy and isopropyl alaninate) |
| 7013 | (structure of uridine analog with 4'-ethynyl, 3'-OH, 5'-O-phosphorothioate with 1-naphthyloxy and isopropyl alaninate) |

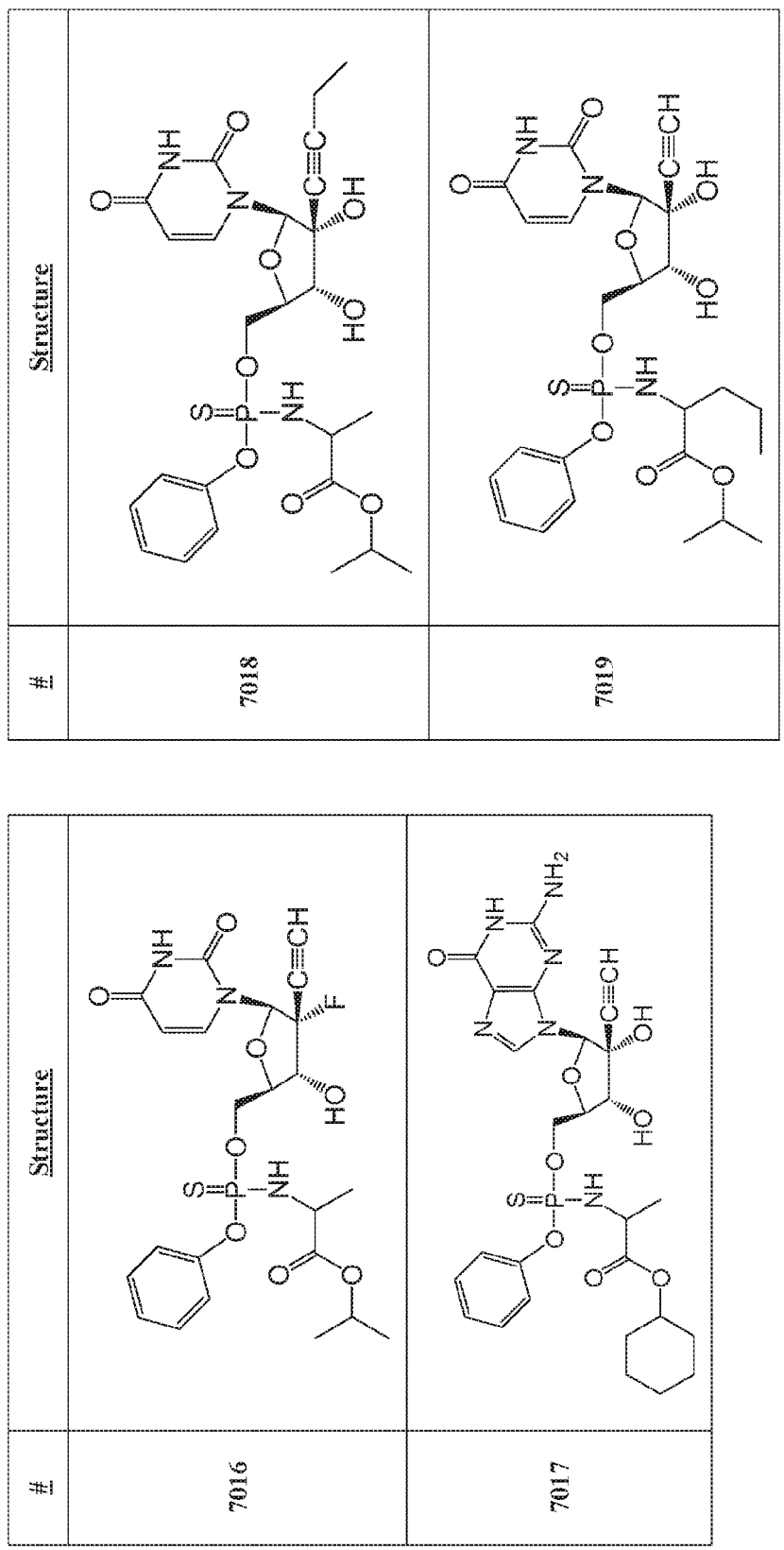
Figure 7 (cont.): Compounds of Formula (AA)

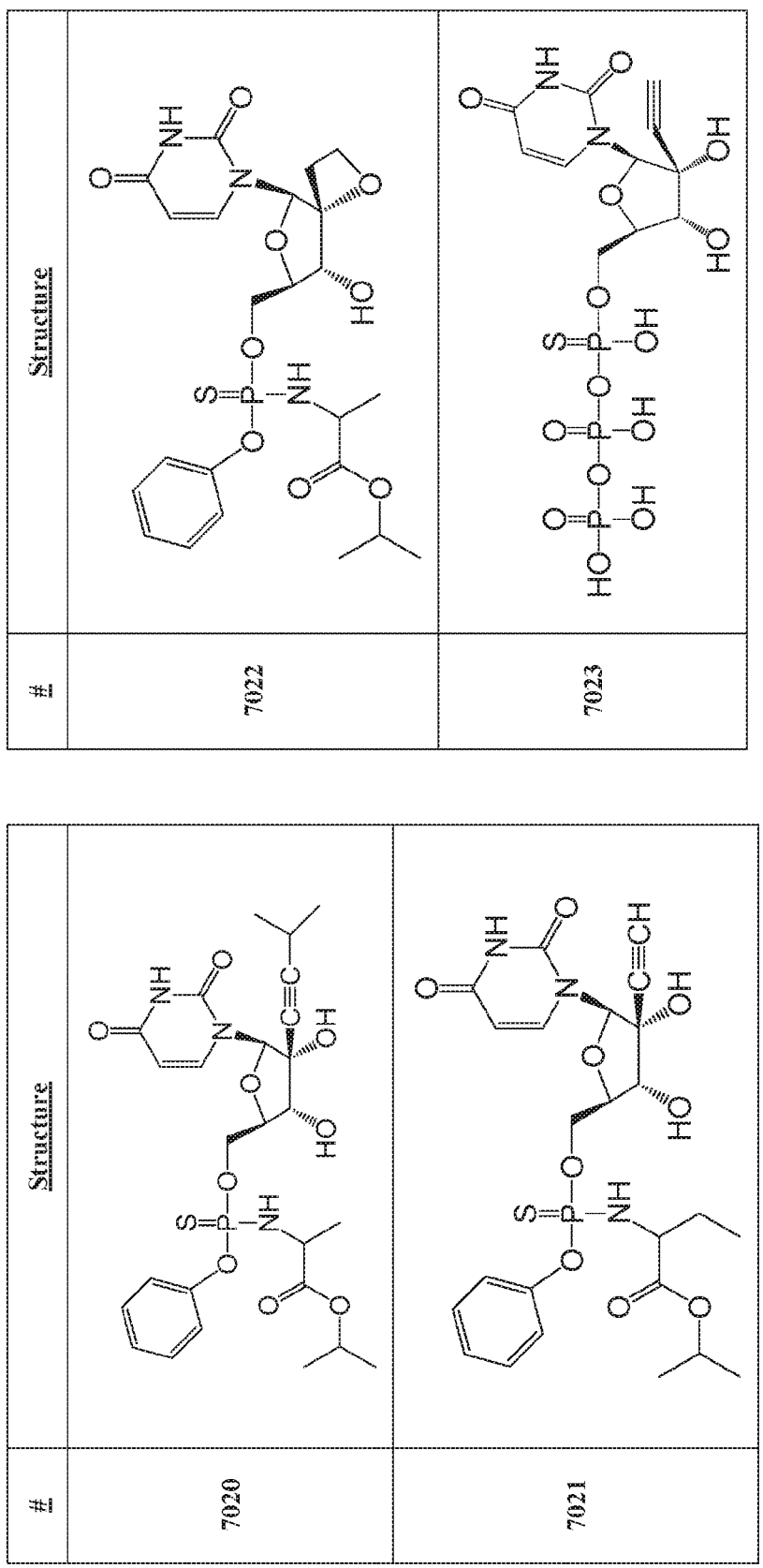
Figure 7 (cont.): Compounds of Formula (AA)

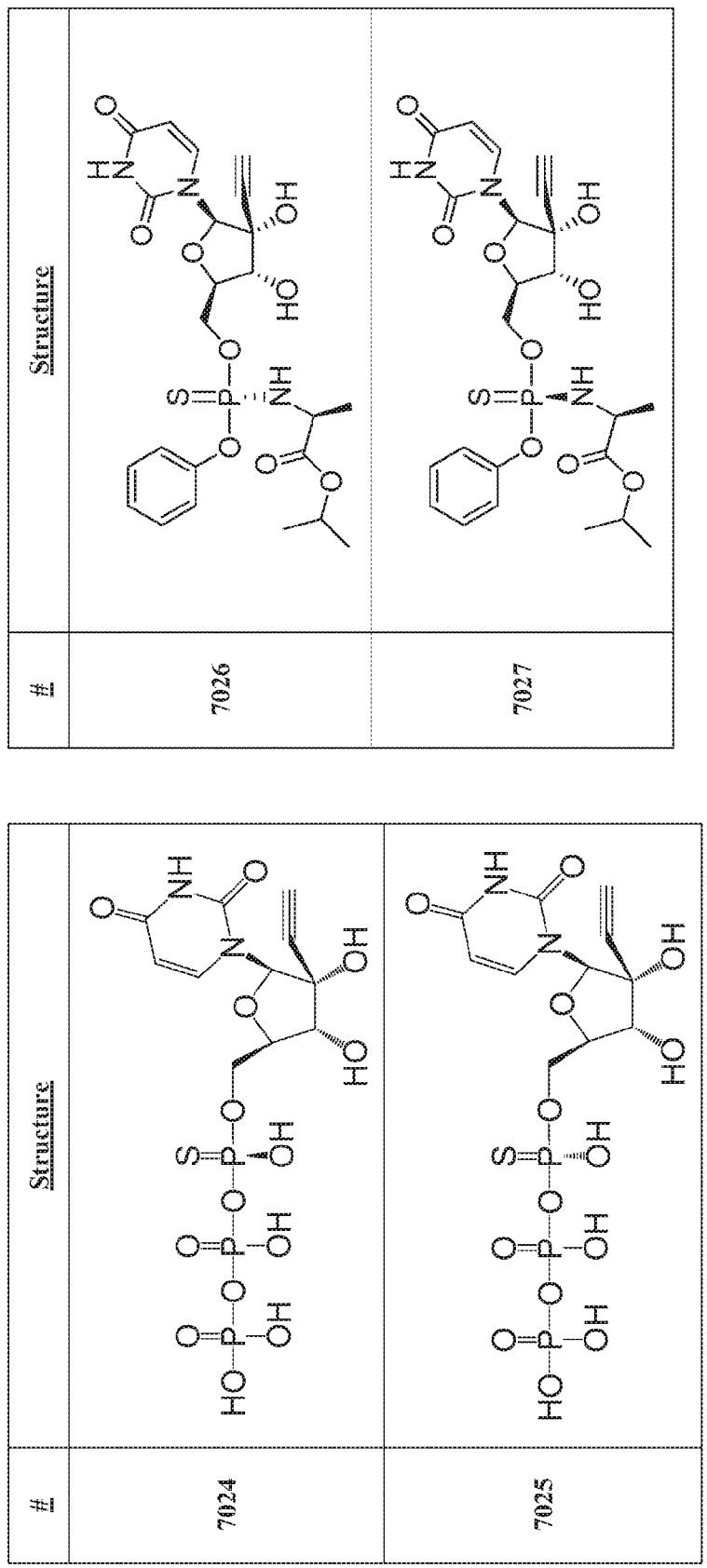
Figure 7 (cont.): Compounds of Formula (AA)

Figure 8: Compounds of Formula (BB)
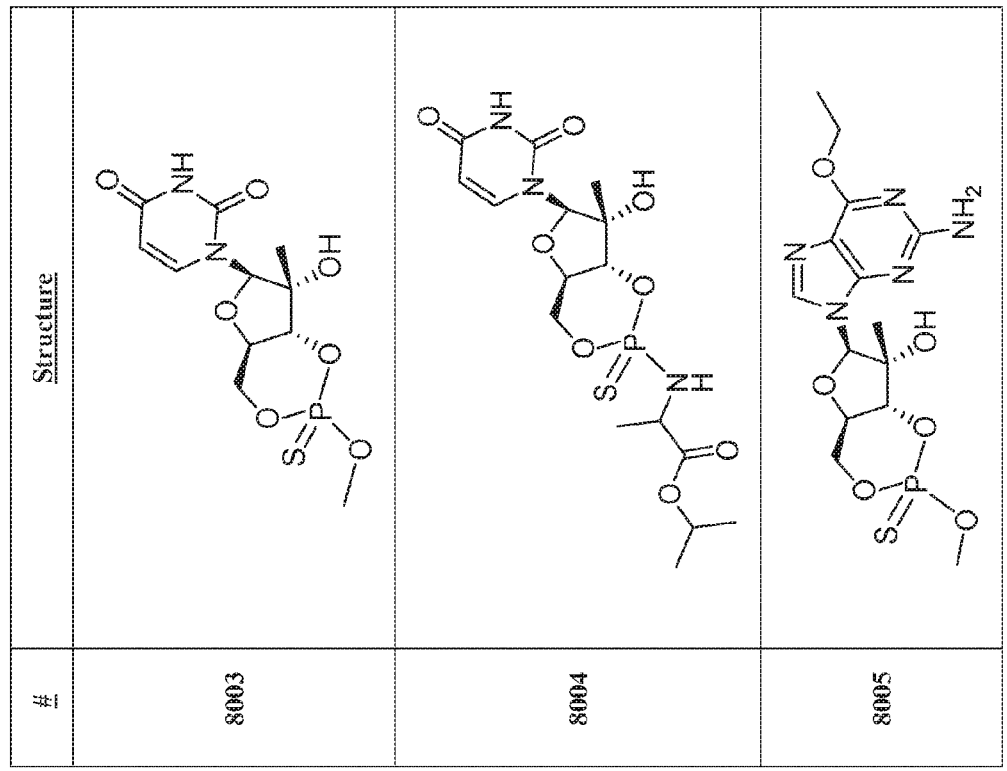
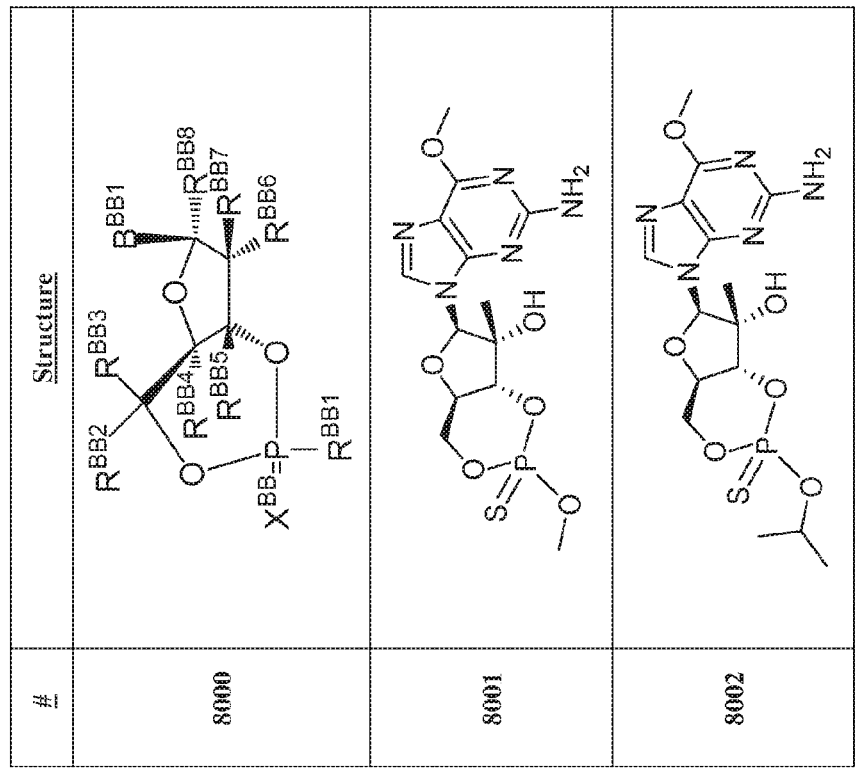

Figure 8 (cont.): Compounds of Formula (BB)
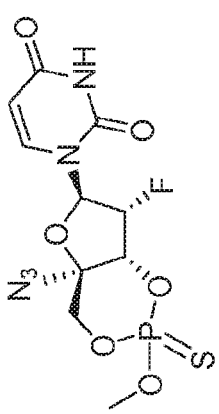

Figure 8 (cont.): Compounds of Formula (BB)
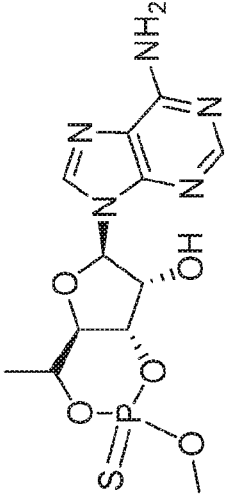

Figure 9: Compounds of Formula (DD)

Figure 9 (cont.): Compounds of Formula (DD)

| # | Structure |
|---|---|
| 9007 | (structure) |
| 9008 | (structure) |
| 9009 | (structure) |
| 9010 | (structure) |

Figure 9 (cont.): Compounds of Formula (DD)

Figure 9 (cont.): Compounds of Formula (DD)

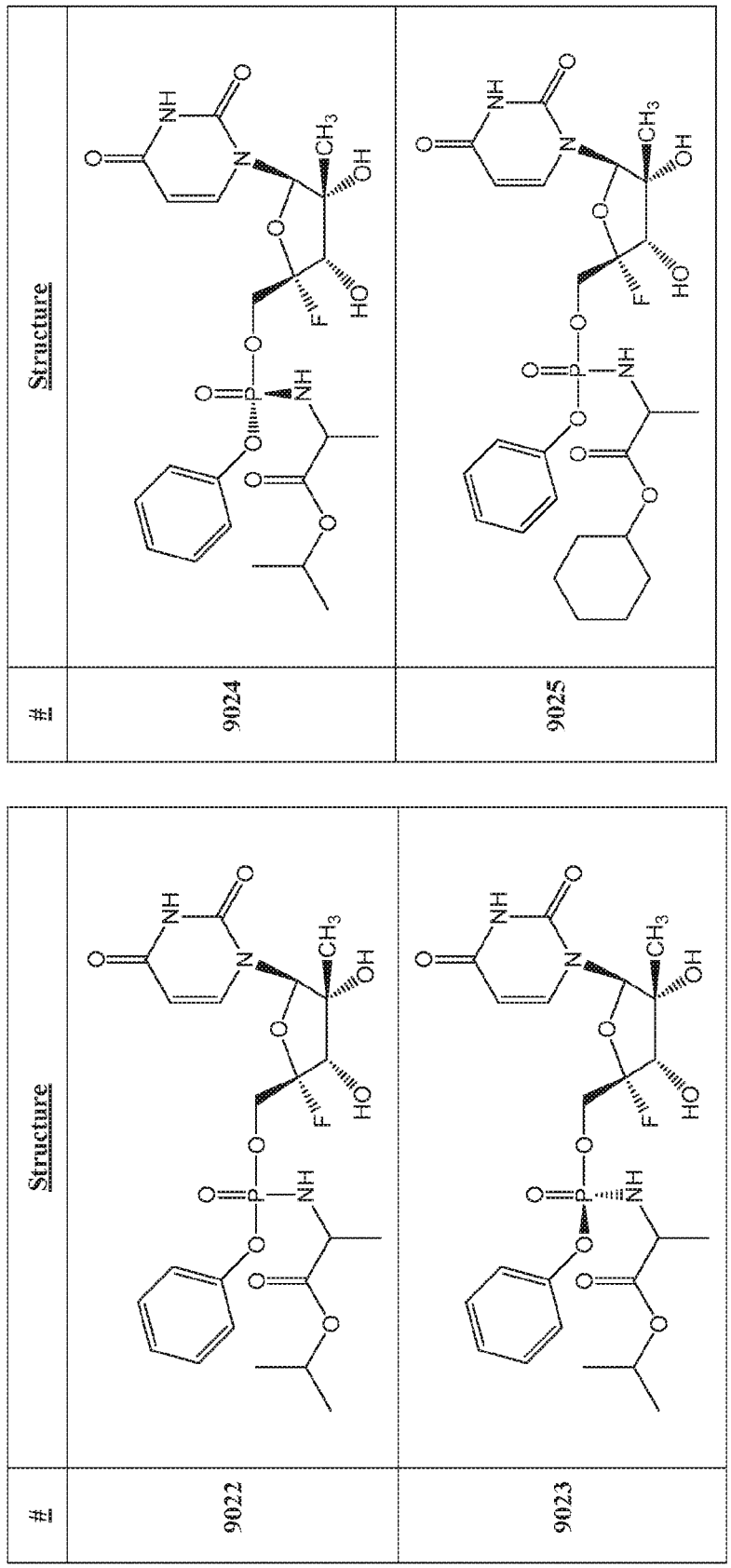
Figure 9 (cont.): Compounds of Formula (DD)

Figure 9 (cont.): Compounds of Formula (DD)

| # | Structure |
|---|---|
| 9028 | |
| 9029 | |
| 9026 | 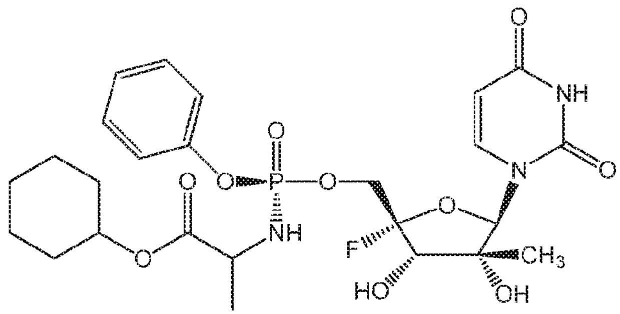 |
| 9027 | 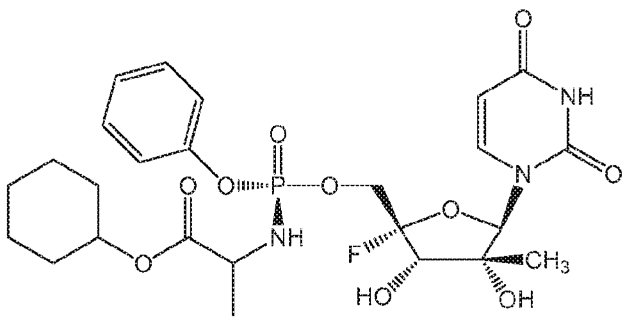 |

Figure 9 (cont.): Compounds of Formula (DD)
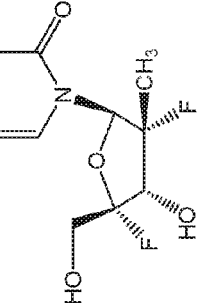

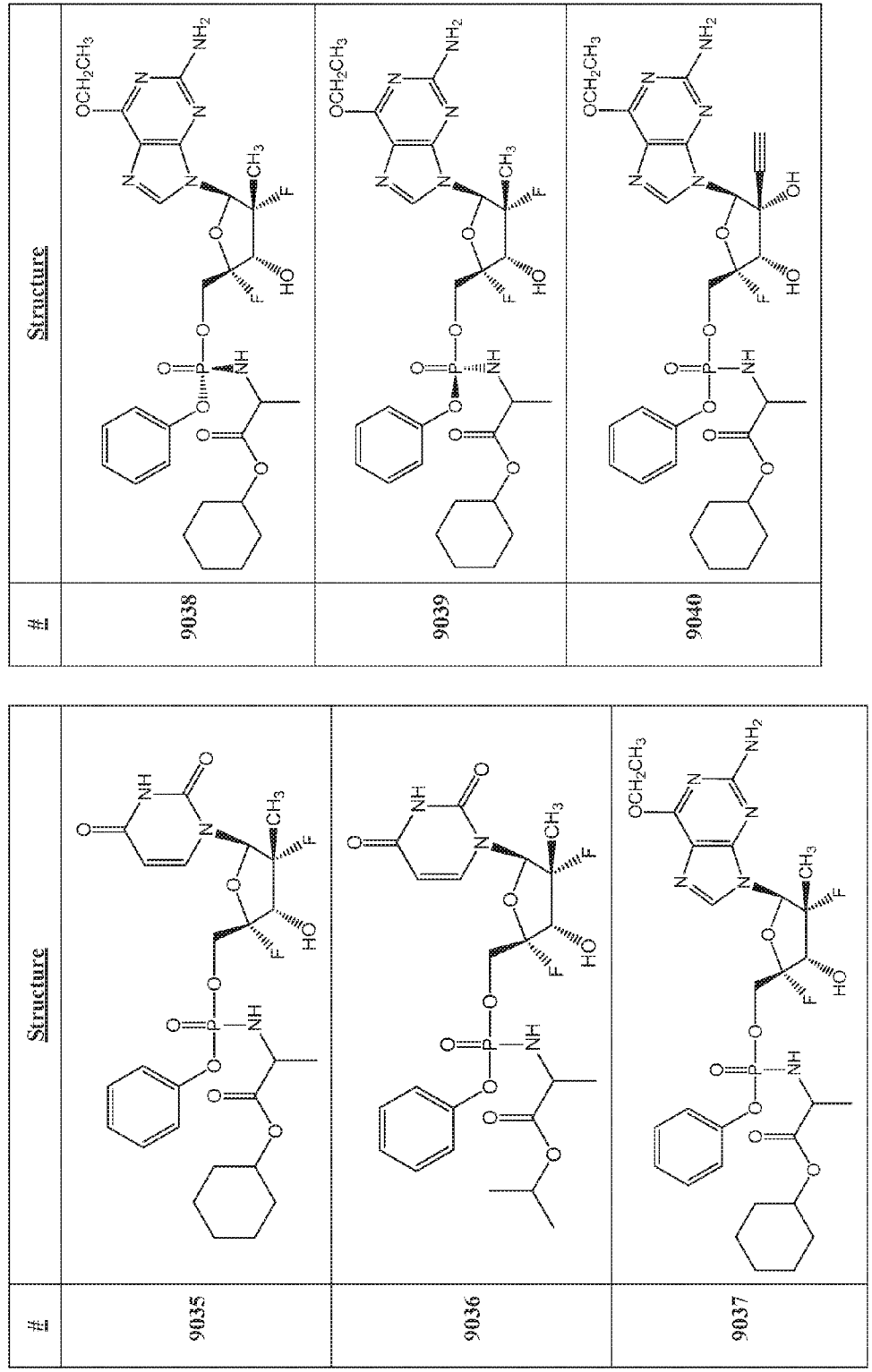
Figure 9 (cont.): Compounds of Formula (DD)

Figure 9 (cont.): Compounds of Formula (DD)
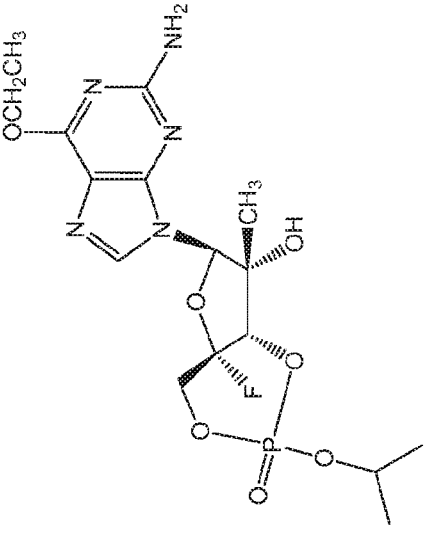
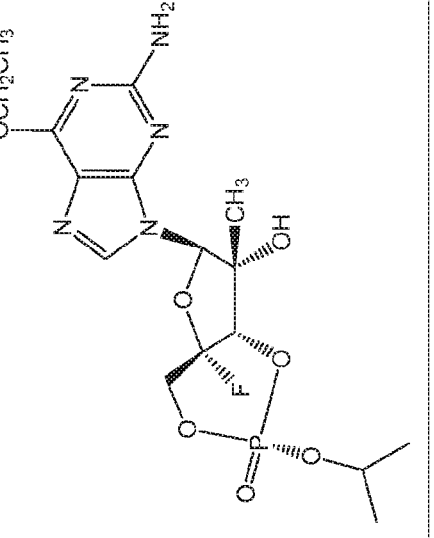
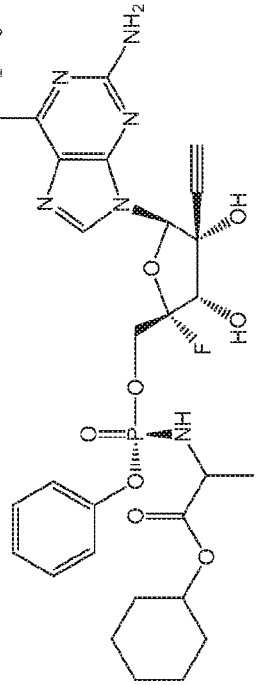
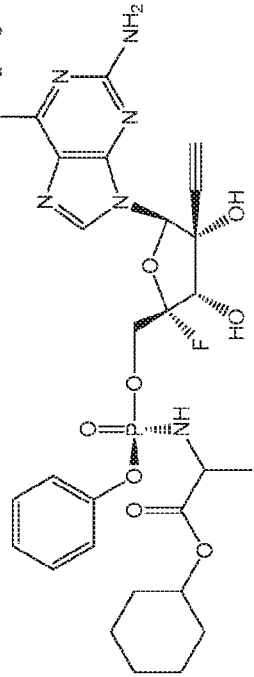

Figure 9 (cont.): Compounds of Formula (DD)
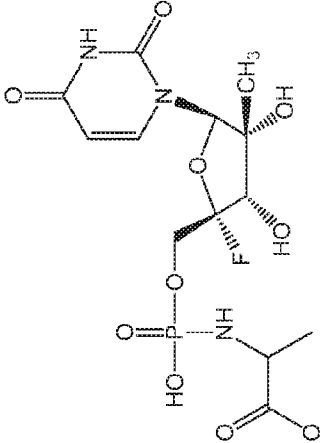

Figure 9 (cont.): Compounds of Formula (DD)

Figure 9 (cont.): Compounds of Formula (DD)

| # | Structure |
|---|---|
| 9057 | (structure: cytosine nucleoside with 2'-CH₃, 2'-N₃, 4'-F) |
| 9058 | (structure: cytosine nucleoside with 2'-CH₃, 2'-OH, 4'-F) |

| # | Structure |
|---|---|
| 9054 | (structure: guanosine triphosphate analog with 2'-C≡CH, 2'-F) |
| 9055 | (structure: uridine nucleoside with 2'-CH₃, 2'-Cl, 4'-F) |
| 9056 | (structure: uridine triphosphate analog with 2'-CH₃, 2'-Cl, 4'-F) |

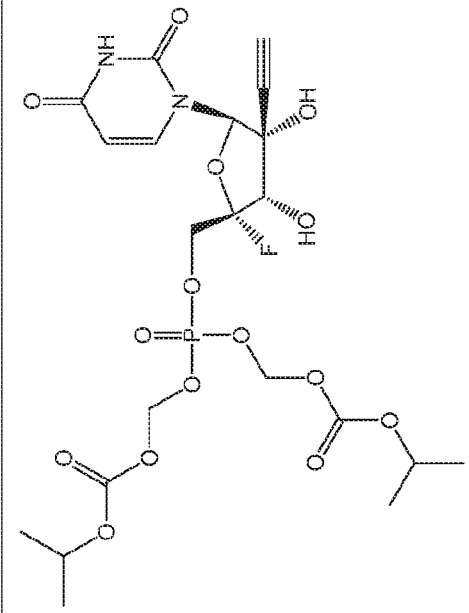
Figure 9 (cont.): Compounds of Formula (DD)

Figure 9 (cont.): Compounds of Formula (DD)

| # | Structure |
|---|---|
| 9065 | |
| 9066 | |
| 9063 | 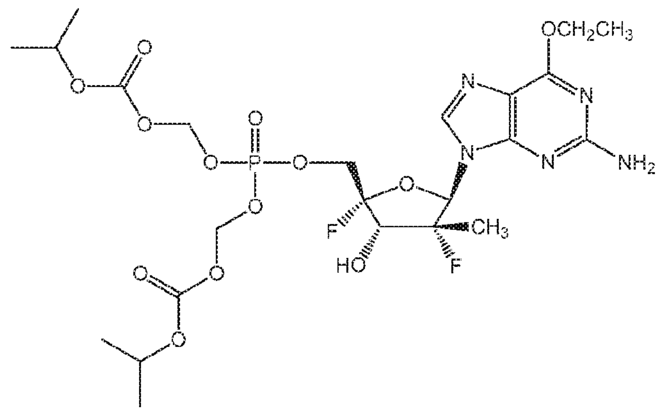 |
| 9064 | 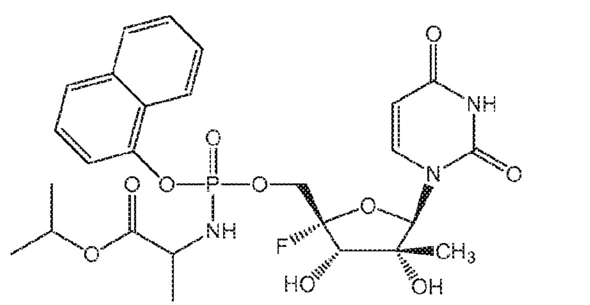 |

Figure 9 (cont.): Compounds of Formula (DD)

| # | Structure |
|---|---|
| 9069 | |
| 9070 | |
| 9067 | 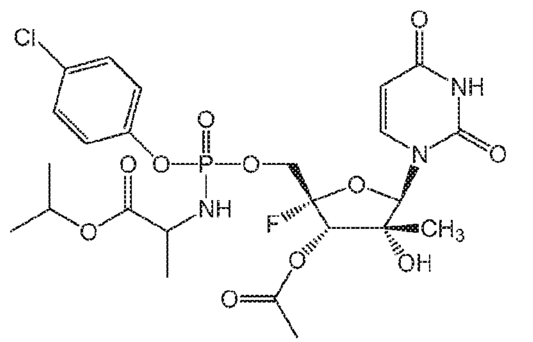 |
| 9068 | 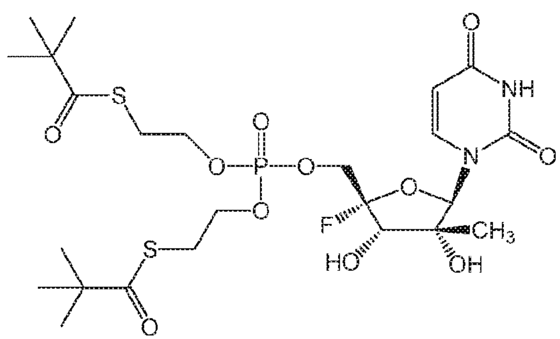 |

Figure 9 (cont.): Compounds of Formula (DD)
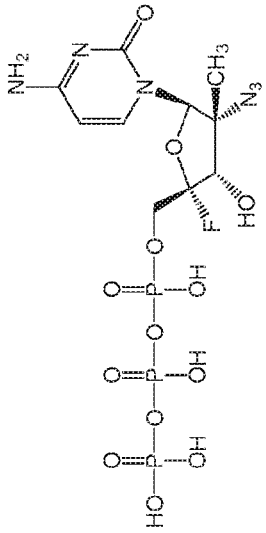
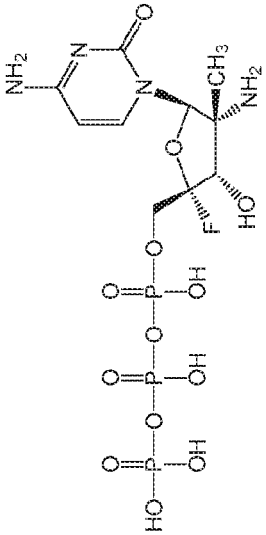
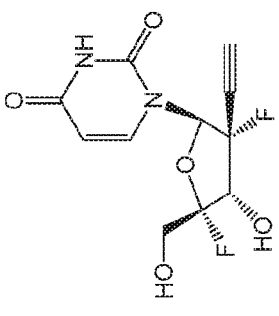
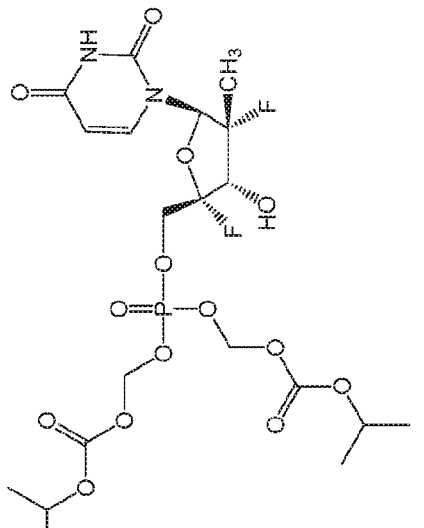
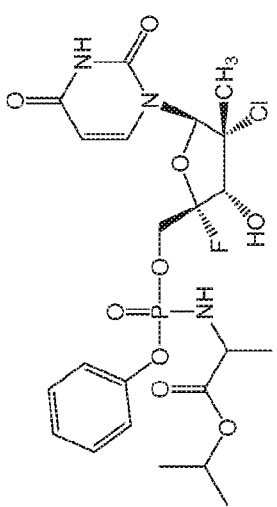

Figure 9 (cont.): Compounds of Formula (DD)

Figure 9 (cont.): Compounds of Formula (DD)

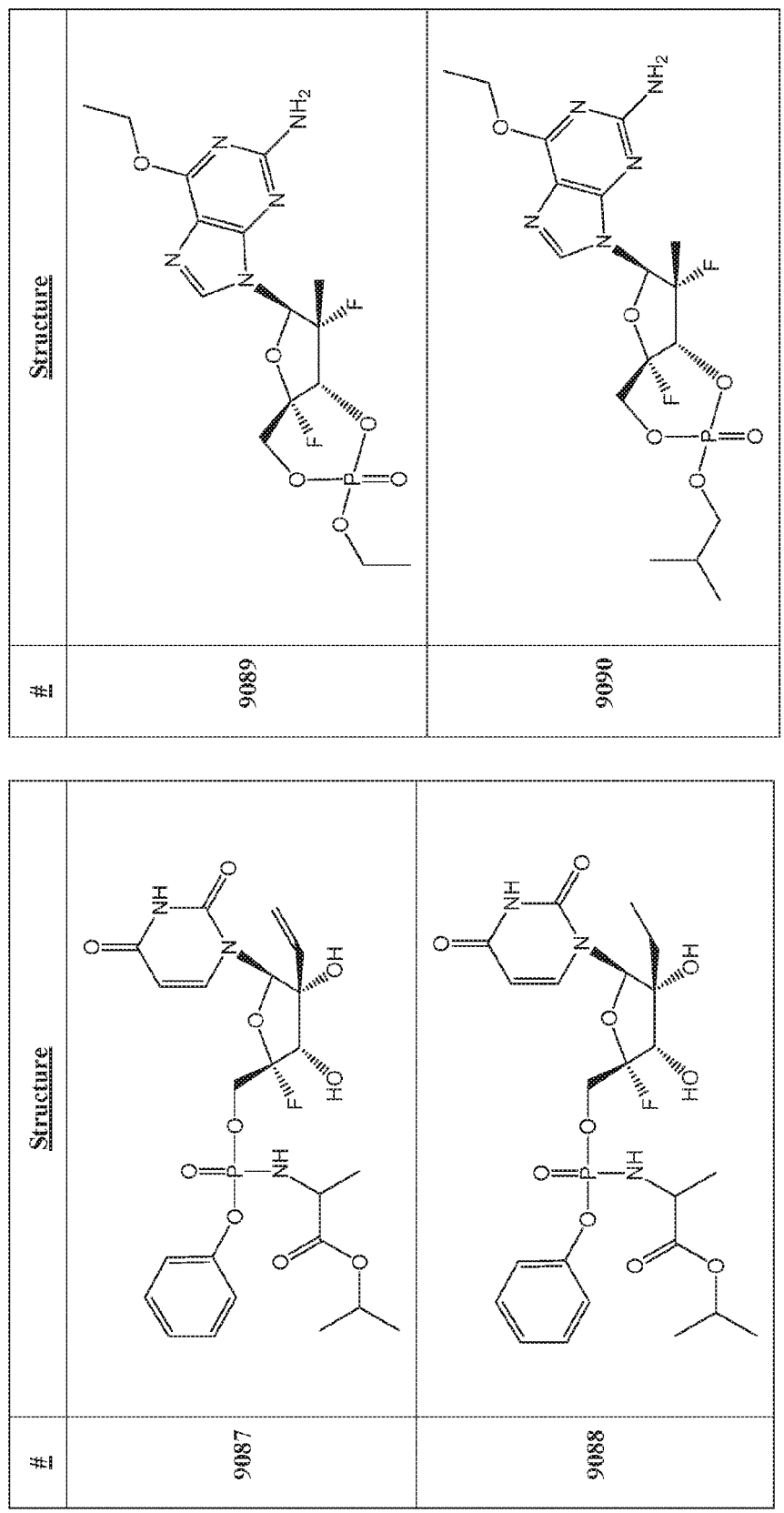
Figure 9 (cont.): Compounds of Formula (DD)

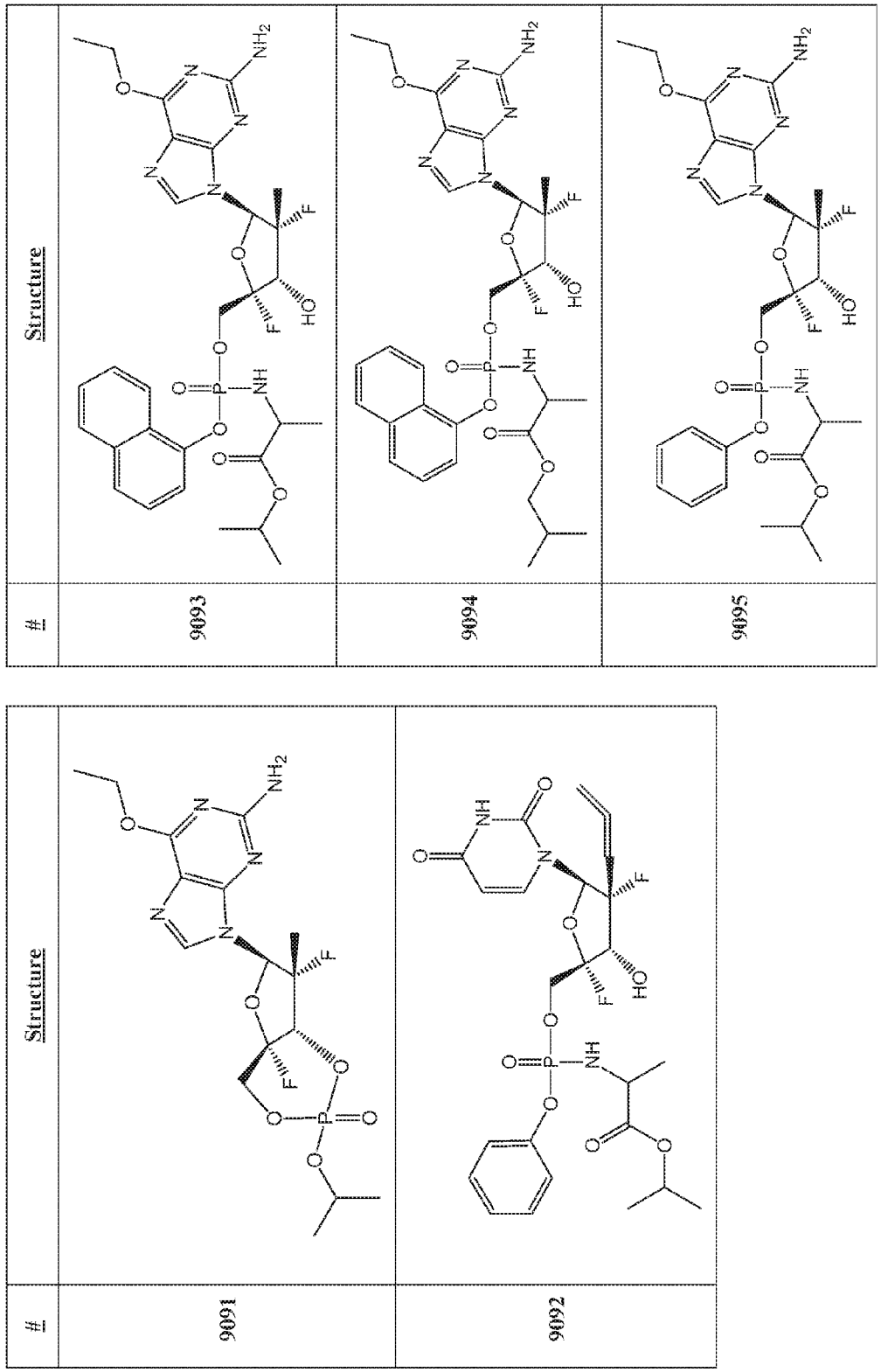
Figure 9 (cont.): Compounds of Formula (DD)

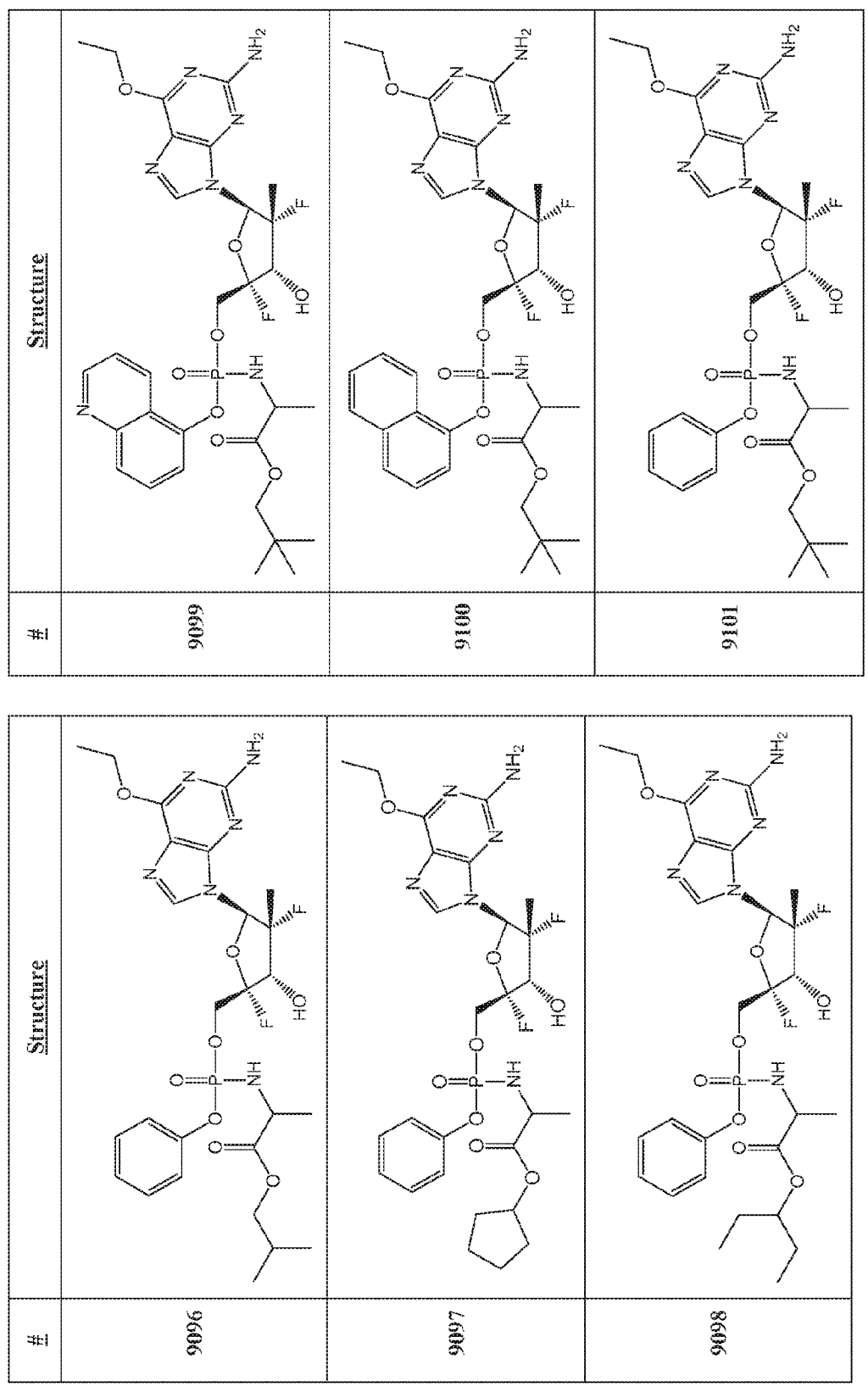
Figure 9 (cont.): Compounds of Formula (IDD)

Figure 9 (cont.): Compounds of Formula (DD)

SUBSTITUTED NUCLEOSIDES, NUCLEOTIDES AND ANALOGS THEREOF

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present application relates to the fields of chemistry, biochemistry and medicine. More particularly, disclosed herein are nucleotide analogs, pharmaceutical compositions that include one or more nucleotide analogs and methods of synthesizing the same. Also disclosed herein are methods of treating diseases and/or conditions with a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof.

Some embodiments disclosed herein relate to a method of ameliorating and/or treating a hepatitis C viral (HCV) infection that can include administering to a subject identified as suffering from the HCV infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a HCV infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a HCV infection.

Some embodiments disclosed herein relate to a method of ameliorating and/or treating a HCV infection that can include contacting a cell infected with the hepatitis C virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a HCV infection that can include contacting a cell infected with the hepatitis C virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for ameliorating and/or treating a HCV infection by contacting a cell infected with the hepatitis C virus with an effective amount of said compound(s).

Some embodiments disclosed herein relate to a method of inhibiting replication of a hepatitis C virus that can include contacting a cell infected with the hepatitis C virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a hepatitis C virus that can include contacting a cell infected with the hepatitis C virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for inhibiting replication of a hepatitis C virus by contacting a cell infected with the hepatitis C virus with an effective amount of said compound(s).

Some embodiments disclosed herein relate to a method of ameliorating and/or treating a HCV infection that can include administering to a subject identified as suffering from the HCV infection an effective amount of a compound described herein or a pharmaceutically acceptable salt thereof (for example, one or more compounds of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, another antiviral compound, a compound of Formula (AA), a compound of Formula (BB), a compound of Formula (CC) and a compound of Formula (DD), or a pharmaceutically acceptable salt of any of the foregoing. Some embodiments disclosed herein relate to a method of ameliorating and/or treating a HCV infection that can include contacting a cell infected with the HCV infection with an effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, another antiviral compound, a compound of Formula (AA), a compound of Formula (BB), a compound of Formula (CC) and a compound of Formula (DD), or a pharmaceutically acceptable salt of any of the foregoing. Some embodiments disclosed herein relate to a method of inhibiting replication of a hepatitis C virus that can include administering to a subject identified as suffering from a HCV infection an effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, another antiviral compound, a compound of Formula (AA), a compound of Formula (BB), a compound of Formula (CC) and a compound of Formula (DD), or a pharmaceutically acceptable salt of any of the foregoing. In some embodiments, the agent can be a compound, or a pharmaceutically acceptable salt thereof, selected from Compound 1001-1016, 2001-2012, 3001-3014, 4001-4012, 5001-5011, 6001-6078, 7000-7027, 8000-8016 and 9000-9105, or a pharmaceutical composition that includes one or more of the aforementioned compounds, or a pharmaceutically acceptable salt of the foregoing. In some embodiments, the method can include administering a second agent selected from an interferon, ribavirin, a HCV protease inhibitor, a HCV polymerase inhibitor, a NS5A inhibitor, another antiviral compound, a compound of Formula (AA), a compound of Formula (BB), a compound of Formula (CC) and a compound of Formula (DD), or a pharmaceutically acceptable salt of any of the foregoing.

BRIEF DESCRIPTION OF THE DRAWINGS

FIG. 1 shows example HCV protease inhibitors.

FIG. 2 shows example nucleoside HCV polymerase inhibitors.

FIG. 3 shows example non-nucleoside HCV polymerase inhibitors.

FIG. 4 shows example NS5A inhibitors.

FIG. 5 shows example other antivirals.

FIG. 6 shows example compounds of Formula (CC) and alpha-thiotriphosphates thereof, wherein Formula (CC) and alpha-thiotriphosphates thereof are described herein.

FIG. 7 shows example compounds of Formula (AA), wherein Formula (AA) is described herein.

FIG. 8 shows example compounds of Formula (BB), wherein Formula (BB) is described herein.

Figure 9:
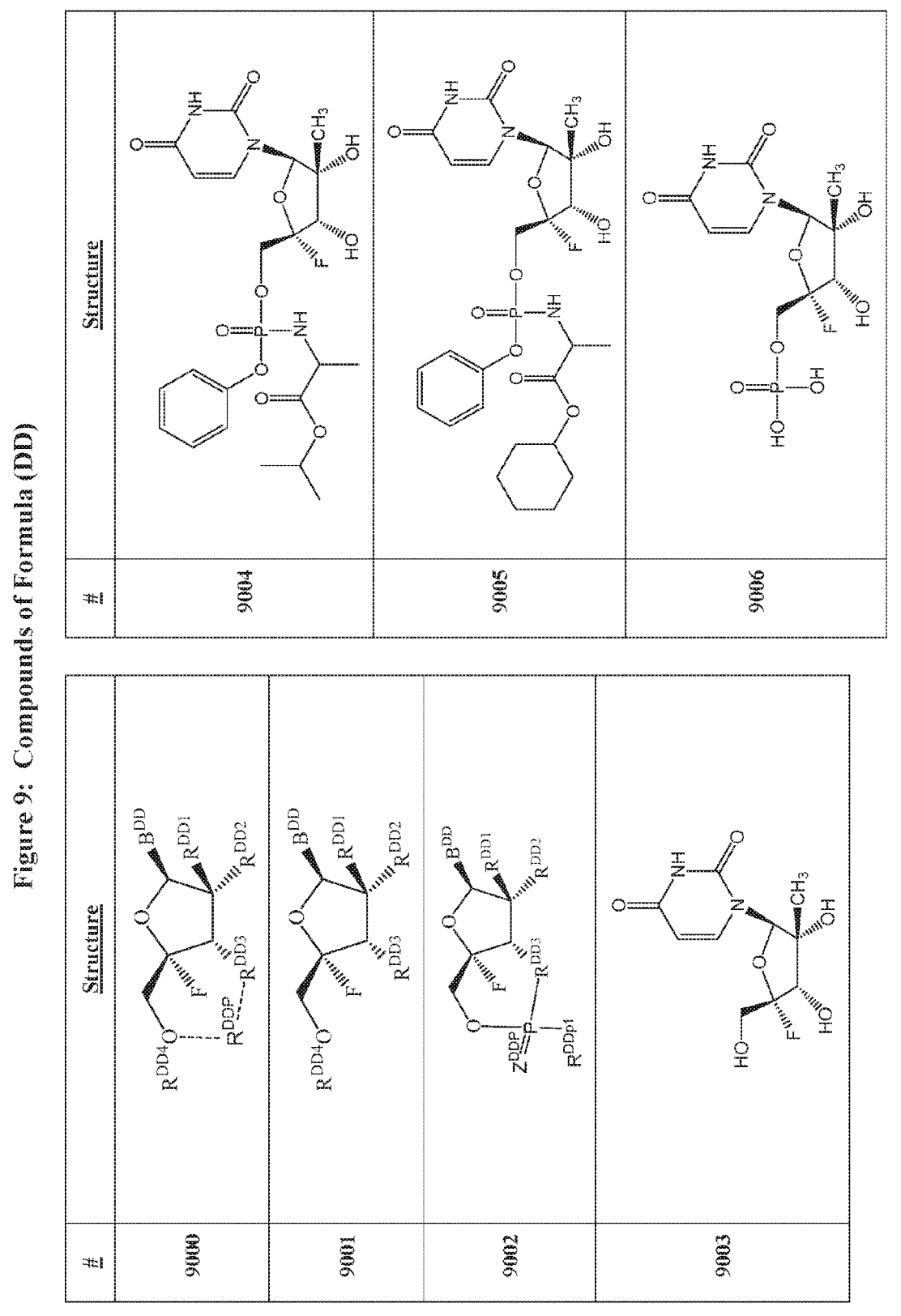
Figure 9:
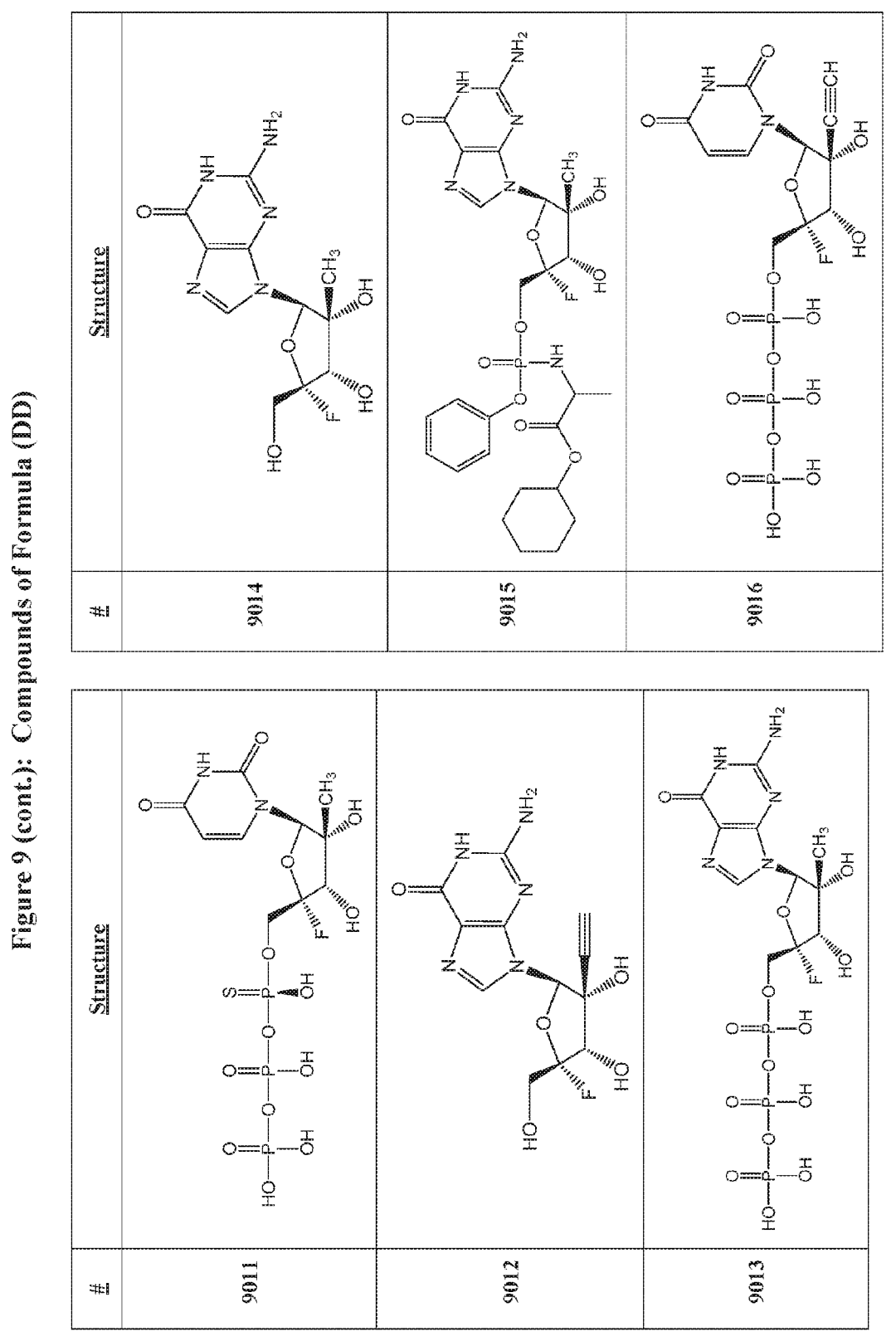
Figure 9:
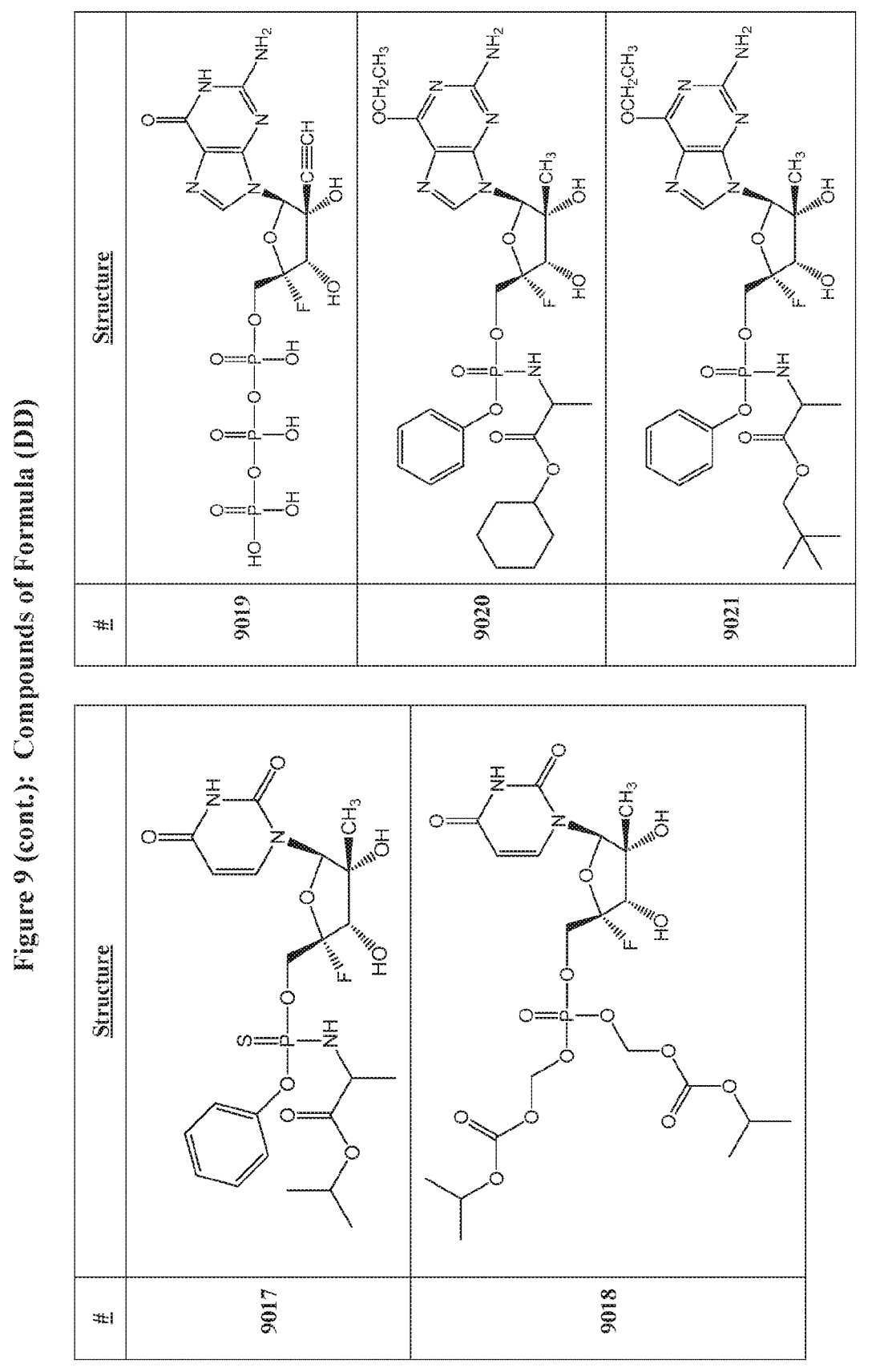
Figure 9:
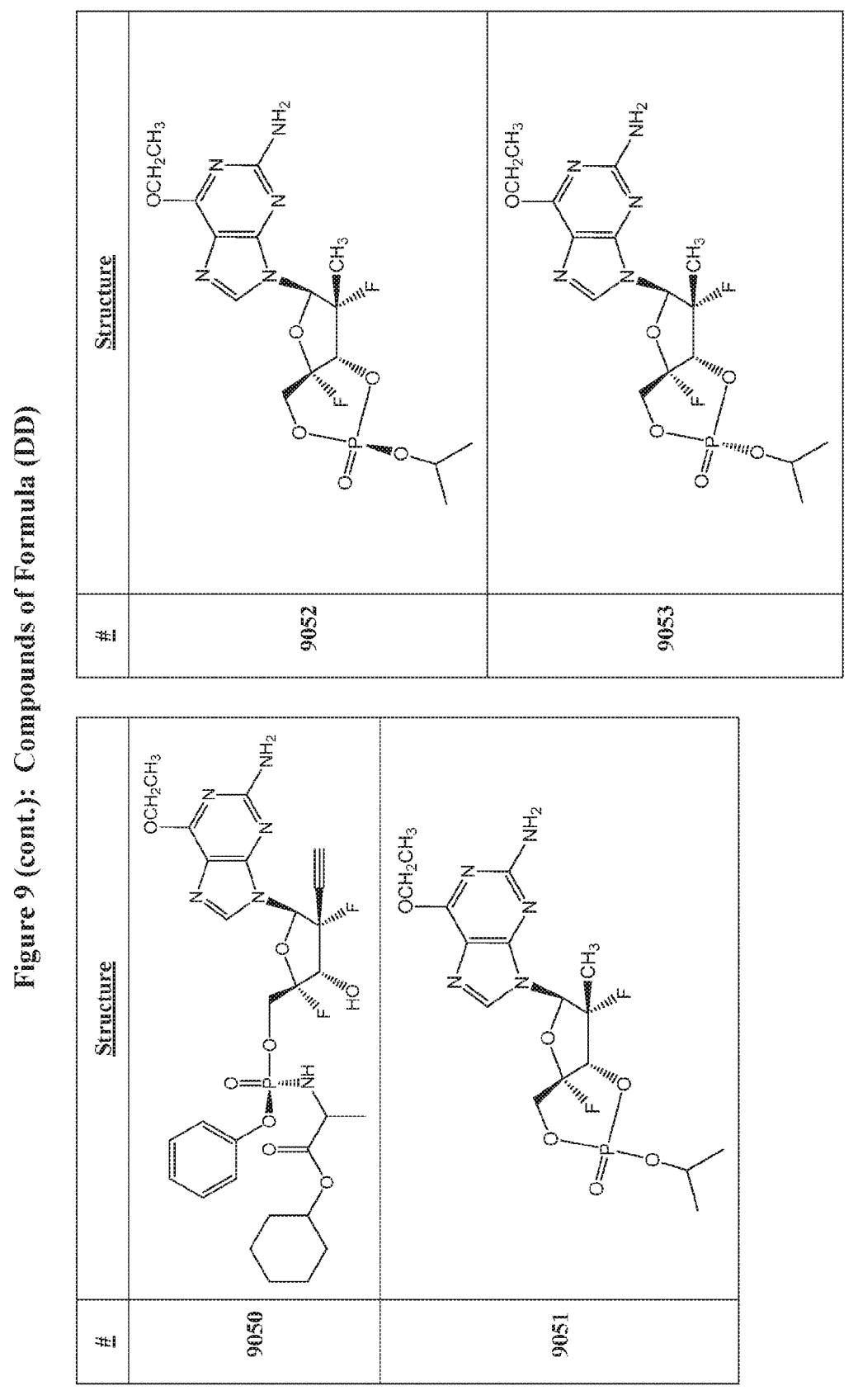
Figure 9:
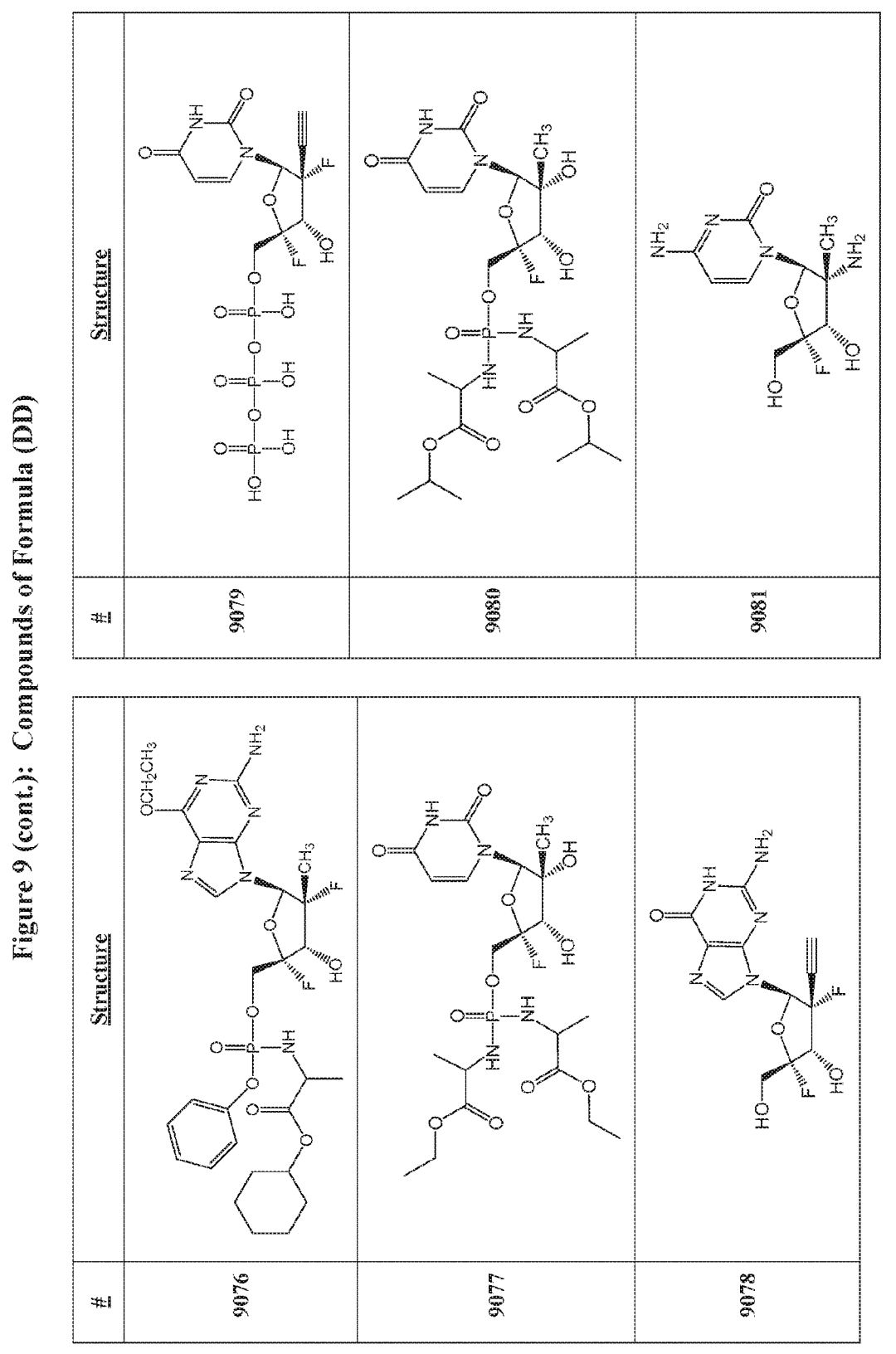
Figure 9:
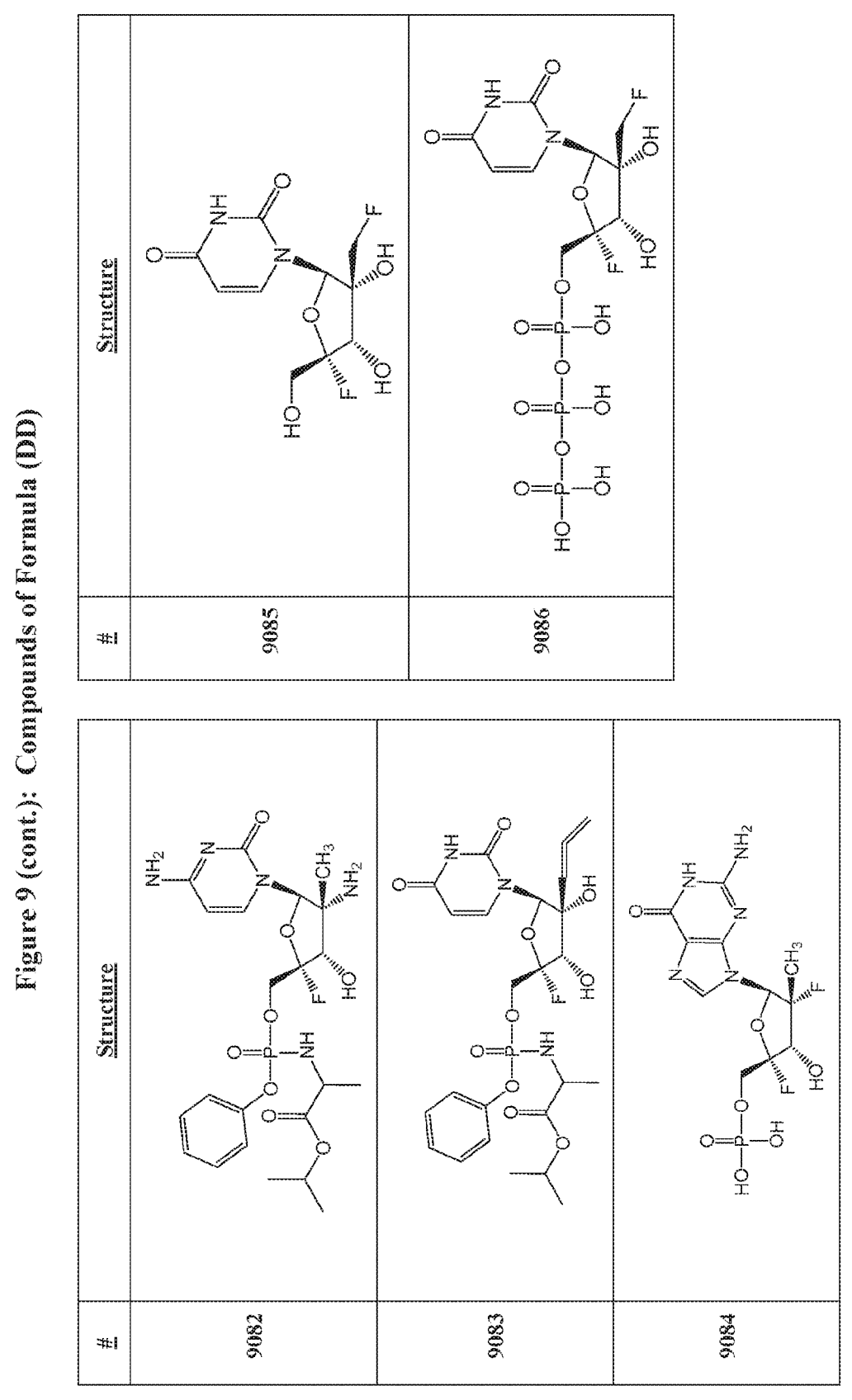
Figure 9:
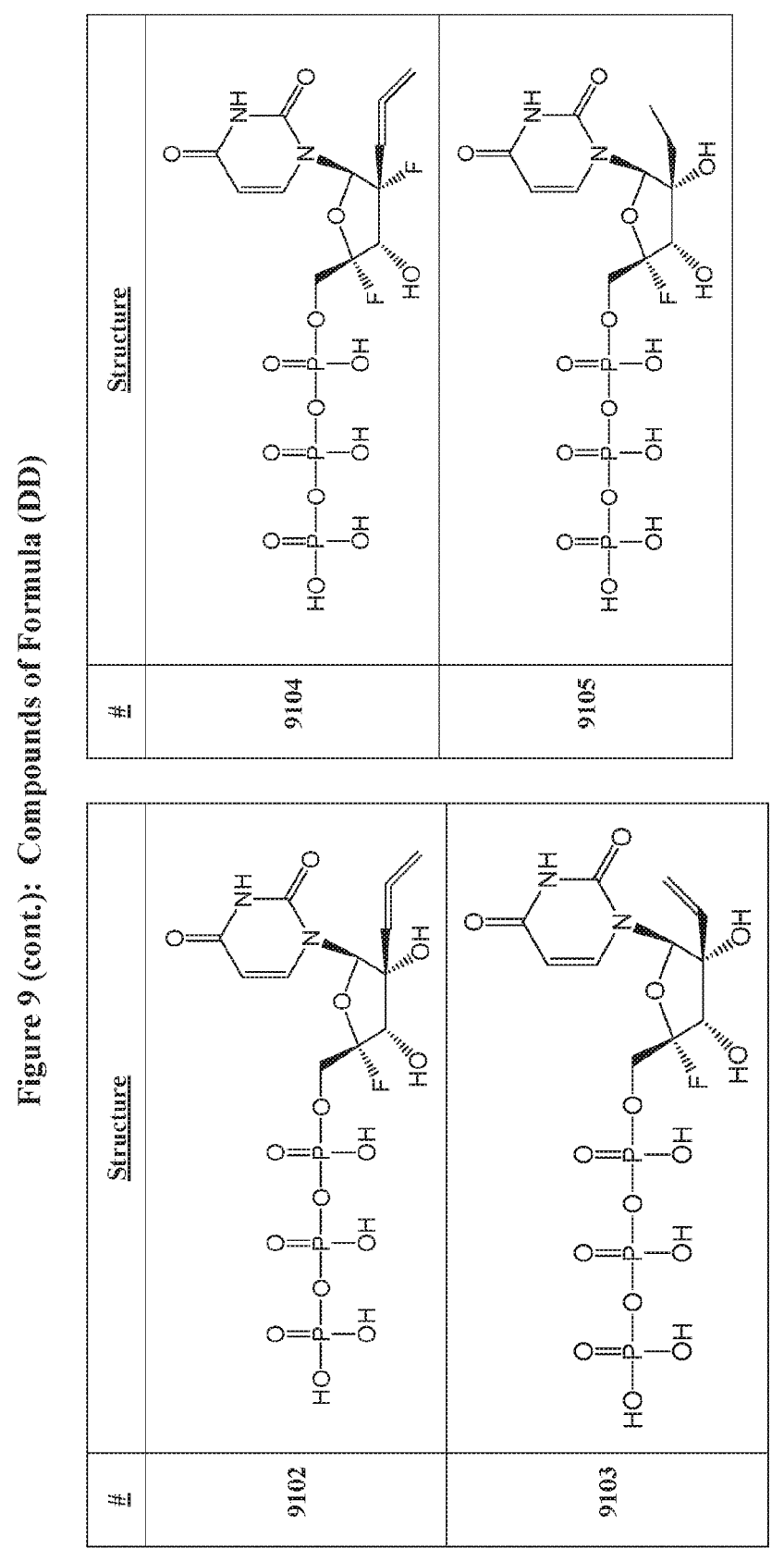

FIG. 9 shows example compounds of Formula (DD), wherein Formula (DD) is described herein.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$ and $R^{13}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

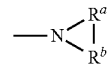

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl) and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), (heteroaryl)alkyl or (heterocyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl.

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

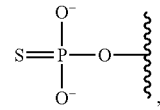

its protonated forms (for example,

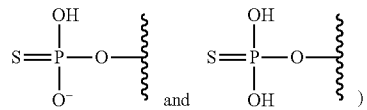

and its tautomers (such as

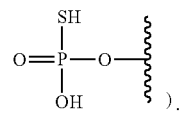

As used herein, the term "phosphate" is used in its ordinary sense as understood by those skilled in the art, and includes its protonated forms (for example,

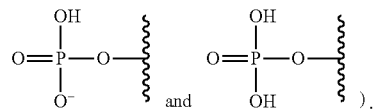

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

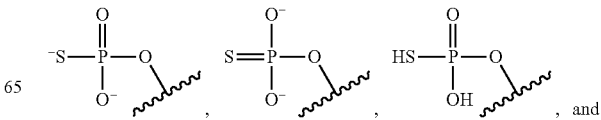
, and

-continued

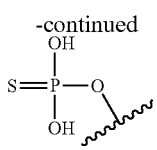

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

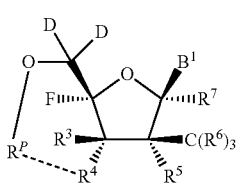

(I)

wherein: $B^1$ can be selected from an optionally substituted

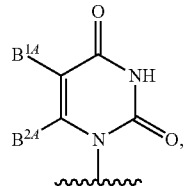

an optionally substituted

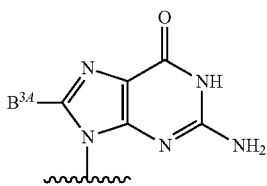

and an optionally substituted

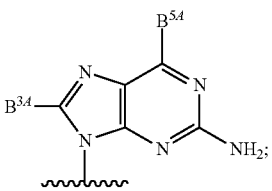

-------- can be absent or a single bond; when ------ is a single bond, then $R^P$ can be

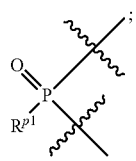

and $R^4$ can be O; when ------ is absent, then $R^P$ can be hydrogen or

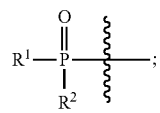

and $R^4$ can be —OH or F; $R^1$ can be selected from an —O-optionally substituted aryl,

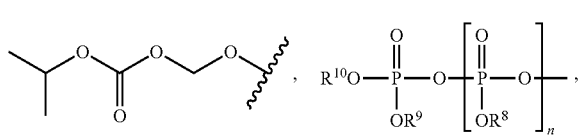

O⁻, and —OH; $R^2$ can be selected from O⁻, —OH, an optionally substituted N-linked amino acid, an optionally substituted N-linked amino acid ester derivative and

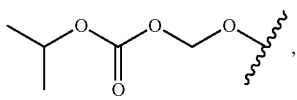

provided that when $R^2$ is $O^-$ or —OH, $R^1$ is selected from

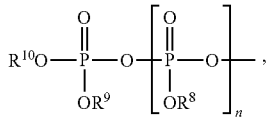

$O^-$ and —OH; $R^3$, each $R^6$ and $R^7$ can be independently hydrogen or deuterium; $R^5$ can be —OH or F; $R^8$, $R^9$ and $R^{10}$ can be independently absent or hydrogen; $B^{1A}$, $B^{2A}$, $B^{3A}$ and $B^{4A}$ can be independently hydrogen or deuterium; $B^{5A}$ can be —O-optionally substituted $C_{1-6}$ alkyl or —NH$_2$, $R^{p1}$ can be selected from $O^-$, OH, an —O-optionally substituted $C_{1-6}$ alkyl, an —O-optionally substituted aryl,

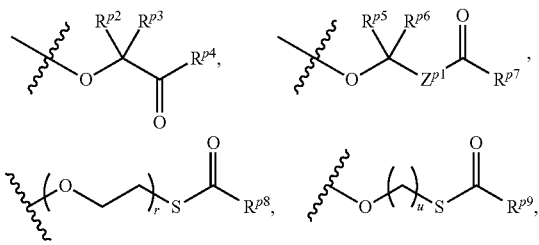

an optionally substituted N-linked amino acid and an optionally substituted N-linked amino acid ester derivative; $R^{p1}$, $R^{p3}$, $R^{p5}$ and $R^{p6}$ can be independently selected from hydrogen, an optionally substituted $C_{1-24}$ alkyl and an optionally substituted aryl; $R^{p4}$ and $R^{p7}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{p8}$ and $R^{p9}$ can be independently selected from hydrogen, an optionally substituted $C_{1-24}$ alkyl and an optionally substituted aryl; n can be 0 or 1; r can be 1 or 2; u can be 3, 4, or 5; and $Z^{p1}$ can be O or S.

In some embodiments, -------- can be absent, $R^P$ can be

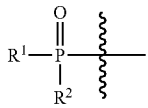

and $R^4$ can be —OH or F, and the compound of Formula (I) can have the structure of Formula (II), or a pharmaceutically acceptable salt thereof:

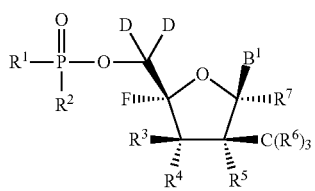

(II)

wherein: $B^1$, $R^1$, $R^2$, $R^3$, $R^4$, $R^5$, each $R^6$ and $R^7$ are provided herein.

A variety of groups can be attached to the phosphorus atom of

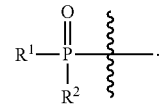

In some embodiments, $R^1$ can be an —O-optionally substituted aryl. For example, $R^1$ can be an —O-optionally substituted phenyl. When the phenyl is substituted, the ring can be substituted 1, 2, 3 or more than 3 times. Suitable mono-substituted phenyl groups include, ortho-substituted phenyl, meta-substituted phenyl and para-substituted phenyl. In some embodiments, $R^1$ can be an —O-unsubstituted aryl. In some embodiments, $R^1$ can be an —O-optionally substituted naphthyl. In some embodiments, $R^1$ can be an —O-unsubstituted phenyl. In some embodiments, $R^1$ can be an —O-unsubstituted naphthyl.

In some embodiments, $R^2$ can be an optionally substituted N-linked amino acid or an optionally substituted N-linked amino acid ester derivative. Various amino acids are suitable, including those described herein. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. In other embodiments, $R^2$ can be an optionally substituted N-linked amino acid ester derivative. Examples of suitable amino acid ester derivatives include, but are not limited to, an ester derivative of any of the following amino acids, alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. Additional examples of N-linked amino acid ester derivatives include, but are not limited to, an ester derivative of any of the following amino acids: alpha-ethyl-glycine, alpha-propyl-glycine and beta-alanine. In some embodiments, the N-linked amino acid ester derivative can be selected from alanine isopropyl ester, alanine cyclohexyl ester, alanine neopentyl ester, valine isopropyl ester, isoleucine isopropyl ester, methionine isopropyl ester and leucine isopropyl ester.

In some embodiments, $R^2$ can be

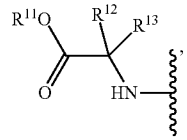

wherein $R^{11}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{12}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{13}$ can be hydrogen or an optionally substituted $C_{1-4}$-alkyl; or $R^{12}$ and $R^{13}$ are taken together to form an optionally substituted $C_{3-6}$ cycloalkyl.

In some embodiments, $R^{12}$ can be substituted by a variety of substituents. Suitable examples of substituents include, but are not limited to, N-amido, mercapto, alkylthio, an optionally substituted aryl, hydroxyl, an optionally substituted heteroaryl, O-carboxy and amino. In some embodiments $R^{12}$ can be hydrogen. In some embodiments, $R^{12}$ can be an optionally substituted $C_{1-6}$-alkyl. In some embodiments, $R^{13}$ can be hydrogen. In some embodiments $R^{13}$ can be an optionally substituted $C_{1-4}$ alkyl, such as methyl, ethyl, n-propyl, isopropyl, n-butyl, isobutyl or tert-butyl. In some embodiments $R^{13}$ can be methyl. In some embodiments, $R^{11}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{11}$ can be methyl or isopropyl. In some embodiments, $R^{11}$ can be ethyl or neopentyl. In some embodiments, $R^{11}$ can be an optionally substituted $C_{3-6}$ cycloalkyl. Examples of optionally substituted $C_{3-6}$ cycloalkyls include optionally substituted variants of the following: cyclopropyl, cyclobutyl, cyclopentyl and cyclohexyl. Depending on the groups that are selected for $R^{12}$ and $R^{13}$, the carbon to which $R^{12}$ and $R^{13}$ are attached may be a chiral center. In some embodiments, the carbon to which $R^{12}$ and $R^{13}$ are attached may be a (R)-chiral center. In other embodiments, the carbon to which $R^{12}$ and $R^{13}$ are attached may be a (S)-chiral center.

Examples of suitable

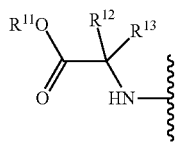

groups include the following:

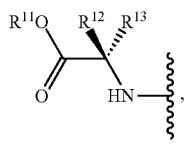

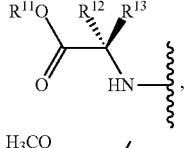

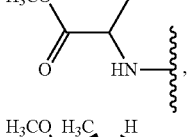

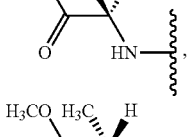

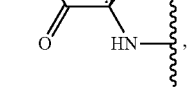

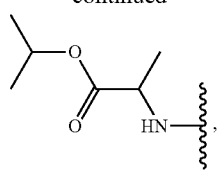

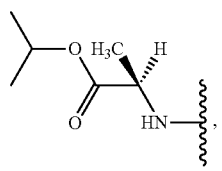

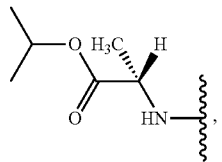

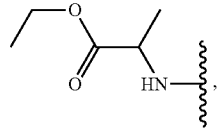

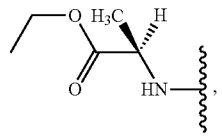

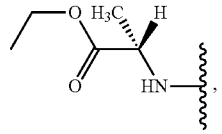

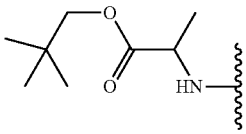

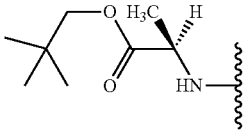

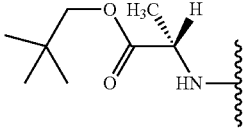

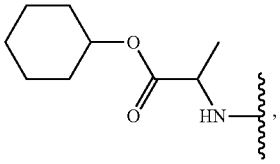

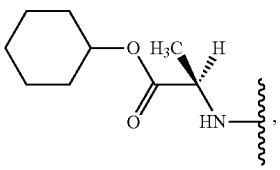

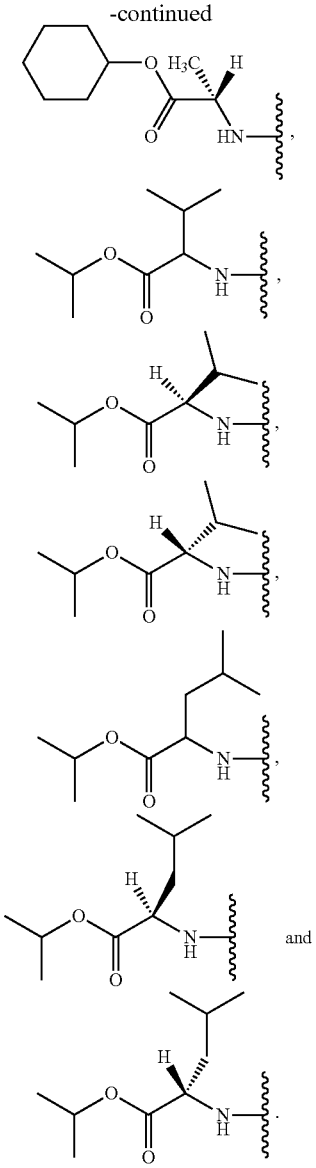

and

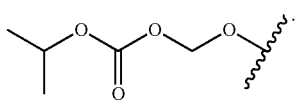

In some embodiments, a compound of Formula (I), or a pharmaceutically acceptable salt thereof, can be a phosphoramidate prodrug. For example, $R^1$ can be an —O-optionally substituted aryl, and $R^2$ can be an optionally substituted N-linked amino acid or an optionally substituted N-linked amino acid ester derivative.

In some embodiments, $R^1$ and/or $R^2$ can be

In some embodiments $R^1$ and $R^2$ can both be a isopropyloxycarbonyloxymethoxy (POC) group, and form a bis(POC) prodrug.

In some embodiments, $R^1$ and $R^2$ can independently be $O^-$ or —OH, and a compound of Formula (I), or a pharmaceutically acceptable salt thereof, can be a monophosphate. In other embodiments, $R^1$ can be

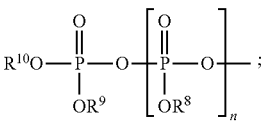

wherein $R^8$, $R^9$ and $R^{10}$ can be independently absent or hydrogen, n can be 0 and $R^2$ can be $O^-$ or —OH. Those skilled in the art understand that when $R^8$, $R^9$ and/or $R^{10}$ are absent, the associated oxygen can have a negative charge. For example, when $R^9$ is absent, then the associated oxygen can have a negative charge, such that $R^1$ can be

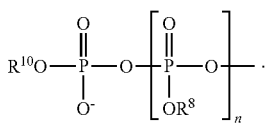

When $R^1$ is

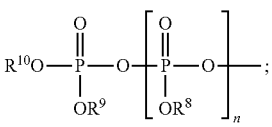

$R^9$ and $R^{10}$ are independently absent or hydrogen, n is 0 and $R^2$ is $O^-$ or —OH, a compound of Formula (I), or a pharmaceutically acceptable salt thereof, can be a diphosphate. In yet other embodiments $R^1$ can be

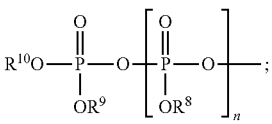

wherein $R^8$, $R^9$ and $R^{10}$ can be independently absent or hydrogen, n can be 1 and $R^2$ can be $O^-$ or —OH. When $R^1$ is

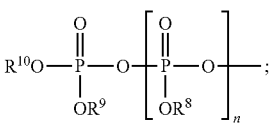

$R^8$, $R^9$ and $R^{10}$ are independently absent or hydrogen, n is 1 and $R^2$ is $O^-$ or —OH, a compound of Formula (I), or a pharmaceutically acceptable salt thereof, can be a triphosphate.

In some embodiments of a compound of Formula (I) or Formula (II), or a pharmaceutically acceptable salt of the foregoing, $R^4$ is —OH. In other embodiments, $R^4$ is F.

In some embodiments of Formula (I), ------ can be a single bond, $R^P$ can be

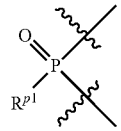

and $R^4$ can be O, and the compound of Formula (I) can have the structure of Formula (III), or a pharmaceutically acceptable salt thereof:

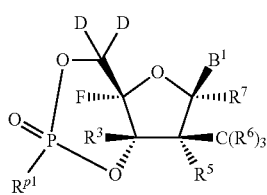

(III)

wherein: $B^1$, $R^3$, $R^5$, each $R^6$, $R^7$ and $R^{p1}$ are provided herein.

In some embodiments, $R^{p1}$ can be O⁻. In other embodiments, $R^{p1}$ can be OH. In other embodiments, $R^{p1}$ can be an —O-optionally substituted $C_{1-6}$ alkyl. For example, $R^{p1}$ can be a substituted or an unsubstituted version of the following: methoxy, ethoxy, n-propoxy, iso-propoxy, n-butoxy, iso-butoxy, tert-butoxy, pentoxy (branched or straight chained) and hexoxy (branched or straight chained).

In some embodiments, $R^{p1}$ can be an —O-optionally substituted aryl. For example, $R^{p1}$ can be an —O-optionally substituted phenyl. When the phenyl is substituted, the ring can be substituted 1, 2, 3 or more than 3 times. Suitable mono-substituted phenyl groups include ortho-substituted phenyl, meta-substituted phenyl and para-substituted phenyl. In some embodiments, $R^{p1}$ can be an —O-unsubstituted aryl. In some embodiments, $R^{p1}$ can be an —O-optionally substituted naphthyl. In some embodiments, $R^{p1}$ can be an —O-unsubstituted phenyl. In some embodiments, $R^{p1}$ can be an —O-unsubstituted naphthyl.

In some embodiments, $R^{p1}$ can be

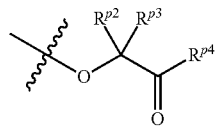

wherein $R^{p1}$ and $R^{p3}$ can be independently selected from hydrogen, an optionally substituted $C_{1-24}$ alkyl and an optionally substituted aryl; and $R^{p4}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, at least one of $R^{p2}$ and $R^{p3}$ can be hydrogen. In other embodiments, both $R^{p2}$ and $R^{p3}$ can be hydrogen. In other embodiments, at least one of $R^{p2}$ and $R^{p3}$ can be an optionally substituted $C_{1-24}$ alkyl or an optionally substituted aryl. In some embodiments, $R^{p4}$ can be an optionally substituted $C_{1-24}$ alkyl. In some embodiments, $R^{p4}$ can be an unsubstituted $C_{1-4}$ alkyl. In other embodiments, $R^{p4}$ can be an optionally substituted aryl. In still other embodiments, $R^{p4}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{p4}$ can be an unsubstituted —O—$C_{1-4}$ alkyl.

In some embodiments, $R^{p1}$ can be

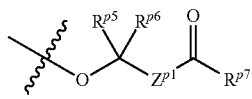

wherein $R^{p5}$ and $R^{p6}$ can be independently selected from hydrogen, an optionally substituted $C_{1-24}$ alkyl and an optionally substituted aryl; $R^{p7}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; and $Z^{p1}$ can be independently O (oxygen) or S (sulfur). In some embodiments, at least one of $R^{p5}$ and $R^{p6}$ can be hydrogen. In other embodiments, both $R^{p5}$ and $R^{p6}$ can be hydrogen. In other embodiments, at least one of $R^{p5}$ and $R^{p6}$ can be an optionally substituted $C_{1-24}$ alkyl or an optionally substituted aryl. In some embodiments, $R^{p7}$ can be an optionally substituted $C_{1-24}$ alkyl. In some embodiments, $R^{p7}$ can be an unsubstituted $C_{1-4}$ alkyl. In other embodiments, $R^{p7}$ can be an optionally substituted aryl. In still other embodiments, $R^{p7}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{p7}$ can be an unsubstituted —O—$C_{1-4}$ alkyl. In some embodiments, $Z^{p1}$ can be O (oxygen). In other embodiments, $Z^{p1}$ can be or S (sulfur). In some embodiments, $R^{p1}$ can be isopropyloxycarbonyloxymethyloxy (POC) group. In some embodiments, $R^{p1}$ can be pivaloyloxymethyloxy (POM) group.

In some embodiments, $R^{p1}$ can be

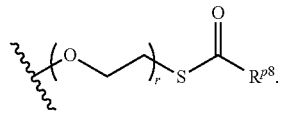

In some embodiments, $R^{p8}$ can be hydrogen. In other embodiments, $R^{p8}$ can be an optionally substituted $C_{1-24}$ alkyl. In still other embodiments, $R^{p8}$ can be an optionally substituted aryl. In some embodiments, $R^{p8}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, r can be 1. In other embodiments, r can be 2.

In some embodiments, $R^{p1}$ can be

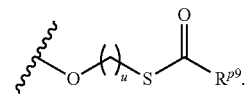

In some embodiments, $R^{p9}$ can be hydrogen. In other embodiments, $R^{p9}$ can be an optionally substituted $C_{1-24}$ alkyl. In still other embodiments, $R^{p9}$ can be an optionally substituted aryl, for example, an optionally substituted phenyl. In some embodiments, $R^{p9}$ can be an optionally substituted $C_{1-6}$ alkyl. In some embodiments, $R^{p9}$ can be an unsubstituted $C_{1-6}$ alkyl. In some embodiments, u can be 3. In other embodiments, u can be 4. In still other embodiments, u can be 5. In some embodiments, $R^{p1}$ can be a S-acylthioethoxy (SATE) group and form a SATE ester prodrug.

In some embodiments, $R^{p1}$ can be an optionally substituted N-linked amino acid or an optionally substituted N-linked amino acid ester derivative. For example, $R^{p1}$ can be optionally substituted version of the following: alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{p1}$ can be selected from N-alanine isopropyl ester, N-alanine cyclohexyl ester, N-alanine neopentyl ester, N-valine isopropyl ester and N-leucine isopropyl ester. In some embodiments, $R^{p1}$ can have the structure

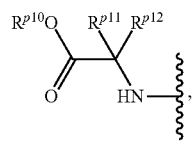

wherein $R^{p10}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{p11}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{p12}$ can be hydrogen or an optionally substituted $C_{1-4}$-alkyl; or $R^{p11}$ and $R^{p12}$ can be taken together to form an optionally substituted $C_{3-6}$ cycloalkyl.

When $R^{p11}$ is substituted, $R^{p11}$ can be substituted with one or more substituents selected from N-amido, mercapto, alkylthio, an optionally substituted aryl, hydroxy, an optionally substituted heteroaryl, O-carboxy, and amino. In some embodiments, $R^{p11}$ can be an unsubstituted $C_{1-6}$-alkyl, such as those described herein. In some embodiments, $R^{p11}$ can be hydrogen. In other embodiments, $R^{p11}$ can be methyl. In some embodiments, $R^{p10}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{p10}$ can be methyl or isopropyl. In some embodiments, $R^{p10}$ can be ethyl or neopentyl. In other embodiments, $R^{p10}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In some embodiments, $R^{p10}$ can be an optionally substituted cyclohexyl. In still other embodiments, $R^{p10}$ can be an optionally substituted aryl, such as phenyl and naphthyl. In yet still other embodiments, $R^{p10}$ can be an optionally substituted aryl($C_{1-6}$ alkyl). In some embodiments, $R^{p10}$ can be an optionally substituted benzyl. In some embodiments, $R^{p10}$ can be an optionally substituted $C_{1-6}$ haloalkyl, for example, $CF_3$. In some embodiments, $R^{p12}$ can be hydrogen. In other embodiments, $R^{p12}$ can be an optionally substituted $C_{1-4}$-alkyl, such as methyl, ethyl, n-propyl, isopropyl, n-butyl, isobutyl and tert-butyl. In some embodiments, $R^{p12}$ can be methyl. In some embodiments, $R^{p11}$ and $R^{p12}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{p11}$ and $R^{p12}$, the carbon to which $R^{p11}$ and $R^{p12}$ are attached may be a chiral center. In some embodiment, the carbon to which $R^{p11}$ and $R^{p12}$ are attached may be a (R)-chiral center. In other embodiments, the carbon to which $R^{p11}$ and $R^{p12}$ are attached may be a (S)-chiral center.

Examples of suitable

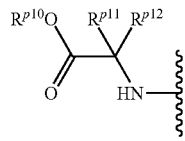

groups include the following:

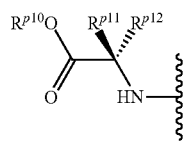

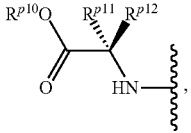

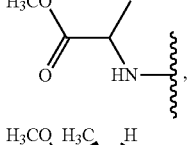

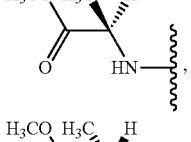

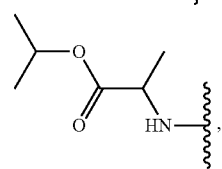

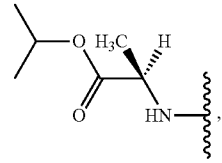

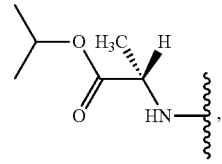

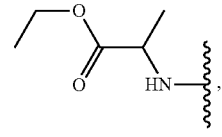

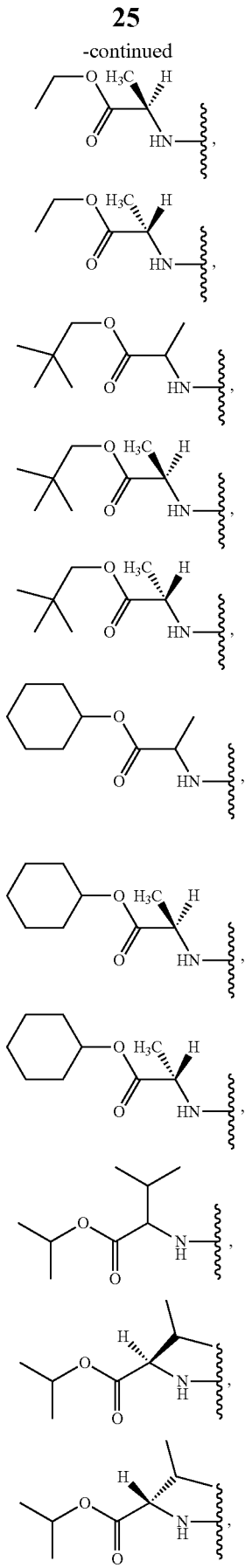

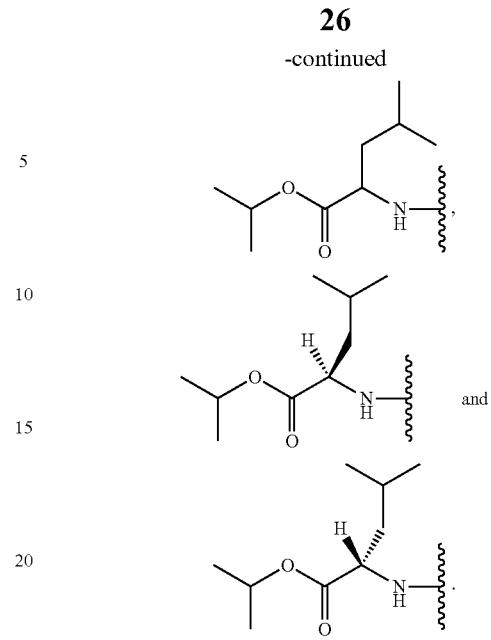

The $R^3$ attached to the 3'-carbon of the pentose ring of a compound described herein can vary. In some embodiments, $R^3$ can be hydrogen. In other embodiments, $R^3$ can be deuterium.

Likewise, various substituents can be attached at the 2'-carbon of the pentose ring. In some embodiments $R^5$ can be —OH. In other embodiments, $R^5$ can be F.

In some embodiments, at least one $R^6$ substituent of the 2'-methyl group can be hydrogen. In other embodiments, at least two $R^6$ can be hydrogen. In yet other embodiments, each $R^6$ can be hydrogen. In some embodiments, at least one $R^6$ can be deuterium. In other embodiments, at least two $R^6$ can be deuterium. In yet other embodiments, each $R^6$ can be deuterium.

In some embodiments, $R^7$ can be hydrogen. In other embodiments, $R^7$ can be deuterium.

The nucleobase of a compound described herein can vary. In some embodiments, the nucleobase can be an optionally substituted deuterated nucleobase. For example, $B^1$ can be an optionally deuterated uracil. In some embodiments $B^1$ can be an optionally substituted

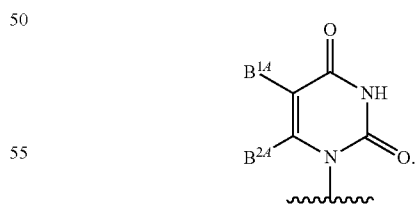

In some embodiments at least one of $B^{1A}$ and $B^{2A}$ can be hydrogen. In some embodiments, both $B^{1A}$ and $B^{2A}$ can be hydrogen. In other embodiments, at least one of $B^{1A}$ and $B^{2A}$ can be deuterium. In yet other embodiments, both $B^{1A}$ and $B^{2A}$ can be deuterium.

In some embodiments, B can be an optionally deuterated guanine or a 6-oxygen protected guanine. For example, $B^1$ can be an optionally substituted

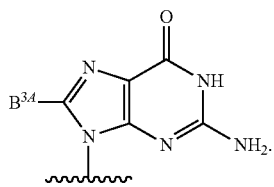

In some embodiments, $B^{3A}$ can be hydrogen. In other embodiments, $B^{3A}$ can be deuterium. In other embodiments, $B^1$ can be an optionally substituted

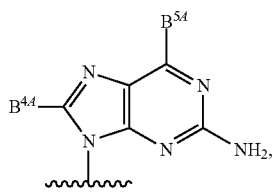

wherein $B^{5A}$ can be an —O-optionally substituted $C_{1-6}$ alkyl. In some embodiments of this paragraph, $B^{4A}$ can be hydrogen. In other embodiments of this paragraph, $B^{4A}$ can be deuterium. In some embodiments, $B^{5A}$ can be an optionally substituted methoxy, an optionally substituted ethoxy, an optionally substituted n-propyloxy, an optionally substituted isopropyloxy, an optionally substituted n-butyloxy, an optionally substituted isobutyloxy, an optionally substituted tert-butyloxy, an optionally substituted pentyloxy (branched and straight-chained) or an optionally substituted hexyloxy (branched and straight-chained). In some embodiments, $B^{5A}$ can be —OCH$_2$CH$_3$.

In some embodiments, B can be an optionally deuterated 2,6-diaminopurine. In some embodiments, $B^1$ can be an optionally substituted

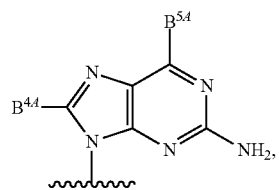

wherein $B^{5A}$ can be —NH$_2$. In some embodiments of this paragraph, $B^{4A}$ can be hydrogen. In other embodiments of this paragraph, $B^{4A}$ can be deuterium.

Examples of a compound of Formula (I), or a pharmaceutically acceptable salt thereof, include the following:

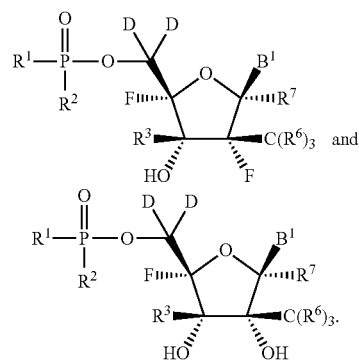

Additional examples of a compound of Formula (I), or a pharmaceutically acceptable salt thereof, include the following:

TABLE 1

| Formula No. | Structure |
|---|---|
| Ia | 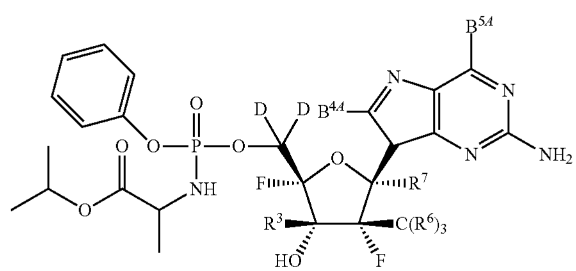 |
| Ib | 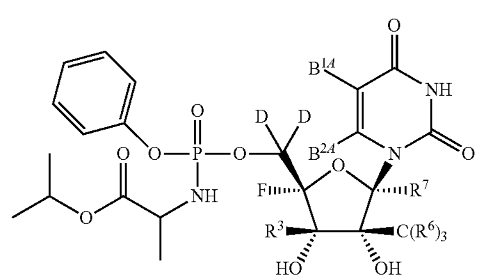 |

TABLE 1-continued

| Formula No. | Structure |
|---|---|
| Ic | (structure shown) |

In some embodiments of Formulae (Ia), (Ib) and/or (Ic), or a pharmaceutically acceptable salt of the foregoing, $R^3$ can be hydrogen. In other embodiments of Formulae (Ia), (Ib) and/or (Ic), or a pharmaceutically acceptable salt of the foregoing, $R^3$ can be deuterium. In some embodiments of Formulae (Ia), (Ib) and/or (Ic), or a pharmaceutically acceptable salt of the foregoing, each $R^6$ can independently be hydrogen or deuterium. In some embodiments of Formulae (Ia), (Ib) and/or (Ic), or a pharmaceutically acceptable salt of the foregoing, at least one $R^6$ can be hydrogen. In some embodiments of Formulae (Ia), (Ib) and/or (Ic), or a pharmaceutically acceptable salt of the foregoing, at least two $R^6$ can be hydrogen. In some embodiments of Formulae (Ia), (Ib) and/or (Ic), or a pharmaceutically acceptable salt of the foregoing, each $R^6$ can be hydrogen. In other embodiments of Formulae (Ia), (Ib) and/or (Ic), or a pharmaceutically acceptable salt of the foregoing, at least one $R^6$ can be deuterium. In yet other embodiments of Formulae (Ia), (Ib) and/or (Ic), or a pharmaceutically acceptable salt of the foregoing, at least two $R^6$ can be deuterium. In yet other embodiments of Formulae (Ia), (Ib) and/or (Ic), or a pharmaceutically acceptable salt of the foregoing, each $R^6$ can be deuterium. In some embodiments of Formulae (Ia), (Ib) and/or (Ic), or a pharmaceutically acceptable salt of the foregoing, $R^7$ can be hydrogen. In other embodiments of Formulae (Ia), (Ib) and/or (Ic), or a pharmaceutically acceptable salt of the foregoing, $R^7$ can be deuterium. In some embodiments of Formulae (Ia) and/or (Ic), or a pharmaceutically acceptable salt of the foregoing, $B^{4A}$ can be hydrogen. In other embodiments of Formulae (Ia) and/or (Ic), or a pharmaceutically acceptable salt of the foregoing, $B^{4A}$ can be deuterium. In some embodiments of Formulae (Ia) and/or (Ic), or a pharmaceutically acceptable salt of the foregoing, $B^{5A}$ can be an —O-optionally substituted alkyl. In other embodiments of Formulae (Ia) and/or (Ic), or a pharmaceutically acceptable salt of the foregoing, $B^{5A}$ can be —NH$_2$. In some embodiments of Formula (Ib), or a pharmaceutically acceptable salt thereof, at least one of $B^{1A}$ and $B^{2A}$ can be hydrogen. In other embodiments of Formula (Ib), or a pharmaceutically acceptable salt thereof, both $B^{1A}$ and $B^{2A}$ can be hydrogen. In other embodiments of Formula (Ib), or a pharmaceutically acceptable salt thereof, at least one of $B^{1A}$ and $B^{2A}$ can be deuterium. In yet other embodiments of Formula (Ib), or a pharmaceutically acceptable salt thereof, both $B^{1A}$ and $B^{2A}$ can be deuterium.

Further examples of a compound of Formula (I), or a pharmaceutically acceptable salt thereof, include:

TABLE 2

| Formula No. | Structure |
|---|---|
| Id | (structure shown) |

TABLE 2-continued

| Formula No. | Structure |
|---|---|
| Ie | (chemical structure) |
| If | (chemical structure) |
| Ig | (chemical structure) |
| Ih | (chemical structure) |
| Ii | (chemical structure) |

TABLE 2-continued

| Formula No. | Structure |
|---|---|
| Ij | 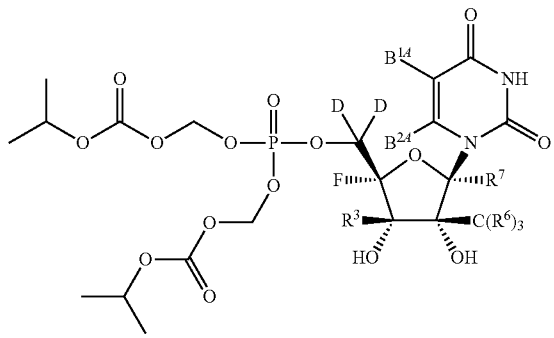 |
| Ik | 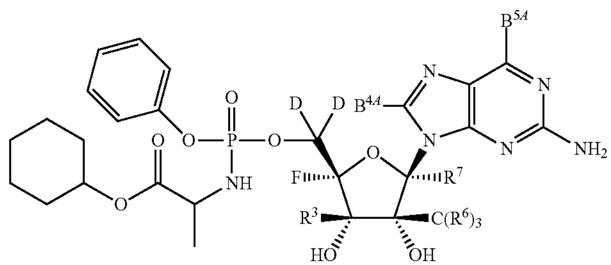 |
| Il | 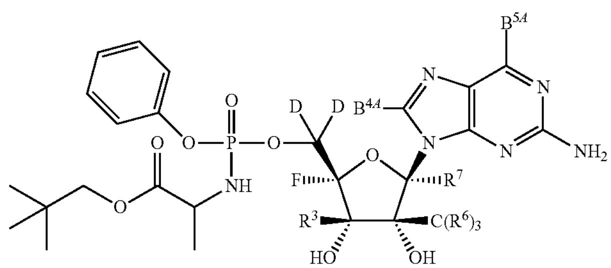 |
| Im | 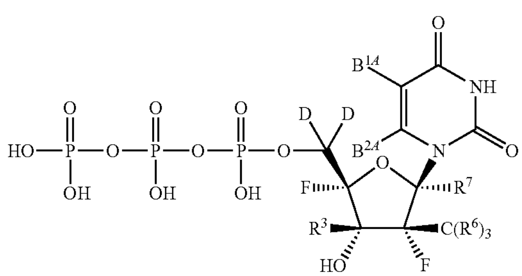 |
| In | 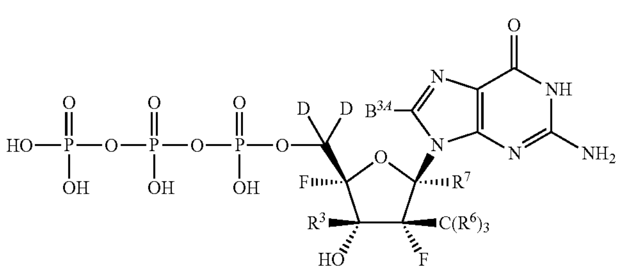 |

TABLE 2-continued
| Formula No. | Structure |
|---|---|
| Io | 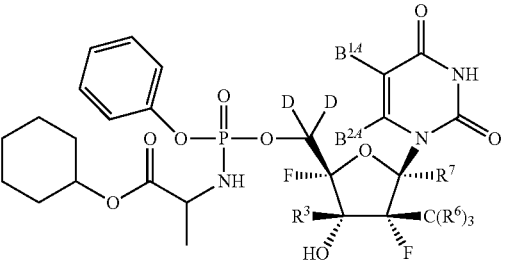 |
| Ip | 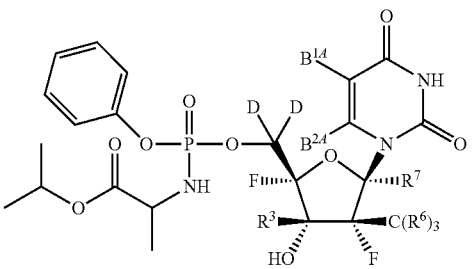 |
| Iq | 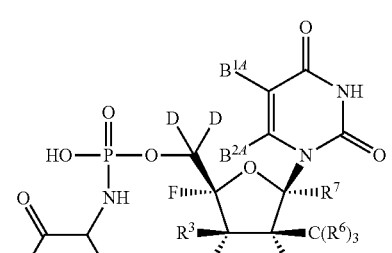 |
| Ir | 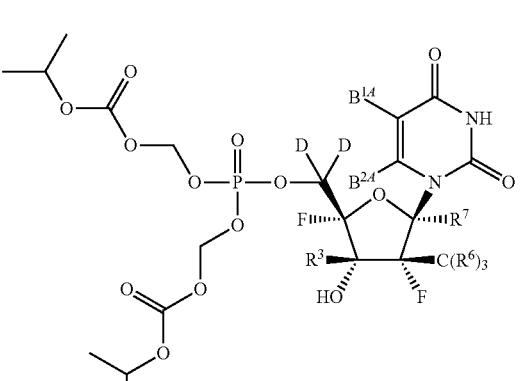 |
| Is | 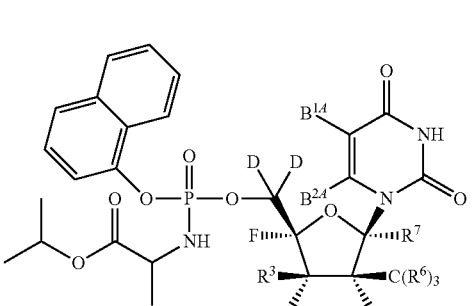 |

TABLE 2-continued

| Formula No. | Structure |
| --- | --- |
| It | 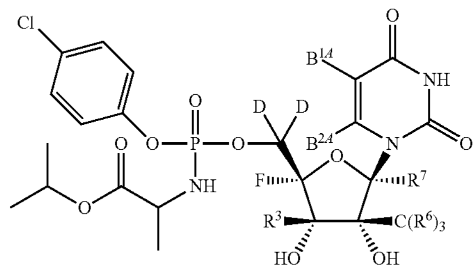 |
| Iu | 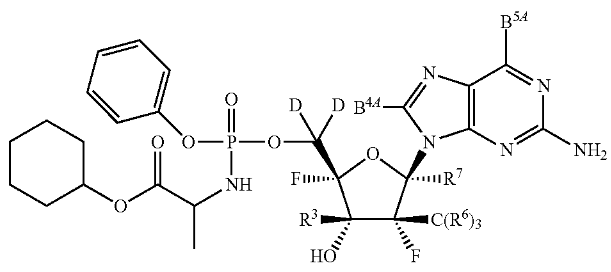 |
| Iv | 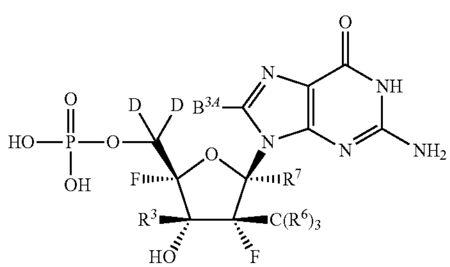 |
| Iw | 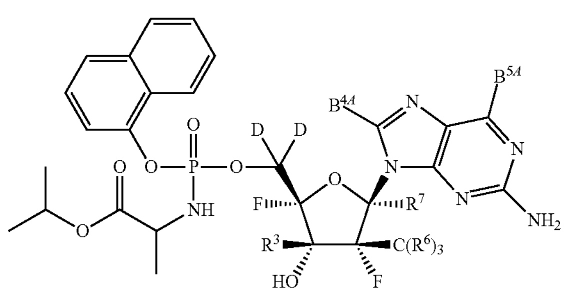 |
| Ix | 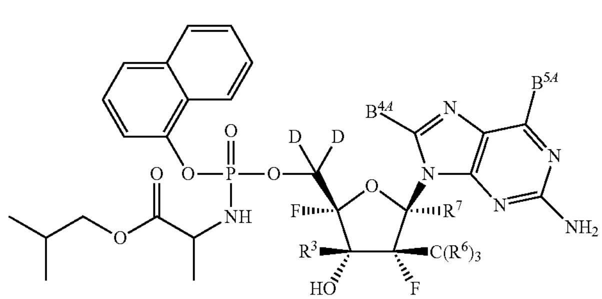 |

TABLE 2-continued

| Formula No. | Structure |
| --- | --- |
| Iy | 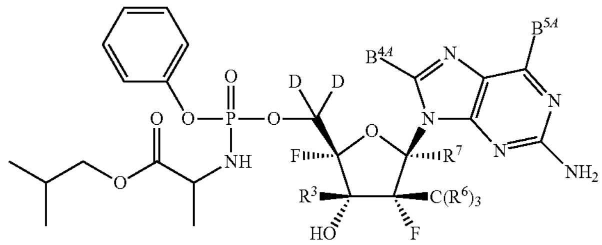 |
| Iz | 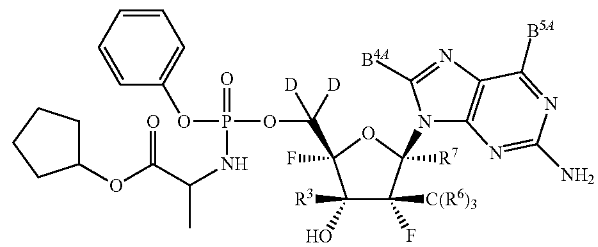 |
| Iaa | 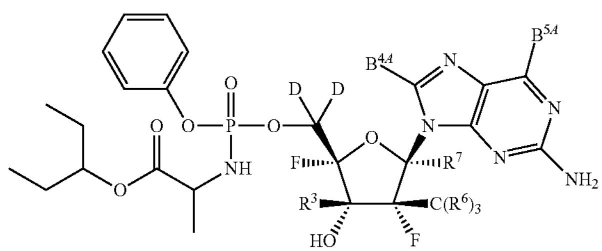 |
| Ibb | 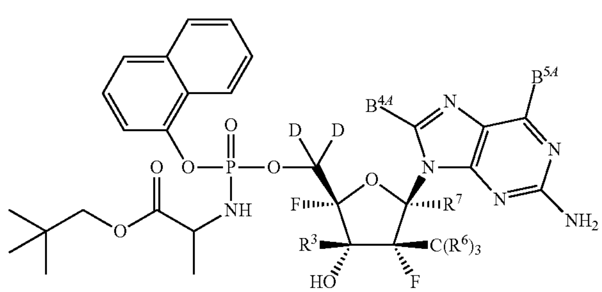 |
| Icc | 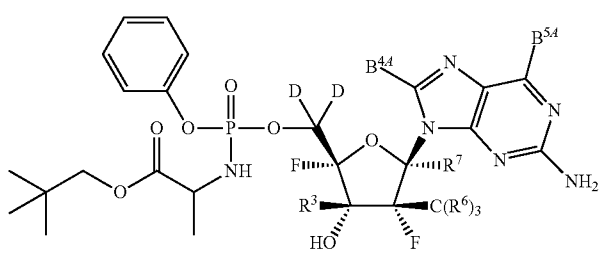 |

TABLE 2-continued

| Formula No. | Structure |
|---|---|
| Idd | [Structure: isopropyl carbonate-oxymethyl phosphate linked nucleoside with guanine base $B^{3A}$, D,D on CH, F, R$^3$, HO, OH, R$^7$, C(R$^6$)$_3$ substituents] |
| Iee | [Structure: isopropyl carbonate-oxymethyl phosphate linked nucleoside with purine base $B^{5A}$, $B^{4A}$, NH$_2$, D,D on CH, F, R$^3$, HO, OH, R$^7$, C(R$^6$)$_3$ substituents] |

In some embodiments of the Formulae in Table 2, or a pharmaceutically acceptable salt of the foregoing, $R^3$ can be hydrogen. In other embodiments of the Formulae in Table 2, or a pharmaceutically acceptable salt of the foregoing, $R^3$ can be deuterium. In some embodiments of the Formulae in Table 2, or a pharmaceutically acceptable salt of the foregoing, each $R^6$ can independently be hydrogen or deuterium. In some embodiments of the Formulae in Table 2, or a pharmaceutically acceptable salt of the foregoing, at least one $R^6$ can be hydrogen. In some embodiments of the Formulae in Table 2, or a pharmaceutically acceptable salt of the foregoing, at least two $R^6$ can be hydrogen. In some embodiments of the Formulae in Table 2, or a pharmaceutically acceptable salt of the foregoing, each $R^6$ can be hydrogen. In other embodiments of the Formulae in Table 2, or a pharmaceutically acceptable salt of the foregoing, at least one $R^6$ can be deuterium. In yet other embodiments of the Formulae in Table 2, or a pharmaceutically acceptable salt of the foregoing, at least two $R^6$ can be deuterium. In yet other embodiments of the Formulae in Table 2, or a pharmaceutically acceptable salt of the foregoing, each $R^6$ can be deuterium. In some embodiments of the Formulae in Table 2, or a pharmaceutically acceptable salt of the foregoing, $R^7$ can be hydrogen. In other embodiments of the Formulae in Table 2, or a pharmaceutically acceptable salt of the foregoing, $R^7$ can be deuterium. In some embodiments of Formulae (Ic), (Il), (Iu), (Iw), (Iy), (Iz), (Iaa), (Ibb), (Icc) and/or (Iee), $B^{4A}$ can be hydrogen. In other embodiments of Formulae (Ik), (Il), (Iu), (Iw), (Iy), (Iz), (Iaa), (Ibb), (Icc) and/or (Iee), $B^{4A}$ can be deuterium. In some embodiments of Formulae (Ik), (Il), (Iu), (Iw), (Iy), (Iz), (Iaa), (Ibb), (Icc) and/or (Iee), or a pharmaceutically acceptable salt of the foregoing, $B^{5A}$ can be an —O-optionally substituted alkyl. In other embodiments of Formulae (Ik), (Il), (Iu), (Iw), (Iy), (Iz), (Iaa), (Ibb), (Icc) and/or (Tee), or a pharmaceutically acceptable salt of the foregoing, $B^{5A}$ can be —NH$_2$. In some embodiments of Formulae (Id), (Ig), (Ih), (Ii), (Ij), (Im), (Io), (Ip), (Iq), (Ir), (Is) and (It), or a pharmaceutically acceptable salt of the foregoing, at least one of $B^{1A}$ and $B^{2A}$ can be hydrogen. In other embodiments of Formulae (Id), (Ig), (Ih), (Ii), (Ij), (Im), (Io), (Ip), (Iq), (Ir), (Is) and (It), or a pharmaceutically acceptable salt of the foregoing, both $B^{1A}$ and $B^{2A}$ can be hydrogen. In still other embodiments of Formulae (Id), (Ig), (Ih), (Ii), (Ij), (Im), (Io), (Ip), (Iq), (Ir), (Is) and (It), or a pharmaceutically acceptable salt of the foregoing, at least one of $B^{1A}$ and $B^{2A}$ can be deuterium. In yet other embodiments of Formulae (Id), (Ig), (Ih), (Ii), (Ij), (Im), (Io), (Ip), (Iq), (Ir), (Is) and (It), or a pharmaceutically acceptable salt of the foregoing, both $B^{1A}$ and $B^{2A}$ can be deuterium. In some embodiments of Formulae (Ie), (If), (In), (Iv) and (Idd), or a pharmaceutically acceptable salt of the foregoing, $B^{3A}$ can be hydrogen. In some embodiments of Formulae (Ie), (If), (In), (Iv) and (Idd), or a pharmaceutically acceptable salt of the foregoing, $B^{3A}$ can be deuterium.

It will be appreciated by one of ordinary skill in the art that the structures of Formulae (Ia)-(Idd), or a pharmaceutically acceptable salt of the foregoing can be prepared in a similar manner to the preparation of their respective non-deuterated analogs as described in PCT Publication No. WO 2014/100505, which is hereby incorporated by reference in its entirety.

As described herein, any position of Formula (I), or pharmaceutically acceptable salt thereof, as well as a compounds of Formulae (Ia)-(Idd) that is hydrogen can be replaced with an isotope of hydrogen, such as hydrogen-2 (deuterium). Some embodiments of Formula (I), or a pharmaceutically acceptable salt thereof, are provided in each row of Table 3.

TABLE 3

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^A$ | Ph | N-AA | OH | OH | $U^1$ | H | HHH | H | H | H | — | — | — |
| $P^A$ | Ph | N-AA | OH | OH | $U^1$ | H | HHD | H | H | H | — | — | — |
| $P^A$ | Ph | N-AA | OH | OH | $U^1$ | H | HDD | H | H | H | — | — | — |
| $P^A$ | Ph | N-AA | OH | OH | $U^1$ | H | DDD | H | H | H | — | — | — |
| $P^A$ | Ph | N-AA | OH | OH | $U^1$ | H | HHH | D | H | H | — | — | — |
| $P^A$ | Ph | N-AA | OH | OH | $U^1$ | H | HHD | D | H | H | — | — | — |
| $P^A$ | Ph | N-AA | OH | OH | $U^1$ | H | HDD | D | H | H | — | — | — |
| $P^A$ | Ph | N-AA | OH | OH | $U^1$ | H | DDD | D | H | H | — | — | — |
| $P^A$ | Ph | N-AA | OH | OH | $U^1$ | D | HHH | H | H | H | — | — | — |
| $P^A$ | Ph | N-AA | OH | OH | $U^1$ | D | HHD | H | H | H | — | — | — |
| $P^A$ | Ph | N-AA | OH | OH | $U^1$ | D | HDD | H | H | H | — | — | — |
| $P^A$ | Ph | N-AA | OH | OH | $U^1$ | D | DDD | H | H | H | — | — | — |
| $P^A$ | Ph | N-AA | OH | OH | $U^1$ | D | HHH | D | H | H | — | — | — |
| $P^A$ | Ph | N-AA | OH | OH | $U^1$ | D | HHD | D | H | H | — | — | — |
| $P^A$ | Ph | N-AA | OH | OH | $U^1$ | D | HDD | D | H | H | — | — | — |
| $P^A$ | Ph | N-AA | OH | OH | $U^1$ | D | DDD | D | H | H | — | — | — |
| $P^A$ | Ph | N-AA | OH | OH | $U^1$ | H | HHH | H | H | D | — | — | — |
| $P^A$ | Ph | N-AA | OH | OH | $U^1$ | H | HHD | H | H | D | — | — | — |
| $P^A$ | Ph | N-AA | OH | OH | $U^1$ | H | HDD | H | H | D | — | — | — |
| $P^A$ | Ph | N-AA | OH | OH | $U^1$ | H | DDD | H | H | D | — | — | — |
| $P^A$ | Ph | N-AA | OH | OH | $U^1$ | H | HHH | D | H | D | — | — | — |
| $P^A$ | Ph | N-AA | OH | OH | $U^1$ | H | HHD | D | H | D | — | — | — |
| $P^A$ | Ph | N-AA | OH | OH | $U^1$ | H | HDD | D | H | D | — | — | — |
| $P^A$ | Ph | N-AA | OH | OH | $U^1$ | H | DDD | D | H | D | — | — | — |
| $P^A$ | Ph | N-AA | OH | OH | $U^1$ | D | HHH | H | H | D | — | — | — |
| $P^A$ | Ph | N-AA | OH | OH | $U^1$ | D | HHD | H | H | D | — | — | — |
| $P^A$ | Ph | N-AA | OH | OH | $U^1$ | D | HDD | H | H | D | — | — | — |
| $P^A$ | Ph | N-AA | OH | OH | $U^1$ | D | DDD | H | H | D | — | — | — |
| $P^A$ | Ph | N-AA | OH | OH | $U^1$ | D | HHH | D | H | D | — | — | — |
| $P^A$ | Ph | N-AA | OH | OH | $U^1$ | D | HHD | D | H | D | — | — | — |
| $P^A$ | Ph | N-AA | OH | OH | $U^1$ | D | HDD | D | H | D | — | — | — |
| $P^A$ | Ph | N-AA | OH | OH | $U^1$ | D | DDD | D | H | D | — | — | — |
| $P^A$ | Ph | N-AA | OH | OH | $U^1$ | H | HHH | H | D | H | — | — | — |
| $P^A$ | Ph | N-AA | OH | OH | $U^1$ | H | HHD | H | D | H | — | — | — |
| $P^A$ | Ph | N-AA | OH | OH | $U^1$ | H | HDD | H | D | H | — | — | — |
| $P^A$ | Ph | N-AA | OH | OH | $U^1$ | H | DDD | H | D | H | — | — | — |
| $P^A$ | Ph | N-AA | OH | OH | $U^1$ | H | HHH | D | D | H | — | — | — |
| $P^A$ | Ph | N-AA | OH | OH | $U^1$ | H | HHD | D | D | H | — | — | — |
| $P^A$ | Ph | N-AA | OH | OH | $U^1$ | H | HDD | D | D | H | — | — | — |
| $P^A$ | Ph | N-AA | OH | OH | $U^1$ | H | DDD | D | D | H | — | — | — |
| $P^A$ | Ph | N-AA | OH | OH | $U^1$ | D | HHH | H | D | H | — | — | — |
| $P^A$ | Ph | N-AA | OH | OH | $U^1$ | D | HHD | H | D | H | — | — | — |
| $P^A$ | Ph | N-AA | OH | OH | $U^1$ | D | HDD | H | D | H | — | — | — |
| $P^A$ | Ph | N-AA | OH | OH | $U^1$ | D | DDD | H | D | H | — | — | — |
| $P^A$ | Ph | N-AA | OH | OH | $U^1$ | D | HHH | D | D | H | — | — | — |
| $P^A$ | Ph | N-AA | OH | OH | $U^1$ | D | HHD | D | D | H | — | — | — |
| $P^A$ | Ph | N-AA | OH | OH | $U^1$ | D | HDD | D | D | H | — | — | — |
| $P^A$ | Ph | N-AA | OH | OH | $U^1$ | D | DDD | D | D | H | — | — | — |
| $P^A$ | Ph | N-AA | OH | OH | $U^1$ | H | HHH | H | D | D | — | — | — |
| $P^A$ | Ph | N-AA | OH | OH | $U^1$ | H | HHD | H | D | D | — | — | — |
| $P^A$ | Ph | N-AA | OH | OH | $U^1$ | H | HDD | H | D | D | — | — | — |
| $P^A$ | Ph | N-AA | OH | OH | $U^1$ | H | DDD | H | D | D | — | — | — |
| $P^A$ | Ph | N-AA | OH | OH | $U^1$ | H | HHH | D | D | D | — | — | — |
| $P^A$ | Ph | N-AA | OH | OH | $U^1$ | H | HHD | D | D | D | — | — | — |
| $P^A$ | Ph | N-AA | OH | OH | $U^1$ | H | HDD | D | D | D | — | — | — |
| $P^A$ | Ph | N-AA | OH | OH | $U^1$ | H | DDD | D | D | D | — | — | — |
| $P^A$ | Ph | N-AA | OH | OH | $U^1$ | D | HHH | H | D | D | — | — | — |
| $P^A$ | Ph | N-AA | OH | OH | $U^1$ | D | HHD | H | D | D | — | — | — |
| $P^A$ | Ph | N-AA | OH | OH | $U^1$ | D | HDD | H | D | D | — | — | — |
| $P^A$ | Ph | N-AA | OH | OH | $U^1$ | D | DDD | H | D | D | — | — | — |
| $P^A$ | Ph | N-AA | OH | OH | $U^1$ | D | HHH | D | D | D | — | — | — |
| $P^A$ | Ph | N-AA | OH | OH | $U^1$ | D | HHD | D | D | D | — | — | — |
| $P^A$ | Ph | N-AA | OH | OH | $U^1$ | D | HDD | D | D | D | — | — | — |
| $P^A$ | Ph | N-AA | OH | OH | $U^1$ | D | DDD | D | D | D | — | — | — |
| $P^A$ | Ph | N-AA | OH | F | $U^1$ | H | HHH | H | H | H | — | — | — |
| $P^A$ | Ph | N-AA | OH | F | $U^1$ | H | HHD | H | H | H | — | — | — |
| $P^A$ | Ph | N-AA | OH | F | $U^1$ | H | HDD | H | H | H | — | — | — |
| $P^A$ | Ph | N-AA | OH | F | $U^1$ | H | DDD | H | H | H | — | — | — |
| $P^A$ | Ph | N-AA | OH | F | $U^1$ | H | HHH | D | H | H | — | — | — |
| $P^A$ | Ph | N-AA | OH | F | $U^1$ | H | HDD | D | H | H | — | — | — |
| $P^A$ | Ph | N-AA | OH | F | $U^1$ | H | DDD | D | H | H | — | — | — |
| $P^A$ | Ph | N-AA | OH | F | $U^1$ | D | HHH | H | H | H | — | — | — |
| $P^A$ | Ph | N-AA | OH | F | $U^1$ | D | HDD | H | H | H | — | — | — |
| $P^A$ | Ph | N-AA | OH | F | $U^1$ | D | DDD | H | H | H | — | — | — |
| $P^A$ | Ph | N-AA | OH | F | $U^1$ | D | HHH | D | H | H | — | — | — |
| $P^A$ | Ph | N-AA | OH | F | $U^1$ | D | HHD | D | H | H | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^A$ | Ph | N-AA | OH | F | $U^1$ | D | HDD | D | H | H | — | — | — |
| $P^A$ | Ph | N-AA | OH | F | $U^1$ | D | DDD | D | H | H | — | — | — |
| $P^A$ | Ph | N-AA | OH | F | $U^1$ | H | HHH | H | H | D | — | — | — |
| $P^A$ | Ph | N-AA | OH | F | $U^1$ | H | HHD | H | H | D | — | — | — |
| $P^A$ | Ph | N-AA | OH | F | $U^1$ | H | HDD | H | H | D | — | — | — |
| $P^A$ | Ph | N-AA | OH | F | $U^1$ | H | DDD | H | H | D | — | — | — |
| $P^A$ | Ph | N-AA | OH | F | $U^1$ | H | HHH | D | H | D | — | — | — |
| $P^A$ | Ph | N-AA | OH | F | $U^1$ | H | HHD | D | H | D | — | — | — |
| $P^A$ | Ph | N-AA | OH | F | $U^1$ | H | HDD | D | H | D | — | — | — |
| $P^A$ | Ph | N-AA | OH | F | $U^1$ | H | DDD | D | H | D | — | — | — |
| $P^A$ | Ph | N-AA | OH | F | $U^1$ | D | HHH | H | H | D | — | — | — |
| $P^A$ | Ph | N-AA | OH | F | $U^1$ | D | HHD | H | H | D | — | — | — |
| $P^A$ | Ph | N-AA | OH | F | $U^1$ | D | HDD | H | H | D | — | — | — |
| $P^A$ | Ph | N-AA | OH | F | $U^1$ | D | DDD | H | H | D | — | — | — |
| $P^A$ | Ph | N-AA | OH | F | $U^1$ | D | HHH | D | H | D | — | — | — |
| $P^A$ | Ph | N-AA | OH | F | $U^1$ | D | HHD | D | H | D | — | — | — |
| $P^A$ | Ph | N-AA | OH | F | $U^1$ | D | HDD | D | H | D | — | — | — |
| $P^A$ | Ph | N-AA | OH | F | $U^1$ | D | DDD | D | H | D | — | — | — |
| $P^A$ | Ph | N-AA | OH | F | $U^1$ | H | HHH | H | D | H | — | — | — |
| $P^A$ | Ph | N-AA | OH | F | $U^1$ | H | HHD | H | D | H | — | — | — |
| $P^A$ | Ph | N-AA | OH | F | $U^1$ | H | HDD | H | D | H | — | — | — |
| $P^A$ | Ph | N-AA | OH | F | $U^1$ | H | DDD | H | D | H | — | — | — |
| $P^A$ | Ph | N-AA | OH | F | $U^1$ | H | HHH | D | D | H | — | — | — |
| $P^A$ | Ph | N-AA | OH | F | $U^1$ | H | HHD | D | D | H | — | — | — |
| $P^A$ | Ph | N-AA | OH | F | $U^1$ | H | HDD | D | D | H | — | — | — |
| $P^A$ | Ph | N-AA | OH | F | $U^1$ | H | DDD | D | D | H | — | — | — |
| $P^A$ | Ph | N-AA | OH | F | $U^1$ | D | HHH | H | D | H | — | — | — |
| $P^A$ | Ph | N-AA | OH | F | $U^1$ | D | HHD | H | D | H | — | — | — |
| $P^A$ | Ph | N-AA | OH | F | $U^1$ | D | HDD | H | D | H | — | — | — |
| $P^A$ | Ph | N-AA | OH | F | $U^1$ | D | DDD | H | D | H | — | — | — |
| $P^A$ | Ph | N-AA | OH | F | $U^1$ | D | HHH | D | D | H | — | — | — |
| $P^A$ | Ph | N-AA | OH | F | $U^1$ | D | HHD | D | D | H | — | — | — |
| $P^A$ | Ph | N-AA | OH | F | $U^1$ | D | HDD | D | D | H | — | — | — |
| $P^A$ | Ph | N-AA | OH | F | $U^1$ | D | DDD | D | D | H | — | — | — |
| $P^A$ | Ph | N-AA | OH | F | $U^1$ | H | HHH | H | D | D | — | — | — |
| $P^A$ | Ph | N-AA | OH | F | $U^1$ | H | HHD | H | D | D | — | — | — |
| $P^A$ | Ph | N-AA | OH | F | $U^1$ | H | HDD | H | D | D | — | — | — |
| $P^A$ | Ph | N-AA | OH | F | $U^1$ | H | DDD | H | D | D | — | — | — |
| $P^A$ | Ph | N-AA | OH | F | $U^1$ | H | HHH | D | D | D | — | — | — |
| $P^A$ | Ph | N-AA | OH | F | $U^1$ | H | HHD | D | D | D | — | — | — |
| $P^A$ | Ph | N-AA | OH | F | $U^1$ | H | HDD | D | D | D | — | — | — |
| $P^A$ | Ph | N-AA | OH | F | $U^1$ | H | DDD | D | D | D | — | — | — |
| $P^A$ | Ph | N-AA | OH | F | $U^1$ | D | HHH | H | D | D | — | — | — |
| $P^A$ | Ph | N-AA | OH | F | $U^1$ | D | HHD | H | D | D | — | — | — |
| $P^A$ | Ph | N-AA | OH | F | $U^1$ | D | HDD | H | D | D | — | — | — |
| $P^A$ | Ph | N-AA | OH | F | $U^1$ | D | DDD | H | D | D | — | — | — |
| $P^A$ | Ph | N-AA | OH | F | $U^1$ | D | HHH | D | D | D | — | — | — |
| $P^A$ | Ph | N-AA | OH | F | $U^1$ | D | HHD | D | D | D | — | — | — |
| $P^A$ | Ph | N-AA | OH | F | $U^1$ | D | HDD | D | D | D | — | — | — |
| $P^A$ | Ph | N-AA | OH | F | $U^1$ | D | DDD | D | D | D | — | — | — |
| $P^A$ | Ph | N-AA | F | OH | $U^1$ | H | HHH | H | H | H | — | — | — |
| $P^A$ | Ph | N-AA | F | OH | $U^1$ | H | HHD | H | H | H | — | — | — |
| $P^A$ | Ph | N-AA | F | OH | $U^1$ | H | HDD | H | H | H | — | — | — |
| $P^A$ | Ph | N-AA | F | OH | $U^1$ | H | DDD | H | H | H | — | — | — |
| $P^A$ | Ph | N-AA | F | OH | $U^1$ | H | HHH | D | H | H | — | — | — |
| $P^A$ | Ph | N-AA | F | OH | $U^1$ | H | HHD | D | H | H | — | — | — |
| $P^A$ | Ph | N-AA | F | OH | $U^1$ | H | HDD | D | H | H | — | — | — |
| $P^A$ | Ph | N-AA | F | OH | $U^1$ | H | DDD | D | H | H | — | — | — |
| $P^A$ | Ph | N-AA | F | OH | $U^1$ | D | HHH | H | H | H | — | — | — |
| $P^A$ | Ph | N-AA | F | OH | $U^1$ | D | HHD | H | H | H | — | — | — |
| $P^A$ | Ph | N-AA | F | OH | $U^1$ | D | HDD | H | H | H | — | — | — |
| $P^A$ | Ph | N-AA | F | OH | $U^1$ | D | DDD | H | H | H | — | — | — |
| $P^A$ | Ph | N-AA | F | OH | $U^1$ | D | HHH | D | H | H | — | — | — |
| $P^A$ | Ph | N-AA | F | OH | $U^1$ | D | HHD | D | H | H | — | — | — |
| $P^A$ | Ph | N-AA | F | OH | $U^1$ | D | HDD | D | H | H | — | — | — |
| $P^A$ | Ph | N-AA | F | OH | $U^1$ | D | DDD | D | H | H | — | — | — |
| $P^A$ | Ph | N-AA | F | OH | $U^1$ | H | HHH | H | H | D | — | — | — |
| $P^A$ | Ph | N-AA | F | OH | $U^1$ | H | HHD | H | H | D | — | — | — |
| $P^A$ | Ph | N-AA | F | OH | $U^1$ | H | HDD | H | H | D | — | — | — |
| $P^A$ | Ph | N-AA | F | OH | $U^1$ | H | DDD | H | H | D | — | — | — |
| $P^A$ | Ph | N-AA | F | OH | $U^1$ | H | HHH | D | H | D | — | — | — |
| $P^A$ | Ph | N-AA | F | OH | $U^1$ | H | HHD | D | H | D | — | — | — |
| $P^A$ | Ph | N-AA | F | OH | $U^1$ | H | HDD | D | H | D | — | — | — |
| $P^A$ | Ph | N-AA | F | OH | $U^1$ | H | DDD | D | H | D | — | — | — |
| $P^A$ | Ph | N-AA | F | OH | $U^1$ | D | HHH | H | H | D | — | — | — |
| $P^A$ | Ph | N-AA | F | OH | $U^1$ | D | HHD | H | H | D | — | — | — |
| $P^A$ | Ph | N-AA | F | OH | $U^1$ | D | HDD | H | H | D | — | — | — |
| $P^A$ | Ph | N-AA | F | OH | $U^1$ | D | DDD | H | H | D | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^A$ | Ph | N-AA | F | OH | $U^1$ | D | HHH | D | H | D | — | — | — |
| $P^A$ | Ph | N-AA | F | OH | $U^1$ | D | HHD | D | H | D | — | — | — |
| $P^A$ | Ph | N-AA | F | OH | $U^1$ | D | HDD | D | H | D | — | — | — |
| $P^A$ | Ph | N-AA | F | OH | $U^1$ | D | DDD | D | H | D | — | — | — |
| $P^A$ | Ph | N-AA | F | OH | $U^1$ | H | HHH | H | D | H | — | — | — |
| $P^A$ | Ph | N-AA | F | OH | $U^1$ | H | HHD | H | D | H | — | — | — |
| $P^A$ | Ph | N-AA | F | OH | $U^1$ | H | HDD | H | D | H | — | — | — |
| $P^A$ | Ph | N-AA | F | OH | $U^1$ | H | DDD | H | D | H | — | — | — |
| $P^A$ | Ph | N-AA | F | OH | $U^1$ | H | HHH | D | D | H | — | — | — |
| $P^A$ | Ph | N-AA | F | OH | $U^1$ | H | HHD | D | D | H | — | — | — |
| $P^A$ | Ph | N-AA | F | OH | $U^1$ | H | HDD | D | D | H | — | — | — |
| $P^A$ | Ph | N-AA | F | OH | $U^1$ | H | DDD | D | D | H | — | — | — |
| $P^A$ | Ph | N-AA | F | OH | $U^1$ | D | HHH | H | D | H | — | — | — |
| $P^A$ | Ph | N-AA | F | OH | $U^1$ | D | HHD | H | D | H | — | — | — |
| $P^A$ | Ph | N-AA | F | OH | $U^1$ | D | HDD | H | D | H | — | — | — |
| $P^A$ | Ph | N-AA | F | OH | $U^1$ | D | DDD | H | D | H | — | — | — |
| $P^A$ | Ph | N-AA | F | OH | $U^1$ | D | HHH | D | D | H | — | — | — |
| $P^A$ | Ph | N-AA | F | OH | $U^1$ | D | HHD | D | D | H | — | — | — |
| $P^A$ | Ph | N-AA | F | OH | $U^1$ | D | HDD | D | D | H | — | — | — |
| $P^A$ | Ph | N-AA | F | OH | $U^1$ | D | DDD | D | D | H | — | — | — |
| $P^A$ | Ph | N-AA | F | OH | $U^1$ | H | HHH | H | D | D | — | — | — |
| $P^A$ | Ph | N-AA | F | OH | $U^1$ | H | HHD | H | D | D | — | — | — |
| $P^A$ | Ph | N-AA | F | OH | $U^1$ | H | HDD | H | D | D | — | — | — |
| $P^A$ | Ph | N-AA | F | OH | $U^1$ | H | DDD | H | D | D | — | — | — |
| $P^A$ | Ph | N-AA | F | OH | $U^1$ | H | HHH | D | D | D | — | — | — |
| $P^A$ | Ph | N-AA | F | OH | $U^1$ | H | HHD | D | D | D | — | — | — |
| $P^A$ | Ph | N-AA | F | OH | $U^1$ | H | HDD | D | D | D | — | — | — |
| $P^A$ | Ph | N-AA | F | OH | $U^1$ | H | DDD | D | D | D | — | — | — |
| $P^A$ | Ph | N-AA | F | OH | $U^1$ | D | HHH | H | D | D | — | — | — |
| $P^A$ | Ph | N-AA | F | OH | $U^1$ | D | HHD | H | D | D | — | — | — |
| $P^A$ | Ph | N-AA | F | OH | $U^1$ | D | HDD | H | D | D | — | — | — |
| $P^A$ | Ph | N-AA | F | OH | $U^1$ | D | DDD | H | D | D | — | — | — |
| $P^A$ | Ph | N-AA | F | OH | $U^1$ | D | HHH | D | D | D | — | — | — |
| $P^A$ | Ph | N-AA | F | OH | $U^1$ | D | HHD | D | D | D | — | — | — |
| $P^A$ | Ph | N-AA | F | OH | $U^1$ | D | HDD | D | D | D | — | — | — |
| $P^A$ | Ph | N-AA | F | OH | $U^1$ | D | DDD | D | D | D | — | — | — |
| $P^A$ | Ph | N-AA | F | F | $U^1$ | H | HHH | H | H | H | — | — | — |
| $P^A$ | Ph | N-AA | F | F | $U^1$ | H | HHD | H | H | H | — | — | — |
| $P^A$ | Ph | N-AA | F | F | $U^1$ | H | HDD | H | H | H | — | — | — |
| $P^A$ | Ph | N-AA | F | F | $U^1$ | H | DDD | H | H | H | — | — | — |
| $P^A$ | Ph | N-AA | F | F | $U^1$ | H | HHH | D | H | H | — | — | — |
| $P^A$ | Ph | N-AA | F | F | $U^1$ | H | HHD | D | H | H | — | — | — |
| $P^A$ | Ph | N-AA | F | F | $U^1$ | H | HDD | D | H | H | — | — | — |
| $P^A$ | Ph | N-AA | F | F | $U^1$ | H | DDD | D | H | H | — | — | — |
| $P^A$ | Ph | N-AA | F | F | $U^1$ | D | HHH | H | H | H | — | — | — |
| $P^A$ | Ph | N-AA | F | F | $U^1$ | D | HHD | H | H | H | — | — | — |
| $P^A$ | Ph | N-AA | F | F | $U^1$ | D | HDD | H | H | H | — | — | — |
| $P^A$ | Ph | N-AA | F | F | $U^1$ | D | DDD | H | H | H | — | — | — |
| $P^A$ | Ph | N-AA | F | F | $U^1$ | D | HHH | D | H | H | — | — | — |
| $P^A$ | Ph | N-AA | F | F | $U^1$ | D | HHD | D | H | H | — | — | — |
| $P^A$ | Ph | N-AA | F | F | $U^1$ | D | HDD | D | H | H | — | — | — |
| $P^A$ | Ph | N-AA | F | F | $U^1$ | D | DDD | D | H | H | — | — | — |
| $P^A$ | Ph | N-AA | F | F | $U^1$ | H | HHH | H | H | D | — | — | — |
| $P^A$ | Ph | N-AA | F | F | $U^1$ | H | HHD | H | H | D | — | — | — |
| $P^A$ | Ph | N-AA | F | F | $U^1$ | H | HDD | H | H | D | — | — | — |
| $P^A$ | Ph | N-AA | F | F | $U^1$ | H | DDD | H | H | D | — | — | — |
| $P^A$ | Ph | N-AA | F | F | $U^1$ | H | HHH | D | H | D | — | — | — |
| $P^A$ | Ph | N-AA | F | F | $U^1$ | H | HHD | D | H | D | — | — | — |
| $P^A$ | Ph | N-AA | F | F | $U^1$ | H | HDD | D | H | D | — | — | — |
| $P^A$ | Ph | N-AA | F | F | $U^1$ | H | DDD | D | H | D | — | — | — |
| $P^A$ | Ph | N-AA | F | F | $U^1$ | D | HHH | H | H | D | — | — | — |
| $P^A$ | Ph | N-AA | F | F | $U^1$ | D | HHD | H | H | D | — | — | — |
| $P^A$ | Ph | N-AA | F | F | $U^1$ | D | HDD | H | H | D | — | — | — |
| $P^A$ | Ph | N-AA | F | F | $U^1$ | D | DDD | H | H | D | — | — | — |
| $P^A$ | Ph | N-AA | F | F | $U^1$ | D | HHH | D | H | D | — | — | — |
| $P^A$ | Ph | N-AA | F | F | $U^1$ | D | HHD | D | H | D | — | — | — |
| $P^A$ | Ph | N-AA | F | F | $U^1$ | D | HDD | D | H | D | — | — | — |
| $P^A$ | Ph | N-AA | F | F | $U^1$ | D | DDD | D | H | D | — | — | — |
| $P^A$ | Ph | N-AA | F | F | $U^1$ | H | HHH | H | D | H | — | — | — |
| $P^A$ | Ph | N-AA | F | F | $U^1$ | H | HHD | H | D | H | — | — | — |
| $P^A$ | Ph | N-AA | F | F | $U^1$ | H | HDD | H | D | H | — | — | — |
| $P^A$ | Ph | N-AA | F | F | $U^1$ | H | DDD | H | D | H | — | — | — |
| $P^A$ | Ph | N-AA | F | F | $U^1$ | H | HHH | D | D | H | — | — | — |
| $P^A$ | Ph | N-AA | F | F | $U^1$ | H | HHD | D | D | H | — | — | — |
| $P^A$ | Ph | N-AA | F | F | $U^1$ | H | HDD | D | D | H | — | — | — |
| $P^A$ | Ph | N-AA | F | F | $U^1$ | H | DDD | D | D | H | — | — | — |
| $P^A$ | Ph | N-AA | F | F | $U^1$ | D | HHH | H | D | H | — | — | — |
| $P^A$ | Ph | N-AA | F | F | $U^1$ | D | HHD | H | D | H | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^A$ | Ph | N-AA | F | F | $U^1$ | D | HDD | H | D | H | — | — | — |
| $P^A$ | Ph | N-AA | F | F | $U^1$ | D | DDD | H | D | H | — | — | — |
| $P^A$ | Ph | N-AA | F | F | $U^1$ | D | HHH | D | D | H | — | — | — |
| $P^A$ | Ph | N-AA | F | F | $U^1$ | D | HHD | D | D | H | — | — | — |
| $P^A$ | Ph | N-AA | F | F | $U^1$ | D | HDD | D | D | H | — | — | — |
| $P^A$ | Ph | N-AA | F | F | $U^1$ | D | DDD | D | D | H | — | — | — |
| $P^A$ | Ph | N-AA | F | F | $U^1$ | H | HHH | H | D | D | — | — | — |
| $P^A$ | Ph | N-AA | F | F | $U^1$ | H | HHD | H | D | D | — | — | — |
| $P^A$ | Ph | N-AA | F | F | $U^1$ | H | HDD | H | D | D | — | — | — |
| $P^A$ | Ph | N-AA | F | F | $U^1$ | H | DDD | H | D | D | — | — | — |
| $P^A$ | Ph | N-AA | F | F | $U^1$ | H | HHH | D | D | D | — | — | — |
| $P^A$ | Ph | N-AA | F | F | $U^1$ | H | HHD | D | D | D | — | — | — |
| $P^A$ | Ph | N-AA | F | F | $U^1$ | H | HDD | D | D | D | — | — | — |
| $P^A$ | Ph | N-AA | F | F | $U^1$ | H | DDD | D | D | D | — | — | — |
| $P^A$ | Ph | N-AA | F | F | $U^1$ | D | HHH | H | D | D | — | — | — |
| $P^A$ | Ph | N-AA | F | F | $U^1$ | D | HHD | H | D | D | — | — | — |
| $P^A$ | Ph | N-AA | F | F | $U^1$ | D | HDD | H | D | D | — | — | — |
| $P^A$ | Ph | N-AA | F | F | $U^1$ | D | DDD | H | D | D | — | — | — |
| $P^A$ | Ph | N-AA | F | F | $U^1$ | D | HHH | D | D | D | — | — | — |
| $P^A$ | Ph | N-AA | F | F | $U^1$ | D | HHD | D | D | D | — | — | — |
| $P^A$ | Ph | N-AA | F | F | $U^1$ | D | HDD | D | D | D | — | — | — |
| $P^A$ | Ph | N-AA | F | F | $U^1$ | D | DDD | D | D | D | — | — | — |
| $P^A$ | Naph | N-AA | OH | OH | $U^1$ | H | HHH | H | H | H | — | — | — |
| $P^A$ | Naph | N-AA | OH | OH | $U^1$ | H | HHD | H | H | H | — | — | — |
| $P^A$ | Naph | N-AA | OH | OH | $U^1$ | H | HDD | H | H | H | — | — | — |
| $P^A$ | Naph | N-AA | OH | OH | $U^1$ | H | DDD | H | H | H | — | — | — |
| $P^A$ | Naph | N-AA | OH | OH | $U^1$ | H | HHH | D | H | H | — | — | — |
| $P^A$ | Naph | N-AA | OH | OH | $U^1$ | H | HHD | D | H | H | — | — | — |
| $P^A$ | Naph | N-AA | OH | OH | $U^1$ | H | HDD | D | H | H | — | — | — |
| $P^A$ | Naph | N-AA | OH | OH | $U^1$ | H | DDD | D | H | H | — | — | — |
| $P^A$ | Naph | N-AA | OH | OH | $U^1$ | D | HHH | H | H | H | — | — | — |
| $P^A$ | Naph | N-AA | OH | OH | $U^1$ | D | HHD | H | H | H | — | — | — |
| $P^A$ | Naph | N-AA | OH | OH | $U^1$ | D | HDD | H | H | H | — | — | — |
| $P^A$ | Naph | N-AA | OH | OH | $U^1$ | D | DDD | H | H | H | — | — | — |
| $P^A$ | Naph | N-AA | OH | OH | $U^1$ | D | HHH | D | H | H | — | — | — |
| $P^A$ | Naph | N-AA | OH | OH | $U^1$ | D | HHD | D | H | H | — | — | — |
| $P^A$ | Naph | N-AA | OH | OH | $U^1$ | D | HDD | D | H | H | — | — | — |
| $P^A$ | Naph | N-AA | OH | OH | $U^1$ | D | DDD | D | H | H | — | — | — |
| $P^A$ | Naph | N-AA | OH | OH | $U^1$ | H | HHH | H | H | D | — | — | — |
| $P^A$ | Naph | N-AA | OH | OH | $U^1$ | H | HHD | H | H | D | — | — | — |
| $P^A$ | Naph | N-AA | OH | OH | $U^1$ | H | HDD | H | H | D | — | — | — |
| $P^A$ | Naph | N-AA | OH | OH | $U^1$ | H | DDD | H | H | D | — | — | — |
| $P^A$ | Naph | N-AA | OH | OH | $U^1$ | H | HHH | D | H | D | — | — | — |
| $P^A$ | Naph | N-AA | OH | OH | $U^1$ | H | HHD | D | H | D | — | — | — |
| $P^A$ | Naph | N-AA | OH | OH | $U^1$ | H | HDD | D | H | D | — | — | — |
| $P^A$ | Naph | N-AA | OH | OH | $U^1$ | H | DDD | D | H | D | — | — | — |
| $P^A$ | Naph | N-AA | OH | OH | $U^1$ | D | HHH | H | H | D | — | — | — |
| $P^A$ | Naph | N-AA | OH | OH | $U^1$ | D | HHD | H | H | D | — | — | — |
| $P^A$ | Naph | N-AA | OH | OH | $U^1$ | D | HDD | H | H | D | — | — | — |
| $P^A$ | Naph | N-AA | OH | OH | $U^1$ | D | DDD | H | H | D | — | — | — |
| $P^A$ | Naph | N-AA | OH | OH | $U^1$ | D | HHH | D | H | D | — | — | — |
| $P^A$ | Naph | N-AA | OH | OH | $U^1$ | D | HHD | D | H | D | — | — | — |
| $P^A$ | Naph | N-AA | OH | OH | $U^1$ | D | HDD | D | H | D | — | — | — |
| $P^A$ | Naph | N-AA | OH | OH | $U^1$ | D | DDD | D | H | D | — | — | — |
| $P^A$ | Naph | N-AA | OH | OH | $U^1$ | H | HHH | H | D | H | — | — | — |
| $P^A$ | Naph | N-AA | OH | OH | $U^1$ | H | HHD | H | D | H | — | — | — |
| $P^A$ | Naph | N-AA | OH | OH | $U^1$ | H | HDD | H | D | H | — | — | — |
| $P^A$ | Naph | N-AA | OH | OH | $U^1$ | H | DDD | H | D | H | — | — | — |
| $P^A$ | Naph | N-AA | OH | OH | $U^1$ | H | HHH | D | D | H | — | — | — |
| $P^A$ | Naph | N-AA | OH | OH | $U^1$ | H | HHD | D | D | H | — | — | — |
| $P^A$ | Naph | N-AA | OH | OH | $U^1$ | H | HDD | D | D | H | — | — | — |
| $P^A$ | Naph | N-AA | OH | OH | $U^1$ | H | DDD | D | D | H | — | — | — |
| $P^A$ | Naph | N-AA | OH | OH | $U^1$ | D | HHH | H | D | H | — | — | — |
| $P^A$ | Naph | N-AA | OH | OH | $U^1$ | D | HHD | H | D | H | — | — | — |
| $P^A$ | Naph | N-AA | OH | OH | $U^1$ | D | HDD | H | D | H | — | — | — |
| $P^A$ | Naph | N-AA | OH | OH | $U^1$ | D | DDD | H | D | H | — | — | — |
| $P^A$ | Naph | N-AA | OH | OH | $U^1$ | D | HHH | D | D | H | — | — | — |
| $P^A$ | Naph | N-AA | OH | OH | $U^1$ | D | HHD | D | D | H | — | — | — |
| $P^A$ | Naph | N-AA | OH | OH | $U^1$ | D | HDD | D | D | H | — | — | — |
| $P^A$ | Naph | N-AA | OH | OH | $U^1$ | D | DDD | D | D | H | — | — | — |
| $P^A$ | Naph | N-AA | OH | OH | $U^1$ | H | HHH | H | D | D | — | — | — |
| $P^A$ | Naph | N-AA | OH | OH | $U^1$ | H | HHD | H | D | D | — | — | — |
| $P^A$ | Naph | N-AA | OH | OH | $U^1$ | H | HDD | H | D | D | — | — | — |
| $P^A$ | Naph | N-AA | OH | OH | $U^1$ | H | DDD | H | D | D | — | — | — |
| $P^A$ | Naph | N-AA | OH | OH | $U^1$ | H | HHH | D | D | D | — | — | — |
| $P^A$ | Naph | N-AA | OH | OH | $U^1$ | H | HHD | D | D | D | — | — | — |
| $P^A$ | Naph | N-AA | OH | OH | $U^1$ | H | HDD | D | D | D | — | — | — |
| $P^A$ | Naph | N-AA | OH | OH | $U^1$ | H | DDD | D | D | D | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^4$ | Naph | N-AA | OH | OH | $U^1$ | D | HHH | H | D | D | — | — | — |
| $P^4$ | Naph | N-AA | OH | OH | $U^1$ | D | HHD | H | D | D | — | — | — |
| $P^4$ | Naph | N-AA | OH | OH | $U^1$ | D | HDD | H | D | D | — | — | — |
| $P^4$ | Naph | N-AA | OH | OH | $U^1$ | D | DDD | H | D | D | — | — | — |
| $P^4$ | Naph | N-AA | OH | OH | $U^1$ | D | HHH | D | D | D | — | — | — |
| $P^4$ | Naph | N-AA | OH | OH | $U^1$ | D | HHD | D | D | D | — | — | — |
| $P^4$ | Naph | N-AA | OH | OH | $U^1$ | D | HDD | D | D | D | — | — | — |
| $P^4$ | Naph | N-AA | OH | OH | $U^1$ | D | DDD | D | D | D | — | — | — |
| $P^4$ | Naph | N-AA | OH | F | $U^1$ | H | HHH | H | H | H | — | — | — |
| $P^4$ | Naph | N-AA | OH | F | $U^1$ | H | HHD | H | H | H | — | — | — |
| $P^4$ | Naph | N-AA | OH | F | $U^1$ | H | HDD | H | H | H | — | — | — |
| $P^4$ | Naph | N-AA | OH | F | $U^1$ | H | DDD | H | H | H | — | — | — |
| $P^4$ | Naph | N-AA | OH | F | $U^1$ | H | HHH | D | H | H | — | — | — |
| $P^4$ | Naph | N-AA | OH | F | $U^1$ | H | HHD | D | H | H | — | — | — |
| $P^4$ | Naph | N-AA | OH | F | $U^1$ | H | HDD | D | H | H | — | — | — |
| $P^4$ | Naph | N-AA | OH | F | $U^1$ | H | DDD | D | H | H | — | — | — |
| $P^4$ | Naph | N-AA | OH | F | $U^1$ | D | HHH | H | H | H | — | — | — |
| $P^4$ | Naph | N-AA | OH | F | $U^1$ | D | HHD | H | H | H | — | — | — |
| $P^4$ | Naph | N-AA | OH | F | $U^1$ | D | HDD | H | H | H | — | — | — |
| $P^4$ | Naph | N-AA | OH | F | $U^1$ | D | DDD | H | H | H | — | — | — |
| $P^4$ | Naph | N-AA | OH | F | $U^1$ | D | HHH | D | H | H | — | — | — |
| $P^4$ | Naph | N-AA | OH | F | $U^1$ | D | HHD | D | H | H | — | — | — |
| $P^4$ | Naph | N-AA | OH | F | $U^1$ | D | HDD | D | H | H | — | — | — |
| $P^4$ | Naph | N-AA | OH | F | $U^1$ | D | DDD | D | H | H | — | — | — |
| $P^4$ | Naph | N-AA | OH | F | $U^1$ | H | HHH | H | H | D | — | — | — |
| $P^4$ | Naph | N-AA | OH | F | $U^1$ | H | HHD | H | H | D | — | — | — |
| $P^4$ | Naph | N-AA | OH | F | $U^1$ | H | HDD | H | H | D | — | — | — |
| $P^4$ | Naph | N-AA | OH | F | $U^1$ | H | DDD | H | H | D | — | — | — |
| $P^4$ | Naph | N-AA | OH | F | $U^1$ | H | HHH | D | H | D | — | — | — |
| $P^4$ | Naph | N-AA | OH | F | $U^1$ | H | HHD | D | H | D | — | — | — |
| $P^4$ | Naph | N-AA | OH | F | $U^1$ | H | HDD | D | H | D | — | — | — |
| $P^4$ | Naph | N-AA | OH | F | $U^1$ | H | DDD | D | H | D | — | — | — |
| $P^4$ | Naph | N-AA | OH | F | $U^1$ | D | HHH | H | H | D | — | — | — |
| $P^4$ | Naph | N-AA | OH | F | $U^1$ | D | HHD | H | H | D | — | — | — |
| $P^4$ | Naph | N-AA | OH | F | $U^1$ | D | HDD | H | H | D | — | — | — |
| $P^4$ | Naph | N-AA | OH | F | $U^1$ | D | DDD | H | H | D | — | — | — |
| $P^4$ | Naph | N-AA | OH | F | $U^1$ | D | HHH | D | H | D | — | — | — |
| $P^4$ | Naph | N-AA | OH | F | $U^1$ | D | HHD | D | H | D | — | — | — |
| $P^4$ | Naph | N-AA | OH | F | $U^1$ | D | HDD | D | H | D | — | — | — |
| $P^4$ | Naph | N-AA | OH | F | $U^1$ | D | DDD | D | H | D | — | — | — |
| $P^4$ | Naph | N-AA | OH | F | $U^1$ | H | HHH | H | D | H | — | — | — |
| $P^4$ | Naph | N-AA | OH | F | $U^1$ | H | HHD | H | D | H | — | — | — |
| $P^4$ | Naph | N-AA | OH | F | $U^1$ | H | HDD | H | D | H | — | — | — |
| $P^4$ | Naph | N-AA | OH | F | $U^1$ | H | DDD | H | D | H | — | — | — |
| $P^4$ | Naph | N-AA | OH | F | $U^1$ | H | HHH | D | D | H | — | — | — |
| $P^4$ | Naph | N-AA | OH | F | $U^1$ | H | HHD | D | D | H | — | — | — |
| $P^4$ | Naph | N-AA | OH | F | $U^1$ | H | HDD | D | D | H | — | — | — |
| $P^4$ | Naph | N-AA | OH | F | $U^1$ | H | DDD | D | D | H | — | — | — |
| $P^4$ | Naph | N-AA | OH | F | $U^1$ | D | HHH | H | D | H | — | — | — |
| $P^4$ | Naph | N-AA | OH | F | $U^1$ | D | HHD | H | D | H | — | — | — |
| $P^4$ | Naph | N-AA | OH | F | $U^1$ | D | HDD | H | D | H | — | — | — |
| $P^4$ | Naph | N-AA | OH | F | $U^1$ | D | DDD | H | D | H | — | — | — |
| $P^4$ | Naph | N-AA | OH | F | $U^1$ | D | HHH | D | D | H | — | — | — |
| $P^4$ | Naph | N-AA | OH | F | $U^1$ | D | HHD | D | D | H | — | — | — |
| $P^4$ | Naph | N-AA | OH | F | $U^1$ | D | HDD | D | D | H | — | — | — |
| $P^4$ | Naph | N-AA | OH | F | $U^1$ | D | DDD | D | D | H | — | — | — |
| $P^4$ | Naph | N-AA | OH | F | $U^1$ | H | HHH | H | D | D | — | — | — |
| $P^4$ | Naph | N-AA | OH | F | $U^1$ | H | HHD | H | D | D | — | — | — |
| $P^4$ | Naph | N-AA | OH | F | $U^1$ | H | HDD | H | D | D | — | — | — |
| $P^4$ | Naph | N-AA | OH | F | $U^1$ | H | DDD | H | D | D | — | — | — |
| $P^4$ | Naph | N-AA | OH | F | $U^1$ | H | HHH | D | D | D | — | — | — |
| $P^4$ | Naph | N-AA | OH | F | $U^1$ | H | HHD | D | D | D | — | — | — |
| $P^4$ | Naph | N-AA | OH | F | $U^1$ | H | HDD | D | D | D | — | — | — |
| $P^4$ | Naph | N-AA | OH | F | $U^1$ | H | DDD | D | D | D | — | — | — |
| $P^4$ | Naph | N-AA | OH | F | $U^1$ | D | HHH | H | D | D | — | — | — |
| $P^4$ | Naph | N-AA | OH | F | $U^1$ | D | HHD | H | D | D | — | — | — |
| $P^4$ | Naph | N-AA | OH | F | $U^1$ | D | HDD | H | D | D | — | — | — |
| $P^4$ | Naph | N-AA | OH | F | $U^1$ | D | DDD | H | D | D | — | — | — |
| $P^4$ | Naph | N-AA | OH | F | $U^1$ | D | HHH | D | D | D | — | — | — |
| $P^4$ | Naph | N-AA | OH | F | $U^1$ | D | HHD | D | D | D | — | — | — |
| $P^4$ | Naph | N-AA | OH | F | $U^1$ | D | HDD | D | D | D | — | — | — |
| $P^4$ | Naph | N-AA | OH | F | $U^1$ | D | DDD | D | D | D | — | — | — |
| $P^4$ | Naph | N-AA | F | OH | $U^1$ | H | HHH | H | H | H | — | — | — |
| $P^4$ | Naph | N-AA | F | OH | $U^1$ | H | HHD | H | H | H | — | — | — |
| $P^4$ | Naph | N-AA | F | OH | $U^1$ | H | HDD | H | H | H | — | — | — |
| $P^4$ | Naph | N-AA | F | OH | $U^1$ | H | DDD | H | H | H | — | — | — |
| $P^4$ | Naph | N-AA | F | OH | $U^1$ | H | HHH | D | H | H | — | — | — |
| $P^4$ | Naph | N-AA | F | OH | $U^1$ | H | HHD | D | H | H | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^4$ | Naph | N-AA | F | OH | $U^1$ | H | HDD | D | H | H | — | — | — |
| $P^4$ | Naph | N-AA | F | OH | $U^1$ | D | HHH | H | H | H | — | — | — |
| $P^4$ | Naph | N-AA | F | OH | $U^1$ | D | HHD | H | H | H | — | — | — |
| $P^4$ | Naph | N-AA | F | OH | $U^1$ | D | HDD | H | H | H | — | — | — |
| $P^4$ | Naph | N-AA | F | OH | $U^1$ | D | DDD | H | H | H | — | — | — |
| $P^4$ | Naph | N-AA | F | OH | $U^1$ | D | HHH | D | H | H | — | — | — |
| $P^4$ | Naph | N-AA | F | OH | $U^1$ | D | HHD | D | H | H | — | — | — |
| $P^4$ | Naph | N-AA | F | OH | $U^1$ | D | HDD | D | H | H | — | — | — |
| $P^4$ | Naph | N-AA | F | OH | $U^1$ | D | DDD | D | H | H | — | — | — |
| $P^4$ | Naph | N-AA | F | OH | $U^1$ | H | HHH | H | H | D | — | — | — |
| $P^4$ | Naph | N-AA | F | OH | $U^1$ | H | HHD | H | H | D | — | — | — |
| $P^4$ | Naph | N-AA | F | OH | $U^1$ | H | HDD | H | H | D | — | — | — |
| $P^4$ | Naph | N-AA | F | OH | $U^1$ | H | DDD | H | H | D | — | — | — |
| $P^4$ | Naph | N-AA | F | OH | $U^1$ | H | HHH | D | H | D | — | — | — |
| $P^4$ | Naph | N-AA | F | OH | $U^1$ | H | HHD | D | H | D | — | — | — |
| $P^4$ | Naph | N-AA | F | OH | $U^1$ | H | HDD | D | H | D | — | — | — |
| $P^4$ | Naph | N-AA | F | OH | $U^1$ | H | DDD | D | H | D | — | — | — |
| $P^4$ | Naph | N-AA | F | OH | $U^1$ | D | HHH | H | H | D | — | — | — |
| $P^4$ | Naph | N-AA | F | OH | $U^1$ | D | HHD | H | H | D | — | — | — |
| $P^4$ | Naph | N-AA | F | OH | $U^1$ | D | HDD | H | H | D | — | — | — |
| $P^4$ | Naph | N-AA | F | OH | $U^1$ | D | DDD | H | H | D | — | — | — |
| $P^4$ | Naph | N-AA | F | OH | $U^1$ | D | HHH | D | H | D | — | — | — |
| $P^4$ | Naph | N-AA | F | OH | $U^1$ | D | HHD | D | H | D | — | — | — |
| $P^4$ | Naph | N-AA | F | OH | $U^1$ | D | HDD | D | H | D | — | — | — |
| $P^4$ | Naph | N-AA | F | OH | $U^1$ | D | DDD | D | H | D | — | — | — |
| $P^4$ | Naph | N-AA | F | OH | $U^1$ | H | HHH | H | D | H | — | — | — |
| $P^4$ | Naph | N-AA | F | OH | $U^1$ | H | HHD | H | D | H | — | — | — |
| $P^4$ | Naph | N-AA | F | OH | $U^1$ | H | HDD | H | D | H | — | — | — |
| $P^4$ | Naph | N-AA | F | OH | $U^1$ | H | DDD | H | D | H | — | — | — |
| $P^4$ | Naph | N-AA | F | OH | $U^1$ | H | HHH | D | D | H | — | — | — |
| $P^4$ | Naph | N-AA | F | OH | $U^1$ | H | HHD | D | D | H | — | — | — |
| $P^4$ | Naph | N-AA | F | OH | $U^1$ | H | HDD | D | D | H | — | — | — |
| $P^4$ | Naph | N-AA | F | OH | $U^1$ | H | DDD | D | D | H | — | — | — |
| $P^4$ | Naph | N-AA | F | OH | $U^1$ | D | HHH | H | D | H | — | — | — |
| $P^4$ | Naph | N-AA | F | OH | $U^1$ | D | HHD | H | D | H | — | — | — |
| $P^4$ | Naph | N-AA | F | OH | $U^1$ | D | HDD | H | D | H | — | — | — |
| $P^4$ | Naph | N-AA | F | OH | $U^1$ | D | DDD | H | D | H | — | — | — |
| $P^4$ | Naph | N-AA | F | OH | $U^1$ | D | HHH | D | D | H | — | — | — |
| $P^4$ | Naph | N-AA | F | OH | $U^1$ | D | HHD | D | D | H | — | — | — |
| $P^4$ | Naph | N-AA | F | OH | $U^1$ | D | HDD | D | D | H | — | — | — |
| $P^4$ | Naph | N-AA | F | OH | $U^1$ | D | DDD | D | D | H | — | — | — |
| $P^4$ | Naph | N-AA | F | OH | $U^1$ | H | HHH | H | D | D | — | — | — |
| $P^4$ | Naph | N-AA | F | OH | $U^1$ | H | HHD | H | D | D | — | — | — |
| $P^4$ | Naph | N-AA | F | OH | $U^1$ | H | HDD | H | D | D | — | — | — |
| $P^4$ | Naph | N-AA | F | OH | $U^1$ | H | DDD | H | D | D | — | — | — |
| $P^4$ | Naph | N-AA | F | OH | $U^1$ | H | HHH | D | D | D | — | — | — |
| $P^4$ | Naph | N-AA | F | OH | $U^1$ | H | HHD | D | D | D | — | — | — |
| $P^4$ | Naph | N-AA | F | OH | $U^1$ | H | HDD | D | D | D | — | — | — |
| $P^4$ | Naph | N-AA | F | OH | $U^1$ | H | DDD | D | D | D | — | — | — |
| $P^4$ | Naph | N-AA | F | OH | $U^1$ | D | HHH | H | D | D | — | — | — |
| $P^4$ | Naph | N-AA | F | OH | $U^1$ | D | HHD | H | D | D | — | — | — |
| $P^4$ | Naph | N-AA | F | OH | $U^1$ | D | HDD | H | D | D | — | — | — |
| $P^4$ | Naph | N-AA | F | OH | $U^1$ | D | DDD | H | D | D | — | — | — |
| $P^4$ | Naph | N-AA | F | OH | $U^1$ | D | HHH | D | D | D | — | — | — |
| $P^4$ | Naph | N-AA | F | OH | $U^1$ | D | HHD | D | D | D | — | — | — |
| $P^4$ | Naph | N-AA | F | OH | $U^1$ | D | HDD | D | D | D | — | — | — |
| $P^4$ | Naph | N-AA | F | OH | $U^1$ | D | DDD | D | D | D | — | — | — |
| $P^4$ | Naph | N-AA | F | F | $U^1$ | H | HHH | H | H | H | — | — | — |
| $P^4$ | Naph | N-AA | F | F | $U^1$ | H | HHD | H | H | H | — | — | — |
| $P^4$ | Naph | N-AA | F | F | $U^1$ | H | HDD | H | H | H | — | — | — |
| $P^4$ | Naph | N-AA | F | F | $U^1$ | H | HHH | H | H | H | — | — | — |
| $P^4$ | Naph | N-AA | F | F | $U^1$ | H | HHD | D | H | H | — | — | — |
| $P^4$ | Naph | N-AA | F | F | $U^1$ | H | HDD | D | H | H | — | — | — |
| $P^4$ | Naph | N-AA | F | F | $U^1$ | H | DDD | D | H | H | — | — | — |
| $P^4$ | Naph | N-AA | F | F | $U^1$ | D | HHH | H | H | H | — | — | — |
| $P^4$ | Naph | N-AA | F | F | $U^1$ | D | HHD | H | H | H | — | — | — |
| $P^4$ | Naph | N-AA | F | F | $U^1$ | D | HDD | H | H | H | — | — | — |
| $P^4$ | Naph | N-AA | F | F | $U^1$ | D | DDD | H | H | H | — | — | — |
| $P^4$ | Naph | N-AA | F | F | $U^1$ | D | HHH | D | H | H | — | — | — |
| $P^4$ | Naph | N-AA | F | F | $U^1$ | D | HHD | D | H | H | — | — | — |
| $P^4$ | Naph | N-AA | F | F | $U^1$ | D | HDD | D | H | H | — | — | — |
| $P^4$ | Naph | N-AA | F | F | $U^1$ | D | DDD | D | H | H | — | — | — |
| $P^4$ | Naph | N-AA | F | F | $U^1$ | H | HHH | H | H | D | — | — | — |
| $P^4$ | Naph | N-AA | F | F | $U^1$ | H | HHD | H | H | D | — | — | — |
| $P^4$ | Naph | N-AA | F | F | $U^1$ | H | HDD | H | H | D | — | — | — |
| $P^4$ | Naph | N-AA | F | F | $U^1$ | H | DDD | H | H | D | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^4$ | Naph | N-AA | F | F | $U^1$ | H | HHH | D | H | D | — | — | — |
| $P^4$ | Naph | N-AA | F | F | $U^1$ | H | HHD | D | H | D | — | — | — |
| $P^4$ | Naph | N-AA | F | F | $U^1$ | H | HDD | D | H | D | — | — | — |
| $P^4$ | Naph | N-AA | F | F | $U^1$ | H | DDD | D | H | D | — | — | — |
| $P^4$ | Naph | N-AA | F | F | $U^1$ | D | HHH | H | H | D | — | — | — |
| $P^4$ | Naph | N-AA | F | F | $U^1$ | D | HHD | H | H | D | — | — | — |
| $P^4$ | Naph | N-AA | F | F | $U^1$ | D | HDD | H | H | D | — | — | — |
| $P^4$ | Naph | N-AA | F | F | $U^1$ | D | DDD | H | H | D | — | — | — |
| $P^4$ | Naph | N-AA | F | F | $U^1$ | D | HHH | D | H | D | — | — | — |
| $P^4$ | Naph | N-AA | F | F | $U^1$ | D | HHD | D | H | D | — | — | — |
| $P^4$ | Naph | N-AA | F | F | $U^1$ | D | HDD | D | H | D | — | — | — |
| $P^4$ | Naph | N-AA | F | F | $U^1$ | D | DDD | D | H | D | — | — | — |
| $P^4$ | Naph | N-AA | F | F | $U^1$ | H | HHH | H | D | H | — | — | — |
| $P^4$ | Naph | N-AA | F | F | $U^1$ | H | HHD | H | D | H | — | — | — |
| $P^4$ | Naph | N-AA | F | F | $U^1$ | H | HDD | H | D | H | — | — | — |
| $P^4$ | Naph | N-AA | F | F | $U^1$ | H | DDD | H | D | H | — | — | — |
| $P^4$ | Naph | N-AA | F | F | $U^1$ | H | HHH | D | D | H | — | — | — |
| $P^4$ | Naph | N-AA | F | F | $U^1$ | H | HHD | D | D | H | — | — | — |
| $P^4$ | Naph | N-AA | F | F | $U^1$ | H | HDD | D | D | H | — | — | — |
| $P^4$ | Naph | N-AA | F | F | $U^1$ | H | DDD | D | D | H | — | — | — |
| $P^4$ | Naph | N-AA | F | F | $U^1$ | D | HHH | H | D | H | — | — | — |
| $P^4$ | Naph | N-AA | F | F | $U^1$ | D | HHD | H | D | H | — | — | — |
| $P^4$ | Naph | N-AA | F | F | $U^1$ | D | HDD | H | D | H | — | — | — |
| $P^4$ | Naph | N-AA | F | F | $U^1$ | D | DDD | H | D | H | — | — | — |
| $P^4$ | Naph | N-AA | F | F | $U^1$ | D | HHH | D | D | H | — | — | — |
| $P^4$ | Naph | N-AA | F | F | $U^1$ | D | HHD | D | D | H | — | — | — |
| $P^4$ | Naph | N-AA | F | F | $U^1$ | D | HDD | D | D | H | — | — | — |
| $P^4$ | Naph | N-AA | F | F | $U^1$ | D | DDD | D | D | H | — | — | — |
| $P^4$ | Naph | N-AA | F | F | $U^1$ | H | HHH | H | D | D | — | — | — |
| $P^4$ | Naph | N-AA | F | F | $U^1$ | H | HHD | H | D | D | — | — | — |
| $P^4$ | Naph | N-AA | F | F | $U^1$ | H | HDD | H | D | D | — | — | — |
| $P^4$ | Naph | N-AA | F | F | $U^1$ | H | DDD | H | D | D | — | — | — |
| $P^4$ | Naph | N-AA | F | F | $U^1$ | H | HHH | D | D | D | — | — | — |
| $P^4$ | Naph | N-AA | F | F | $U^1$ | H | HHD | D | D | D | — | — | — |
| $P^4$ | Naph | N-AA | F | F | $U^1$ | H | HDD | D | D | D | — | — | — |
| $P^4$ | Naph | N-AA | F | F | $U^1$ | H | DDD | D | D | D | — | — | — |
| $P^4$ | Naph | N-AA | F | F | $U^1$ | D | HHH | H | D | D | — | — | — |
| $P^4$ | Naph | N-AA | F | F | $U^1$ | D | HHD | H | D | D | — | — | — |
| $P^4$ | Naph | N-AA | F | F | $U^1$ | D | HDD | H | D | D | — | — | — |
| $P^4$ | Naph | N-AA | F | F | $U^1$ | D | DDD | H | D | D | — | — | — |
| $P^4$ | Naph | N-AA | F | F | $U^1$ | D | HHH | D | D | D | — | — | — |
| $P^4$ | Naph | N-AA | F | F | $U^1$ | D | HHD | D | D | D | — | — | — |
| $P^4$ | Naph | N-AA | F | F | $U^1$ | D | HDD | D | D | D | — | — | — |
| $P^4$ | Naph | N-AA | F | F | $U^1$ | D | DDD | D | D | D | — | — | — |
| $P^4$ | POC | POC | OH | OH | $U^1$ | H | HHH | H | H | H | — | — | — |
| $P^4$ | POC | POC | OH | OH | $U^1$ | H | HHD | H | H | H | — | — | — |
| $P^4$ | POC | POC | OH | OH | $U^1$ | H | HDD | H | H | H | — | — | — |
| $P^4$ | POC | POC | OH | OH | $U^1$ | H | DDD | H | H | H | — | — | — |
| $P^4$ | POC | POC | OH | OH | $U^1$ | H | HHH | D | H | H | — | — | — |
| $P^4$ | POC | POC | OH | OH | $U^1$ | H | HHD | D | H | H | — | — | — |
| $P^4$ | POC | POC | OH | OH | $U^1$ | H | HDD | D | H | H | — | — | — |
| $P^4$ | POC | POC | OH | OH | $U^1$ | H | DDD | D | H | H | — | — | — |
| $P^4$ | POC | POC | OH | OH | $U^1$ | D | HHH | H | H | H | — | — | — |
| $P^4$ | POC | POC | OH | OH | $U^1$ | D | HHD | H | H | H | — | — | — |
| $P^4$ | POC | POC | OH | OH | $U^1$ | D | HDD | H | H | H | — | — | — |
| $P^4$ | POC | POC | OH | OH | $U^1$ | D | DDD | H | H | H | — | — | — |
| $P^4$ | POC | POC | OH | OH | $U^1$ | D | HHH | D | H | H | — | — | — |
| $P^4$ | POC | POC | OH | OH | $U^1$ | D | HHD | D | H | H | — | — | — |
| $P^4$ | POC | POC | OH | OH | $U^1$ | D | HDD | D | H | H | — | — | — |
| $P^4$ | POC | POC | OH | OH | $U^1$ | D | DDD | D | H | H | — | — | — |
| $P^4$ | POC | POC | OH | OH | $U^1$ | H | HHH | H | H | D | — | — | — |
| $P^4$ | POC | POC | OH | OH | $U^1$ | H | HHD | H | H | D | — | — | — |
| $P^4$ | POC | POC | OH | OH | $U^1$ | H | HDD | H | H | D | — | — | — |
| $P^4$ | POC | POC | OH | OH | $U^1$ | H | DDD | H | H | D | — | — | — |
| $P^4$ | POC | POC | OH | OH | $U^1$ | H | HHH | D | H | D | — | — | — |
| $P^4$ | POC | POC | OH | OH | $U^1$ | H | HHD | D | H | D | — | — | — |
| $P^4$ | POC | POC | OH | OH | $U^1$ | H | HDD | D | H | D | — | — | — |
| $P^4$ | POC | POC | OH | OH | $U^1$ | H | DDD | D | H | D | — | — | — |
| $P^4$ | POC | POC | OH | OH | $U^1$ | D | HHH | H | H | D | — | — | — |
| $P^4$ | POC | POC | OH | OH | $U^1$ | D | HHD | H | H | D | — | — | — |
| $P^4$ | POC | POC | OH | OH | $U^1$ | D | HDD | H | H | D | — | — | — |
| $P^4$ | POC | POC | OH | OH | $U^1$ | D | DDD | H | H | D | — | — | — |
| $P^4$ | POC | POC | OH | OH | $U^1$ | D | HHH | D | H | D | — | — | — |
| $P^4$ | POC | POC | OH | OH | $U^1$ | D | HHD | D | H | D | — | — | — |
| $P^4$ | POC | POC | OH | OH | $U^1$ | D | HDD | D | H | D | — | — | — |
| $P^4$ | POC | POC | OH | OH | $U^1$ | D | DDD | D | H | D | — | — | — |
| $P^4$ | POC | POC | OH | OH | $U^1$ | H | HHH | H | D | H | — | — | — |
| $P^4$ | POC | POC | OH | OH | $U^1$ | H | HHD | H | D | H | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | POC | POC | OH | OH | $U^1$ | H | HDD | H | D | H | — | — | — |
| $P^4$ | POC | POC | OH | OH | $U^1$ | H | DDD | H | D | H | — | — | — |
| $P^4$ | POC | POC | OH | OH | $U^1$ | H | HHD | D | D | H | — | — | — |
| $P^4$ | POC | POC | OH | OH | $U^1$ | H | HDD | D | D | H | — | — | — |
| $P^4$ | POC | POC | OH | OH | $U^1$ | H | DDD | D | D | H | — | — | — |
| $P^4$ | POC | POC | OH | OH | $U^1$ | D | HHH | H | D | H | — | — | — |
| $P^4$ | POC | POC | OH | OH | $U^1$ | D | HHD | H | D | H | — | — | — |
| $P^4$ | POC | POC | OH | OH | $U^1$ | D | HDD | H | D | H | — | — | — |
| $P^4$ | POC | POC | OH | OH | $U^1$ | D | DDD | H | D | H | — | — | — |
| $P^4$ | POC | POC | OH | OH | $U^1$ | D | HHH | D | D | H | — | — | — |
| $P^4$ | POC | POC | OH | OH | $U^1$ | D | HHD | D | D | H | — | — | — |
| $P^4$ | POC | POC | OH | OH | $U^1$ | D | HDD | D | D | H | — | — | — |
| $P^4$ | POC | POC | OH | OH | $U^1$ | D | DDD | D | D | H | — | — | — |
| $P^4$ | POC | POC | OH | OH | $U^1$ | H | HHH | H | D | D | — | — | — |
| $P^4$ | POC | POC | OH | OH | $U^1$ | H | HHD | H | D | D | — | — | — |
| $P^4$ | POC | POC | OH | OH | $U^1$ | H | HDD | H | D | D | — | — | — |
| $P^4$ | POC | POC | OH | OH | $U^1$ | H | DDD | H | D | D | — | — | — |
| $P^4$ | POC | POC | OH | OH | $U^1$ | H | HHD | D | D | D | — | — | — |
| $P^4$ | POC | POC | OH | OH | $U^1$ | H | HDD | D | D | D | — | — | — |
| $P^4$ | POC | POC | OH | OH | $U^1$ | H | DDD | D | D | D | — | — | — |
| $P^4$ | POC | POC | OH | OH | $U^1$ | D | HHH | H | D | D | — | — | — |
| $P^4$ | POC | POC | OH | OH | $U^1$ | D | HHD | H | D | D | — | — | — |
| $P^4$ | POC | POC | OH | OH | $U^1$ | D | HDD | H | D | D | — | — | — |
| $P^4$ | POC | POC | OH | OH | $U^1$ | D | DDD | H | D | D | — | — | — |
| $P^4$ | POC | POC | OH | OH | $U^1$ | D | HHH | D | D | D | — | — | — |
| $P^4$ | POC | POC | OH | OH | $U^1$ | D | HHD | D | D | D | — | — | — |
| $P^4$ | POC | POC | OH | OH | $U^1$ | D | HDD | D | D | D | — | — | — |
| $P^4$ | POC | POC | OH | OH | $U^1$ | D | DDD | D | D | D | — | — | — |
| $P^4$ | POC | POC | OH | F | $U^1$ | H | HHH | H | H | H | — | — | — |
| $P^4$ | POC | POC | OH | F | $U^1$ | H | HHD | H | H | H | — | — | — |
| $P^4$ | POC | POC | OH | F | $U^1$ | H | HDD | H | H | H | — | — | — |
| $P^4$ | POC | POC | OH | F | $U^1$ | H | DDD | H | H | H | — | — | — |
| $P^4$ | POC | POC | OH | F | $U^1$ | H | HHH | D | H | H | — | — | — |
| $P^4$ | POC | POC | OH | F | $U^1$ | H | HDD | D | H | H | — | — | — |
| $P^4$ | POC | POC | OH | F | $U^1$ | H | DDD | D | H | H | — | — | — |
| $P^4$ | POC | POC | OH | F | $U^1$ | D | HHH | H | H | H | — | — | — |
| $P^4$ | POC | POC | OH | F | $U^1$ | D | HHD | H | H | H | — | — | — |
| $P^4$ | POC | POC | OH | F | $U^1$ | D | HDD | H | H | H | — | — | — |
| $P^4$ | POC | POC | OH | F | $U^1$ | D | DDD | H | H | H | — | — | — |
| $P^4$ | POC | POC | OH | F | $U^1$ | D | HHH | D | H | H | — | — | — |
| $P^4$ | POC | POC | OH | F | $U^1$ | D | HHD | D | H | H | — | — | — |
| $P^4$ | POC | POC | OH | F | $U^1$ | D | HDD | D | H | H | — | — | — |
| $P^4$ | POC | POC | OH | F | $U^1$ | D | DDD | D | H | H | — | — | — |
| $P^4$ | POC | POC | OH | F | $U^1$ | H | HHH | H | H | D | — | — | — |
| $P^4$ | POC | POC | OH | F | $U^1$ | H | HHD | H | H | D | — | — | — |
| $P^4$ | POC | POC | OH | F | $U^1$ | H | HDD | H | H | D | — | — | — |
| $P^4$ | POC | POC | OH | F | $U^1$ | H | DDD | H | H | D | — | — | — |
| $P^4$ | POC | POC | OH | F | $U^1$ | H | HHH | D | H | D | — | — | — |
| $P^4$ | POC | POC | OH | F | $U^1$ | H | HHD | D | H | D | — | — | — |
| $P^4$ | POC | POC | OH | F | $U^1$ | H | HDD | D | H | D | — | — | — |
| $P^4$ | POC | POC | OH | F | $U^1$ | H | DDD | D | H | D | — | — | — |
| $P^4$ | POC | POC | OH | F | $U^1$ | D | HHH | H | H | D | — | — | — |
| $P^4$ | POC | POC | OH | F | $U^1$ | D | HHD | H | H | D | — | — | — |
| $P^4$ | POC | POC | OH | F | $U^1$ | D | HDD | H | H | D | — | — | — |
| $P^4$ | POC | POC | OH | F | $U^1$ | D | DDD | H | H | D | — | — | — |
| $P^4$ | POC | POC | OH | F | $U^1$ | D | HHH | D | H | D | — | — | — |
| $P^4$ | POC | POC | OH | F | $U^1$ | D | HHD | D | H | D | — | — | — |
| $P^4$ | POC | POC | OH | F | $U^1$ | D | HDD | D | H | D | — | — | — |
| $P^4$ | POC | POC | OH | F | $U^1$ | D | DDD | D | H | D | — | — | — |
| $P^4$ | POC | POC | OH | F | $U^1$ | H | HHH | H | D | H | — | — | — |
| $P^4$ | POC | POC | OH | F | $U^1$ | H | HHD | H | D | H | — | — | — |
| $P^4$ | POC | POC | OH | F | $U^1$ | H | HDD | H | D | H | — | — | — |
| $P^4$ | POC | POC | OH | F | $U^1$ | H | DDD | H | D | H | — | — | — |
| $P^4$ | POC | POC | OH | F | $U^1$ | H | HHH | D | D | H | — | — | — |
| $P^4$ | POC | POC | OH | F | $U^1$ | H | HHD | D | D | H | — | — | — |
| $P^4$ | POC | POC | OH | F | $U^1$ | H | DDD | D | D | H | — | — | — |
| $P^4$ | POC | POC | OH | F | $U^1$ | D | HHH | H | D | H | — | — | — |
| $P^4$ | POC | POC | OH | F | $U^1$ | D | HHD | H | D | H | — | — | — |
| $P^4$ | POC | POC | OH | F | $U^1$ | D | HDD | H | D | H | — | — | — |
| $P^4$ | POC | POC | OH | F | $U^1$ | D | DDD | H | D | H | — | — | — |
| $P^4$ | POC | POC | OH | F | $U^1$ | D | HHH | D | D | H | — | — | — |
| $P^4$ | POC | POC | OH | F | $U^1$ | D | HHD | D | D | H | — | — | — |
| $P^4$ | POC | POC | OH | F | $U^1$ | D | HDD | D | D | H | — | — | — |
| $P^4$ | POC | POC | OH | F | $U^1$ | D | DDD | D | D | H | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^A$ | POC | POC | OH | F | $U^1$ | H | HHH | H | D | D | — | — | — |
| $P^A$ | POC | POC | OH | F | $U^1$ | H | HHD | H | D | D | — | — | — |
| $P^A$ | POC | POC | OH | F | $U^1$ | H | HDD | H | D | D | — | — | — |
| $P^A$ | POC | POC | OH | F | $U^1$ | H | DDD | H | D | D | — | — | — |
| $P^A$ | POC | POC | OH | F | $U^1$ | H | HHH | D | D | D | — | — | — |
| $P^A$ | POC | POC | OH | F | $U^1$ | H | HHD | D | D | D | — | — | — |
| $P^A$ | POC | POC | OH | F | $U^1$ | H | HDD | D | D | D | — | — | — |
| $P^A$ | POC | POC | OH | F | $U^1$ | H | DDD | D | D | D | — | — | — |
| $P^A$ | POC | POC | OH | F | $U^1$ | D | HHH | H | D | D | — | — | — |
| $P^A$ | POC | POC | OH | F | $U^1$ | D | HHD | H | D | D | — | — | — |
| $P^A$ | POC | POC | OH | F | $U^1$ | D | HDD | H | D | D | — | — | — |
| $P^A$ | POC | POC | OH | F | $U^1$ | D | DDD | H | D | D | — | — | — |
| $P^A$ | POC | POC | OH | F | $U^1$ | D | HHH | D | D | D | — | — | — |
| $P^A$ | POC | POC | OH | F | $U^1$ | D | HHD | D | D | D | — | — | — |
| $P^A$ | POC | POC | OH | F | $U^1$ | D | HDD | D | D | D | — | — | — |
| $P^A$ | POC | POC | OH | F | $U^1$ | D | DDD | D | D | D | — | — | — |
| $P^A$ | POC | POC | F | OH | $U^1$ | H | HHH | H | H | H | — | — | — |
| $P^A$ | POC | POC | F | OH | $U^1$ | H | HHD | H | H | H | — | — | — |
| $P^A$ | POC | POC | F | OH | $U^1$ | H | HDD | H | H | H | — | — | — |
| $P^A$ | POC | POC | F | OH | $U^1$ | H | DDD | H | H | H | — | — | — |
| $P^A$ | POC | POC | F | OH | $U^1$ | H | HHH | D | H | H | — | — | — |
| $P^A$ | POC | POC | F | OH | $U^1$ | H | HHD | D | H | H | — | — | — |
| $P^A$ | POC | POC | F | OH | $U^1$ | H | HDD | D | H | H | — | — | — |
| $P^A$ | POC | POC | F | OH | $U^1$ | H | DDD | D | H | H | — | — | — |
| $P^A$ | POC | POC | F | OH | $U^1$ | D | HHH | H | H | H | — | — | — |
| $P^A$ | POC | POC | F | OH | $U^1$ | D | HHD | H | H | H | — | — | — |
| $P^A$ | POC | POC | F | OH | $U^1$ | D | HDD | H | H | H | — | — | — |
| $P^A$ | POC | POC | F | OH | $U^1$ | D | DDD | H | H | H | — | — | — |
| $P^A$ | POC | POC | F | OH | $U^1$ | D | HHH | D | H | H | — | — | — |
| $P^A$ | POC | POC | F | OH | $U^1$ | D | HHD | D | H | H | — | — | — |
| $P^A$ | POC | POC | F | OH | $U^1$ | D | HDD | D | H | H | — | — | — |
| $P^A$ | POC | POC | F | OH | $U^1$ | D | DDD | D | H | H | — | — | — |
| $P^A$ | POC | POC | F | OH | $U^1$ | H | HHH | H | H | D | — | — | — |
| $P^A$ | POC | POC | F | OH | $U^1$ | H | HHD | H | H | D | — | — | — |
| $P^A$ | POC | POC | F | OH | $U^1$ | H | HDD | H | H | D | — | — | — |
| $P^A$ | POC | POC | F | OH | $U^1$ | H | DDD | H | H | D | — | — | — |
| $P^A$ | POC | POC | F | OH | $U^1$ | H | HHH | D | H | D | — | — | — |
| $P^A$ | POC | POC | F | OH | $U^1$ | H | HHD | D | H | D | — | — | — |
| $P^A$ | POC | POC | F | OH | $U^1$ | H | HDD | D | H | D | — | — | — |
| $P^A$ | POC | POC | F | OH | $U^1$ | H | DDD | D | H | D | — | — | — |
| $P^A$ | POC | POC | F | OH | $U^1$ | D | HHH | H | H | D | — | — | — |
| $P^A$ | POC | POC | F | OH | $U^1$ | D | HHD | H | H | D | — | — | — |
| $P^A$ | POC | POC | F | OH | $U^1$ | D | HDD | H | H | D | — | — | — |
| $P^A$ | POC | POC | F | OH | $U^1$ | D | DDD | H | H | D | — | — | — |
| $P^A$ | POC | POC | F | OH | $U^1$ | D | HHH | D | H | D | — | — | — |
| $P^A$ | POC | POC | F | OH | $U^1$ | D | HHD | D | H | D | — | — | — |
| $P^A$ | POC | POC | F | OH | $U^1$ | D | HDD | D | H | D | — | — | — |
| $P^A$ | POC | POC | F | OH | $U^1$ | D | DDD | D | H | D | — | — | — |
| $P^A$ | POC | POC | F | OH | $U^1$ | H | HHH | H | D | H | — | — | — |
| $P^A$ | POC | POC | F | OH | $U^1$ | H | HHD | H | D | H | — | — | — |
| $P^A$ | POC | POC | F | OH | $U^1$ | H | HDD | H | D | H | — | — | — |
| $P^A$ | POC | POC | F | OH | $U^1$ | H | DDD | H | D | H | — | — | — |
| $P^A$ | POC | POC | F | OH | $U^1$ | H | HHH | D | D | H | — | — | — |
| $P^A$ | POC | POC | F | OH | $U^1$ | H | HHD | D | D | H | — | — | — |
| $P^A$ | POC | POC | F | OH | $U^1$ | H | HDD | D | D | H | — | — | — |
| $P^A$ | POC | POC | F | OH | $U^1$ | H | DDD | D | D | H | — | — | — |
| $P^A$ | POC | POC | F | OH | $U^1$ | D | HHH | H | D | H | — | — | — |
| $P^A$ | POC | POC | F | OH | $U^1$ | D | HHD | H | D | H | — | — | — |
| $P^A$ | POC | POC | F | OH | $U^1$ | D | HDD | H | D | H | — | — | — |
| $P^A$ | POC | POC | F | OH | $U^1$ | D | DDD | H | D | H | — | — | — |
| $P^A$ | POC | POC | F | OH | $U^1$ | D | HHH | D | D | H | — | — | — |
| $P^A$ | POC | POC | F | OH | $U^1$ | D | HHD | D | D | H | — | — | — |
| $P^A$ | POC | POC | F | OH | $U^1$ | D | HDD | D | D | H | — | — | — |
| $P^A$ | POC | POC | F | OH | $U^1$ | D | DDD | D | D | H | — | — | — |
| $P^A$ | POC | POC | F | OH | $U^1$ | H | HHH | H | D | D | — | — | — |
| $P^A$ | POC | POC | F | OH | $U^1$ | H | HHD | H | D | D | — | — | — |
| $P^A$ | POC | POC | F | OH | $U^1$ | H | HDD | H | D | D | — | — | — |
| $P^A$ | POC | POC | F | OH | $U^1$ | H | DDD | H | D | D | — | — | — |
| $P^A$ | POC | POC | F | OH | $U^1$ | H | HHH | D | D | D | — | — | — |
| $P^A$ | POC | POC | F | OH | $U^1$ | H | HHD | D | D | D | — | — | — |
| $P^A$ | POC | POC | F | OH | $U^1$ | H | DDD | D | D | D | — | — | — |
| $P^A$ | POC | POC | F | OH | $U^1$ | D | HHH | H | D | D | — | — | — |
| $P^A$ | POC | POC | F | OH | $U^1$ | D | HDD | H | D | D | — | — | — |
| $P^A$ | POC | POC | F | OH | $U^1$ | D | DDD | H | D | D | — | — | — |
| $P^A$ | POC | POC | F | OH | $U^1$ | D | HHH | D | D | D | — | — | — |
| $P^A$ | POC | POC | F | OH | $U^1$ | D | HHD | D | D | D | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | POC | POC | F | OH | $U^1$ | D | HDD | D | D | D | — | — | — |
| $P^4$ | POC | POC | F | OH | $U^1$ | D | DDD | D | D | D | — | — | — |
| $P^4$ | POC | POC | F | F | $U^1$ | H | HHH | H | H | H | — | — | — |
| $P^4$ | POC | POC | F | F | $U^1$ | H | HHD | H | H | H | — | — | — |
| $P^4$ | POC | POC | F | F | $U^1$ | H | HDD | H | H | H | — | — | — |
| $P^4$ | POC | POC | F | F | $U^1$ | H | DDD | H | H | H | — | — | — |
| $P^4$ | POC | POC | F | F | $U^1$ | H | HHH | D | H | H | — | — | — |
| $P^4$ | POC | POC | F | F | $U^1$ | H | HHD | D | H | H | — | — | — |
| $P^4$ | POC | POC | F | F | $U^1$ | H | HDD | D | H | H | — | — | — |
| $P^4$ | POC | POC | F | F | $U^1$ | H | DDD | D | H | H | — | — | — |
| $P^4$ | POC | POC | F | F | $U^1$ | D | HHH | H | H | H | — | — | — |
| $P^4$ | POC | POC | F | F | $U^1$ | D | HHD | H | H | H | — | — | — |
| $P^4$ | POC | POC | F | F | $U^1$ | D | HDD | H | H | H | — | — | — |
| $P^4$ | POC | POC | F | F | $U^1$ | D | DDD | H | H | H | — | — | — |
| $P^4$ | POC | POC | F | F | $U^1$ | D | HHH | D | H | H | — | — | — |
| $P^4$ | POC | POC | F | F | $U^1$ | D | HHD | D | H | H | — | — | — |
| $P^4$ | POC | POC | F | F | $U^1$ | D | HDD | D | H | H | — | — | — |
| $P^4$ | POC | POC | F | F | $U^1$ | D | DDD | D | H | H | — | — | — |
| $P^4$ | POC | POC | F | F | $U^1$ | H | HHH | H | H | D | — | — | — |
| $P^4$ | POC | POC | F | F | $U^1$ | H | HHD | H | H | D | — | — | — |
| $P^4$ | POC | POC | F | F | $U^1$ | H | HDD | H | H | D | — | — | — |
| $P^4$ | POC | POC | F | F | $U^1$ | H | DDD | H | H | D | — | — | — |
| $P^4$ | POC | POC | F | F | $U^1$ | H | HHH | D | H | D | — | — | — |
| $P^4$ | POC | POC | F | F | $U^1$ | H | HHD | D | H | D | — | — | — |
| $P^4$ | POC | POC | F | F | $U^1$ | H | HDD | D | H | D | — | — | — |
| $P^4$ | POC | POC | F | F | $U^1$ | H | DDD | D | H | D | — | — | — |
| $P^4$ | POC | POC | F | F | $U^1$ | D | HHH | H | H | D | — | — | — |
| $P^4$ | POC | POC | F | F | $U^1$ | D | HHD | H | H | D | — | — | — |
| $P^4$ | POC | POC | F | F | $U^1$ | D | HDD | H | H | D | — | — | — |
| $P^4$ | POC | POC | F | F | $U^1$ | D | DDD | H | H | D | — | — | — |
| $P^4$ | POC | POC | F | F | $U^1$ | D | HHH | D | H | D | — | — | — |
| $P^4$ | POC | POC | F | F | $U^1$ | D | HHD | D | H | D | — | — | — |
| $P^4$ | POC | POC | F | F | $U^1$ | D | HDD | D | H | D | — | — | — |
| $P^4$ | POC | POC | F | F | $U^1$ | D | DDD | D | H | D | — | — | — |
| $P^4$ | POC | POC | F | F | $U^1$ | H | HHH | H | D | H | — | — | — |
| $P^4$ | POC | POC | F | F | $U^1$ | H | HHD | H | D | H | — | — | — |
| $P^4$ | POC | POC | F | F | $U^1$ | H | HDD | H | D | H | — | — | — |
| $P^4$ | POC | POC | F | F | $U^1$ | H | DDD | H | D | H | — | — | — |
| $P^4$ | POC | POC | F | F | $U^1$ | H | HHH | D | D | H | — | — | — |
| $P^4$ | POC | POC | F | F | $U^1$ | H | HHD | D | D | H | — | — | — |
| $P^4$ | POC | POC | F | F | $U^1$ | H | HDD | D | D | H | — | — | — |
| $P^4$ | POC | POC | F | F | $U^1$ | H | DDD | D | D | H | — | — | — |
| $P^4$ | POC | POC | F | F | $U^1$ | D | HHH | H | D | H | — | — | — |
| $P^4$ | POC | POC | F | F | $U^1$ | D | HHD | H | D | H | — | — | — |
| $P^4$ | POC | POC | F | F | $U^1$ | D | HDD | H | D | H | — | — | — |
| $P^4$ | POC | POC | F | F | $U^1$ | D | DDD | H | D | H | — | — | — |
| $P^4$ | POC | POC | F | F | $U^1$ | D | HHH | D | D | H | — | — | — |
| $P^4$ | POC | POC | F | F | $U^1$ | D | HHD | D | D | H | — | — | — |
| $P^4$ | POC | POC | F | F | $U^1$ | D | HDD | D | D | H | — | — | — |
| $P^4$ | POC | POC | F | F | $U^1$ | D | DDD | D | D | H | — | — | — |
| $P^4$ | POC | POC | F | F | $U^1$ | H | HHH | H | D | D | — | — | — |
| $P^4$ | POC | POC | F | F | $U^1$ | H | HHD | H | D | D | — | — | — |
| $P^4$ | POC | POC | F | F | $U^1$ | H | HDD | H | D | D | — | — | — |
| $P^4$ | POC | POC | F | F | $U^1$ | H | DDD | H | D | D | — | — | — |
| $P^4$ | POC | POC | F | F | $U^1$ | H | HHH | D | D | D | — | — | — |
| $P^4$ | POC | POC | F | F | $U^1$ | H | HHD | D | D | D | — | — | — |
| $P^4$ | POC | POC | F | F | $U^1$ | H | HDD | D | D | D | — | — | — |
| $P^4$ | POC | POC | F | F | $U^1$ | H | DDD | D | D | D | — | — | — |
| $P^4$ | POC | POC | F | F | $U^1$ | D | HHH | H | D | D | — | — | — |
| $P^4$ | POC | POC | F | F | $U^1$ | D | HHD | H | D | D | — | — | — |
| $P^4$ | POC | POC | F | F | $U^1$ | D | HDD | H | D | D | — | — | — |
| $P^4$ | POC | POC | F | F | $U^1$ | D | DDD | H | D | D | — | — | — |
| $P^4$ | POC | POC | F | F | $U^1$ | D | HHH | D | D | D | — | — | — |
| $P^4$ | POC | POC | F | F | $U^1$ | D | HHD | D | D | D | — | — | — |
| $P^4$ | POC | POC | F | F | $U^1$ | D | HDD | D | D | D | — | — | — |
| $P^4$ | POC | POC | F | F | $U^1$ | D | DDD | D | D | D | — | — | — |
| $P^4$ | $P^1$ | OH/O$^-$ | OH | OH | $U^1$ | H | HHH | H | H | H | — | — | — |
| $P^4$ | $P^1$ | OH/O$^-$ | OH | OH | $U^1$ | H | HHD | H | H | H | — | — | — |
| $P^4$ | $P^1$ | OH/O$^-$ | OH | OH | $U^1$ | H | HDD | H | H | H | — | — | — |
| $P^4$ | $P^1$ | OH/O$^-$ | OH | OH | $U^1$ | H | DDD | H | H | H | — | — | — |
| $P^4$ | $P^1$ | OH/O$^-$ | OH | OH | $U^1$ | H | HHH | D | H | H | — | — | — |
| $P^4$ | $P^1$ | OH/O$^-$ | OH | OH | $U^1$ | H | HHD | D | H | H | — | — | — |
| $P^4$ | $P^1$ | OH/O$^-$ | OH | OH | $U^1$ | H | HDD | D | H | H | — | — | — |
| $P^4$ | $P^1$ | OH/O$^-$ | OH | OH | $U^1$ | H | DDD | D | H | H | — | — | — |
| $P^4$ | $P^1$ | OH/O$^-$ | OH | OH | $U^1$ | D | HHH | H | H | H | — | — | — |
| $P^4$ | $P^1$ | OH/O$^-$ | OH | OH | $U^1$ | D | HHD | H | H | H | — | — | — |
| $P^4$ | $P^1$ | OH/O$^-$ | OH | OH | $U^1$ | D | HDD | H | H | H | — | — | — |
| $P^4$ | $P^1$ | OH/O$^-$ | OH | OH | $U^1$ | D | DDD | H | H | H | — | — | — |

TABLE 3-continued

| R$^P$ | R$^1$ | R$^2$ | R$^4$ | R$^5$ | B$^1$ | R$^3$ | (R$^6$)$_3$ | R$^7$ | B$^{1A}$ | B$^{2A}$ | B$^{3A}$ | B$^{4A}$ | B$^{5A}$ |
|---|---|---|---|---|---|---|---|---|---|---|---|---|---|
| P$^4$ | P$^1$ | OH/O$^-$ | OH | OH | U$^1$ | D | HHH | D | H | H | — | — | — |
| P$^4$ | P$^1$ | OH/O$^-$ | OH | OH | U$^1$ | D | HHD | D | H | H | — | — | — |
| P$^4$ | P$^1$ | OH/O$^-$ | OH | OH | U$^1$ | D | HDD | D | H | H | — | — | — |
| P$^4$ | P$^1$ | OH/O$^-$ | OH | OH | U$^1$ | D | DDD | D | H | H | — | — | — |
| P$^4$ | P$^1$ | OH/O$^-$ | OH | OH | U$^1$ | H | HHH | H | H | D | — | — | — |
| P$^4$ | P$^1$ | OH/O$^-$ | OH | OH | U$^1$ | H | HHD | H | H | D | — | — | — |
| P$^4$ | P$^1$ | OH/O$^-$ | OH | OH | U$^1$ | H | HDD | H | H | D | — | — | — |
| P$^4$ | P$^1$ | OH/O$^-$ | OH | OH | U$^1$ | H | DDD | H | H | D | — | — | — |
| P$^4$ | P$^1$ | OH/O$^-$ | OH | OH | U$^1$ | H | HHH | D | H | D | — | — | — |
| P$^4$ | P$^1$ | OH/O$^-$ | OH | OH | U$^1$ | H | HHD | D | H | D | — | — | — |
| P$^4$ | P$^1$ | OH/O$^-$ | OH | OH | U$^1$ | H | HDD | D | H | D | — | — | — |
| P$^4$ | P$^1$ | OH/O$^-$ | OH | OH | U$^1$ | H | DDD | D | H | D | — | — | — |
| P$^4$ | P$^1$ | OH/O$^-$ | OH | OH | U$^1$ | D | HHH | H | H | D | — | — | — |
| P$^4$ | P$^1$ | OH/O$^-$ | OH | OH | U$^1$ | D | HHD | H | H | D | — | — | — |
| P$^4$ | P$^1$ | OH/O$^-$ | OH | OH | U$^1$ | D | HDD | H | H | D | — | — | — |
| P$^4$ | P$^1$ | OH/O$^-$ | OH | OH | U$^1$ | D | DDD | H | H | D | — | — | — |
| P$^4$ | P$^1$ | OH/O$^-$ | OH | OH | U$^1$ | D | HHH | D | H | D | — | — | — |
| P$^4$ | P$^1$ | OH/O$^-$ | OH | OH | U$^1$ | D | HHD | D | H | D | — | — | — |
| P$^4$ | P$^1$ | OH/O$^-$ | OH | OH | U$^1$ | D | HDD | D | H | D | — | — | — |
| P$^4$ | P$^1$ | OH/O$^-$ | OH | OH | U$^1$ | D | DDD | D | H | D | — | — | — |
| P$^4$ | P$^1$ | OH/O$^-$ | OH | OH | U$^1$ | H | HHH | H | D | H | — | — | — |
| P$^4$ | P$^1$ | OH/O$^-$ | OH | OH | U$^1$ | H | HHD | H | D | H | — | — | — |
| P$^4$ | P$^1$ | OH/O$^-$ | OH | OH | U$^1$ | H | HDD | H | D | H | — | — | — |
| P$^4$ | P$^1$ | OH/O$^-$ | OH | OH | U$^1$ | H | DDD | H | D | H | — | — | — |
| P$^4$ | P$^1$ | OH/O$^-$ | OH | OH | U$^1$ | H | HHH | D | D | H | — | — | — |
| P$^4$ | P$^1$ | OH/O$^-$ | OH | OH | U$^1$ | H | HHD | D | D | H | — | — | — |
| P$^4$ | P$^1$ | OH/O$^-$ | OH | OH | U$^1$ | H | HDD | D | D | H | — | — | — |
| P$^4$ | P$^1$ | OH/O$^-$ | OH | OH | U$^1$ | H | DDD | D | D | H | — | — | — |
| P$^4$ | P$^1$ | OH/O$^-$ | OH | OH | U$^1$ | D | HHH | H | D | H | — | — | — |
| P$^4$ | P$^1$ | OH/O$^-$ | OH | OH | U$^1$ | D | HHD | H | D | H | — | — | — |
| P$^4$ | P$^1$ | OH/O$^-$ | OH | OH | U$^1$ | D | HDD | H | D | H | — | — | — |
| P$^4$ | P$^1$ | OH/O$^-$ | OH | OH | U$^1$ | D | DDD | H | D | H | — | — | — |
| P$^4$ | P$^1$ | OH/O$^-$ | OH | OH | U$^1$ | D | HHH | D | D | H | — | — | — |
| P$^4$ | P$^1$ | OH/O$^-$ | OH | OH | U$^1$ | D | HHD | D | D | H | — | — | — |
| P$^4$ | P$^1$ | OH/O$^-$ | OH | OH | U$^1$ | D | HDD | D | D | H | — | — | — |
| P$^4$ | P$^1$ | OH/O$^-$ | OH | OH | U$^1$ | D | DDD | D | D | H | — | — | — |
| P$^4$ | P$^1$ | OH/O$^-$ | OH | OH | U$^1$ | H | HHH | H | D | D | — | — | — |
| P$^4$ | P$^1$ | OH/O$^-$ | OH | OH | U$^1$ | H | HHD | H | D | D | — | — | — |
| P$^4$ | P$^1$ | OH/O$^-$ | OH | OH | U$^1$ | H | HDD | H | D | D | — | — | — |
| P$^4$ | P$^1$ | OH/O$^-$ | OH | OH | U$^1$ | H | DDD | H | D | D | — | — | — |
| P$^4$ | P$^1$ | OH/O$^-$ | OH | OH | U$^1$ | H | HHH | D | D | D | — | — | — |
| P$^4$ | P$^1$ | OH/O$^-$ | OH | OH | U$^1$ | H | HHD | D | D | D | — | — | — |
| P$^4$ | P$^1$ | OH/O$^-$ | OH | OH | U$^1$ | H | HDD | D | D | D | — | — | — |
| P$^4$ | P$^1$ | OH/O$^-$ | OH | OH | U$^1$ | H | DDD | D | D | D | — | — | — |
| P$^4$ | P$^1$ | OH/O$^-$ | OH | OH | U$^1$ | D | HHH | H | D | D | — | — | — |
| P$^4$ | P$^1$ | OH/O$^-$ | OH | OH | U$^1$ | D | HHD | H | D | D | — | — | — |
| P$^4$ | P$^1$ | OH/O$^-$ | OH | OH | U$^1$ | D | HDD | H | D | D | — | — | — |
| P$^4$ | P$^1$ | OH/O$^-$ | OH | OH | U$^1$ | D | DDD | H | D | D | — | — | — |
| P$^4$ | P$^1$ | OH/O$^-$ | OH | OH | U$^1$ | D | HHH | D | D | D | — | — | — |
| P$^4$ | P$^1$ | OH/O$^-$ | OH | OH | U$^1$ | D | HHD | D | D | D | — | — | — |
| P$^4$ | P$^1$ | OH/O$^-$ | OH | OH | U$^1$ | D | HDD | D | D | D | — | — | — |
| P$^4$ | P$^1$ | OH/O$^-$ | OH | OH | U$^1$ | D | DDD | D | D | D | — | — | — |
| P$^4$ | P$^1$ | OH/O$^-$ | OH | F | U$^1$ | H | HHH | H | H | H | — | — | — |
| P$^4$ | P$^1$ | OH/O$^-$ | OH | F | U$^1$ | H | HHD | H | H | H | — | — | — |
| P$^4$ | P$^1$ | OH/O$^-$ | OH | F | U$^1$ | H | HDD | H | H | H | — | — | — |
| P$^4$ | P$^1$ | OH/O$^-$ | OH | F | U$^1$ | H | DDD | H | H | H | — | — | — |
| P$^4$ | P$^1$ | OH/O$^-$ | OH | F | U$^1$ | H | HHH | D | H | H | — | — | — |
| P$^4$ | P$^1$ | OH/O$^-$ | OH | F | U$^1$ | H | HDD | D | H | H | — | — | — |
| P$^4$ | P$^1$ | OH/O$^-$ | OH | F | U$^1$ | H | DDD | D | H | H | — | — | — |
| P$^4$ | P$^1$ | OH/O$^-$ | OH | F | U$^1$ | D | HHH | H | H | H | — | — | — |
| P$^4$ | P$^1$ | OH/O$^-$ | OH | F | U$^1$ | D | HHD | H | H | H | — | — | — |
| P$^4$ | P$^1$ | OH/O$^-$ | OH | F | U$^1$ | D | HDD | H | H | H | — | — | — |
| P$^4$ | P$^1$ | OH/O$^-$ | OH | F | U$^1$ | D | DDD | H | H | H | — | — | — |
| P$^4$ | P$^1$ | OH/O$^-$ | OH | F | U$^1$ | D | HHH | D | H | H | — | — | — |
| P$^4$ | P$^1$ | OH/O$^-$ | OH | F | U$^1$ | D | HHD | D | H | H | — | — | — |
| P$^4$ | P$^1$ | OH/O$^-$ | OH | F | U$^1$ | D | HDD | D | H | H | — | — | — |
| P$^4$ | P$^1$ | OH/O$^-$ | OH | F | U$^1$ | D | DDD | D | H | H | — | — | — |
| P$^4$ | P$^1$ | OH/O$^-$ | OH | F | U$^1$ | H | HHH | H | H | D | — | — | — |
| P$^4$ | P$^1$ | OH/O$^-$ | OH | F | U$^1$ | H | HHD | H | H | D | — | — | — |
| P$^4$ | P$^1$ | OH/O$^-$ | OH | F | U$^1$ | H | HDD | H | H | D | — | — | — |
| P$^4$ | P$^1$ | OH/O$^-$ | OH | F | U$^1$ | H | DDD | H | H | D | — | — | — |
| P$^4$ | P$^1$ | OH/O$^-$ | OH | F | U$^1$ | H | HHH | D | H | D | — | — | — |
| P$^4$ | P$^1$ | OH/O$^-$ | OH | F | U$^1$ | H | HDD | D | H | D | — | — | — |
| P$^4$ | P$^1$ | OH/O$^-$ | OH | F | U$^1$ | H | DDD | D | H | D | — | — | — |
| P$^4$ | P$^1$ | OH/O$^-$ | OH | F | U$^1$ | D | HHH | H | H | D | — | — | — |
| P$^4$ | P$^1$ | OH/O$^-$ | OH | F | U$^1$ | D | HHD | H | H | D | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^4$ | $P^1$ | OH/O$^-$ | OH | F | $U^1$ | D | HDD | H | H | D | — | — | — |
| $P^4$ | $P^1$ | OH/O$^-$ | OH | F | $U^1$ | D | DDD | H | H | D | — | — | — |
| $P^4$ | $P^1$ | OH/O$^-$ | OH | F | $U^1$ | D | HHH | D | H | D | — | — | — |
| $P^4$ | $P^1$ | OH/O$^-$ | OH | F | $U^1$ | D | HHD | D | H | D | — | — | — |
| $P^4$ | $P^1$ | OH/O$^-$ | OH | F | $U^1$ | D | HDD | D | H | D | — | — | — |
| $P^4$ | $P^1$ | OH/O$^-$ | OH | F | $U^1$ | D | DDD | D | H | D | — | — | — |
| $P^4$ | $P^1$ | OH/O$^-$ | OH | F | $U^1$ | H | HHH | H | D | H | — | — | — |
| $P^4$ | $P^1$ | OH/O$^-$ | OH | F | $U^1$ | H | HHD | H | D | H | — | — | — |
| $P^4$ | $P^1$ | OH/O$^-$ | OH | F | $U^1$ | H | HDD | H | D | H | — | — | — |
| $P^4$ | $P^1$ | OH/O$^-$ | OH | F | $U^1$ | H | DDD | H | D | H | — | — | — |
| $P^4$ | $P^1$ | OH/O$^-$ | OH | F | $U^1$ | H | HHD | D | D | H | — | — | — |
| $P^4$ | $P^1$ | OH/O$^-$ | OH | F | $U^1$ | H | HDD | D | D | H | — | — | — |
| $P^4$ | $P^1$ | OH/O$^-$ | OH | F | $U^1$ | H | DDD | D | D | H | — | — | — |
| $P^4$ | $P^1$ | OH/O$^-$ | OH | F | $U^1$ | D | HHH | H | D | H | — | — | — |
| $P^4$ | $P^1$ | OH/O$^-$ | OH | F | $U^1$ | D | HHD | H | D | H | — | — | — |
| $P^4$ | $P^1$ | OH/O$^-$ | OH | F | $U^1$ | D | HDD | H | D | H | — | — | — |
| $P^4$ | $P^1$ | OH/O$^-$ | OH | F | $U^1$ | D | DDD | H | D | H | — | — | — |
| $P^4$ | $P^1$ | OH/O$^-$ | OH | F | $U^1$ | D | HHH | D | D | H | — | — | — |
| $P^4$ | $P^1$ | OH/O$^-$ | OH | F | $U^1$ | D | HHD | D | D | H | — | — | — |
| $P^4$ | $P^1$ | OH/O$^-$ | OH | F | $U^1$ | D | HDD | D | D | H | — | — | — |
| $P^4$ | $P^1$ | OH/O$^-$ | OH | F | $U^1$ | D | DDD | D | D | H | — | — | — |
| $P^4$ | $P^1$ | OH/O$^-$ | OH | F | $U^1$ | H | HHH | H | H | D | — | — | — |
| $P^4$ | $P^1$ | OH/O$^-$ | OH | F | $U^1$ | H | HHD | H | H | D | — | — | — |
| $P^4$ | $P^1$ | OH/O$^-$ | OH | F | $U^1$ | H | HDD | H | H | D | — | — | — |
| $P^4$ | $P^1$ | OH/O$^-$ | OH | F | $U^1$ | H | DDD | H | H | D | — | — | — |
| $P^4$ | $P^1$ | OH/O$^-$ | OH | F | $U^1$ | H | HHH | D | H | D | — | — | — |
| $P^4$ | $P^1$ | OH/O$^-$ | OH | F | $U^1$ | H | HHD | D | H | D | — | — | — |
| $P^4$ | $P^1$ | OH/O$^-$ | OH | F | $U^1$ | H | HDD | D | H | D | — | — | — |
| $P^4$ | $P^1$ | OH/O$^-$ | OH | F | $U^1$ | H | DDD | D | H | D | — | — | — |
| $P^4$ | $P^1$ | OH/O$^-$ | OH | F | $U^1$ | D | HHH | H | H | D | — | — | — |
| $P^4$ | $P^1$ | OH/O$^-$ | OH | F | $U^1$ | D | HHD | H | H | D | — | — | — |
| $P^4$ | $P^1$ | OH/O$^-$ | OH | F | $U^1$ | D | HDD | H | H | D | — | — | — |
| $P^4$ | $P^1$ | OH/O$^-$ | OH | F | $U^1$ | D | DDD | H | H | D | — | — | — |
| $P^4$ | $P^1$ | OH/O$^-$ | OH | F | $U^1$ | D | HHH | D | H | D | — | — | — |
| $P^4$ | $P^1$ | OH/O$^-$ | OH | F | $U^1$ | D | HHD | D | H | D | — | — | — |
| $P^4$ | $P^1$ | OH/O$^-$ | OH | F | $U^1$ | D | HDD | D | H | D | — | — | — |
| $P^4$ | $P^1$ | OH/O$^-$ | OH | F | $U^1$ | D | DDD | D | H | D | — | — | — |
| $P^4$ | $P^1$ | OH/O$^-$ | F | OH | $U^1$ | H | HHH | H | H | H | — | — | — |
| $P^4$ | $P^1$ | OH/O$^-$ | F | OH | $U^1$ | H | HHD | H | H | H | — | — | — |
| $P^4$ | $P^1$ | OH/O$^-$ | F | OH | $U^1$ | H | HDD | H | H | H | — | — | — |
| $P^4$ | $P^1$ | OH/O$^-$ | F | OH | $U^1$ | H | DDD | H | H | H | — | — | — |
| $P^4$ | $P^1$ | OH/O$^-$ | F | OH | $U^1$ | H | HHH | D | H | H | — | — | — |
| $P^4$ | $P^1$ | OH/O$^-$ | F | OH | $U^1$ | H | HHD | D | H | H | — | — | — |
| $P^4$ | $P^1$ | OH/O$^-$ | F | OH | $U^1$ | H | HDD | D | H | H | — | — | — |
| $P^4$ | $P^1$ | OH/O$^-$ | F | OH | $U^1$ | H | DDD | D | H | H | — | — | — |
| $P^4$ | $P^1$ | OH/O$^-$ | F | OH | $U^1$ | D | HHH | H | H | H | — | — | — |
| $P^4$ | $P^1$ | OH/O$^-$ | F | OH | $U^1$ | D | HDD | H | H | H | — | — | — |
| $P^4$ | $P^1$ | OH/O$^-$ | F | OH | $U^1$ | D | DDD | H | H | H | — | — | — |
| $P^4$ | $P^1$ | OH/O$^-$ | F | OH | $U^1$ | D | HHD | D | H | H | — | — | — |
| $P^4$ | $P^1$ | OH/O$^-$ | F | OH | $U^1$ | D | HDD | D | H | H | — | — | — |
| $P^4$ | $P^1$ | OH/O$^-$ | F | OH | $U^1$ | D | DDD | D | H | H | — | — | — |
| $P^4$ | $P^1$ | OH/O$^-$ | F | OH | $U^1$ | H | HHH | H | H | D | — | — | — |
| $P^4$ | $P^1$ | OH/O$^-$ | F | OH | $U^1$ | H | HHD | H | H | D | — | — | — |
| $P^4$ | $P^1$ | OH/O$^-$ | F | OH | $U^1$ | H | HDD | H | H | D | — | — | — |
| $P^4$ | $P^1$ | OH/O$^-$ | F | OH | $U^1$ | H | DDD | H | H | D | — | — | — |
| $P^4$ | $P^1$ | OH/O$^-$ | F | OH | $U^1$ | H | HHH | D | H | D | — | — | — |
| $P^4$ | $P^1$ | OH/O$^-$ | F | OH | $U^1$ | H | HHD | D | H | D | — | — | — |
| $P^4$ | $P^1$ | OH/O$^-$ | F | OH | $U^1$ | H | HDD | D | H | D | — | — | — |
| $P^4$ | $P^1$ | OH/O$^-$ | F | OH | $U^1$ | H | DDD | D | H | D | — | — | — |
| $P^4$ | $P^1$ | OH/O$^-$ | F | OH | $U^1$ | D | HHH | H | H | D | — | — | — |
| $P^4$ | $P^1$ | OH/O$^-$ | F | OH | $U^1$ | D | HHD | H | H | D | — | — | — |
| $P^4$ | $P^1$ | OH/O$^-$ | F | OH | $U^1$ | D | HDD | H | H | D | — | — | — |
| $P^4$ | $P^1$ | OH/O$^-$ | F | OH | $U^1$ | D | DDD | H | H | D | — | — | — |
| $P^4$ | $P^1$ | OH/O$^-$ | F | OH | $U^1$ | D | HHH | D | H | D | — | — | — |
| $P^4$ | $P^1$ | OH/O$^-$ | F | OH | $U^1$ | D | HHD | D | H | D | — | — | — |
| $P^4$ | $P^1$ | OH/O$^-$ | F | OH | $U^1$ | D | HDD | D | H | D | — | — | — |
| $P^4$ | $P^1$ | OH/O$^-$ | F | OH | $U^1$ | D | DDD | D | H | D | — | — | — |
| $P^4$ | $P^1$ | OH/O$^-$ | F | OH | $U^1$ | H | HHH | H | D | H | — | — | — |
| $P^4$ | $P^1$ | OH/O$^-$ | F | OH | $U^1$ | H | HDD | H | D | H | — | — | — |
| $P^4$ | $P^1$ | OH/O$^-$ | F | OH | $U^1$ | H | DDD | H | D | H | — | — | — |
| $P^4$ | $P^1$ | OH/O$^-$ | F | OH | $U^1$ | H | HHH | D | D | H | — | — | — |
| $P^4$ | $P^1$ | OH/O$^-$ | F | OH | $U^1$ | H | HHD | D | D | H | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | $P^1$ | OH/O⁻ | F | OH | $U^1$ | H | HDD | D | D | H | — | — | — |
| $P^4$ | $P^1$ | OH/O⁻ | F | OH | $U^1$ | H | DDD | D | D | H | — | — | — |
| $P^4$ | $P^1$ | OH/O⁻ | F | OH | $U^1$ | D | HHH | H | D | H | — | — | — |
| $P^4$ | $P^1$ | OH/O⁻ | F | OH | $U^1$ | D | HHD | H | D | H | — | — | — |
| $P^4$ | $P^1$ | OH/O⁻ | F | OH | $U^1$ | D | HDD | H | D | H | — | — | — |
| $P^4$ | $P^1$ | OH/O⁻ | F | OH | $U^1$ | D | DDD | H | D | H | — | — | — |
| $P^4$ | $P^1$ | OH/O⁻ | F | OH | $U^1$ | D | HHH | D | D | H | — | — | — |
| $P^4$ | $P^1$ | OH/O⁻ | F | OH | $U^1$ | D | HHD | D | D | H | — | — | — |
| $P^4$ | $P^1$ | OH/O⁻ | F | OH | $U^1$ | D | HDD | D | D | H | — | — | — |
| $P^4$ | $P^1$ | OH/O⁻ | F | OH | $U^1$ | D | DDD | D | D | H | — | — | — |
| $P^4$ | $P^1$ | OH/O⁻ | F | OH | $U^1$ | H | HHH | H | D | D | — | — | — |
| $P^4$ | $P^1$ | OH/O⁻ | F | OH | $U^1$ | H | HHD | H | D | D | — | — | — |
| $P^4$ | $P^1$ | OH/O⁻ | F | OH | $U^1$ | H | HDD | H | D | D | — | — | — |
| $P^4$ | $P^1$ | OH/O⁻ | F | OH | $U^1$ | H | DDD | H | D | D | — | — | — |
| $P^4$ | $P^1$ | OH/O⁻ | F | OH | $U^1$ | H | HHH | D | D | D | — | — | — |
| $P^4$ | $P^1$ | OH/O⁻ | F | OH | $U^1$ | H | HHD | D | D | D | — | — | — |
| $P^4$ | $P^1$ | OH/O⁻ | F | OH | $U^1$ | H | HDD | D | D | D | — | — | — |
| $P^4$ | $P^1$ | OH/O⁻ | F | OH | $U^1$ | H | DDD | D | D | D | — | — | — |
| $P^4$ | $P^1$ | OH/O⁻ | F | OH | $U^1$ | D | HHH | H | D | D | — | — | — |
| $P^4$ | $P^1$ | OH/O⁻ | F | OH | $U^1$ | D | HHD | H | D | D | — | — | — |
| $P^4$ | $P^1$ | OH/O⁻ | F | OH | $U^1$ | D | HDD | H | D | D | — | — | — |
| $P^4$ | $P^1$ | OH/O⁻ | F | OH | $U^1$ | D | DDD | H | D | D | — | — | — |
| $P^4$ | $P^1$ | OH/O⁻ | F | OH | $U^1$ | D | HHH | D | D | D | — | — | — |
| $P^4$ | $P^1$ | OH/O⁻ | F | OH | $U^1$ | D | HHD | D | D | D | — | — | — |
| $P^4$ | $P^1$ | OH/O⁻ | F | OH | $U^1$ | D | HDD | D | D | D | — | — | — |
| $P^4$ | $P^1$ | OH/O⁻ | F | OH | $U^1$ | D | DDD | D | D | D | — | — | — |
| $P^4$ | $P^1$ | OH/O⁻ | F | F | $U^1$ | H | HHH | H | H | H | — | — | — |
| $P^4$ | $P^1$ | OH/O⁻ | F | F | $U^1$ | H | HHD | H | H | H | — | — | — |
| $P^4$ | $P^1$ | OH/O⁻ | F | F | $U^1$ | H | HDD | H | H | H | — | — | — |
| $P^4$ | $P^1$ | OH/O⁻ | F | F | $U^1$ | H | DDD | H | H | H | — | — | — |
| $P^4$ | $P^1$ | OH/O⁻ | F | F | $U^1$ | H | HHH | D | H | H | — | — | — |
| $P^4$ | $P^1$ | OH/O⁻ | F | F | $U^1$ | H | HHD | D | H | H | — | — | — |
| $P^4$ | $P^1$ | OH/O⁻ | F | F | $U^1$ | H | HDD | D | H | H | — | — | — |
| $P^4$ | $P^1$ | OH/O⁻ | F | F | $U^1$ | H | DDD | D | H | H | — | — | — |
| $P^4$ | $P^1$ | OH/O⁻ | F | F | $U^1$ | D | HHH | H | H | H | — | — | — |
| $P^4$ | $P^1$ | OH/O⁻ | F | F | $U^1$ | D | HHD | H | H | H | — | — | — |
| $P^4$ | $P^1$ | OH/O⁻ | F | F | $U^1$ | D | HDD | H | H | H | — | — | — |
| $P^4$ | $P^1$ | OH/O⁻ | F | F | $U^1$ | D | DDD | H | H | H | — | — | — |
| $P^4$ | $P^1$ | OH/O⁻ | F | F | $U^1$ | D | HHH | D | H | H | — | — | — |
| $P^4$ | $P^1$ | OH/O⁻ | F | F | $U^1$ | D | HHD | D | H | H | — | — | — |
| $P^4$ | $P^1$ | OH/O⁻ | F | F | $U^1$ | D | HDD | D | H | H | — | — | — |
| $P^4$ | $P^1$ | OH/O⁻ | F | F | $U^1$ | D | DDD | D | H | H | — | — | — |
| $P^4$ | $P^1$ | OH/O⁻ | F | F | $U^1$ | H | HHH | H | H | D | — | — | — |
| $P^4$ | $P^1$ | OH/O⁻ | F | F | $U^1$ | H | HHD | H | H | D | — | — | — |
| $P^4$ | $P^1$ | OH/O⁻ | F | F | $U^1$ | H | HDD | H | H | D | — | — | — |
| $P^4$ | $P^1$ | OH/O⁻ | F | F | $U^1$ | H | DDD | H | H | D | — | — | — |
| $P^4$ | $P^1$ | OH/O⁻ | F | F | $U^1$ | H | HHH | D | H | D | — | — | — |
| $P^4$ | $P^1$ | OH/O⁻ | F | F | $U^1$ | H | HHD | D | H | D | — | — | — |
| $P^4$ | $P^1$ | OH/O⁻ | F | F | $U^1$ | H | HDD | D | H | D | — | — | — |
| $P^4$ | $P^1$ | OH/O⁻ | F | F | $U^1$ | H | DDD | D | H | D | — | — | — |
| $P^4$ | $P^1$ | OH/O⁻ | F | F | $U^1$ | D | HHH | H | H | D | — | — | — |
| $P^4$ | $P^1$ | OH/O⁻ | F | F | $U^1$ | D | HHD | H | H | D | — | — | — |
| $P^4$ | $P^1$ | OH/O⁻ | F | F | $U^1$ | D | HDD | H | H | D | — | — | — |
| $P^4$ | $P^1$ | OH/O⁻ | F | F | $U^1$ | D | DDD | H | H | D | — | — | — |
| $P^4$ | $P^1$ | OH/O⁻ | F | F | $U^1$ | D | HHH | D | H | D | — | — | — |
| $P^4$ | $P^1$ | OH/O⁻ | F | F | $U^1$ | D | HHD | D | H | D | — | — | — |
| $P^4$ | $P^1$ | OH/O⁻ | F | F | $U^1$ | D | HDD | D | H | D | — | — | — |
| $P^4$ | $P^1$ | OH/O⁻ | F | F | $U^1$ | D | DDD | D | H | D | — | — | — |
| $P^4$ | $P^1$ | OH/O⁻ | F | F | $U^1$ | H | HHH | H | D | H | — | — | — |
| $P^4$ | $P^1$ | OH/O⁻ | F | F | $U^1$ | H | HHD | H | D | H | — | — | — |
| $P^4$ | $P^1$ | OH/O⁻ | F | F | $U^1$ | H | HDD | H | D | H | — | — | — |
| $P^4$ | $P^1$ | OH/O⁻ | F | F | $U^1$ | H | DDD | H | D | H | — | — | — |
| $P^4$ | $P^1$ | OH/O⁻ | F | F | $U^1$ | H | HHH | D | D | H | — | — | — |
| $P^4$ | $P^1$ | OH/O⁻ | F | F | $U^1$ | H | HHD | D | D | H | — | — | — |
| $P^4$ | $P^1$ | OH/O⁻ | F | F | $U^1$ | H | HDD | D | D | H | — | — | — |
| $P^4$ | $P^1$ | OH/O⁻ | F | F | $U^1$ | H | DDD | D | D | H | — | — | — |
| $P^4$ | $P^1$ | OH/O⁻ | F | F | $U^1$ | D | HHH | H | D | H | — | — | — |
| $P^4$ | $P^1$ | OH/O⁻ | F | F | $U^1$ | D | HHD | H | D | H | — | — | — |
| $P^4$ | $P^1$ | OH/O⁻ | F | F | $U^1$ | D | HDD | H | D | H | — | — | — |
| $P^4$ | $P^1$ | OH/O⁻ | F | F | $U^1$ | D | DDD | H | D | H | — | — | — |
| $P^4$ | $P^1$ | OH/O⁻ | F | F | $U^1$ | D | HHH | D | D | H | — | — | — |
| $P^4$ | $P^1$ | OH/O⁻ | F | F | $U^1$ | D | HHD | D | D | H | — | — | — |
| $P^4$ | $P^1$ | OH/O⁻ | F | F | $U^1$ | D | HDD | D | D | H | — | — | — |
| $P^4$ | $P^1$ | OH/O⁻ | F | F | $U^1$ | D | DDD | D | D | H | — | — | — |
| $P^4$ | $P^1$ | OH/O⁻ | F | F | $U^1$ | H | HHH | H | D | D | — | — | — |
| $P^4$ | $P^1$ | OH/O⁻ | F | F | $U^1$ | H | HHD | H | D | D | — | — | — |
| $P^4$ | $P^1$ | OH/O⁻ | F | F | $U^1$ | H | HDD | H | D | D | — | — | — |
| $P^4$ | $P^1$ | OH/O⁻ | F | F | $U^1$ | H | DDD | H | D | D | — | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^A$ | $P^1$ | OH/O⁻ | F | F | $U^1$ | H | HHH | D | D | D | — | — | — |
| $P^A$ | $P^1$ | OH/O⁻ | F | F | $U^1$ | H | HHD | D | D | D | — | — | — |
| $P^A$ | $P^1$ | OH/O⁻ | F | F | $U^1$ | H | HDD | D | D | D | — | — | — |
| $P^A$ | $P^1$ | OH/O⁻ | F | F | $U^1$ | H | DDD | D | D | D | — | — | — |
| $P^A$ | $P^1$ | OH/O⁻ | F | F | $U^1$ | D | HHH | H | D | D | — | — | — |
| $P^A$ | $P^1$ | OH/O⁻ | F | F | $U^1$ | D | HHD | H | D | D | — | — | — |
| $P^A$ | $P^1$ | OH/O⁻ | F | F | $U^1$ | D | HDD | H | D | D | — | — | — |
| $P^A$ | $P^1$ | OH/O⁻ | F | F | $U^1$ | D | DDD | H | D | D | — | — | — |
| $P^A$ | $P^1$ | OH/O⁻ | F | F | $U^1$ | D | HHH | D | D | D | — | — | — |
| $P^A$ | $P^1$ | OH/O⁻ | F | F | $U^1$ | D | HHD | D | D | D | — | — | — |
| $P^A$ | $P^1$ | OH/O⁻ | F | F | $U^1$ | D | HDD | D | D | D | — | — | — |
| $P^A$ | $P^1$ | OH/O⁻ | F | F | $U^1$ | D | DDD | D | D | D | — | — | — |
| $P^A$ | Ph | N-AA | OH | OH | $G^1$ | H | HHH | H | — | — | H | — | — |
| $P^A$ | Ph | N-AA | OH | OH | $G^1$ | H | HHD | H | — | — | H | — | — |
| $P^A$ | Ph | N-AA | OH | OH | $G^1$ | H | HDD | H | — | — | H | — | — |
| $P^A$ | Ph | N-AA | OH | OH | $G^1$ | H | DDD | H | — | — | H | — | — |
| $P^A$ | Ph | N-AA | OH | OH | $G^1$ | H | HHH | D | — | — | H | — | — |
| $P^A$ | Ph | N-AA | OH | OH | $G^1$ | H | HHD | D | — | — | H | — | — |
| $P^A$ | Ph | N-AA | OH | OH | $G^1$ | H | HDD | D | — | — | H | — | — |
| $P^A$ | Ph | N-AA | OH | OH | $G^1$ | H | DDD | D | — | — | H | — | — |
| $P^A$ | Ph | N-AA | OH | OH | $G^1$ | D | HHH | H | — | — | H | — | — |
| $P^A$ | Ph | N-AA | OH | OH | $G^1$ | D | HHD | H | — | — | H | — | — |
| $P^A$ | Ph | N-AA | OH | OH | $G^1$ | D | HDD | H | — | — | H | — | — |
| $P^A$ | Ph | N-AA | OH | OH | $G^1$ | D | DDD | H | — | — | H | — | — |
| $P^A$ | Ph | N-AA | OH | OH | $G^1$ | D | HHH | D | — | — | H | — | — |
| $P^A$ | Ph | N-AA | OH | OH | $G^1$ | D | HHD | D | — | — | H | — | — |
| $P^A$ | Ph | N-AA | OH | OH | $G^1$ | D | HDD | D | — | — | H | — | — |
| $P^A$ | Ph | N-AA | OH | OH | $G^1$ | D | DDD | D | — | — | H | — | — |
| $P^A$ | Ph | N-AA | OH | OH | $G^1$ | H | HHH | H | — | — | D | — | — |
| $P^A$ | Ph | N-AA | OH | OH | $G^1$ | H | HHD | H | — | — | D | — | — |
| $P^A$ | Ph | N-AA | OH | OH | $G^1$ | H | HDD | H | — | — | D | — | — |
| $P^A$ | Ph | N-AA | OH | OH | $G^1$ | H | DDD | H | — | — | D | — | — |
| $P^A$ | Ph | N-AA | OH | OH | $G^1$ | H | HHH | D | — | — | D | — | — |
| $P^A$ | Ph | N-AA | OH | OH | $G^1$ | H | HHD | D | — | — | D | — | — |
| $P^A$ | Ph | N-AA | OH | OH | $G^1$ | H | HDD | D | — | — | D | — | — |
| $P^A$ | Ph | N-AA | OH | OH | $G^1$ | H | DDD | D | — | — | D | — | — |
| $P^A$ | Ph | N-AA | OH | OH | $G^1$ | D | HHH | H | — | — | D | — | — |
| $P^A$ | Ph | N-AA | OH | OH | $G^1$ | D | HHD | H | — | — | D | — | — |
| $P^A$ | Ph | N-AA | OH | OH | $G^1$ | D | HDD | H | — | — | D | — | — |
| $P^A$ | Ph | N-AA | OH | OH | $G^1$ | D | DDD | H | — | — | D | — | — |
| $P^A$ | Ph | N-AA | OH | OH | $G^1$ | D | HHH | D | — | — | D | — | — |
| $P^A$ | Ph | N-AA | OH | OH | $G^1$ | D | HHD | D | — | — | D | — | — |
| $P^A$ | Ph | N-AA | OH | OH | $G^1$ | D | HDD | D | — | — | D | — | — |
| $P^A$ | Ph | N-AA | OH | OH | $G^1$ | D | DDD | D | — | — | D | — | — |
| $P^A$ | Ph | N-AA | OH | F | $G^1$ | H | HHH | H | — | — | H | — | — |
| $P^A$ | Ph | N-AA | OH | F | $G^1$ | H | HHD | H | — | — | H | — | — |
| $P^A$ | Ph | N-AA | OH | F | $G^1$ | H | HDD | H | — | — | H | — | — |
| $P^A$ | Ph | N-AA | OH | F | $G^1$ | H | DDD | H | — | — | H | — | — |
| $P^A$ | Ph | N-AA | OH | F | $G^1$ | H | HHH | D | — | — | H | — | — |
| $P^A$ | Ph | N-AA | OH | F | $G^1$ | H | HHD | D | — | — | H | — | — |
| $P^A$ | Ph | N-AA | OH | F | $G^1$ | H | HDD | D | — | — | H | — | — |
| $P^A$ | Ph | N-AA | OH | F | $G^1$ | H | DDD | D | — | — | H | — | — |
| $P^A$ | Ph | N-AA | OH | F | $G^1$ | D | HHH | H | — | — | H | — | — |
| $P^A$ | Ph | N-AA | OH | F | $G^1$ | D | HHD | H | — | — | H | — | — |
| $P^A$ | Ph | N-AA | OH | F | $G^1$ | D | HDD | H | — | — | H | — | — |
| $P^A$ | Ph | N-AA | OH | F | $G^1$ | D | DDD | H | — | — | H | — | — |
| $P^A$ | Ph | N-AA | OH | F | $G^1$ | D | HHH | D | — | — | H | — | — |
| $P^A$ | Ph | N-AA | OH | F | $G^1$ | D | HHD | D | — | — | H | — | — |
| $P^A$ | Ph | N-AA | OH | F | $G^1$ | D | HDD | D | — | — | H | — | — |
| $P^A$ | Ph | N-AA | OH | F | $G^1$ | D | DDD | D | — | — | H | — | — |
| $P^A$ | Ph | N-AA | OH | F | $G^1$ | H | HHH | H | — | — | D | — | — |
| $P^A$ | Ph | N-AA | OH | F | $G^1$ | H | HHD | H | — | — | D | — | — |
| $P^A$ | Ph | N-AA | OH | F | $G^1$ | H | HDD | H | — | — | D | — | — |
| $P^A$ | Ph | N-AA | OH | F | $G^1$ | H | DDD | H | — | — | D | — | — |
| $P^A$ | Ph | N-AA | OH | F | $G^1$ | H | HHH | D | — | — | D | — | — |
| $P^A$ | Ph | N-AA | OH | F | $G^1$ | H | HHD | D | — | — | D | — | — |
| $P^A$ | Ph | N-AA | OH | F | $G^1$ | H | HDD | D | — | — | D | — | — |
| $P^A$ | Ph | N-AA | OH | F | $G^1$ | H | DDD | D | — | — | D | — | — |
| $P^A$ | Ph | N-AA | OH | F | $G^1$ | D | HHH | H | — | — | D | — | — |
| $P^A$ | Ph | N-AA | OH | F | $G^1$ | D | HHD | H | — | — | D | — | — |
| $P^A$ | Ph | N-AA | OH | F | $G^1$ | D | HDD | H | — | — | D | — | — |
| $P^A$ | Ph | N-AA | OH | F | $G^1$ | D | DDD | H | — | — | D | — | — |
| $P^A$ | Ph | N-AA | OH | F | $G^1$ | D | HHH | D | — | — | D | — | — |
| $P^A$ | Ph | N-AA | OH | F | $G^1$ | D | HHD | D | — | — | D | — | — |
| $P^A$ | Ph | N-AA | OH | F | $G^1$ | D | HDD | D | — | — | D | — | — |
| $P^A$ | Ph | N-AA | OH | F | $G^1$ | D | DDD | D | — | — | D | — | — |
| $P^A$ | Ph | N-AA | F | OH | $G^1$ | H | HHH | H | — | — | H | — | — |
| $P^A$ | Ph | N-AA | F | OH | $G^1$ | H | HHD | H | — | — | H | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | Ph | N-AA | F | OH | $G^1$ | H | HDD | H | — | — | H | — | — |
| $P^4$ | Ph | N-AA | F | OH | $G^1$ | H | DDD | H | — | — | H | — | — |
| $P^4$ | Ph | N-AA | F | OH | $G^1$ | H | HHH | D | — | — | H | — | — |
| $P^4$ | Ph | N-AA | F | OH | $G^1$ | H | HHD | D | — | — | H | — | — |
| $P^4$ | Ph | N-AA | F | OH | $G^1$ | H | HDD | D | — | — | H | — | — |
| $P^4$ | Ph | N-AA | F | OH | $G^1$ | H | DDD | D | — | — | H | — | — |
| $P^4$ | Ph | N-AA | F | OH | $G^1$ | D | HHH | H | — | — | H | — | — |
| $P^4$ | Ph | N-AA | F | OH | $G^1$ | D | HHD | H | — | — | H | — | — |
| $P^4$ | Ph | N-AA | F | OH | $G^1$ | D | HDD | H | — | — | H | — | — |
| $P^4$ | Ph | N-AA | F | OH | $G^1$ | D | DDD | H | — | — | H | — | — |
| $P^4$ | Ph | N-AA | F | OH | $G^1$ | D | HHH | D | — | — | H | — | — |
| $P^4$ | Ph | N-AA | F | OH | $G^1$ | D | HHD | D | — | — | H | — | — |
| $P^4$ | Ph | N-AA | F | OH | $G^1$ | D | HDD | D | — | — | H | — | — |
| $P^4$ | Ph | N-AA | F | OH | $G^1$ | D | DDD | D | — | — | H | — | — |
| $P^4$ | Ph | N-AA | F | OH | $G^1$ | H | HHH | H | — | — | D | — | — |
| $P^4$ | Ph | N-AA | F | OH | $G^1$ | H | HHD | H | — | — | D | — | — |
| $P^4$ | Ph | N-AA | F | OH | $G^1$ | H | HDD | H | — | — | D | — | — |
| $P^4$ | Ph | N-AA | F | OH | $G^1$ | H | DDD | H | — | — | D | — | — |
| $P^4$ | Ph | N-AA | F | OH | $G^1$ | H | HHH | D | — | — | D | — | — |
| $P^4$ | Ph | N-AA | F | OH | $G^1$ | H | HHD | D | — | — | D | — | — |
| $P^4$ | Ph | N-AA | F | OH | $G^1$ | H | HDD | D | — | — | D | — | — |
| $P^4$ | Ph | N-AA | F | OH | $G^1$ | H | DDD | D | — | — | D | — | — |
| $P^4$ | Ph | N-AA | F | OH | $G^1$ | D | HHH | H | — | — | D | — | — |
| $P^4$ | Ph | N-AA | F | OH | $G^1$ | D | HHD | H | — | — | D | — | — |
| $P^4$ | Ph | N-AA | F | OH | $G^1$ | D | HDD | H | — | — | D | — | — |
| $P^4$ | Ph | N-AA | F | OH | $G^1$ | D | DDD | H | — | — | D | — | — |
| $P^4$ | Ph | N-AA | F | OH | $G^1$ | D | HHH | D | — | — | D | — | — |
| $P^4$ | Ph | N-AA | F | OH | $G^1$ | D | HHD | D | — | — | D | — | — |
| $P^4$ | Ph | N-AA | F | OH | $G^1$ | D | HDD | D | — | — | D | — | — |
| $P^4$ | Ph | N-AA | F | OH | $G^1$ | D | DDD | D | — | — | D | — | — |
| $P^4$ | Ph | N-AA | F | F | $G^1$ | H | HHH | H | — | — | H | — | — |
| $P^4$ | Ph | N-AA | F | F | $G^1$ | H | HHD | H | — | — | H | — | — |
| $P^4$ | Ph | N-AA | F | F | $G^1$ | H | HDD | H | — | — | H | — | — |
| $P^4$ | Ph | N-AA | F | F | $G^1$ | H | DDD | H | — | — | H | — | — |
| $P^4$ | Ph | N-AA | F | F | $G^1$ | H | HHH | D | — | — | H | — | — |
| $P^4$ | Ph | N-AA | F | F | $G^1$ | H | HHD | D | — | — | H | — | — |
| $P^4$ | Ph | N-AA | F | F | $G^1$ | H | HDD | D | — | — | H | — | — |
| $P^4$ | Ph | N-AA | F | F | $G^1$ | H | DDD | D | — | — | H | — | — |
| $P^4$ | Ph | N-AA | F | F | $G^1$ | D | HHH | H | — | — | H | — | — |
| $P^4$ | Ph | N-AA | F | F | $G^1$ | D | HHD | H | — | — | H | — | — |
| $P^4$ | Ph | N-AA | F | F | $G^1$ | D | HDD | H | — | — | H | — | — |
| $P^4$ | Ph | N-AA | F | F | $G^1$ | D | DDD | H | — | — | H | — | — |
| $P^4$ | Ph | N-AA | F | F | $G^1$ | D | HHH | D | — | — | H | — | — |
| $P^4$ | Ph | N-AA | F | F | $G^1$ | D | HHD | D | — | — | H | — | — |
| $P^4$ | Ph | N-AA | F | F | $G^1$ | D | HDD | D | — | — | H | — | — |
| $P^4$ | Ph | N-AA | F | F | $G^1$ | D | DDD | D | — | — | H | — | — |
| $P^4$ | Ph | N-AA | F | F | $G^1$ | H | HHH | H | — | — | D | — | — |
| $P^4$ | Ph | N-AA | F | F | $G^1$ | H | HHD | H | — | — | D | — | — |
| $P^4$ | Ph | N-AA | F | F | $G^1$ | H | HDD | H | — | — | D | — | — |
| $P^4$ | Ph | N-AA | F | F | $G^1$ | H | DDD | H | — | — | D | — | — |
| $P^4$ | Ph | N-AA | F | F | $G^1$ | H | HHH | D | — | — | D | — | — |
| $P^4$ | Ph | N-AA | F | F | $G^1$ | H | HHD | D | — | — | D | — | — |
| $P^4$ | Ph | N-AA | F | F | $G^1$ | H | HDD | D | — | — | D | — | — |
| $P^4$ | Ph | N-AA | F | F | $G^1$ | H | DDD | D | — | — | D | — | — |
| $P^4$ | Ph | N-AA | F | F | $G^1$ | D | HHH | H | — | — | D | — | — |
| $P^4$ | Ph | N-AA | F | F | $G^1$ | D | HHD | H | — | — | D | — | — |
| $P^4$ | Ph | N-AA | F | F | $G^1$ | D | HDD | H | — | — | D | — | — |
| $P^4$ | Ph | N-AA | F | F | $G^1$ | D | DDD | H | — | — | D | — | — |
| $P^4$ | Ph | N-AA | F | F | $G^1$ | D | HHH | D | — | — | D | — | — |
| $P^4$ | Ph | N-AA | F | F | $G^1$ | D | HHD | D | — | — | D | — | — |
| $P^4$ | Ph | N-AA | F | F | $G^1$ | D | HDD | D | — | — | D | — | — |
| $P^4$ | Ph | N-AA | F | F | $G^1$ | D | DDD | D | — | — | D | — | — |
| $P^4$ | Naph | N-AA | OH | OH | $G^1$ | H | HHH | H | — | — | H | — | — |
| $P^4$ | Naph | N-AA | OH | OH | $G^1$ | H | HHD | H | — | — | H | — | — |
| $P^4$ | Naph | N-AA | OH | OH | $G^1$ | H | HDD | H | — | — | H | — | — |
| $P^4$ | Naph | N-AA | OH | OH | $G^1$ | H | DDD | H | — | — | H | — | — |
| $P^4$ | Naph | N-AA | OH | OH | $G^1$ | H | HHH | D | — | — | H | — | — |
| $P^4$ | Naph | N-AA | OH | OH | $G^1$ | H | HHD | D | — | — | H | — | — |
| $P^4$ | Naph | N-AA | OH | OH | $G^1$ | H | HDD | D | — | — | H | — | — |
| $P^4$ | Naph | N-AA | OH | OH | $G^1$ | H | DDD | D | — | — | H | — | — |
| $P^4$ | Naph | N-AA | OH | OH | $G^1$ | D | HHH | H | — | — | H | — | — |
| $P^4$ | Naph | N-AA | OH | OH | $G^1$ | D | HHD | H | — | — | H | — | — |
| $P^4$ | Naph | N-AA | OH | OH | $G^1$ | D | HDD | H | — | — | H | — | — |
| $P^4$ | Naph | N-AA | OH | OH | $G^1$ | D | DDD | H | — | — | H | — | — |
| $P^4$ | Naph | N-AA | OH | OH | $G^1$ | D | HHH | D | — | — | H | — | — |
| $P^4$ | Naph | N-AA | OH | OH | $G^1$ | D | HHD | D | — | — | H | — | — |
| $P^4$ | Naph | N-AA | OH | OH | $G^1$ | D | HDD | D | — | — | H | — | — |
| $P^4$ | Naph | N-AA | OH | OH | $G^1$ | D | DDD | D | — | — | H | — | — |

TABLE 3-continued

| R$^P$ | R$^1$ | R$^2$ | R$^4$ | R$^5$ | B$^1$ | R$^3$ | (R$^6$)$_3$ | R$^7$ | B$^{1A}$ | B$^{2A}$ | B$^{3A}$ | B$^{4A}$ | B$^{5A}$ |
|---|---|---|---|---|---|---|---|---|---|---|---|---|---|
| P$^4$ | Naph | N-AA | OH | OH | G$^1$ | H | HHH | H | — | — | D | — | — |
| P$^4$ | Naph | N-AA | OH | OH | G$^1$ | H | HHD | H | — | — | D | — | — |
| P$^4$ | Naph | N-AA | OH | OH | G$^1$ | H | HDD | H | — | — | D | — | — |
| P$^4$ | Naph | N-AA | OH | OH | G$^1$ | H | DDD | H | — | — | D | — | — |
| P$^4$ | Naph | N-AA | OH | OH | G$^1$ | H | HHH | D | — | — | D | — | — |
| P$^4$ | Naph | N-AA | OH | OH | G$^1$ | H | HHD | D | — | — | D | — | — |
| P$^4$ | Naph | N-AA | OH | OH | G$^1$ | H | HDD | D | — | — | D | — | — |
| P$^4$ | Naph | N-AA | OH | OH | G$^1$ | H | DDD | D | — | — | D | — | — |
| P$^4$ | Naph | N-AA | OH | OH | G$^1$ | D | HHH | H | — | — | D | — | — |
| P$^4$ | Naph | N-AA | OH | OH | G$^1$ | D | HHD | H | — | — | D | — | — |
| P$^4$ | Naph | N-AA | OH | OH | G$^1$ | D | HDD | H | — | — | D | — | — |
| P$^4$ | Naph | N-AA | OH | OH | G$^1$ | D | DDD | H | — | — | D | — | — |
| P$^4$ | Naph | N-AA | OH | OH | G$^1$ | D | HHH | D | — | — | D | — | — |
| P$^4$ | Naph | N-AA | OH | OH | G$^1$ | D | HHD | D | — | — | D | — | — |
| P$^4$ | Naph | N-AA | OH | OH | G$^1$ | D | HDD | D | — | — | D | — | — |
| P$^4$ | Naph | N-AA | OH | OH | G$^1$ | D | DDD | D | — | — | D | — | — |
| P$^4$ | Naph | N-AA | OH | F | G$^1$ | H | HHH | H | — | — | H | — | — |
| P$^4$ | Naph | N-AA | OH | F | G$^1$ | H | HHD | H | — | — | H | — | — |
| P$^4$ | Naph | N-AA | OH | F | G$^1$ | H | HDD | H | — | — | H | — | — |
| P$^4$ | Naph | N-AA | OH | F | G$^1$ | H | DDD | H | — | — | H | — | — |
| P$^4$ | Naph | N-AA | OH | F | G$^1$ | H | HHH | D | — | — | H | — | — |
| P$^4$ | Naph | N-AA | OH | F | G$^1$ | H | HHD | D | — | — | H | — | — |
| P$^4$ | Naph | N-AA | OH | F | G$^1$ | H | HDD | D | — | — | H | — | — |
| P$^4$ | Naph | N-AA | OH | F | G$^1$ | H | DDD | D | — | — | H | — | — |
| P$^4$ | Naph | N-AA | OH | F | G$^1$ | D | HHH | H | — | — | H | — | — |
| P$^4$ | Naph | N-AA | OH | F | G$^1$ | D | HHD | H | — | — | H | — | — |
| P$^4$ | Naph | N-AA | OH | F | G$^1$ | D | HDD | H | — | — | H | — | — |
| P$^4$ | Naph | N-AA | OH | F | G$^1$ | D | DDD | H | — | — | H | — | — |
| P$^4$ | Naph | N-AA | OH | F | G$^1$ | D | HHH | D | — | — | H | — | — |
| P$^4$ | Naph | N-AA | OH | F | G$^1$ | D | HHD | D | — | — | H | — | — |
| P$^4$ | Naph | N-AA | OH | F | G$^1$ | D | HDD | D | — | — | H | — | — |
| P$^4$ | Naph | N-AA | OH | F | G$^1$ | D | DDD | D | — | — | H | — | — |
| P$^4$ | Naph | N-AA | OH | F | G$^1$ | H | HHH | H | — | — | D | — | — |
| P$^4$ | Naph | N-AA | OH | F | G$^1$ | H | HHD | H | — | — | D | — | — |
| P$^4$ | Naph | N-AA | OH | F | G$^1$ | H | HDD | H | — | — | D | — | — |
| P$^4$ | Naph | N-AA | OH | F | G$^1$ | H | DDD | H | — | — | D | — | — |
| P$^4$ | Naph | N-AA | OH | F | G$^1$ | H | HHH | D | — | — | D | — | — |
| P$^4$ | Naph | N-AA | OH | F | G$^1$ | H | HHD | D | — | — | D | — | — |
| P$^4$ | Naph | N-AA | OH | F | G$^1$ | H | HDD | D | — | — | D | — | — |
| P$^4$ | Naph | N-AA | OH | F | G$^1$ | H | DDD | D | — | — | D | — | — |
| P$^4$ | Naph | N-AA | OH | F | G$^1$ | D | HHH | H | — | — | D | — | — |
| P$^4$ | Naph | N-AA | OH | F | G$^1$ | D | HHD | H | — | — | D | — | — |
| P$^4$ | Naph | N-AA | OH | F | G$^1$ | D | HDD | H | — | — | D | — | — |
| P$^4$ | Naph | N-AA | OH | F | G$^1$ | D | DDD | H | — | — | D | — | — |
| P$^4$ | Naph | N-AA | OH | F | G$^1$ | D | HHH | D | — | — | D | — | — |
| P$^4$ | Naph | N-AA | OH | F | G$^1$ | D | HHD | D | — | — | D | — | — |
| P$^4$ | Naph | N-AA | OH | F | G$^1$ | D | HDD | D | — | — | D | — | — |
| P$^4$ | Naph | N-AA | OH | F | G$^1$ | D | DDD | D | — | — | D | — | — |
| P$^4$ | Naph | N-AA | F | OH | G$^1$ | H | HHH | H | — | — | H | — | — |
| P$^4$ | Naph | N-AA | F | OH | G$^1$ | H | HHD | H | — | — | H | — | — |
| P$^4$ | Naph | N-AA | F | OH | G$^1$ | H | HDD | H | — | — | H | — | — |
| P$^4$ | Naph | N-AA | F | OH | G$^1$ | H | DDD | H | — | — | H | — | — |
| P$^4$ | Naph | N-AA | F | OH | G$^1$ | H | HHH | D | — | — | H | — | — |
| P$^4$ | Naph | N-AA | F | OH | G$^1$ | H | HHD | D | — | — | H | — | — |
| P$^4$ | Naph | N-AA | F | OH | G$^1$ | H | HDD | D | — | — | H | — | — |
| P$^4$ | Naph | N-AA | F | OH | G$^1$ | H | DDD | D | — | — | H | — | — |
| P$^4$ | Naph | N-AA | F | OH | G$^1$ | D | HHH | H | — | — | H | — | — |
| P$^4$ | Naph | N-AA | F | OH | G$^1$ | D | HHD | H | — | — | H | — | — |
| P$^4$ | Naph | N-AA | F | OH | G$^1$ | D | HDD | H | — | — | H | — | — |
| P$^4$ | Naph | N-AA | F | OH | G$^1$ | D | DDD | H | — | — | H | — | — |
| P$^4$ | Naph | N-AA | F | OH | G$^1$ | D | HHH | D | — | — | H | — | — |
| P$^4$ | Naph | N-AA | F | OH | G$^1$ | D | HHD | D | — | — | H | — | — |
| P$^4$ | Naph | N-AA | F | OH | G$^1$ | D | HDD | D | — | — | H | — | — |
| P$^4$ | Naph | N-AA | F | OH | G$^1$ | D | DDD | D | — | — | H | — | — |
| P$^4$ | Naph | N-AA | F | OH | G$^1$ | H | HHH | H | — | — | D | — | — |
| P$^4$ | Naph | N-AA | F | OH | G$^1$ | H | HHD | H | — | — | D | — | — |
| P$^4$ | Naph | N-AA | F | OH | G$^1$ | H | HDD | H | — | — | D | — | — |
| P$^4$ | Naph | N-AA | F | OH | G$^1$ | H | DDD | H | — | — | D | — | — |
| P$^4$ | Naph | N-AA | F | OH | G$^1$ | H | HHH | D | — | — | D | — | — |
| P$^4$ | Naph | N-AA | F | OH | G$^1$ | H | HHD | D | — | — | D | — | — |
| P$^4$ | Naph | N-AA | F | OH | G$^1$ | H | HDD | D | — | — | D | — | — |
| P$^4$ | Naph | N-AA | F | OH | G$^1$ | H | DDD | D | — | — | D | — | — |
| P$^4$ | Naph | N-AA | F | OH | G$^1$ | D | HHH | H | — | — | D | — | — |
| P$^4$ | Naph | N-AA | F | OH | G$^1$ | D | HHD | H | — | — | D | — | — |
| P$^4$ | Naph | N-AA | F | OH | G$^1$ | D | HDD | H | — | — | D | — | — |
| P$^4$ | Naph | N-AA | F | OH | G$^1$ | D | DDD | H | — | — | D | — | — |
| P$^4$ | Naph | N-AA | F | OH | G$^1$ | D | HHH | D | — | — | D | — | — |
| P$^4$ | Naph | N-AA | F | OH | G$^1$ | D | HHD | D | — | — | D | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^A$ | Naph | N-AA | F | OH | $G^1$ | D | HDD | D | — | — | D | — | — |
| $P^A$ | Naph | N-AA | F | OH | $G^1$ | D | DDD | D | — | — | D | — | — |
| $P^A$ | Naph | N-AA | F | F | $G^1$ | H | HHH | H | — | — | H | — | — |
| $P^A$ | Naph | N-AA | F | F | $G^1$ | H | HHD | H | — | — | H | — | — |
| $P^A$ | Naph | N-AA | F | F | $G^1$ | H | HDD | H | — | — | H | — | — |
| $P^A$ | Naph | N-AA | F | F | $G^1$ | H | DDD | H | — | — | H | — | — |
| $P^A$ | Naph | N-AA | F | F | $G^1$ | H | HHH | D | — | — | H | — | — |
| $P^A$ | Naph | N-AA | F | F | $G^1$ | H | HHD | D | — | — | H | — | — |
| $P^A$ | Naph | N-AA | F | F | $G^1$ | H | HDD | D | — | — | H | — | — |
| $P^A$ | Naph | N-AA | F | F | $G^1$ | H | DDD | D | — | — | H | — | — |
| $P^A$ | Naph | N-AA | F | F | $G^1$ | D | HHH | H | — | — | H | — | — |
| $P^A$ | Naph | N-AA | F | F | $G^1$ | D | HHD | H | — | — | H | — | — |
| $P^A$ | Naph | N-AA | F | F | $G^1$ | D | HDD | H | — | — | H | — | — |
| $P^A$ | Naph | N-AA | F | F | $G^1$ | D | DDD | H | — | — | H | — | — |
| $P^A$ | Naph | N-AA | F | F | $G^1$ | D | HHH | D | — | — | H | — | — |
| $P^A$ | Naph | N-AA | F | F | $G^1$ | D | HHD | D | — | — | H | — | — |
| $P^A$ | Naph | N-AA | F | F | $G^1$ | D | HDD | D | — | — | H | — | — |
| $P^A$ | Naph | N-AA | F | F | $G^1$ | D | DDD | D | — | — | H | — | — |
| $P^A$ | Naph | N-AA | F | F | $G^1$ | H | HHH | H | — | — | D | — | — |
| $P^A$ | Naph | N-AA | F | F | $G^1$ | H | HHD | H | — | — | D | — | — |
| $P^A$ | Naph | N-AA | F | F | $G^1$ | H | HDD | H | — | — | D | — | — |
| $P^A$ | Naph | N-AA | F | F | $G^1$ | H | DDD | H | — | — | D | — | — |
| $P^A$ | Naph | N-AA | F | F | $G^1$ | H | HHH | D | — | — | D | — | — |
| $P^A$ | Naph | N-AA | F | F | $G^1$ | H | HHD | D | — | — | D | — | — |
| $P^A$ | Naph | N-AA | F | F | $G^1$ | H | HDD | D | — | — | D | — | — |
| $P^A$ | Naph | N-AA | F | F | $G^1$ | H | DDD | D | — | — | D | — | — |
| $P^A$ | Naph | N-AA | F | F | $G^1$ | D | HHH | H | — | — | D | — | — |
| $P^A$ | Naph | N-AA | F | F | $G^1$ | D | HHD | H | — | — | D | — | — |
| $P^A$ | Naph | N-AA | F | F | $G^1$ | D | HDD | H | — | — | D | — | — |
| $P^A$ | Naph | N-AA | F | F | $G^1$ | D | DDD | H | — | — | D | — | — |
| $P^A$ | Naph | N-AA | F | F | $G^1$ | D | HHH | D | — | — | D | — | — |
| $P^A$ | Naph | N-AA | F | F | $G^1$ | D | HHD | D | — | — | D | — | — |
| $P^A$ | Naph | N-AA | F | F | $G^1$ | D | HDD | D | — | — | D | — | — |
| $P^A$ | Naph | N-AA | F | F | $G^1$ | D | DDD | D | — | — | D | — | — |
| $P^A$ | POC | POC | OH | OH | $G^1$ | H | HHH | H | — | — | H | — | — |
| $P^A$ | POC | POC | OH | OH | $G^1$ | H | HHD | H | — | — | H | — | — |
| $P^A$ | POC | POC | OH | OH | $G^1$ | H | HDD | H | — | — | H | — | — |
| $P^A$ | POC | POC | OH | OH | $G^1$ | H | DDD | H | — | — | H | — | — |
| $P^A$ | POC | POC | OH | OH | $G^1$ | H | HHH | D | — | — | H | — | — |
| $P^A$ | POC | POC | OH | OH | $G^1$ | H | HHD | D | — | — | H | — | — |
| $P^A$ | POC | POC | OH | OH | $G^1$ | H | HDD | D | — | — | H | — | — |
| $P^A$ | POC | POC | OH | OH | $G^1$ | H | DDD | D | — | — | H | — | — |
| $P^A$ | POC | POC | OH | OH | $G^1$ | D | HHH | H | — | — | H | — | — |
| $P^A$ | POC | POC | OH | OH | $G^1$ | D | HHD | H | — | — | H | — | — |
| $P^A$ | POC | POC | OH | OH | $G^1$ | D | HDD | H | — | — | H | — | — |
| $P^A$ | POC | POC | OH | OH | $G^1$ | D | DDD | H | — | — | H | — | — |
| $P^A$ | POC | POC | OH | OH | $G^1$ | D | HHH | D | — | — | H | — | — |
| $P^A$ | POC | POC | OH | OH | $G^1$ | D | HHD | D | — | — | H | — | — |
| $P^A$ | POC | POC | OH | OH | $G^1$ | D | HDD | D | — | — | H | — | — |
| $P^A$ | POC | POC | OH | OH | $G^1$ | D | DDD | D | — | — | H | — | — |
| $P^A$ | POC | POC | OH | OH | $G^1$ | H | HHH | H | — | — | D | — | — |
| $P^A$ | POC | POC | OH | OH | $G^1$ | H | HHD | H | — | — | D | — | — |
| $P^A$ | POC | POC | OH | OH | $G^1$ | H | HDD | H | — | — | D | — | — |
| $P^A$ | POC | POC | OH | OH | $G^1$ | H | DDD | H | — | — | D | — | — |
| $P^A$ | POC | POC | OH | OH | $G^1$ | H | HHH | D | — | — | D | — | — |
| $P^A$ | POC | POC | OH | OH | $G^1$ | H | HHD | D | — | — | D | — | — |
| $P^A$ | POC | POC | OH | OH | $G^1$ | H | HDD | D | — | — | D | — | — |
| $P^A$ | POC | POC | OH | OH | $G^1$ | H | DDD | D | — | — | D | — | — |
| $P^A$ | POC | POC | OH | OH | $G^1$ | D | HHH | H | — | — | D | — | — |
| $P^A$ | POC | POC | OH | OH | $G^1$ | D | HHD | H | — | — | D | — | — |
| $P^A$ | POC | POC | OH | OH | $G^1$ | D | HDD | H | — | — | D | — | — |
| $P^A$ | POC | POC | OH | OH | $G^1$ | D | DDD | H | — | — | D | — | — |
| $P^A$ | POC | POC | OH | OH | $G^1$ | D | HHH | D | — | — | D | — | — |
| $P^A$ | POC | POC | OH | OH | $G^1$ | D | HHD | D | — | — | D | — | — |
| $P^A$ | POC | POC | OH | OH | $G^1$ | D | HDD | D | — | — | D | — | — |
| $P^A$ | POC | POC | OH | OH | $G^1$ | D | DDD | D | — | — | D | — | — |
| $P^A$ | POC | POC | OH | F | $G^1$ | H | HHH | H | — | — | H | — | — |
| $P^A$ | POC | POC | OH | F | $G^1$ | H | HHD | H | — | — | H | — | — |
| $P^A$ | POC | POC | OH | F | $G^1$ | H | HDD | H | — | — | H | — | — |
| $P^A$ | POC | POC | OH | F | $G^1$ | H | DDD | H | — | — | H | — | — |
| $P^A$ | POC | POC | OH | F | $G^1$ | H | HHH | H | — | — | H | — | — |
| $P^A$ | POC | POC | OH | F | $G^1$ | H | HHD | H | — | — | H | — | — |
| $P^A$ | POC | POC | OH | F | $G^1$ | H | HDD | D | — | — | H | — | — |
| $P^A$ | POC | POC | OH | F | $G^1$ | H | DDD | D | — | — | H | — | — |
| $P^A$ | POC | POC | OH | F | $G^1$ | D | HHH | H | — | — | H | — | — |
| $P^A$ | POC | POC | OH | F | $G^1$ | D | HHD | H | — | — | H | — | — |
| $P^A$ | POC | POC | OH | F | $G^1$ | D | HDD | H | — | — | H | — | — |
| $P^A$ | POC | POC | OH | F | $G^1$ | D | DDD | H | — | — | H | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^A$ | POC | POC | OH | F | $G^1$ | D | HHH | D | — | — | H | — | — |
| $P^A$ | POC | POC | OH | F | $G^1$ | D | HHD | D | — | — | H | — | — |
| $P^A$ | POC | POC | OH | F | $G^1$ | D | HDD | D | — | — | H | — | — |
| $P^A$ | POC | POC | OH | F | $G^1$ | D | DDD | D | — | — | H | — | — |
| $P^A$ | POC | POC | OH | F | $G^1$ | H | HHH | H | — | — | D | — | — |
| $P^A$ | POC | POC | OH | F | $G^1$ | H | HHD | H | — | — | D | — | — |
| $P^A$ | POC | POC | OH | F | $G^1$ | H | HDD | H | — | — | D | — | — |
| $P^A$ | POC | POC | OH | F | $G^1$ | H | DDD | H | — | — | D | — | — |
| $P^A$ | POC | POC | OH | F | $G^1$ | H | HHH | D | — | — | D | — | — |
| $P^A$ | POC | POC | OH | F | $G^1$ | H | HHD | D | — | — | D | — | — |
| $P^A$ | POC | POC | OH | F | $G^1$ | H | HDD | D | — | — | D | — | — |
| $P^A$ | POC | POC | OH | F | $G^1$ | H | DDD | D | — | — | D | — | — |
| $P^A$ | POC | POC | OH | F | $G^1$ | D | HHH | H | — | — | D | — | — |
| $P^A$ | POC | POC | OH | F | $G^1$ | D | HHD | H | — | — | D | — | — |
| $P^A$ | POC | POC | OH | F | $G^1$ | D | HDD | H | — | — | D | — | — |
| $P^A$ | POC | POC | OH | F | $G^1$ | D | DDD | H | — | — | D | — | — |
| $P^A$ | POC | POC | OH | F | $G^1$ | D | HHH | D | — | — | D | — | — |
| $P^A$ | POC | POC | OH | F | $G^1$ | D | HHD | D | — | — | D | — | — |
| $P^A$ | POC | POC | OH | F | $G^1$ | D | HDD | D | — | — | D | — | — |
| $P^A$ | POC | POC | OH | F | $G^1$ | D | DDD | D | — | — | D | — | — |
| $P^A$ | POC | POC | F | OH | $G^1$ | H | HHH | H | — | — | H | — | — |
| $P^A$ | POC | POC | F | OH | $G^1$ | H | HHD | H | — | — | H | — | — |
| $P^A$ | POC | POC | F | OH | $G^1$ | H | HDD | H | — | — | H | — | — |
| $P^A$ | POC | POC | F | OH | $G^1$ | H | DDD | H | — | — | H | — | — |
| $P^A$ | POC | POC | F | OH | $G^1$ | H | HHH | D | — | — | H | — | — |
| $P^A$ | POC | POC | F | OH | $G^1$ | H | HHD | D | — | — | H | — | — |
| $P^A$ | POC | POC | F | OH | $G^1$ | H | HDD | D | — | — | H | — | — |
| $P^A$ | POC | POC | F | OH | $G^1$ | H | DDD | D | — | — | H | — | — |
| $P^A$ | POC | POC | F | OH | $G^1$ | D | HHH | H | — | — | H | — | — |
| $P^A$ | POC | POC | F | OH | $G^1$ | D | HHD | H | — | — | H | — | — |
| $P^A$ | POC | POC | F | OH | $G^1$ | D | HDD | H | — | — | H | — | — |
| $P^A$ | POC | POC | F | OH | $G^1$ | D | DDD | H | — | — | H | — | — |
| $P^A$ | POC | POC | F | OH | $G^1$ | D | HHH | D | — | — | H | — | — |
| $P^A$ | POC | POC | F | OH | $G^1$ | D | HHD | D | — | — | H | — | — |
| $P^A$ | POC | POC | F | OH | $G^1$ | D | HDD | D | — | — | H | — | — |
| $P^A$ | POC | POC | F | OH | $G^1$ | D | DDD | D | — | — | H | — | — |
| $P^A$ | POC | POC | F | OH | $G^1$ | H | HHH | H | — | — | D | — | — |
| $P^A$ | POC | POC | F | OH | $G^1$ | H | HHD | H | — | — | D | — | — |
| $P^A$ | POC | POC | F | OH | $G^1$ | H | HDD | H | — | — | D | — | — |
| $P^A$ | POC | POC | F | OH | $G^1$ | H | DDD | H | — | — | D | — | — |
| $P^A$ | POC | POC | F | OH | $G^1$ | H | HHH | D | — | — | D | — | — |
| $P^A$ | POC | POC | F | OH | $G^1$ | H | HHD | D | — | — | D | — | — |
| $P^A$ | POC | POC | F | OH | $G^1$ | H | HDD | D | — | — | D | — | — |
| $P^A$ | POC | POC | F | OH | $G^1$ | H | DDD | D | — | — | D | — | — |
| $P^A$ | POC | POC | F | OH | $G^1$ | D | HHH | H | — | — | D | — | — |
| $P^A$ | POC | POC | F | OH | $G^1$ | D | HHD | H | — | — | D | — | — |
| $P^A$ | POC | POC | F | OH | $G^1$ | D | HDD | H | — | — | D | — | — |
| $P^A$ | POC | POC | F | OH | $G^1$ | D | DDD | H | — | — | D | — | — |
| $P^A$ | POC | POC | F | OH | $G^1$ | D | HHH | D | — | — | D | — | — |
| $P^A$ | POC | POC | F | OH | $G^1$ | D | HHD | D | — | — | D | — | — |
| $P^A$ | POC | POC | F | OH | $G^1$ | D | HDD | D | — | — | D | — | — |
| $P^A$ | POC | POC | F | OH | $G^1$ | D | DDD | D | — | — | D | — | — |
| $P^A$ | POC | POC | F | F | $G^1$ | H | HHH | H | — | — | H | — | — |
| $P^A$ | POC | POC | F | F | $G^1$ | H | HHD | H | — | — | H | — | — |
| $P^A$ | POC | POC | F | F | $G^1$ | H | HDD | H | — | — | H | — | — |
| $P^A$ | POC | POC | F | F | $G^1$ | H | DDD | H | — | — | H | — | — |
| $P^A$ | POC | POC | F | F | $G^1$ | H | HHH | D | — | — | H | — | — |
| $P^A$ | POC | POC | F | F | $G^1$ | H | HHD | D | — | — | H | — | — |
| $P^A$ | POC | POC | F | F | $G^1$ | H | HDD | D | — | — | H | — | — |
| $P^A$ | POC | POC | F | F | $G^1$ | H | DDD | D | — | — | H | — | — |
| $P^A$ | POC | POC | F | F | $G^1$ | D | HHH | H | — | — | H | — | — |
| $P^A$ | POC | POC | F | F | $G^1$ | D | HHD | H | — | — | H | — | — |
| $P^A$ | POC | POC | F | F | $G^1$ | D | HDD | H | — | — | H | — | — |
| $P^A$ | POC | POC | F | F | $G^1$ | D | DDD | H | — | — | H | — | — |
| $P^A$ | POC | POC | F | F | $G^1$ | D | HHH | D | — | — | H | — | — |
| $P^A$ | POC | POC | F | F | $G^1$ | D | HHD | D | — | — | H | — | — |
| $P^A$ | POC | POC | F | F | $G^1$ | D | HDD | D | — | — | H | — | — |
| $P^A$ | POC | POC | F | F | $G^1$ | D | DDD | D | — | — | H | — | — |
| $P^A$ | POC | POC | F | F | $G^1$ | H | HHH | H | — | — | D | — | — |
| $P^A$ | POC | POC | F | F | $G^1$ | H | HHD | H | — | — | D | — | — |
| $P^A$ | POC | POC | F | F | $G^1$ | H | HDD | H | — | — | D | — | — |
| $P^A$ | POC | POC | F | F | $G^1$ | H | DDD | H | — | — | D | — | — |
| $P^A$ | POC | POC | F | F | $G^1$ | H | HHH | D | — | — | D | — | — |
| $P^A$ | POC | POC | F | F | $G^1$ | H | HHD | D | — | — | D | — | — |
| $P^A$ | POC | POC | F | F | $G^1$ | H | HDD | D | — | — | D | — | — |
| $P^A$ | POC | POC | F | F | $G^1$ | H | DDD | D | — | — | D | — | — |
| $P^A$ | POC | POC | F | F | $G^1$ | D | HHH | H | — | — | D | — | — |
| $P^A$ | POC | POC | F | F | $G^1$ | D | HHD | H | — | — | D | — | — |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^4$ | POC | POC | F | F | $G^1$ | D | HDD | H | — | — | D | — | — |
| $P^4$ | POC | POC | F | F | $G^1$ | D | DDD | H | — | — | D | — | — |
| $P^4$ | POC | POC | F | F | $G^1$ | D | HHH | D | — | — | D | — | — |
| $P^4$ | POC | POC | F | F | $G^1$ | D | HHD | D | — | — | D | — | — |
| $P^4$ | POC | POC | F | F | $G^1$ | D | HDD | D | — | — | D | — | — |
| $P^4$ | POC | POC | F | F | $G^1$ | D | DDD | D | — | — | D | — | — |
| $P^4$ | $P^1$ | OH/O$^-$ | OH | OH | $G^1$ | H | HHH | H | — | — | H | — | — |
| $P^4$ | $P^1$ | OH/O$^-$ | OH | OH | $G^1$ | H | HHD | H | — | — | H | — | — |
| $P^4$ | $P^1$ | OH/O$^-$ | OH | OH | $G^1$ | H | HDD | H | — | — | H | — | — |
| $P^4$ | $P^1$ | OH/O$^-$ | OH | OH | $G^1$ | H | DDD | H | — | — | H | — | — |
| $P^4$ | $P^1$ | OH/O$^-$ | OH | OH | $G^1$ | H | HHH | D | — | — | H | — | — |
| $P^4$ | $P^1$ | OH/O$^-$ | OH | OH | $G^1$ | H | HHD | D | — | — | H | — | — |
| $P^4$ | $P^1$ | OH/O$^-$ | OH | OH | $G^1$ | H | HDD | D | — | — | H | — | — |
| $P^4$ | $P^1$ | OH/O$^-$ | OH | OH | $G^1$ | H | DDD | D | — | — | H | — | — |
| $P^4$ | $P^1$ | OH/O$^-$ | OH | OH | $G^1$ | D | HHH | H | — | — | H | — | — |
| $P^4$ | $P^1$ | OH/O$^-$ | OH | OH | $G^1$ | D | HHD | H | — | — | H | — | — |
| $P^4$ | $P^1$ | OH/O$^-$ | OH | OH | $G^1$ | D | HDD | H | — | — | H | — | — |
| $P^4$ | $P^1$ | OH/O$^-$ | OH | OH | $G^1$ | D | DDD | H | — | — | H | — | — |
| $P^4$ | $P^1$ | OH/O$^-$ | OH | OH | $G^1$ | D | HHH | D | — | — | H | — | — |
| $P^4$ | $P^1$ | OH/O$^-$ | OH | OH | $G^1$ | D | HHD | D | — | — | H | — | — |
| $P^4$ | $P^1$ | OH/O$^-$ | OH | OH | $G^1$ | D | HDD | D | — | — | H | — | — |
| $P^4$ | $P^1$ | OH/O$^-$ | OH | OH | $G^1$ | D | DDD | D | — | — | H | — | — |
| $P^4$ | $P^1$ | OH/O$^-$ | OH | OH | $G^1$ | H | HHH | H | — | — | D | — | — |
| $P^4$ | $P^1$ | OH/O$^-$ | OH | OH | $G^1$ | H | HHD | H | — | — | D | — | — |
| $P^4$ | $P^1$ | OH/O$^-$ | OH | OH | $G^1$ | H | HDD | H | — | — | D | — | — |
| $P^4$ | $P^1$ | OH/O$^-$ | OH | OH | $G^1$ | H | DDD | H | — | — | D | — | — |
| $P^4$ | $P^1$ | OH/O$^-$ | OH | OH | $G^1$ | H | HHH | D | — | — | D | — | — |
| $P^4$ | $P^1$ | OH/O$^-$ | OH | OH | $G^1$ | H | HHD | D | — | — | D | — | — |
| $P^4$ | $P^1$ | OH/O$^-$ | OH | OH | $G^1$ | H | HDD | D | — | — | D | — | — |
| $P^4$ | $P^1$ | OH/O$^-$ | OH | OH | $G^1$ | H | DDD | D | — | — | D | — | — |
| $P^4$ | $P^1$ | OH/O$^-$ | OH | OH | $G^1$ | D | HHH | H | — | — | D | — | — |
| $P^4$ | $P^1$ | OH/O$^-$ | OH | OH | $G^1$ | D | HHD | H | — | — | D | — | — |
| $P^4$ | $P^1$ | OH/O$^-$ | OH | OH | $G^1$ | D | HDD | H | — | — | D | — | — |
| $P^4$ | $P^1$ | OH/O$^-$ | OH | OH | $G^1$ | D | DDD | H | — | — | D | — | — |
| $P^4$ | $P^1$ | OH/O$^-$ | OH | OH | $G^1$ | D | HHH | D | — | — | D | — | — |
| $P^4$ | $P^1$ | OH/O$^-$ | OH | OH | $G^1$ | D | HHD | D | — | — | D | — | — |
| $P^4$ | $P^1$ | OH/O$^-$ | OH | OH | $G^1$ | D | HDD | D | — | — | D | — | — |
| $P^4$ | $P^1$ | OH/O$^-$ | OH | OH | $G^1$ | D | DDD | D | — | — | D | — | — |
| $P^4$ | $P^1$ | OH/O$^-$ | OH | F | $G^1$ | H | HHH | H | — | — | H | — | — |
| $P^4$ | $P^1$ | OH/O$^-$ | OH | F | $G^1$ | H | HHD | H | — | — | H | — | — |
| $P^4$ | $P^1$ | OH/O$^-$ | OH | F | $G^1$ | H | HDD | H | — | — | H | — | — |
| $P^4$ | $P^1$ | OH/O$^-$ | OH | F | $G^1$ | H | DDD | H | — | — | H | — | — |
| $P^4$ | $P^1$ | OH/O$^-$ | OH | F | $G^1$ | H | HHH | D | — | — | H | — | — |
| $P^4$ | $P^1$ | OH/O$^-$ | OH | F | $G^1$ | H | HHD | D | — | — | H | — | — |
| $P^4$ | $P^1$ | OH/O$^-$ | OH | F | $G^1$ | H | HDD | D | — | — | H | — | — |
| $P^4$ | $P^1$ | OH/O$^-$ | OH | F | $G^1$ | H | DDD | D | — | — | H | — | — |
| $P^4$ | $P^1$ | OH/O$^-$ | OH | F | $G^1$ | D | HHH | H | — | — | H | — | — |
| $P^4$ | $P^1$ | OH/O$^-$ | OH | F | $G^1$ | D | HHD | H | — | — | H | — | — |
| $P^4$ | $P^1$ | OH/O$^-$ | OH | F | $G^1$ | D | HDD | H | — | — | H | — | — |
| $P^4$ | $P^1$ | OH/O$^-$ | OH | F | $G^1$ | D | DDD | H | — | — | H | — | — |
| $P^4$ | $P^1$ | OH/O$^-$ | OH | F | $G^1$ | D | HHH | D | — | — | H | — | — |
| $P^4$ | $P^1$ | OH/O$^-$ | OH | F | $G^1$ | D | HHD | D | — | — | H | — | — |
| $P^4$ | $P^1$ | OH/O$^-$ | OH | F | $G^1$ | D | HDD | D | — | — | H | — | — |
| $P^4$ | $P^1$ | OH/O$^-$ | OH | F | $G^1$ | D | DDD | D | — | — | H | — | — |
| $P^4$ | $P^1$ | OH/O$^-$ | OH | F | $G^1$ | H | HHH | H | — | — | D | — | — |
| $P^4$ | $P^1$ | OH/O$^-$ | OH | F | $G^1$ | H | HHD | H | — | — | D | — | — |
| $P^4$ | $P^1$ | OH/O$^-$ | OH | F | $G^1$ | H | HDD | H | — | — | D | — | — |
| $P^4$ | $P^1$ | OH/O$^-$ | OH | F | $G^1$ | H | DDD | H | — | — | D | — | — |
| $P^4$ | $P^1$ | OH/O$^-$ | OH | F | $G^1$ | H | HHH | D | — | — | D | — | — |
| $P^4$ | $P^1$ | OH/O$^-$ | OH | F | $G^1$ | H | HHD | D | — | — | D | — | — |
| $P^4$ | $P^1$ | OH/O$^-$ | OH | F | $G^1$ | H | HDD | D | — | — | D | — | — |
| $P^4$ | $P^1$ | OH/O$^-$ | OH | F | $G^1$ | H | DDD | D | — | — | D | — | — |
| $P^4$ | $P^1$ | OH/O$^-$ | OH | F | $G^1$ | D | HHH | H | — | — | D | — | — |
| $P^4$ | $P^1$ | OH/O$^-$ | OH | F | $G^1$ | D | HHD | H | — | — | D | — | — |
| $P^4$ | $P^1$ | OH/O$^-$ | OH | F | $G^1$ | D | HDD | H | — | — | D | — | — |
| $P^4$ | $P^1$ | OH/O$^-$ | OH | F | $G^1$ | D | DDD | H | — | — | D | — | — |
| $P^4$ | $P^1$ | OH/O$^-$ | OH | F | $G^1$ | D | HHH | D | — | — | D | — | — |
| $P^4$ | $P^1$ | OH/O$^-$ | OH | F | $G^1$ | D | HHD | D | — | — | D | — | — |
| $P^4$ | $P^1$ | OH/O$^-$ | OH | F | $G^1$ | D | HDD | D | — | — | D | — | — |
| $P^4$ | $P^1$ | OH/O$^-$ | OH | F | $G^1$ | D | DDD | D | — | — | D | — | — |
| $P^4$ | $P^1$ | OH/O$^-$ | F | OH | $G^1$ | H | HHH | H | — | — | H | — | — |
| $P^4$ | $P^1$ | OH/O$^-$ | F | OH | $G^1$ | H | HHD | H | — | — | H | — | — |
| $P^4$ | $P^1$ | OH/O$^-$ | F | OH | $G^1$ | H | HDD | H | — | — | H | — | — |
| $P^4$ | $P^1$ | OH/O$^-$ | F | OH | $G^1$ | H | DDD | H | — | — | H | — | — |
| $P^4$ | $P^1$ | OH/O$^-$ | F | OH | $G^1$ | H | HHH | D | — | — | H | — | — |
| $P^4$ | $P^1$ | OH/O$^-$ | F | OH | $G^1$ | H | HHD | D | — | — | H | — | — |
| $P^4$ | $P^1$ | OH/O$^-$ | F | OH | $G^1$ | H | HDD | D | — | — | H | — | — |
| $P^4$ | $P^1$ | OH/O$^-$ | F | OH | $G^1$ | H | DDD | D | — | — | H | — | — |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | $P^1$ | OH/O$^-$ | F | OH | $G^1$ | D | HHH | H | — | — | H | — | — |
| $P^4$ | $P^1$ | OH/O$^-$ | F | OH | $G^1$ | D | HHD | H | — | — | H | — | — |
| $P^4$ | $P^1$ | OH/O$^-$ | F | OH | $G^1$ | D | HDD | H | — | — | H | — | — |
| $P^4$ | $P^1$ | OH/O$^-$ | F | OH | $G^1$ | D | DDD | H | — | — | H | — | — |
| $P^4$ | $P^1$ | OH/O$^-$ | F | OH | $G^1$ | D | HHH | D | — | — | H | — | — |
| $P^4$ | $P^1$ | OH/O$^-$ | F | OH | $G^1$ | D | HHD | D | — | — | H | — | — |
| $P^4$ | $P^1$ | OH/O$^-$ | F | OH | $G^1$ | D | HDD | D | — | — | H | — | — |
| $P^4$ | $P^1$ | OH/O$^-$ | F | OH | $G^1$ | D | DDD | D | — | — | H | — | — |
| $P^4$ | $P^1$ | OH/O$^-$ | F | OH | $G^1$ | H | HHH | H | — | — | D | — | — |
| $P^4$ | $P^1$ | OH/O$^-$ | F | OH | $G^1$ | H | HHD | H | — | — | D | — | — |
| $P^4$ | $P^1$ | OH/O$^-$ | F | OH | $G^1$ | H | HDD | H | — | — | D | — | — |
| $P^4$ | $P^1$ | OH/O$^-$ | F | OH | $G^1$ | H | DDD | H | — | — | D | — | — |
| $P^4$ | $P^1$ | OH/O$^-$ | F | OH | $G^1$ | H | HHH | D | — | — | D | — | — |
| $P^4$ | $P^1$ | OH/O$^-$ | F | OH | $G^1$ | H | HHD | D | — | — | D | — | — |
| $P^4$ | $P^1$ | OH/O$^-$ | F | OH | $G^1$ | H | HDD | D | — | — | D | — | — |
| $P^4$ | $P^1$ | OH/O$^-$ | F | OH | $G^1$ | H | DDD | D | — | — | D | — | — |
| $P^4$ | $P^1$ | OH/O$^-$ | F | OH | $G^1$ | D | HHH | H | — | — | D | — | — |
| $P^4$ | $P^1$ | OH/O$^-$ | F | OH | $G^1$ | D | HHD | H | — | — | D | — | — |
| $P^4$ | $P^1$ | OH/O$^-$ | F | OH | $G^1$ | D | HDD | H | — | — | D | — | — |
| $P^4$ | $P^1$ | OH/O$^-$ | F | OH | $G^1$ | D | DDD | H | — | — | D | — | — |
| $P^4$ | $P^1$ | OH/O$^-$ | F | OH | $G^1$ | D | HHH | D | — | — | D | — | — |
| $P^4$ | $P^1$ | OH/O$^-$ | F | OH | $G^1$ | D | HHD | D | — | — | D | — | — |
| $P^4$ | $P^1$ | OH/O$^-$ | F | OH | $G^1$ | D | HDD | D | — | — | D | — | — |
| $P^4$ | $P^1$ | OH/O$^-$ | F | OH | $G^1$ | D | DDD | D | — | — | D | — | — |
| $P^4$ | $P^1$ | OH/O$^-$ | F | F | $G^1$ | H | HHH | H | — | — | H | — | — |
| $P^4$ | $P^1$ | OH/O$^-$ | F | F | $G^1$ | H | HHD | H | — | — | H | — | — |
| $P^4$ | $P^1$ | OH/O$^-$ | F | F | $G^1$ | H | HDD | H | — | — | H | — | — |
| $P^4$ | $P^1$ | OH/O$^-$ | F | F | $G^1$ | H | DDD | H | — | — | H | — | — |
| $P^4$ | $P^1$ | OH/O$^-$ | F | F | $G^1$ | H | HHH | D | — | — | H | — | — |
| $P^4$ | $P^1$ | OH/O$^-$ | F | F | $G^1$ | H | HHD | D | — | — | H | — | — |
| $P^4$ | $P^1$ | OH/O$^-$ | F | F | $G^1$ | H | HDD | D | — | — | H | — | — |
| $P^4$ | $P^1$ | OH/O$^-$ | F | F | $G^1$ | H | DDD | D | — | — | H | — | — |
| $P^4$ | $P^1$ | OH/O$^-$ | F | F | $G^1$ | D | HHH | H | — | — | H | — | — |
| $P^4$ | $P^1$ | OH/O$^-$ | F | F | $G^1$ | D | HHD | H | — | — | H | — | — |
| $P^4$ | $P^1$ | OH/O$^-$ | F | F | $G^1$ | D | HDD | H | — | — | H | — | — |
| $P^4$ | $P^1$ | OH/O$^-$ | F | F | $G^1$ | D | DDD | H | — | — | H | — | — |
| $P^4$ | $P^1$ | OH/O$^-$ | F | F | $G^1$ | D | HHH | D | — | — | H | — | — |
| $P^4$ | $P^1$ | OH/O$^-$ | F | F | $G^1$ | D | HHD | D | — | — | H | — | — |
| $P^4$ | $P^1$ | OH/O$^-$ | F | F | $G^1$ | D | HDD | D | — | — | H | — | — |
| $P^4$ | $P^1$ | OH/O$^-$ | F | F | $G^1$ | D | DDD | D | — | — | H | — | — |
| $P^4$ | $P^1$ | OH/O$^-$ | F | F | $G^1$ | H | HHH | H | — | — | D | — | — |
| $P^4$ | $P^1$ | OH/O$^-$ | F | F | $G^1$ | H | HHD | H | — | — | D | — | — |
| $P^4$ | $P^1$ | OH/O$^-$ | F | F | $G^1$ | H | HDD | H | — | — | D | — | — |
| $P^4$ | $P^1$ | OH/O$^-$ | F | F | $G^1$ | H | DDD | H | — | — | D | — | — |
| $P^4$ | $P^1$ | OH/O$^-$ | F | F | $G^1$ | H | HHH | D | — | — | D | — | — |
| $P^4$ | $P^1$ | OH/O$^-$ | F | F | $G^1$ | H | HHD | D | — | — | D | — | — |
| $P^4$ | $P^1$ | OH/O$^-$ | F | F | $G^1$ | H | HDD | D | — | — | D | — | — |
| $P^4$ | $P^1$ | OH/O$^-$ | F | F | $G^1$ | H | DDD | D | — | — | D | — | — |
| $P^4$ | $P^1$ | OH/O$^-$ | F | F | $G^1$ | D | HHH | H | — | — | D | — | — |
| $P^4$ | $P^1$ | OH/O$^-$ | F | F | $G^1$ | D | HHD | H | — | — | D | — | — |
| $P^4$ | $P^1$ | OH/O$^-$ | F | F | $G^1$ | D | HDD | H | — | — | D | — | — |
| $P^4$ | $P^1$ | OH/O$^-$ | F | F | $G^1$ | D | DDD | H | — | — | D | — | — |
| $P^4$ | $P^1$ | OH/O$^-$ | F | F | $G^1$ | D | HHH | D | — | — | D | — | — |
| $P^4$ | $P^1$ | OH/O$^-$ | F | F | $G^1$ | D | HHD | D | — | — | D | — | — |
| $P^4$ | $P^1$ | OH/O$^-$ | F | F | $G^1$ | D | HDD | D | — | — | D | — | — |
| $P^4$ | $P^1$ | OH/O$^-$ | F | F | $G^1$ | D | DDD | D | — | — | D | — | — |
| $P^4$ | Ph | N-AA | OH | OH | $G^2$ | H | HHH | H | — | — | — | H | OCH$_2$CH$_3$ |
| $P^4$ | Ph | N-AA | OH | OH | $G^2$ | H | HHD | H | — | — | — | H | OCH$_2$CH$_3$ |
| $P^4$ | Ph | N-AA | OH | OH | $G^2$ | H | HDD | H | — | — | — | H | OCH$_2$CH$_3$ |
| $P^4$ | Ph | N-AA | OH | OH | $G^2$ | H | DDD | H | — | — | — | H | OCH$_2$CH$_3$ |
| $P^4$ | Ph | N-AA | OH | OH | $G^2$ | H | HHH | D | — | — | — | H | OCH$_2$CH$_3$ |
| $P^4$ | Ph | N-AA | OH | OH | $G^2$ | H | HHD | D | — | — | — | H | OCH$_2$CH$_3$ |
| $P^4$ | Ph | N-AA | OH | OH | $G^2$ | H | HDD | D | — | — | — | H | OCH$_2$CH$_3$ |
| $P^4$ | Ph | N-AA | OH | OH | $G^2$ | H | DDD | D | — | — | — | H | OCH$_2$CH$_3$ |
| $P^4$ | Ph | N-AA | OH | OH | $G^2$ | D | HHH | H | — | — | — | H | OCH$_2$CH$_3$ |
| $P^4$ | Ph | N-AA | OH | OH | $G^2$ | D | HHD | H | — | — | — | H | OCH$_2$CH$_3$ |
| $P^4$ | Ph | N-AA | OH | OH | $G^2$ | D | HDD | H | — | — | — | H | OCH$_2$CH$_3$ |
| $P^4$ | Ph | N-AA | OH | OH | $G^2$ | D | DDD | H | — | — | — | H | OCH$_2$CH$_3$ |
| $P^4$ | Ph | N-AA | OH | OH | $G^2$ | D | HHH | D | — | — | — | H | OCH$_2$CH$_3$ |
| $P^4$ | Ph | N-AA | OH | OH | $G^2$ | D | HHD | D | — | — | — | H | OCH$_2$CH$_3$ |
| $P^4$ | Ph | N-AA | OH | OH | $G^2$ | D | HDD | D | — | — | — | H | OCH$_2$CH$_3$ |
| $P^4$ | Ph | N-AA | OH | OH | $G^2$ | D | DDD | D | — | — | — | H | OCH$_2$CH$_3$ |
| $P^4$ | Ph | N-AA | OH | OH | $G^2$ | H | HHH | H | — | — | — | H | NH$_2$ |
| $P^4$ | Ph | N-AA | OH | OH | $G^2$ | H | HHD | H | — | — | — | H | NH$_2$ |
| $P^4$ | Ph | N-AA | OH | OH | $G^2$ | H | HDD | H | — | — | — | H | NH$_2$ |
| $P^4$ | Ph | N-AA | OH | OH | $G^2$ | H | DDD | H | — | — | — | H | NH$_2$ |
| $P^4$ | Ph | N-AA | OH | OH | $G^2$ | H | HHH | D | — | — | — | H | NH$_2$ |
| $P^4$ | Ph | N-AA | OH | OH | $G^2$ | H | HHD | D | — | — | — | H | NH$_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,4}$ | $B^{2,4}$ | $B^{3,4}$ | $B^{4,4}$ | $B^{5,4}$ |
|---|---|---|---|---|---|---|---|---|---|---|---|---|---|
| $P^4$ | Ph | N-AA | OH | OH | $G^2$ | H | HDD | D | — | — | — | H | $NH_2$ |
| $P^4$ | Ph | N-AA | OH | OH | $G^2$ | H | DDD | D | — | — | — | H | $NH_2$ |
| $P^4$ | Ph | N-AA | OH | OH | $G^2$ | D | HHH | H | — | — | — | H | $NH_2$ |
| $P^4$ | Ph | N-AA | OH | OH | $G^2$ | D | HHD | H | — | — | — | H | $NH_2$ |
| $P^4$ | Ph | N-AA | OH | OH | $G^2$ | D | HDD | H | — | — | — | H | $NH_2$ |
| $P^4$ | Ph | N-AA | OH | OH | $G^2$ | D | DDD | H | — | — | — | H | $NH_2$ |
| $P^4$ | Ph | N-AA | OH | OH | $G^2$ | D | HHH | D | — | — | — | H | $NH_2$ |
| $P^4$ | Ph | N-AA | OH | OH | $G^2$ | D | HHD | D | — | — | — | H | $NH_2$ |
| $P^4$ | Ph | N-AA | OH | OH | $G^2$ | D | HDD | D | — | — | — | H | $NH_2$ |
| $P^4$ | Ph | N-AA | OH | OH | $G^2$ | D | DDD | D | — | — | — | H | $NH_2$ |
| $P^4$ | Ph | N-AA | OH | OH | $G^2$ | H | HHH | H | — | — | — | D | $OCH_2CH_3$ |
| $P^4$ | Ph | N-AA | OH | OH | $G^2$ | H | HHD | H | — | — | — | D | $OCH_2CH_3$ |
| $P^4$ | Ph | N-AA | OH | OH | $G^2$ | H | HDD | H | — | — | — | D | $OCH_2CH_3$ |
| $P^4$ | Ph | N-AA | OH | OH | $G^2$ | H | DDD | H | — | — | — | D | $OCH_2CH_3$ |
| $P^4$ | Ph | N-AA | OH | OH | $G^2$ | H | HHH | D | — | — | — | D | $OCH_2CH_3$ |
| $P^4$ | Ph | N-AA | OH | OH | $G^2$ | H | HHD | D | — | — | — | D | $OCH_2CH_3$ |
| $P^4$ | Ph | N-AA | OH | OH | $G^2$ | H | HDD | D | — | — | — | D | $OCH_2CH_3$ |
| $P^4$ | Ph | N-AA | OH | OH | $G^2$ | H | DDD | D | — | — | — | D | $OCH_2CH_3$ |
| $P^4$ | Ph | N-AA | OH | OH | $G^2$ | D | HHH | H | — | — | — | D | $OCH_2CH_3$ |
| $P^4$ | Ph | N-AA | OH | OH | $G^2$ | D | HHD | H | — | — | — | D | $OCH_2CH_3$ |
| $P^4$ | Ph | N-AA | OH | OH | $G^2$ | D | HDD | H | — | — | — | D | $OCH_2CH_3$ |
| $P^4$ | Ph | N-AA | OH | OH | $G^2$ | D | DDD | H | — | — | — | D | $OCH_2CH_3$ |
| $P^4$ | Ph | N-AA | OH | OH | $G^2$ | D | HHH | D | — | — | — | D | $OCH_2CH_3$ |
| $P^4$ | Ph | N-AA | OH | OH | $G^2$ | D | HHD | D | — | — | — | D | $OCH_2CH_3$ |
| $P^4$ | Ph | N-AA | OH | OH | $G^2$ | D | HDD | D | — | — | — | D | $OCH_2CH_3$ |
| $P^4$ | Ph | N-AA | OH | OH | $G^2$ | D | DDD | D | — | — | — | D | $OCH_2CH_3$ |
| $P^4$ | Ph | N-AA | OH | OH | $G^2$ | H | HHH | H | — | — | — | D | $NH_2$ |
| $P^4$ | Ph | N-AA | OH | OH | $G^2$ | H | HHD | H | — | — | — | D | $NH_2$ |
| $P^4$ | Ph | N-AA | OH | OH | $G^2$ | H | HDD | H | — | — | — | D | $NH_2$ |
| $P^4$ | Ph | N-AA | OH | OH | $G^2$ | H | DDD | H | — | — | — | D | $NH_2$ |
| $P^4$ | Ph | N-AA | OH | OH | $G^2$ | H | HHH | D | — | — | — | D | $NH_2$ |
| $P^4$ | Ph | N-AA | OH | OH | $G^2$ | H | HHD | D | — | — | — | D | $NH_2$ |
| $P^4$ | Ph | N-AA | OH | OH | $G^2$ | H | HDD | D | — | — | — | D | $NH_2$ |
| $P^4$ | Ph | N-AA | OH | OH | $G^2$ | H | DDD | D | — | — | — | D | $NH_2$ |
| $P^4$ | Ph | N-AA | OH | OH | $G^2$ | D | HHH | H | — | — | — | D | $NH_2$ |
| $P^4$ | Ph | N-AA | OH | OH | $G^2$ | D | HHD | H | — | — | — | D | $NH_2$ |
| $P^4$ | Ph | N-AA | OH | OH | $G^2$ | D | HDD | H | — | — | — | D | $NH_2$ |
| $P^4$ | Ph | N-AA | OH | OH | $G^2$ | D | DDD | H | — | — | — | D | $NH_2$ |
| $P^4$ | Ph | N-AA | OH | OH | $G^2$ | D | HHH | D | — | — | — | D | $NH_2$ |
| $P^4$ | Ph | N-AA | OH | OH | $G^2$ | D | HHD | D | — | — | — | D | $NH_2$ |
| $P^4$ | Ph | N-AA | OH | OH | $G^2$ | D | HDD | D | — | — | — | D | $NH_2$ |
| $P^4$ | Ph | N-AA | OH | OH | $G^2$ | D | DDD | D | — | — | — | D | $NH_2$ |
| $P^4$ | Ph | N-AA | OH | F | $G^2$ | H | HHH | H | — | — | — | H | $OCH_2CH_3$ |
| $P^4$ | Ph | N-AA | OH | F | $G^2$ | H | HHD | H | — | — | — | H | $OCH_2CH_3$ |
| $P^4$ | Ph | N-AA | OH | F | $G^2$ | H | HDD | H | — | — | — | H | $OCH_2CH_3$ |
| $P^4$ | Ph | N-AA | OH | F | $G^2$ | H | DDD | H | — | — | — | H | $OCH_2CH_3$ |
| $P^4$ | Ph | N-AA | OH | F | $G^2$ | H | HHH | D | — | — | — | H | $OCH_2CH_3$ |
| $P^4$ | Ph | N-AA | OH | F | $G^2$ | H | HHD | D | — | — | — | H | $OCH_2CH_3$ |
| $P^4$ | Ph | N-AA | OH | F | $G^2$ | H | HDD | D | — | — | — | H | $OCH_2CH_3$ |
| $P^4$ | Ph | N-AA | OH | F | $G^2$ | H | DDD | D | — | — | — | H | $OCH_2CH_3$ |
| $P^4$ | Ph | N-AA | OH | F | $G^2$ | D | HHH | H | — | — | — | H | $OCH_2CH_3$ |
| $P^4$ | Ph | N-AA | OH | F | $G^2$ | D | HHD | H | — | — | — | H | $OCH_2CH_3$ |
| $P^4$ | Ph | N-AA | OH | F | $G^2$ | D | HDD | H | — | — | — | H | $OCH_2CH_3$ |
| $P^4$ | Ph | N-AA | OH | F | $G^2$ | D | DDD | H | — | — | — | H | $OCH_2CH_3$ |
| $P^4$ | Ph | N-AA | OH | F | $G^2$ | D | HHH | D | — | — | — | H | $OCH_2CH_3$ |
| $P^4$ | Ph | N-AA | OH | F | $G^2$ | D | HHD | D | — | — | — | H | $OCH_2CH_3$ |
| $P^4$ | Ph | N-AA | OH | F | $G^2$ | D | HDD | D | — | — | — | H | $OCH_2CH_3$ |
| $P^4$ | Ph | N-AA | OH | F | $G^2$ | D | DDD | D | — | — | — | H | $OCH_2CH_3$ |
| $P^4$ | Ph | N-AA | OH | F | $G^2$ | H | HHH | H | — | — | — | H | $NH_2$ |
| $P^4$ | Ph | N-AA | OH | F | $G^2$ | H | HHD | H | — | — | — | H | $NH_2$ |
| $P^4$ | Ph | N-AA | OH | F | $G^2$ | H | HDD | H | — | — | — | H | $NH_2$ |
| $P^4$ | Ph | N-AA | OH | F | $G^2$ | H | DDD | H | — | — | — | H | $NH_2$ |
| $P^4$ | Ph | N-AA | OH | F | $G^2$ | H | HHH | D | — | — | — | H | $NH_2$ |
| $P^4$ | Ph | N-AA | OH | F | $G^2$ | H | HHD | D | — | — | — | H | $NH_2$ |
| $P^4$ | Ph | N-AA | OH | F | $G^2$ | H | HDD | D | — | — | — | H | $NH_2$ |
| $P^4$ | Ph | N-AA | OH | F | $G^2$ | H | DDD | D | — | — | — | H | $NH_2$ |
| $P^4$ | Ph | N-AA | OH | F | $G^2$ | D | HHH | H | — | — | — | H | $NH_2$ |
| $P^4$ | Ph | N-AA | OH | F | $G^2$ | D | HHD | H | — | — | — | H | $NH_2$ |
| $P^4$ | Ph | N-AA | OH | F | $G^2$ | D | HDD | H | — | — | — | H | $NH_2$ |
| $P^4$ | Ph | N-AA | OH | F | $G^2$ | D | DDD | H | — | — | — | H | $NH_2$ |
| $P^4$ | Ph | N-AA | OH | F | $G^2$ | D | HHH | D | — | — | — | H | $NH_2$ |
| $P^4$ | Ph | N-AA | OH | F | $G^2$ | D | HHD | D | — | — | — | H | $NH_2$ |
| $P^4$ | Ph | N-AA | OH | F | $G^2$ | D | HDD | D | — | — | — | H | $NH_2$ |
| $P^4$ | Ph | N-AA | OH | F | $G^2$ | D | DDD | D | — | — | — | H | $NH_2$ |
| $P^4$ | Ph | N-AA | OH | F | $G^2$ | H | HHH | H | — | — | — | D | $OCH_2CH_3$ |
| $P^4$ | Ph | N-AA | OH | F | $G^2$ | H | HHD | H | — | — | — | D | $OCH_2CH_3$ |
| $P^4$ | Ph | N-AA | OH | F | $G^2$ | H | HDD | H | — | — | — | D | $OCH_2CH_3$ |
| $P^4$ | Ph | N-AA | OH | F | $G^2$ | H | DDD | H | — | — | — | D | $OCH_2CH_3$ |

TABLE 3-continued

| $R^P$ | $R^1$ | $R^2$ | $R^4$ | $R^5$ | $B^1$ | $R^3$ | $(R^6)_3$ | $R^7$ | $B^{1A}$ | $B^{2A}$ | $B^{3A}$ | $B^{4A}$ | $B^{5A}$ |
|---|---|---|---|---|---|---|---|---|---|---|---|---|---|
| $P^4$ | Ph | N-AA | OH | F | $G^2$ | H | HHH | D | — | — | — | D | OCH$_2$CH$_3$ |
| $P^4$ | Ph | N-AA | OH | F | $G^2$ | H | HHD | D | — | — | — | D | OCH$_2$CH$_3$ |
| $P^4$ | Ph | N-AA | OH | F | $G^2$ | H | HDD | D | — | — | — | D | OCH$_2$CH$_3$ |
| $P^4$ | Ph | N-AA | OH | F | $G^2$ | H | DDD | D | — | — | — | D | OCH$_2$CH$_3$ |
| $P^4$ | Ph | N-AA | OH | F | $G^2$ | D | HHH | H | — | — | — | D | OCH$_2$CH$_3$ |
| $P^4$ | Ph | N-AA | OH | F | $G^2$ | D | HHD | H | — | — | — | D | OCH$_2$CH$_3$ |
| $P^4$ | Ph | N-AA | OH | F | $G^2$ | D | HDD | H | — | — | — | D | OCH$_2$CH$_3$ |
| $P^4$ | Ph | N-AA | OH | F | $G^2$ | D | DDD | H | — | — | — | D | OCH$_2$CH$_3$ |
| $P^4$ | Ph | N-AA | OH | F | $G^2$ | D | HHH | D | — | — | — | D | OCH$_2$CH$_3$ |
| $P^4$ | Ph | N-AA | OH | F | $G^2$ | D | HHD | D | — | — | — | D | OCH$_2$CH$_3$ |
| $P^4$ | Ph | N-AA | OH | F | $G^2$ | D | HDD | D | — | — | — | D | OCH$_2$CH$_3$ |
| $P^4$ | Ph | N-AA | OH | F | $G^2$ | D | DDD | D | — | — | — | D | OCH$_2$CH$_3$ |
| $P^4$ | Ph | N-AA | OH | F | $G^2$ | H | HHH | H | — | — | — | D | NH$_2$ |
| $P^4$ | Ph | N-AA | OH | F | $G^2$ | H | HHD | H | — | — | — | D | NH$_2$ |
| $P^4$ | Ph | N-AA | OH | F | $G^2$ | H | HDD | H | — | — | — | D | NH$_2$ |
| $P^4$ | Ph | N-AA | OH | F | $G^2$ | H | DDD | H | — | — | — | D | NH$_2$ |
| $P^4$ | Ph | N-AA | OH | F | $G^2$ | H | HHH | D | — | — | — | D | NH$_2$ |
| $P^4$ | Ph | N-AA | OH | F | $G^2$ | H | HHD | D | — | — | — | D | NH$_2$ |
| $P^4$ | Ph | N-AA | OH | F | $G^2$ | H | HDD | D | — | — | — | D | NH$_2$ |
| $P^4$ | Ph | N-AA | OH | F | $G^2$ | H | DDD | D | — | — | — | D | NH$_2$ |
| $P^4$ | Ph | N-AA | OH | F | $G^2$ | D | HHH | H | — | — | — | D | NH$_2$ |
| $P^4$ | Ph | N-AA | OH | F | $G^2$ | D | HHD | H | — | — | — | D | NH$_2$ |
| $P^4$ | Ph | N-AA | OH | F | $G^2$ | D | HDD | H | — | — | — | D | NH$_2$ |
| $P^4$ | Ph | N-AA | OH | F | $G^2$ | D | DDD | H | — | — | — | D | NH$_2$ |
| $P^4$ | Ph | N-AA | OH | F | $G^2$ | D | HHH | D | — | — | — | D | NH$_2$ |
| $P^4$ | Ph | N-AA | OH | F | $G^2$ | D | HHD | D | — | — | — | D | NH$_2$ |
| $P^4$ | Ph | N-AA | OH | F | $G^2$ | D | HDD | D | — | — | — | D | NH$_2$ |
| $P^4$ | Ph | N-AA | OH | F | $G^2$ | D | DDD | D | — | — | — | D | NH$_2$ |
| $P^4$ | Ph | N-AA | F | OH | $G^2$ | H | HHH | H | — | — | — | H | OCH$_2$CH$_3$ |
| $P^4$ | Ph | N-AA | F | OH | $G^2$ | H | HHD | H | — | — | — | H | OCH$_2$CH$_3$ |
| $P^4$ | Ph | N-AA | F | OH | $G^2$ | H | HDD | H | — | — | — | H | OCH$_2$CH$_3$ |
| $P^4$ | Ph | N-AA | F | OH | $G^2$ | H | DDD | H | — | — | — | H | OCH$_2$CH$_3$ |
| $P^4$ | Ph | N-AA | F | OH | $G^2$ | H | HHH | D | — | — | — | H | OCH$_2$CH$_3$ |
| $P^4$ | Ph | N-AA | F | OH | $G^2$ | H | HHD | D | — | — | — | H | OCH$_2$CH$_3$ |
| $P^4$ | Ph | N-AA | F | OH | $G^2$ | H | HDD | D | — | — | — | H | OCH$_2$CH$_3$ |
| $P^4$ | Ph | N-AA | F | OH | $G^2$ | H | DDD | D | — | — | — | H | OCH$_2$CH$_3$ |
| $P^4$ | Ph | N-AA | F | OH | $G^2$ | D | HHH | H | — | — | — | H | OCH$_2$CH$_3$ |
| $P^4$ | Ph | N-AA | F | OH | $G^2$ | D | HHD | H | — | — | — | H | OCH$_2$CH$_3$ |
| $P^4$ | Ph | N-AA | F | OH | $G^2$ | D | HDD | H | — | — | — | H | OCH$_2$CH$_3$ |
| $P^4$ | Ph | N-AA | F | OH | $G^2$ | D | DDD | H | — | — | — | H | OCH$_2$CH$_3$ |
| $P^4$ | Ph | N-AA | F | OH | $G^2$ | D | HHH | D | — | — | — | H | OCH$_2$CH$_3$ |
| $P^4$ | Ph | N-AA | F | OH | $G^2$ | D | HHD | D | — | — | — | H | OCH$_2$CH$_3$ |
| $P^4$ | Ph | N-AA | F | OH | $G^2$ | D | HDD | D | — | — | — | H | OCH$_2$CH$_3$ |
| $P^4$ | Ph | N-AA | F | OH | $G^2$ | D | DDD | D | — | — | — | H | OCH$_2$CH$_3$ |
| $P^4$ | Ph | N-AA | F | OH | $G^2$ | H | HHH | H | — | — | — | H | NH$_2$ |
| $P^4$ | Ph | N-AA | F | OH | $G^2$ | H | HHD | H | — | — | — | H | NH$_2$ |
| $P^4$ | Ph | N-AA | F | OH | $G^2$ | H | HDD | H | — | — | — | H | NH$_2$ |
| $P^4$ | Ph | N-AA | F | OH | $G^2$ | H | DDD | H | — | — | — | H | NH$_2$ |
| $P^4$ | Ph | N-AA | F | OH | $G^2$ | H | HHH | D | — | — | — | H | NH$_2$ |
| $P^4$ | Ph | N-AA | F | OH | $G^2$ | H | HHD | D | — | — | — | H | NH$_2$ |
| $P^4$ | Ph | N-AA | F | OH | $G^2$ | H | HDD | D | — | — | — | H | NH$_2$ |
| $P^4$ | Ph | N-AA | F | OH | $G^2$ | H | DDD | D | — | — | — | H | NH$_2$ |
| $P^4$ | Ph | N-AA | F | OH | $G^2$ | D | HHH | H | — | — | — | H | NH$_2$ |
| $P^4$ | Ph | N-AA | F | OH | $G^2$ | D | HHD | H | — | — | — | H | NH$_2$ |
| $P^4$ | Ph | N-AA | F | OH | $G^2$ | D | HDD | H | — | — | — | H | NH$_2$ |
| $P^4$ | Ph | N-AA | F | OH | $G^2$ | D | DDD | H | — | — | — | H | NH$_2$ |
| $P^4$ | Ph | N-AA | F | OH | $G^2$ | D | HHH | D | — | — | — | H | NH$_2$ |
| $P^4$ | Ph | N-AA | F | OH | $G^2$ | D | HHD | D | — | — | — | H | NH$_2$ |
| $P^4$ | Ph | N-AA | F | OH | $G^2$ | D | HDD | D | — | — | — | H | NH$_2$ |
| $P^4$ | Ph | N-AA | F | OH | $G^2$ | D | DDD | D | — | — | — | H | NH$_2$ |
| $P^4$ | Ph | N-AA | F | OH | $G^2$ | H | HHH | H | — | — | — | D | OCH$_2$CH$_3$ |
| $P^4$ | Ph | N-AA | F | OH | $G^2$ | H | HHD | H | — | — | — | D | OCH$_2$CH$_3$ |
| $P^4$ | Ph | N-AA | F | OH | $G^2$ | H | HDD | H | — | — | — | D | OCH$_2$CH$_3$ |
| $P^4$ | Ph | N-AA | F | OH | $G^2$ | H | DDD | H | — | — | — | D | OCH$_2$CH$_3$ |
| $P^4$ | Ph | N-AA | F | OH | $G^2$ | H | HHH | D | — | — | — | D | OCH$_2$CH$_3$ |
| $P^4$ | Ph | N-AA | F | OH | $G^2$ | H | HHD | D | — | — | — | D | OCH$_2$CH$_3$ |
| $P^4$ | Ph | N-AA | F | OH | $G^2$ | H | HDD | D | — | — | — | D | OCH$_2$CH$_3$ |
| $P^4$ | Ph | N-AA | F | OH | $G^2$ | H | DDD | D | — | — | — | D | OCH$_2$CH$_3$ |
| $P^4$ | Ph | N-AA | F | OH | $G^2$ | D | HHH | H | — | — | — | D | OCH$_2$CH$_3$ |
| $P^4$ | Ph | N-AA | F | OH | $G^2$ | D | HHD | H | — | — | — | D | OCH$_2$CH$_3$ |
| $P^4$ | Ph | N-AA | F | OH | $G^2$ | D | HDD | H | — | — | — | D | OCH$_2$CH$_3$ |
| $P^4$ | Ph | N-AA | F | OH | $G^2$ | D | DDD | H | — | — | — | D | OCH$_2$CH$_3$ |
| $P^4$ | Ph | N-AA | F | OH | $G^2$ | D | HHH | D | — | — | — | D | OCH$_2$CH$_3$ |
| $P^4$ | Ph | N-AA | F | OH | $G^2$ | D | HHD | D | — | — | — | D | OCH$_2$CH$_3$ |
| $P^4$ | Ph | N-AA | F | OH | $G^2$ | D | HDD | D | — | — | — | D | OCH$_2$CH$_3$ |
| $P^4$ | Ph | N-AA | F | OH | $G^2$ | D | DDD | D | — | — | — | D | OCH$_2$CH$_3$ |
| $P^4$ | Ph | N-AA | F | OH | $G^2$ | H | HHH | H | — | — | — | D | NH$_2$ |
| $P^4$ | Ph | N-AA | F | OH | $G^2$ | H | HHD | H | — | — | — | D | NH$_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | Ph | N-AA | F | OH | $G^2$ | H | HDD | H | — | — | — | D | $NH_2$ |
| $P^4$ | Ph | N-AA | F | OH | $G^2$ | H | DDD | H | — | — | — | D | $NH_2$ |
| $P^4$ | Ph | N-AA | F | OH | $G^2$ | H | HHH | D | — | — | — | D | $NH_2$ |
| $P^4$ | Ph | N-AA | F | OH | $G^2$ | H | HHD | D | — | — | — | D | $NH_2$ |
| $P^4$ | Ph | N-AA | F | OH | $G^2$ | H | HDD | D | — | — | — | D | $NH_2$ |
| $P^4$ | Ph | N-AA | F | OH | $G^2$ | H | DDD | D | — | — | — | D | $NH_2$ |
| $P^4$ | Ph | N-AA | F | OH | $G^2$ | D | HHH | H | — | — | — | D | $NH_2$ |
| $P^4$ | Ph | N-AA | F | OH | $G^2$ | D | HHD | H | — | — | — | D | $NH_2$ |
| $P^4$ | Ph | N-AA | F | OH | $G^2$ | D | HDD | H | — | — | — | D | $NH_2$ |
| $P^4$ | Ph | N-AA | F | OH | $G^2$ | D | DDD | H | — | — | — | D | $NH_2$ |
| $P^4$ | Ph | N-AA | F | OH | $G^2$ | D | HHH | D | — | — | — | D | $NH_2$ |
| $P^4$ | Ph | N-AA | F | OH | $G^2$ | D | HHD | D | — | — | — | D | $NH_2$ |
| $P^4$ | Ph | N-AA | F | OH | $G^2$ | D | HDD | D | — | — | — | D | $NH_2$ |
| $P^4$ | Ph | N-AA | F | OH | $G^2$ | D | DDD | D | — | — | — | D | $NH_2$ |
| $P^4$ | Ph | N-AA | F | F | $G^2$ | H | HHH | H | — | — | — | H | $OCH_2CH_3$ |
| $P^4$ | Ph | N-AA | F | F | $G^2$ | H | HHD | H | — | — | — | H | $OCH_2CH_3$ |
| $P^4$ | Ph | N-AA | F | F | $G^2$ | H | HDD | H | — | — | — | H | $OCH_2CH_3$ |
| $P^4$ | Ph | N-AA | F | F | $G^2$ | H | DDD | H | — | — | — | H | $OCH_2CH_3$ |
| $P^4$ | Ph | N-AA | F | F | $G^2$ | H | HHH | D | — | — | — | H | $OCH_2CH_3$ |
| $P^4$ | Ph | N-AA | F | F | $G^2$ | H | HHD | D | — | — | — | H | $OCH_2CH_3$ |
| $P^4$ | Ph | N-AA | F | F | $G^2$ | H | HDD | D | — | — | — | H | $OCH_2CH_3$ |
| $P^4$ | Ph | N-AA | F | F | $G^2$ | H | DDD | D | — | — | — | H | $OCH_2CH_3$ |
| $P^4$ | Ph | N-AA | F | F | $G^2$ | D | HHH | H | — | — | — | H | $OCH_2CH_3$ |
| $P^4$ | Ph | N-AA | F | F | $G^2$ | D | HHD | H | — | — | — | H | $OCH_2CH_3$ |
| $P^4$ | Ph | N-AA | F | F | $G^2$ | D | HDD | H | — | — | — | H | $OCH_2CH_3$ |
| $P^4$ | Ph | N-AA | F | F | $G^2$ | D | DDD | H | — | — | — | H | $OCH_2CH_3$ |
| $P^4$ | Ph | N-AA | F | F | $G^2$ | D | HHH | D | — | — | — | H | $OCH_2CH_3$ |
| $P^4$ | Ph | N-AA | F | F | $G^2$ | D | HHD | D | — | — | — | H | $OCH_2CH_3$ |
| $P^4$ | Ph | N-AA | F | F | $G^2$ | D | HDD | D | — | — | — | H | $OCH_2CH_3$ |
| $P^4$ | Ph | N-AA | F | F | $G^2$ | D | DDD | D | — | — | — | H | $OCH_2CH_3$ |
| $P^4$ | Ph | N-AA | F | F | $G^2$ | H | HHH | H | — | — | — | H | $NH_2$ |
| $P^4$ | Ph | N-AA | F | F | $G^2$ | H | HHD | H | — | — | — | H | $NH_2$ |
| $P^4$ | Ph | N-AA | F | F | $G^2$ | H | HDD | H | — | — | — | H | $NH_2$ |
| $P^4$ | Ph | N-AA | F | F | $G^2$ | H | DDD | H | — | — | — | H | $NH_2$ |
| $P^4$ | Ph | N-AA | F | F | $G^2$ | H | HHH | D | — | — | — | H | $NH_2$ |
| $P^4$ | Ph | N-AA | F | F | $G^2$ | H | HHD | D | — | — | — | H | $NH_2$ |
| $P^4$ | Ph | N-AA | F | F | $G^2$ | H | HDD | D | — | — | — | H | $NH_2$ |
| $P^4$ | Ph | N-AA | F | F | $G^2$ | H | DDD | D | — | — | — | H | $NH_2$ |
| $P^4$ | Ph | N-AA | F | F | $G^2$ | D | HHH | H | — | — | — | H | $NH_2$ |
| $P^4$ | Ph | N-AA | F | F | $G^2$ | D | HHD | H | — | — | — | H | $NH_2$ |
| $P^4$ | Ph | N-AA | F | F | $G^2$ | D | HDD | H | — | — | — | H | $NH_2$ |
| $P^4$ | Ph | N-AA | F | F | $G^2$ | D | DDD | H | — | — | — | H | $NH_2$ |
| $P^4$ | Ph | N-AA | F | F | $G^2$ | D | HHH | D | — | — | — | H | $NH_2$ |
| $P^4$ | Ph | N-AA | F | F | $G^2$ | D | HHD | D | — | — | — | H | $NH_2$ |
| $P^4$ | Ph | N-AA | F | F | $G^2$ | D | HDD | D | — | — | — | H | $NH_2$ |
| $P^4$ | Ph | N-AA | F | F | $G^2$ | D | DDD | D | — | — | — | H | $NH_2$ |
| $P^4$ | Ph | N-AA | F | F | $G^2$ | H | HHH | H | — | — | — | D | $OCH_2CH_3$ |
| $P^4$ | Ph | N-AA | F | F | $G^2$ | H | HHD | H | — | — | — | D | $OCH_2CH_3$ |
| $P^4$ | Ph | N-AA | F | F | $G^2$ | H | HDD | H | — | — | — | D | $OCH_2CH_3$ |
| $P^4$ | Ph | N-AA | F | F | $G^2$ | H | DDD | H | — | — | — | D | $OCH_2CH_3$ |
| $P^4$ | Ph | N-AA | F | F | $G^2$ | H | HHH | D | — | — | — | D | $OCH_2CH_3$ |
| $P^4$ | Ph | N-AA | F | F | $G^2$ | H | HHD | D | — | — | — | D | $OCH_2CH_3$ |
| $P^4$ | Ph | N-AA | F | F | $G^2$ | H | HDD | D | — | — | — | D | $OCH_2CH_3$ |
| $P^4$ | Ph | N-AA | F | F | $G^2$ | H | DDD | D | — | — | — | D | $OCH_2CH_3$ |
| $P^4$ | Ph | N-AA | F | F | $G^2$ | D | HHH | H | — | — | — | D | $OCH_2CH_3$ |
| $P^4$ | Ph | N-AA | F | F | $G^2$ | D | HHD | H | — | — | — | D | $OCH_2CH_3$ |
| $P^4$ | Ph | N-AA | F | F | $G^2$ | D | HDD | H | — | — | — | D | $OCH_2CH_3$ |
| $P^4$ | Ph | N-AA | F | F | $G^2$ | D | DDD | H | — | — | — | D | $OCH_2CH_3$ |
| $P^4$ | Ph | N-AA | F | F | $G^2$ | D | HHH | D | — | — | — | D | $OCH_2CH_3$ |
| $P^4$ | Ph | N-AA | F | F | $G^2$ | D | HHD | D | — | — | — | D | $OCH_2CH_3$ |
| $P^4$ | Ph | N-AA | F | F | $G^2$ | D | HDD | D | — | — | — | D | $OCH_2CH_3$ |
| $P^4$ | Ph | N-AA | F | F | $G^2$ | D | DDD | D | — | — | — | D | $OCH_2CH_3$ |
| $P^4$ | Ph | N-AA | F | F | $G^2$ | H | HHH | H | — | — | — | D | $NH_2$ |
| $P^4$ | Ph | N-AA | F | F | $G^2$ | H | HHD | H | — | — | — | D | $NH_2$ |
| $P^4$ | Ph | N-AA | F | F | $G^2$ | H | HDD | H | — | — | — | D | $NH_2$ |
| $P^4$ | Ph | N-AA | F | F | $G^2$ | H | DDD | H | — | — | — | D | $NH_2$ |
| $P^4$ | Ph | N-AA | F | F | $G^2$ | H | HHH | D | — | — | — | D | $NH_2$ |
| $P^4$ | Ph | N-AA | F | F | $G^2$ | H | HHD | D | — | — | — | D | $NH_2$ |
| $P^4$ | Ph | N-AA | F | F | $G^2$ | H | HDD | D | — | — | — | D | $NH_2$ |
| $P^4$ | Ph | N-AA | F | F | $G^2$ | H | DDD | D | — | — | — | D | $NH_2$ |
| $P^4$ | Ph | N-AA | F | F | $G^2$ | D | HHH | H | — | — | — | D | $NH_2$ |
| $P^4$ | Ph | N-AA | F | F | $G^2$ | D | HHD | H | — | — | — | D | $NH_2$ |
| $P^4$ | Ph | N-AA | F | F | $G^2$ | D | HDD | H | — | — | — | D | $NH_2$ |
| $P^4$ | Ph | N-AA | F | F | $G^2$ | D | DDD | H | — | — | — | D | $NH_2$ |
| $P^4$ | Ph | N-AA | F | F | $G^2$ | D | HHH | D | — | — | — | D | $NH_2$ |
| $P^4$ | Ph | N-AA | F | F | $G^2$ | D | HHD | D | — | — | — | D | $NH_2$ |
| $P^4$ | Ph | N-AA | F | F | $G^2$ | D | HDD | D | — | — | — | D | $NH_2$ |
| $P^4$ | Ph | N-AA | F | F | $G^2$ | D | DDD | D | — | — | — | D | $NH_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,4}$ | $B^{2,4}$ | $B^{3,4}$ | $B^{4,4}$ | $B^{5,4}$ |
|---|---|---|---|---|---|---|---|---|---|---|---|---|---|
| $P^4$ | Naph | N-AA | OH | OH | $G^2$ | H | HHH | H | — | — | — | H | $OCH_2CH_3$ |
| $P^4$ | Naph | N-AA | OH | OH | $G^2$ | H | HHD | H | — | — | — | H | $OCH_2CH_3$ |
| $P^4$ | Naph | N-AA | OH | OH | $G^2$ | H | HDD | H | — | — | — | H | $OCH_2CH_3$ |
| $P^4$ | Naph | N-AA | OH | OH | $G^2$ | H | DDD | H | — | — | — | H | $OCH_2CH_3$ |
| $P^4$ | Naph | N-AA | OH | OH | $G^2$ | H | HHH | D | — | — | — | H | $OCH_2CH_3$ |
| $P^4$ | Naph | N-AA | OH | OH | $G^2$ | H | HHD | D | — | — | — | H | $OCH_2CH_3$ |
| $P^4$ | Naph | N-AA | OH | OH | $G^2$ | H | HDD | D | — | — | — | H | $OCH_2CH_3$ |
| $P^4$ | Naph | N-AA | OH | OH | $G^2$ | H | DDD | D | — | — | — | H | $OCH_2CH_3$ |
| $P^4$ | Naph | N-AA | OH | OH | $G^2$ | D | HHH | H | — | — | — | H | $OCH_2CH_3$ |
| $P^4$ | Naph | N-AA | OH | OH | $G^2$ | D | HHD | H | — | — | — | H | $OCH_2CH_3$ |
| $P^4$ | Naph | N-AA | OH | OH | $G^2$ | D | HDD | H | — | — | — | H | $OCH_2CH_3$ |
| $P^4$ | Naph | N-AA | OH | OH | $G^2$ | D | DDD | H | — | — | — | H | $OCH_2CH_3$ |
| $P^4$ | Naph | N-AA | OH | OH | $G^2$ | D | HHH | D | — | — | — | H | $OCH_2CH_3$ |
| $P^4$ | Naph | N-AA | OH | OH | $G^2$ | D | HHD | D | — | — | — | H | $OCH_2CH_3$ |
| $P^4$ | Naph | N-AA | OH | OH | $G^2$ | D | HDD | D | — | — | — | H | $OCH_2CH_3$ |
| $P^4$ | Naph | N-AA | OH | OH | $G^2$ | D | DDD | D | — | — | — | H | $OCH_2CH_3$ |
| $P^4$ | Naph | N-AA | OH | OH | $G^2$ | H | HHH | H | — | — | — | H | $NH_2$ |
| $P^4$ | Naph | N-AA | OH | OH | $G^2$ | H | HHD | H | — | — | — | H | $NH_2$ |
| $P^4$ | Naph | N-AA | OH | OH | $G^2$ | H | HDD | H | — | — | — | H | $NH_2$ |
| $P^4$ | Naph | N-AA | OH | OH | $G^2$ | H | DDD | H | — | — | — | H | $NH_2$ |
| $P^4$ | Naph | N-AA | OH | OH | $G^2$ | H | HHH | D | — | — | — | H | $NH_2$ |
| $P^4$ | Naph | N-AA | OH | OH | $G^2$ | H | HHD | D | — | — | — | H | $NH_2$ |
| $P^4$ | Naph | N-AA | OH | OH | $G^2$ | H | HDD | D | — | — | — | H | $NH_2$ |
| $P^4$ | Naph | N-AA | OH | OH | $G^2$ | H | DDD | D | — | — | — | H | $NH_2$ |
| $P^4$ | Naph | N-AA | OH | OH | $G^2$ | D | HHH | H | — | — | — | H | $NH_2$ |
| $P^4$ | Naph | N-AA | OH | OH | $G^2$ | D | HHD | H | — | — | — | H | $NH_2$ |
| $P^4$ | Naph | N-AA | OH | OH | $G^2$ | D | HDD | H | — | — | — | H | $NH_2$ |
| $P^4$ | Naph | N-AA | OH | OH | $G^2$ | D | DDD | H | — | — | — | H | $NH_2$ |
| $P^4$ | Naph | N-AA | OH | OH | $G^2$ | D | HHH | D | — | — | — | H | $NH_2$ |
| $P^4$ | Naph | N-AA | OH | OH | $G^2$ | D | HHD | D | — | — | — | H | $NH_2$ |
| $P^4$ | Naph | N-AA | OH | OH | $G^2$ | D | HDD | D | — | — | — | H | $NH_2$ |
| $P^4$ | Naph | N-AA | OH | OH | $G^2$ | D | DDD | D | — | — | — | H | $NH_2$ |
| $P^4$ | Naph | N-AA | OH | OH | $G^2$ | H | HHH | H | — | — | — | D | $OCH_2CH_3$ |
| $P^4$ | Naph | N-AA | OH | OH | $G^2$ | H | HHD | H | — | — | — | D | $OCH_2CH_3$ |
| $P^4$ | Naph | N-AA | OH | OH | $G^2$ | H | HDD | H | — | — | — | D | $OCH_2CH_3$ |
| $P^4$ | Naph | N-AA | OH | OH | $G^2$ | H | DDD | H | — | — | — | D | $OCH_2CH_3$ |
| $P^4$ | Naph | N-AA | OH | OH | $G^2$ | H | HHH | D | — | — | — | D | $OCH_2CH_3$ |
| $P^4$ | Naph | N-AA | OH | OH | $G^2$ | H | HHD | D | — | — | — | D | $OCH_2CH_3$ |
| $P^4$ | Naph | N-AA | OH | OH | $G^2$ | H | HDD | D | — | — | — | D | $OCH_2CH_3$ |
| $P^4$ | Naph | N-AA | OH | OH | $G^2$ | H | DDD | D | — | — | — | D | $OCH_2CH_3$ |
| $P^4$ | Naph | N-AA | OH | OH | $G^2$ | D | HHH | H | — | — | — | D | $OCH_2CH_3$ |
| $P^4$ | Naph | N-AA | OH | OH | $G^2$ | D | HHD | H | — | — | — | D | $OCH_2CH_3$ |
| $P^4$ | Naph | N-AA | OH | OH | $G^2$ | D | HDD | H | — | — | — | D | $OCH_2CH_3$ |
| $P^4$ | Naph | N-AA | OH | OH | $G^2$ | D | DDD | H | — | — | — | D | $OCH_2CH_3$ |
| $P^4$ | Naph | N-AA | OH | OH | $G^2$ | D | HHH | D | — | — | — | D | $OCH_2CH_3$ |
| $P^4$ | Naph | N-AA | OH | OH | $G^2$ | D | HHD | D | — | — | — | D | $OCH_2CH_3$ |
| $P^4$ | Naph | N-AA | OH | OH | $G^2$ | D | HDD | D | — | — | — | D | $OCH_2CH_3$ |
| $P^4$ | Naph | N-AA | OH | OH | $G^2$ | D | DDD | D | — | — | — | D | $OCH_2CH_3$ |
| $P^4$ | Naph | N-AA | OH | OH | $G^2$ | H | HHH | H | — | — | — | D | $NH_2$ |
| $P^4$ | Naph | N-AA | OH | OH | $G^2$ | H | HHD | H | — | — | — | D | $NH_2$ |
| $P^4$ | Naph | N-AA | OH | OH | $G^2$ | H | HDD | H | — | — | — | D | $NH_2$ |
| $P^4$ | Naph | N-AA | OH | OH | $G^2$ | H | DDD | H | — | — | — | D | $NH_2$ |
| $P^4$ | Naph | N-AA | OH | OH | $G^2$ | H | HHH | D | — | — | — | D | $NH_2$ |
| $P^4$ | Naph | N-AA | OH | OH | $G^2$ | H | HHD | D | — | — | — | D | $NH_2$ |
| $P^4$ | Naph | N-AA | OH | OH | $G^2$ | H | HDD | D | — | — | — | D | $NH_2$ |
| $P^4$ | Naph | N-AA | OH | OH | $G^2$ | H | DDD | D | — | — | — | D | $NH_2$ |
| $P^4$ | Naph | N-AA | OH | OH | $G^2$ | D | HHH | H | — | — | — | D | $NH_2$ |
| $P^4$ | Naph | N-AA | OH | OH | $G^2$ | D | HHD | H | — | — | — | D | $NH_2$ |
| $P^4$ | Naph | N-AA | OH | OH | $G^2$ | D | HDD | H | — | — | — | D | $NH_2$ |
| $P^4$ | Naph | N-AA | OH | OH | $G^2$ | D | DDD | H | — | — | — | D | $NH_2$ |
| $P^4$ | Naph | N-AA | OH | OH | $G^2$ | D | HHH | D | — | — | — | D | $NH_2$ |
| $P^4$ | Naph | N-AA | OH | OH | $G^2$ | D | HHD | D | — | — | — | D | $NH_2$ |
| $P^4$ | Naph | N-AA | OH | OH | $G^2$ | D | HDD | D | — | — | — | D | $NH_2$ |
| $P^4$ | Naph | N-AA | OH | OH | $G^2$ | D | DDD | D | — | — | — | D | $NH_2$ |
| $P^4$ | Naph | N-AA | OH | F | $G^2$ | H | HHH | H | — | — | — | H | $OCH_2CH_3$ |
| $P^4$ | Naph | N-AA | OH | F | $G^2$ | H | HHD | H | — | — | — | H | $OCH_2CH_3$ |
| $P^4$ | Naph | N-AA | OH | F | $G^2$ | H | HDD | H | — | — | — | H | $OCH_2CH_3$ |
| $P^4$ | Naph | N-AA | OH | F | $G^2$ | H | DDD | H | — | — | — | H | $OCH_2CH_3$ |
| $P^4$ | Naph | N-AA | OH | F | $G^2$ | H | HHH | D | — | — | — | H | $OCH_2CH_3$ |
| $P^4$ | Naph | N-AA | OH | F | $G^2$ | H | HHD | D | — | — | — | H | $OCH_2CH_3$ |
| $P^4$ | Naph | N-AA | OH | F | $G^2$ | H | HDD | D | — | — | — | H | $OCH_2CH_3$ |
| $P^4$ | Naph | N-AA | OH | F | $G^2$ | H | DDD | D | — | — | — | H | $OCH_2CH_3$ |
| $P^4$ | Naph | N-AA | OH | F | $G^2$ | D | HHH | H | — | — | — | H | $OCH_2CH_3$ |
| $P^4$ | Naph | N-AA | OH | F | $G^2$ | D | HHD | H | — | — | — | H | $OCH_2CH_3$ |
| $P^4$ | Naph | N-AA | OH | F | $G^2$ | D | HDD | H | — | — | — | H | $OCH_2CH_3$ |
| $P^4$ | Naph | N-AA | OH | F | $G^2$ | D | DDD | H | — | — | — | H | $OCH_2CH_3$ |
| $P^4$ | Naph | N-AA | OH | F | $G^2$ | D | HHH | D | — | — | — | H | $OCH_2CH_3$ |
| $P^4$ | Naph | N-AA | OH | F | $G^2$ | D | HHD | D | — | — | — | H | $OCH_2CH_3$ |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^A$ | Naph | N-AA | OH | F | $G^2$ | D | HDD | D | — | — | — | H | $OCH_2CH_3$ |
| $P^A$ | Naph | N-AA | OH | F | $G^2$ | D | DDD | D | — | — | — | H | $OCH_2CH_3$ |
| $P^A$ | Naph | N-AA | OH | F | $G^2$ | H | HHH | H | — | — | — | H | $NH_2$ |
| $P^A$ | Naph | N-AA | OH | F | $G^2$ | H | HHD | H | — | — | — | H | $NH_2$ |
| $P^A$ | Naph | N-AA | OH | F | $G^2$ | H | HDD | H | — | — | — | H | $NH_2$ |
| $P^A$ | Naph | N-AA | OH | F | $G^2$ | H | DDD | H | — | — | — | H | $NH_2$ |
| $P^A$ | Naph | N-AA | OH | F | $G^2$ | H | HHH | D | — | — | — | H | $NH_2$ |
| $P^A$ | Naph | N-AA | OH | F | $G^2$ | H | HHD | D | — | — | — | H | $NH_2$ |
| $P^A$ | Naph | N-AA | OH | F | $G^2$ | H | HDD | D | — | — | — | H | $NH_2$ |
| $P^A$ | Naph | N-AA | OH | F | $G^2$ | H | DDD | D | — | — | — | H | $NH_2$ |
| $P^A$ | Naph | N-AA | OH | F | $G^2$ | D | HHH | H | — | — | — | H | $NH_2$ |
| $P^A$ | Naph | N-AA | OH | F | $G^2$ | D | HHD | H | — | — | — | H | $NH_2$ |
| $P^A$ | Naph | N-AA | OH | F | $G^2$ | D | HDD | H | — | — | — | H | $NH_2$ |
| $P^A$ | Naph | N-AA | OH | F | $G^2$ | D | DDD | H | — | — | — | H | $NH_2$ |
| $P^A$ | Naph | N-AA | OH | F | $G^2$ | D | HHH | D | — | — | — | H | $NH_2$ |
| $P^A$ | Naph | N-AA | OH | F | $G^2$ | D | HHD | D | — | — | — | H | $NH_2$ |
| $P^A$ | Naph | N-AA | OH | F | $G^2$ | D | HDD | D | — | — | — | H | $NH_2$ |
| $P^A$ | Naph | N-AA | OH | F | $G^2$ | D | DDD | D | — | — | — | H | $NH_2$ |
| $P^A$ | Naph | N-AA | OH | F | $G^2$ | H | HHH | H | — | — | — | D | $OCH_2CH_3$ |
| $P^A$ | Naph | N-AA | OH | F | $G^2$ | H | HHD | H | — | — | — | D | $OCH_2CH_3$ |
| $P^A$ | Naph | N-AA | OH | F | $G^2$ | H | HDD | H | — | — | — | D | $OCH_2CH_3$ |
| $P^A$ | Naph | N-AA | OH | F | $G^2$ | H | DDD | H | — | — | — | D | $OCH_2CH_3$ |
| $P^A$ | Naph | N-AA | OH | F | $G^2$ | H | HHH | D | — | — | — | D | $OCH_2CH_3$ |
| $P^A$ | Naph | N-AA | OH | F | $G^2$ | H | HHD | D | — | — | — | D | $OCH_2CH_3$ |
| $P^A$ | Naph | N-AA | OH | F | $G^2$ | H | HDD | D | — | — | — | D | $OCH_2CH_3$ |
| $P^A$ | Naph | N-AA | OH | F | $G^2$ | H | DDD | D | — | — | — | D | $OCH_2CH_3$ |
| $P^A$ | Naph | N-AA | OH | F | $G^2$ | D | HHH | H | — | — | — | D | $OCH_2CH_3$ |
| $P^A$ | Naph | N-AA | OH | F | $G^2$ | D | HHD | H | — | — | — | D | $OCH_2CH_3$ |
| $P^A$ | Naph | N-AA | OH | F | $G^2$ | D | HDD | H | — | — | — | D | $OCH_2CH_3$ |
| $P^A$ | Naph | N-AA | OH | F | $G^2$ | D | DDD | H | — | — | — | D | $OCH_2CH_3$ |
| $P^A$ | Naph | N-AA | OH | F | $G^2$ | D | HHH | D | — | — | — | D | $OCH_2CH_3$ |
| $P^A$ | Naph | N-AA | OH | F | $G^2$ | D | HHD | D | — | — | — | D | $OCH_2CH_3$ |
| $P^A$ | Naph | N-AA | OH | F | $G^2$ | D | HDD | D | — | — | — | D | $OCH_2CH_3$ |
| $P^A$ | Naph | N-AA | OH | F | $G^2$ | D | DDD | D | — | — | — | D | $OCH_2CH_3$ |
| $P^A$ | Naph | N-AA | OH | F | $G^2$ | H | HHH | H | — | — | — | D | $NH_2$ |
| $P^A$ | Naph | N-AA | OH | F | $G^2$ | H | HHD | H | — | — | — | D | $NH_2$ |
| $P^A$ | Naph | N-AA | OH | F | $G^2$ | H | HDD | H | — | — | — | D | $NH_2$ |
| $P^A$ | Naph | N-AA | OH | F | $G^2$ | H | DDD | H | — | — | — | D | $NH_2$ |
| $P^A$ | Naph | N-AA | OH | F | $G^2$ | H | HHH | D | — | — | — | D | $NH_2$ |
| $P^A$ | Naph | N-AA | OH | F | $G^2$ | H | HHD | D | — | — | — | D | $NH_2$ |
| $P^A$ | Naph | N-AA | OH | F | $G^2$ | H | HDD | D | — | — | — | D | $NH_2$ |
| $P^A$ | Naph | N-AA | OH | F | $G^2$ | H | DDD | D | — | — | — | D | $NH_2$ |
| $P^A$ | Naph | N-AA | OH | F | $G^2$ | D | HHH | H | — | — | — | D | $NH_2$ |
| $P^A$ | Naph | N-AA | OH | F | $G^2$ | D | HHD | H | — | — | — | D | $NH_2$ |
| $P^A$ | Naph | N-AA | OH | F | $G^2$ | D | HDD | H | — | — | — | D | $NH_2$ |
| $P^A$ | Naph | N-AA | OH | F | $G^2$ | D | DDD | H | — | — | — | D | $NH_2$ |
| $P^A$ | Naph | N-AA | OH | F | $G^2$ | D | HHH | D | — | — | — | D | $NH_2$ |
| $P^A$ | Naph | N-AA | OH | F | $G^2$ | D | HHD | D | — | — | — | D | $NH_2$ |
| $P^A$ | Naph | N-AA | OH | F | $G^2$ | D | HDD | D | — | — | — | D | $NH_2$ |
| $P^A$ | Naph | N-AA | OH | F | $G^2$ | D | DDD | D | — | — | — | D | $NH_2$ |
| $P^A$ | Naph | N-AA | F | OH | $G^2$ | H | HHH | H | — | — | — | H | $OCH_2CH_3$ |
| $P^A$ | Naph | N-AA | F | OH | $G^2$ | H | HHD | H | — | — | — | H | $OCH_2CH_3$ |
| $P^A$ | Naph | N-AA | F | OH | $G^2$ | H | HDD | H | — | — | — | H | $OCH_2CH_3$ |
| $P^A$ | Naph | N-AA | F | OH | $G^2$ | H | DDD | H | — | — | — | H | $OCH_2CH_3$ |
| $P^A$ | Naph | N-AA | F | OH | $G^2$ | H | HHH | D | — | — | — | H | $OCH_2CH_3$ |
| $P^A$ | Naph | N-AA | F | OH | $G^2$ | H | HHD | D | — | — | — | H | $OCH_2CH_3$ |
| $P^A$ | Naph | N-AA | F | OH | $G^2$ | H | HDD | D | — | — | — | H | $OCH_2CH_3$ |
| $P^A$ | Naph | N-AA | F | OH | $G^2$ | H | DDD | D | — | — | — | H | $OCH_2CH_3$ |
| $P^A$ | Naph | N-AA | F | OH | $G^2$ | D | HHH | H | — | — | — | H | $OCH_2CH_3$ |
| $P^A$ | Naph | N-AA | F | OH | $G^2$ | D | HHD | H | — | — | — | H | $OCH_2CH_3$ |
| $P^A$ | Naph | N-AA | F | OH | $G^2$ | D | HDD | H | — | — | — | H | $OCH_2CH_3$ |
| $P^A$ | Naph | N-AA | F | OH | $G^2$ | D | DDD | H | — | — | — | H | $OCH_2CH_3$ |
| $P^A$ | Naph | N-AA | F | OH | $G^2$ | D | HHH | D | — | — | — | H | $OCH_2CH_3$ |
| $P^A$ | Naph | N-AA | F | OH | $G^2$ | D | HHD | D | — | — | — | H | $OCH_2CH_3$ |
| $P^A$ | Naph | N-AA | F | OH | $G^2$ | D | HDD | D | — | — | — | H | $OCH_2CH_3$ |
| $P^A$ | Naph | N-AA | F | OH | $G^2$ | D | DDD | D | — | — | — | H | $OCH_2CH_3$ |
| $P^A$ | Naph | N-AA | F | OH | $G^2$ | H | HHH | H | — | — | — | H | $NH_2$ |
| $P^A$ | Naph | N-AA | F | OH | $G^2$ | H | HHD | H | — | — | — | H | $NH_2$ |
| $P^A$ | Naph | N-AA | F | OH | $G^2$ | H | HDD | H | — | — | — | H | $NH_2$ |
| $P^A$ | Naph | N-AA | F | OH | $G^2$ | H | DDD | H | — | — | — | H | $NH_2$ |
| $P^A$ | Naph | N-AA | F | OH | $G^2$ | H | HHH | D | — | — | — | H | $NH_2$ |
| $P^A$ | Naph | N-AA | F | OH | $G^2$ | H | HHD | D | — | — | — | H | $NH_2$ |
| $P^A$ | Naph | N-AA | F | OH | $G^2$ | H | HDD | D | — | — | — | H | $NH_2$ |
| $P^A$ | Naph | N-AA | F | OH | $G^2$ | H | DDD | D | — | — | — | H | $NH_2$ |
| $P^A$ | Naph | N-AA | F | OH | $G^2$ | D | HHH | H | — | — | — | H | $NH_2$ |
| $P^A$ | Naph | N-AA | F | OH | $G^2$ | D | HHD | H | — | — | — | H | $NH_2$ |
| $P^A$ | Naph | N-AA | F | OH | $G^2$ | D | HDD | H | — | — | — | H | $NH_2$ |
| $P^A$ | Naph | N-AA | F | OH | $G^2$ | D | DDD | H | — | — | — | H | $NH_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,4}$ | $B^{2,4}$ | $B^{3,4}$ | $B^{4,4}$ | $B^{5,4}$ |
|---|---|---|---|---|---|---|---|---|---|---|---|---|---|
| $P^4$ | Naph | N-AA | F | OH | $G^2$ | D | HHH | D | — | — | — | H | $NH_2$ |
| $P^4$ | Naph | N-AA | F | OH | $G^2$ | D | HHD | D | — | — | — | H | $NH_2$ |
| $P^4$ | Naph | N-AA | F | OH | $G^2$ | D | HDD | D | — | — | — | H | $NH_2$ |
| $P^4$ | Naph | N-AA | F | OH | $G^2$ | D | DDD | D | — | — | — | H | $NH_2$ |
| $P^4$ | Naph | N-AA | F | OH | $G^2$ | H | HHH | H | — | — | — | D | $OCH_2CH_3$ |
| $P^4$ | Naph | N-AA | F | OH | $G^2$ | H | HHD | H | — | — | — | D | $OCH_2CH_3$ |
| $P^4$ | Naph | N-AA | F | OH | $G^2$ | H | HDD | H | — | — | — | D | $OCH_2CH_3$ |
| $P^4$ | Naph | N-AA | F | OH | $G^2$ | H | DDD | H | — | — | — | D | $OCH_2CH_3$ |
| $P^4$ | Naph | N-AA | F | OH | $G^2$ | H | HHH | D | — | — | — | D | $OCH_2CH_3$ |
| $P^4$ | Naph | N-AA | F | OH | $G^2$ | H | HHD | D | — | — | — | D | $OCH_2CH_3$ |
| $P^4$ | Naph | N-AA | F | OH | $G^2$ | H | HDD | D | — | — | — | D | $OCH_2CH_3$ |
| $P^4$ | Naph | N-AA | F | OH | $G^2$ | H | DDD | D | — | — | — | D | $OCH_2CH_3$ |
| $P^4$ | Naph | N-AA | F | OH | $G^2$ | D | HHH | H | — | — | — | D | $OCH_2CH_3$ |
| $P^4$ | Naph | N-AA | F | OH | $G^2$ | D | HHD | H | — | — | — | D | $OCH_2CH_3$ |
| $P^4$ | Naph | N-AA | F | OH | $G^2$ | D | HDD | H | — | — | — | D | $OCH_2CH_3$ |
| $P^4$ | Naph | N-AA | F | OH | $G^2$ | D | DDD | H | — | — | — | D | $OCH_2CH_3$ |
| $P^4$ | Naph | N-AA | F | OH | $G^2$ | D | HHH | D | — | — | — | D | $OCH_2CH_3$ |
| $P^4$ | Naph | N-AA | F | OH | $G^2$ | D | HHD | D | — | — | — | D | $OCH_2CH_3$ |
| $P^4$ | Naph | N-AA | F | OH | $G^2$ | D | HDD | D | — | — | — | D | $OCH_2CH_3$ |
| $P^4$ | Naph | N-AA | F | OH | $G^2$ | D | DDD | D | — | — | — | D | $OCH_2CH_3$ |
| $P^4$ | Naph | N-AA | F | OH | $G^2$ | H | HHH | H | — | — | — | D | $NH_2$ |
| $P^4$ | Naph | N-AA | F | OH | $G^2$ | H | HHD | H | — | — | — | D | $NH_2$ |
| $P^4$ | Naph | N-AA | F | OH | $G^2$ | H | HDD | H | — | — | — | D | $NH_2$ |
| $P^4$ | Naph | N-AA | F | OH | $G^2$ | H | DDD | H | — | — | — | D | $NH_2$ |
| $P^4$ | Naph | N-AA | F | OH | $G^2$ | H | HHH | D | — | — | — | D | $NH_2$ |
| $P^4$ | Naph | N-AA | F | OH | $G^2$ | H | HHD | D | — | — | — | D | $NH_2$ |
| $P^4$ | Naph | N-AA | F | OH | $G^2$ | H | HDD | D | — | — | — | D | $NH_2$ |
| $P^4$ | Naph | N-AA | F | OH | $G^2$ | H | DDD | D | — | — | — | D | $NH_2$ |
| $P^4$ | Naph | N-AA | F | OH | $G^2$ | D | HHH | H | — | — | — | D | $NH_2$ |
| $P^4$ | Naph | N-AA | F | OH | $G^2$ | D | HHD | H | — | — | — | D | $NH_2$ |
| $P^4$ | Naph | N-AA | F | OH | $G^2$ | D | HDD | H | — | — | — | D | $NH_2$ |
| $P^4$ | Naph | N-AA | F | OH | $G^2$ | D | DDD | H | — | — | — | D | $NH_2$ |
| $P^4$ | Naph | N-AA | F | OH | $G^2$ | D | HHH | D | — | — | — | D | $NH_2$ |
| $P^4$ | Naph | N-AA | F | OH | $G^2$ | D | HHD | D | — | — | — | D | $NH_2$ |
| $P^4$ | Naph | N-AA | F | OH | $G^2$ | D | HDD | D | — | — | — | D | $NH_2$ |
| $P^4$ | Naph | N-AA | F | OH | $G^2$ | D | DDD | D | — | — | — | D | $NH_2$ |
| $P^4$ | Naph | N-AA | F | F | $G^2$ | H | HHH | H | — | — | — | H | $OCH_2CH_3$ |
| $P^4$ | Naph | N-AA | F | F | $G^2$ | H | HHD | H | — | — | — | H | $OCH_2CH_3$ |
| $P^4$ | Naph | N-AA | F | F | $G^2$ | H | HDD | H | — | — | — | H | $OCH_2CH_3$ |
| $P^4$ | Naph | N-AA | F | F | $G^2$ | H | DDD | H | — | — | — | H | $OCH_2CH_3$ |
| $P^4$ | Naph | N-AA | F | F | $G^2$ | H | HHH | D | — | — | — | H | $OCH_2CH_3$ |
| $P^4$ | Naph | N-AA | F | F | $G^2$ | H | HHD | D | — | — | — | H | $OCH_2CH_3$ |
| $P^4$ | Naph | N-AA | F | F | $G^2$ | H | HDD | D | — | — | — | H | $OCH_2CH_3$ |
| $P^4$ | Naph | N-AA | F | F | $G^2$ | H | DDD | D | — | — | — | H | $OCH_2CH_3$ |
| $P^4$ | Naph | N-AA | F | F | $G^2$ | D | HHH | H | — | — | — | H | $OCH_2CH_3$ |
| $P^4$ | Naph | N-AA | F | F | $G^2$ | D | HHD | H | — | — | — | H | $OCH_2CH_3$ |
| $P^4$ | Naph | N-AA | F | F | $G^2$ | D | HDD | H | — | — | — | H | $OCH_2CH_3$ |
| $P^4$ | Naph | N-AA | F | F | $G^2$ | D | DDD | H | — | — | — | H | $OCH_2CH_3$ |
| $P^4$ | Naph | N-AA | F | F | $G^2$ | D | HHH | D | — | — | — | H | $OCH_2CH_3$ |
| $P^4$ | Naph | N-AA | F | F | $G^2$ | D | HHD | D | — | — | — | H | $OCH_2CH_3$ |
| $P^4$ | Naph | N-AA | F | F | $G^2$ | D | HDD | D | — | — | — | H | $OCH_2CH_3$ |
| $P^4$ | Naph | N-AA | F | F | $G^2$ | D | DDD | D | — | — | — | H | $OCH_2CH_3$ |
| $P^4$ | Naph | N-AA | F | F | $G^2$ | H | HHH | H | — | — | — | H | $NH_2$ |
| $P^4$ | Naph | N-AA | F | F | $G^2$ | H | HHD | H | — | — | — | H | $NH_2$ |
| $P^4$ | Naph | N-AA | F | F | $G^2$ | H | HDD | H | — | — | — | H | $NH_2$ |
| $P^4$ | Naph | N-AA | F | F | $G^2$ | H | DDD | H | — | — | — | H | $NH_2$ |
| $P^4$ | Naph | N-AA | F | F | $G^2$ | H | HHH | D | — | — | — | H | $NH_2$ |
| $P^4$ | Naph | N-AA | F | F | $G^2$ | H | HHD | D | — | — | — | H | $NH_2$ |
| $P^4$ | Naph | N-AA | F | F | $G^2$ | H | HDD | D | — | — | — | H | $NH_2$ |
| $P^4$ | Naph | N-AA | F | F | $G^2$ | H | DDD | D | — | — | — | H | $NH_2$ |
| $P^4$ | Naph | N-AA | F | F | $G^2$ | D | HHH | H | — | — | — | H | $NH_2$ |
| $P^4$ | Naph | N-AA | F | F | $G^2$ | D | HHD | H | — | — | — | H | $NH_2$ |
| $P^4$ | Naph | N-AA | F | F | $G^2$ | D | HDD | H | — | — | — | H | $NH_2$ |
| $P^4$ | Naph | N-AA | F | F | $G^2$ | D | DDD | H | — | — | — | H | $NH_2$ |
| $P^4$ | Naph | N-AA | F | F | $G^2$ | D | HHH | D | — | — | — | H | $NH_2$ |
| $P^4$ | Naph | N-AA | F | F | $G^2$ | D | HHD | D | — | — | — | H | $NH_2$ |
| $P^4$ | Naph | N-AA | F | F | $G^2$ | D | HDD | D | — | — | — | H | $NH_2$ |
| $P^4$ | Naph | N-AA | F | F | $G^2$ | D | DDD | D | — | — | — | H | $NH_2$ |
| $P^4$ | Naph | N-AA | F | F | $G^2$ | H | HHH | H | — | — | — | D | $OCH_2CH_3$ |
| $P^4$ | Naph | N-AA | F | F | $G^2$ | H | HHD | H | — | — | — | D | $OCH_2CH_3$ |
| $P^4$ | Naph | N-AA | F | F | $G^2$ | H | HDD | H | — | — | — | D | $OCH_2CH_3$ |
| $P^4$ | Naph | N-AA | F | F | $G^2$ | H | DDD | H | — | — | — | D | $OCH_2CH_3$ |
| $P^4$ | Naph | N-AA | F | F | $G^2$ | H | HHH | D | — | — | — | D | $OCH_2CH_3$ |
| $P^4$ | Naph | N-AA | F | F | $G^2$ | H | HHD | D | — | — | — | D | $OCH_2CH_3$ |
| $P^4$ | Naph | N-AA | F | F | $G^2$ | H | DDD | D | — | — | — | D | $OCH_2CH_3$ |
| $P^4$ | Naph | N-AA | F | F | $G^2$ | D | HHH | H | — | — | — | D | $OCH_2CH_3$ |
| $P^4$ | Naph | N-AA | F | F | $G^2$ | D | HHD | H | — | — | — | D | $OCH_2CH_3$ |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | Naph | N-AA | F | F | $G^2$ | D | HDD | H | — | — | — | D | $OCH_2CH_3$ |
| $P^4$ | Naph | N-AA | F | F | $G^2$ | D | DDD | H | — | — | — | D | $OCH_2CH_3$ |
| $P^4$ | Naph | N-AA | F | F | $G^2$ | D | HHH | D | — | — | — | D | $OCH_2CH_3$ |
| $P^4$ | Naph | N-AA | F | F | $G^2$ | D | HHD | D | — | — | — | D | $OCH_2CH_3$ |
| $P^4$ | Naph | N-AA | F | F | $G^2$ | D | HDD | D | — | — | — | D | $OCH_2CH_3$ |
| $P^4$ | Naph | N-AA | F | F | $G^2$ | D | DDD | D | — | — | — | D | $OCH_2CH_3$ |
| $P^4$ | Naph | N-AA | F | F | $G^2$ | H | HHH | H | — | — | — | D | $NH_2$ |
| $P^4$ | Naph | N-AA | F | F | $G^2$ | H | HHD | H | — | — | — | D | $NH_2$ |
| $P^4$ | Naph | N-AA | F | F | $G^2$ | H | HDD | H | — | — | — | D | $NH_2$ |
| $P^4$ | Naph | N-AA | F | F | $G^2$ | H | DDD | H | — | — | — | D | $NH_2$ |
| $P^4$ | Naph | N-AA | F | F | $G^2$ | H | HHD | D | — | — | — | D | $NH_2$ |
| $P^4$ | Naph | N-AA | F | F | $G^2$ | H | HDD | D | — | — | — | D | $NH_2$ |
| $P^4$ | Naph | N-AA | F | F | $G^2$ | H | DDD | D | — | — | — | D | $NH_2$ |
| $P^4$ | Naph | N-AA | F | F | $G^2$ | D | HHH | H | — | — | — | D | $NH_2$ |
| $P^4$ | Naph | N-AA | F | F | $G^2$ | D | HHD | H | — | — | — | D | $NH_2$ |
| $P^4$ | Naph | N-AA | F | F | $G^2$ | D | HDD | H | — | — | — | D | $NH_2$ |
| $P^4$ | Naph | N-AA | F | F | $G^2$ | D | DDD | H | — | — | — | D | $NH_2$ |
| $P^4$ | Naph | N-AA | F | F | $G^2$ | D | HHH | D | — | — | — | D | $NH_2$ |
| $P^4$ | Naph | N-AA | F | F | $G^2$ | D | HHD | D | — | — | — | D | $NH_2$ |
| $P^4$ | Naph | N-AA | F | F | $G^2$ | D | HDD | D | — | — | — | D | $NH_2$ |
| $P^4$ | Naph | N-AA | F | F | $G^2$ | D | DDD | D | — | — | — | D | $NH_2$ |
| $P^4$ | POC | POC | OH | OH | $G^2$ | H | HHH | H | — | — | — | H | $OCH_2CH_3$ |
| $P^4$ | POC | POC | OH | OH | $G^2$ | H | HHD | H | — | — | — | H | $OCH_2CH_3$ |
| $P^4$ | POC | POC | OH | OH | $G^2$ | H | HDD | H | — | — | — | H | $OCH_2CH_3$ |
| $P^4$ | POC | POC | OH | OH | $G^2$ | H | DDD | H | — | — | — | H | $OCH_2CH_3$ |
| $P^4$ | POC | POC | OH | OH | $G^2$ | H | HHH | D | — | — | — | H | $OCH_2CH_3$ |
| $P^4$ | POC | POC | OH | OH | $G^2$ | H | HDD | D | — | — | — | H | $OCH_2CH_3$ |
| $P^4$ | POC | POC | OH | OH | $G^2$ | H | DDD | D | — | — | — | H | $OCH_2CH_3$ |
| $P^4$ | POC | POC | OH | OH | $G^2$ | D | HHH | H | — | — | — | H | $OCH_2CH_3$ |
| $P^4$ | POC | POC | OH | OH | $G^2$ | D | HHD | H | — | — | — | H | $OCH_2CH_3$ |
| $P^4$ | POC | POC | OH | OH | $G^2$ | D | DDD | H | — | — | — | H | $OCH_2CH_3$ |
| $P^4$ | POC | POC | OH | OH | $G^2$ | D | HHH | D | — | — | — | H | $OCH_2CH_3$ |
| $P^4$ | POC | POC | OH | OH | $G^2$ | D | HHD | D | — | — | — | H | $OCH_2CH_3$ |
| $P^4$ | POC | POC | OH | OH | $G^2$ | D | HDD | D | — | — | — | H | $OCH_2CH_3$ |
| $P^4$ | POC | POC | OH | OH | $G^2$ | D | DDD | D | — | — | — | H | $OCH_2CH_3$ |
| $P^4$ | POC | POC | OH | OH | $G^2$ | H | HHH | H | — | — | — | H | $NH_2$ |
| $P^4$ | POC | POC | OH | OH | $G^2$ | H | HHD | H | — | — | — | H | $NH_2$ |
| $P^4$ | POC | POC | OH | OH | $G^2$ | H | HDD | H | — | — | — | H | $NH_2$ |
| $P^4$ | POC | POC | OH | OH | $G^2$ | H | DDD | H | — | — | — | H | $NH_2$ |
| $P^4$ | POC | POC | OH | OH | $G^2$ | H | HHH | D | — | — | — | H | $NH_2$ |
| $P^4$ | POC | POC | OH | OH | $G^2$ | H | HHD | D | — | — | — | H | $NH_2$ |
| $P^4$ | POC | POC | OH | OH | $G^2$ | H | HDD | D | — | — | — | H | $NH_2$ |
| $P^4$ | POC | POC | OH | OH | $G^2$ | H | DDD | D | — | — | — | H | $NH_2$ |
| $P^4$ | POC | POC | OH | OH | $G^2$ | D | HHH | H | — | — | — | H | $NH_2$ |
| $P^4$ | POC | POC | OH | OH | $G^2$ | D | HDD | H | — | — | — | H | $NH_2$ |
| $P^4$ | POC | POC | OH | OH | $G^2$ | D | DDD | H | — | — | — | H | $NH_2$ |
| $P^4$ | POC | POC | OH | OH | $G^2$ | D | HHH | D | — | — | — | H | $NH_2$ |
| $P^4$ | POC | POC | OH | OH | $G^2$ | D | HHD | D | — | — | — | H | $NH_2$ |
| $P^4$ | POC | POC | OH | OH | $G^2$ | D | DDD | D | — | — | — | H | $NH_2$ |
| $P^4$ | POC | POC | OH | OH | $G^2$ | H | HHH | H | — | — | — | D | $OCH_2CH_3$ |
| $P^4$ | POC | POC | OH | OH | $G^2$ | H | HHD | H | — | — | — | D | $OCH_2CH_3$ |
| $P^4$ | POC | POC | OH | OH | $G^2$ | H | HDD | H | — | — | — | D | $OCH_2CH_3$ |
| $P^4$ | POC | POC | OH | OH | $G^2$ | H | DDD | H | — | — | — | D | $OCH_2CH_3$ |
| $P^4$ | POC | POC | OH | OH | $G^2$ | H | HHH | D | — | — | — | D | $OCH_2CH_3$ |
| $P^4$ | POC | POC | OH | OH | $G^2$ | H | HHD | D | — | — | — | D | $OCH_2CH_3$ |
| $P^4$ | POC | POC | OH | OH | $G^2$ | H | HDD | D | — | — | — | D | $OCH_2CH_3$ |
| $P^4$ | POC | POC | OH | OH | $G^2$ | H | DDD | D | — | — | — | D | $OCH_2CH_3$ |
| $P^4$ | POC | POC | OH | OH | $G^2$ | D | HHH | H | — | — | — | D | $OCH_2CH_3$ |
| $P^4$ | POC | POC | OH | OH | $G^2$ | D | HHD | H | — | — | — | D | $OCH_2CH_3$ |
| $P^4$ | POC | POC | OH | OH | $G^2$ | D | HDD | H | — | — | — | D | $OCH_2CH_3$ |
| $P^4$ | POC | POC | OH | OH | $G^2$ | D | DDD | H | — | — | — | D | $OCH_2CH_3$ |
| $P^4$ | POC | POC | OH | OH | $G^2$ | D | HHH | D | — | — | — | D | $OCH_2CH_3$ |
| $P^4$ | POC | POC | OH | OH | $G^2$ | D | HHD | D | — | — | — | D | $OCH_2CH_3$ |
| $P^4$ | POC | POC | OH | OH | $G^2$ | D | HDD | D | — | — | — | D | $OCH_2CH_3$ |
| $P^4$ | POC | POC | OH | OH | $G^2$ | D | DDD | D | — | — | — | D | $OCH_2CH_3$ |
| $P^4$ | POC | POC | OH | OH | $G^2$ | H | HHH | H | — | — | — | D | $NH_2$ |
| $P^4$ | POC | POC | OH | OH | $G^2$ | H | HHD | H | — | — | — | D | $NH_2$ |
| $P^4$ | POC | POC | OH | OH | $G^2$ | H | HDD | H | — | — | — | D | $NH_2$ |
| $P^4$ | POC | POC | OH | OH | $G^2$ | H | DDD | H | — | — | — | D | $NH_2$ |
| $P^4$ | POC | POC | OH | OH | $G^2$ | H | HHH | D | — | — | — | D | $NH_2$ |
| $P^4$ | POC | POC | OH | OH | $G^2$ | H | HHD | D | — | — | — | D | $NH_2$ |
| $P^4$ | POC | POC | OH | OH | $G^2$ | H | HDD | D | — | — | — | D | $NH_2$ |
| $P^4$ | POC | POC | OH | OH | $G^2$ | H | DDD | D | — | — | — | D | $NH_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,4}$ | $B^{2,4}$ | $B^{3,4}$ | $B^{4,4}$ | $B^{5,4}$ |
|---|---|---|---|---|---|---|---|---|---|---|---|---|---|
| $P^4$ | POC | POC | OH | OH | $G^2$ | D | HHH | H | — | — | — | D | $NH_2$ |
| $P^4$ | POC | POC | OH | OH | $G^2$ | D | HHD | H | — | — | — | D | $NH_2$ |
| $P^4$ | POC | POC | OH | OH | $G^2$ | D | HDD | H | — | — | — | D | $NH_2$ |
| $P^4$ | POC | POC | OH | OH | $G^2$ | D | DDD | H | — | — | — | D | $NH_2$ |
| $P^4$ | POC | POC | OH | OH | $G^2$ | D | HHH | D | — | — | — | D | $NH_2$ |
| $P^4$ | POC | POC | OH | OH | $G^2$ | D | HHD | D | — | — | — | D | $NH_2$ |
| $P^4$ | POC | POC | OH | OH | $G^2$ | D | HDD | D | — | — | — | D | $NH_2$ |
| $P^4$ | POC | POC | OH | OH | $G^2$ | D | DDD | D | — | — | — | D | $NH_2$ |
| $P^4$ | POC | POC | OH | F | $G^2$ | H | HHH | H | — | — | — | H | $OCH_2CH_3$ |
| $P^4$ | POC | POC | OH | F | $G^2$ | H | HHD | H | — | — | — | H | $OCH_2CH_3$ |
| $P^4$ | POC | POC | OH | F | $G^2$ | H | HDD | H | — | — | — | H | $OCH_2CH_3$ |
| $P^4$ | POC | POC | OH | F | $G^2$ | H | DDD | H | — | — | — | H | $OCH_2CH_3$ |
| $P^4$ | POC | POC | OH | F | $G^2$ | H | HHH | D | — | — | — | H | $OCH_2CH_3$ |
| $P^4$ | POC | POC | OH | F | $G^2$ | H | HHD | D | — | — | — | H | $OCH_2CH_3$ |
| $P^4$ | POC | POC | OH | F | $G^2$ | H | HDD | D | — | — | — | H | $OCH_2CH_3$ |
| $P^4$ | POC | POC | OH | F | $G^2$ | H | DDD | D | — | — | — | H | $OCH_2CH_3$ |
| $P^4$ | POC | POC | OH | F | $G^2$ | D | HHH | H | — | — | — | H | $OCH_2CH_3$ |
| $P^4$ | POC | POC | OH | F | $G^2$ | D | HHD | H | — | — | — | H | $OCH_2CH_3$ |
| $P^4$ | POC | POC | OH | F | $G^2$ | D | HDD | H | — | — | — | H | $OCH_2CH_3$ |
| $P^4$ | POC | POC | OH | F | $G^2$ | D | DDD | H | — | — | — | H | $OCH_2CH_3$ |
| $P^4$ | POC | POC | OH | F | $G^2$ | D | HHH | D | — | — | — | H | $OCH_2CH_3$ |
| $P^4$ | POC | POC | OH | F | $G^2$ | D | HHD | D | — | — | — | H | $OCH_2CH_3$ |
| $P^4$ | POC | POC | OH | F | $G^2$ | D | HDD | D | — | — | — | H | $OCH_2CH_3$ |
| $P^4$ | POC | POC | OH | F | $G^2$ | D | DDD | D | — | — | — | H | $OCH_2CH_3$ |
| $P^4$ | POC | POC | OH | F | $G^2$ | H | HHH | H | — | — | — | H | $NH_2$ |
| $P^4$ | POC | POC | OH | F | $G^2$ | H | HHD | H | — | — | — | H | $NH_2$ |
| $P^4$ | POC | POC | OH | F | $G^2$ | H | HDD | H | — | — | — | H | $NH_2$ |
| $P^4$ | POC | POC | OH | F | $G^2$ | H | DDD | H | — | — | — | H | $NH_2$ |
| $P^4$ | POC | POC | OH | F | $G^2$ | H | HHH | D | — | — | — | H | $NH_2$ |
| $P^4$ | POC | POC | OH | F | $G^2$ | H | HHD | D | — | — | — | H | $NH_2$ |
| $P^4$ | POC | POC | OH | F | $G^2$ | H | HDD | D | — | — | — | H | $NH_2$ |
| $P^4$ | POC | POC | OH | F | $G^2$ | H | DDD | D | — | — | — | H | $NH_2$ |
| $P^4$ | POC | POC | OH | F | $G^2$ | D | HHH | H | — | — | — | H | $NH_2$ |
| $P^4$ | POC | POC | OH | F | $G^2$ | D | HHD | H | — | — | — | H | $NH_2$ |
| $P^4$ | POC | POC | OH | F | $G^2$ | D | HDD | H | — | — | — | H | $NH_2$ |
| $P^4$ | POC | POC | OH | F | $G^2$ | D | DDD | H | — | — | — | H | $NH_2$ |
| $P^4$ | POC | POC | OH | F | $G^2$ | D | HHH | D | — | — | — | H | $NH_2$ |
| $P^4$ | POC | POC | OH | F | $G^2$ | D | HHD | D | — | — | — | H | $NH_2$ |
| $P^4$ | POC | POC | OH | F | $G^2$ | D | HDD | D | — | — | — | H | $NH_2$ |
| $P^4$ | POC | POC | OH | F | $G^2$ | D | DDD | D | — | — | — | H | $NH_2$ |
| $P^4$ | POC | POC | OH | F | $G^2$ | H | HHH | H | — | — | — | D | $OCH_2CH_3$ |
| $P^4$ | POC | POC | OH | F | $G^2$ | H | HHD | H | — | — | — | D | $OCH_2CH_3$ |
| $P^4$ | POC | POC | OH | F | $G^2$ | H | HDD | H | — | — | — | D | $OCH_2CH_3$ |
| $P^4$ | POC | POC | OH | F | $G^2$ | H | DDD | H | — | — | — | D | $OCH_2CH_3$ |
| $P^4$ | POC | POC | OH | F | $G^2$ | H | HHH | D | — | — | — | D | $OCH_2CH_3$ |
| $P^4$ | POC | POC | OH | F | $G^2$ | H | HHD | D | — | — | — | D | $OCH_2CH_3$ |
| $P^4$ | POC | POC | OH | F | $G^2$ | H | HDD | D | — | — | — | D | $OCH_2CH_3$ |
| $P^4$ | POC | POC | OH | F | $G^2$ | H | DDD | D | — | — | — | D | $OCH_2CH_3$ |
| $P^4$ | POC | POC | OH | F | $G^2$ | D | HHH | H | — | — | — | D | $OCH_2CH_3$ |
| $P^4$ | POC | POC | OH | F | $G^2$ | D | HHD | H | — | — | — | D | $OCH_2CH_3$ |
| $P^4$ | POC | POC | OH | F | $G^2$ | D | HDD | H | — | — | — | D | $OCH_2CH_3$ |
| $P^4$ | POC | POC | OH | F | $G^2$ | D | DDD | H | — | — | — | D | $OCH_2CH_3$ |
| $P^4$ | POC | POC | OH | F | $G^2$ | D | HHH | D | — | — | — | D | $OCH_2CH_3$ |
| $P^4$ | POC | POC | OH | F | $G^2$ | D | HHD | D | — | — | — | D | $OCH_2CH_3$ |
| $P^4$ | POC | POC | OH | F | $G^2$ | D | HDD | D | — | — | — | D | $OCH_2CH_3$ |
| $P^4$ | POC | POC | OH | F | $G^2$ | D | DDD | D | — | — | — | D | $OCH_2CH_3$ |
| $P^4$ | POC | POC | OH | F | $G^2$ | H | HHH | H | — | — | — | D | $NH_2$ |
| $P^4$ | POC | POC | OH | F | $G^2$ | H | HHD | H | — | — | — | D | $NH_2$ |
| $P^4$ | POC | POC | OH | F | $G^2$ | H | HDD | H | — | — | — | D | $NH_2$ |
| $P^4$ | POC | POC | OH | F | $G^2$ | H | DDD | H | — | — | — | D | $NH_2$ |
| $P^4$ | POC | POC | OH | F | $G^2$ | H | HHH | D | — | — | — | D | $NH_2$ |
| $P^4$ | POC | POC | OH | F | $G^2$ | H | HHD | D | — | — | — | D | $NH_2$ |
| $P^4$ | POC | POC | OH | F | $G^2$ | H | HDD | D | — | — | — | D | $NH_2$ |
| $P^4$ | POC | POC | OH | F | $G^2$ | H | DDD | D | — | — | — | D | $NH_2$ |
| $P^4$ | POC | POC | OH | F | $G^2$ | D | HHH | H | — | — | — | D | $NH_2$ |
| $P^4$ | POC | POC | OH | F | $G^2$ | D | HHD | H | — | — | — | D | $NH_2$ |
| $P^4$ | POC | POC | OH | F | $G^2$ | D | HDD | H | — | — | — | D | $NH_2$ |
| $P^4$ | POC | POC | OH | F | $G^2$ | D | DDD | H | — | — | — | D | $NH_2$ |
| $P^4$ | POC | POC | OH | F | $G^2$ | D | HHH | D | — | — | — | D | $NH_2$ |
| $P^4$ | POC | POC | OH | F | $G^2$ | D | HHD | D | — | — | — | D | $NH_2$ |
| $P^4$ | POC | POC | OH | F | $G^2$ | D | HDD | D | — | — | — | D | $NH_2$ |
| $P^4$ | POC | POC | OH | F | $G^2$ | D | DDD | D | — | — | — | D | $NH_2$ |
| $P^4$ | POC | POC | F | OH | $G^2$ | H | HHH | H | — | — | — | H | $OCH_2CH_3$ |
| $P^4$ | POC | POC | F | OH | $G^2$ | H | HHD | H | — | — | — | H | $OCH_2CH_3$ |
| $P^4$ | POC | POC | F | OH | $G^2$ | H | HDD | H | — | — | — | H | $OCH_2CH_3$ |
| $P^4$ | POC | POC | F | OH | $G^2$ | H | DDD | H | — | — | — | H | $OCH_2CH_3$ |
| $P^4$ | POC | POC | F | OH | $G^2$ | H | HHH | D | — | — | — | H | $OCH_2CH_3$ |
| $P^4$ | POC | POC | F | OH | $G^2$ | H | HHD | D | — | — | — | H | $OCH_2CH_3$ |

TABLE 3-continued

| $R^P$ | $R^1$ | $R^2$ | $R^4$ | $R^5$ | $B^1$ | $R^3$ | $(R^6)_3$ | $R^7$ | $B^{1,4}$ | $B^{2,4}$ | $B^{3,4}$ | $B^{4,4}$ | $B^{5,4}$ |
|---|---|---|---|---|---|---|---|---|---|---|---|---|---|
| $P^4$ | POC | POC | F | OH | $G^2$ | H | HDD | D | — | — | — | H | $OCH_2CH_3$ |
| $P^4$ | POC | POC | F | OH | $G^2$ | H | DDD | D | — | — | — | H | $OCH_2CH_3$ |
| $P^4$ | POC | POC | F | OH | $G^2$ | D | HHH | H | — | — | — | H | $OCH_2CH_3$ |
| $P^4$ | POC | POC | F | OH | $G^2$ | D | HHD | H | — | — | — | H | $OCH_2CH_3$ |
| $P^4$ | POC | POC | F | OH | $G^2$ | D | HDD | H | — | — | — | H | $OCH_2CH_3$ |
| $P^4$ | POC | POC | F | OH | $G^2$ | D | DDD | H | — | — | — | H | $OCH_2CH_3$ |
| $P^4$ | POC | POC | F | OH | $G^2$ | D | HHH | D | — | — | — | H | $OCH_2CH_3$ |
| $P^4$ | POC | POC | F | OH | $G^2$ | D | HHD | D | — | — | — | H | $OCH_2CH_3$ |
| $P^4$ | POC | POC | F | OH | $G^2$ | D | HDD | D | — | — | — | H | $OCH_2CH_3$ |
| $P^4$ | POC | POC | F | OH | $G^2$ | D | DDD | D | — | — | — | H | $OCH_2CH_3$ |
| $P^4$ | POC | POC | F | OH | $G^2$ | H | HHH | H | — | — | — | H | $NH_2$ |
| $P^4$ | POC | POC | F | OH | $G^2$ | H | HHD | H | — | — | — | H | $NH_2$ |
| $P^4$ | POC | POC | F | OH | $G^2$ | H | HDD | H | — | — | — | H | $NH_2$ |
| $P^4$ | POC | POC | F | OH | $G^2$ | H | DDD | H | — | — | — | H | $NH_2$ |
| $P^4$ | POC | POC | F | OH | $G^2$ | H | HHH | D | — | — | — | H | $NH_2$ |
| $P^4$ | POC | POC | F | OH | $G^2$ | H | HHD | D | — | — | — | H | $NH_2$ |
| $P^4$ | POC | POC | F | OH | $G^2$ | H | HDD | D | — | — | — | H | $NH_2$ |
| $P^4$ | POC | POC | F | OH | $G^2$ | H | DDD | D | — | — | — | H | $NH_2$ |
| $P^4$ | POC | POC | F | OH | $G^2$ | D | HHH | H | — | — | — | H | $NH_2$ |
| $P^4$ | POC | POC | F | OH | $G^2$ | D | HHD | H | — | — | — | H | $NH_2$ |
| $P^4$ | POC | POC | F | OH | $G^2$ | D | HDD | H | — | — | — | H | $NH_2$ |
| $P^4$ | POC | POC | F | OH | $G^2$ | D | DDD | H | — | — | — | H | $NH_2$ |
| $P^4$ | POC | POC | F | OH | $G^2$ | D | HHH | D | — | — | — | H | $NH_2$ |
| $P^4$ | POC | POC | F | OH | $G^2$ | D | HHD | D | — | — | — | H | $NH_2$ |
| $P^4$ | POC | POC | F | OH | $G^2$ | D | HDD | D | — | — | — | H | $NH_2$ |
| $P^4$ | POC | POC | F | OH | $G^2$ | D | DDD | D | — | — | — | H | $NH_2$ |
| $P^4$ | POC | POC | F | OH | $G^2$ | H | HHH | H | — | — | — | D | $OCH_2CH_3$ |
| $P^4$ | POC | POC | F | OH | $G^2$ | H | HHD | H | — | — | — | D | $OCH_2CH_3$ |
| $P^4$ | POC | POC | F | OH | $G^2$ | H | HDD | H | — | — | — | D | $OCH_2CH_3$ |
| $P^4$ | POC | POC | F | OH | $G^2$ | H | DDD | H | — | — | — | D | $OCH_2CH_3$ |
| $P^4$ | POC | POC | F | OH | $G^2$ | H | HHH | D | — | — | — | D | $OCH_2CH_3$ |
| $P^4$ | POC | POC | F | OH | $G^2$ | H | HHD | D | — | — | — | D | $OCH_2CH_3$ |
| $P^4$ | POC | POC | F | OH | $G^2$ | H | HDD | D | — | — | — | D | $OCH_2CH_3$ |
| $P^4$ | POC | POC | F | OH | $G^2$ | H | DDD | D | — | — | — | D | $OCH_2CH_3$ |
| $P^4$ | POC | POC | F | OH | $G^2$ | D | HHH | H | — | — | — | D | $OCH_2CH_3$ |
| $P^4$ | POC | POC | F | OH | $G^2$ | D | HHD | H | — | — | — | D | $OCH_2CH_3$ |
| $P^4$ | POC | POC | F | OH | $G^2$ | D | HDD | H | — | — | — | D | $OCH_2CH_3$ |
| $P^4$ | POC | POC | F | OH | $G^2$ | D | DDD | H | — | — | — | D | $OCH_2CH_3$ |
| $P^4$ | POC | POC | F | OH | $G^2$ | D | HHH | D | — | — | — | D | $OCH_2CH_3$ |
| $P^4$ | POC | POC | F | OH | $G^2$ | D | HHD | D | — | — | — | D | $OCH_2CH_3$ |
| $P^4$ | POC | POC | F | OH | $G^2$ | D | HDD | D | — | — | — | D | $OCH_2CH_3$ |
| $P^4$ | POC | POC | F | OH | $G^2$ | D | DDD | D | — | — | — | D | $OCH_2CH_3$ |
| $P^4$ | POC | POC | F | OH | $G^2$ | H | HHH | H | — | — | — | D | $NH_2$ |
| $P^4$ | POC | POC | F | OH | $G^2$ | H | HHD | H | — | — | — | D | $NH_2$ |
| $P^4$ | POC | POC | F | OH | $G^2$ | H | HDD | H | — | — | — | D | $NH_2$ |
| $P^4$ | POC | POC | F | OH | $G^2$ | H | DDD | H | — | — | — | D | $NH_2$ |
| $P^4$ | POC | POC | F | OH | $G^2$ | H | HHH | D | — | — | — | D | $NH_2$ |
| $P^4$ | POC | POC | F | OH | $G^2$ | H | HHD | D | — | — | — | D | $NH_2$ |
| $P^4$ | POC | POC | F | OH | $G^2$ | H | HDD | D | — | — | — | D | $NH_2$ |
| $P^4$ | POC | POC | F | OH | $G^2$ | H | DDD | D | — | — | — | D | $NH_2$ |
| $P^4$ | POC | POC | F | OH | $G^2$ | D | HHH | H | — | — | — | D | $NH_2$ |
| $P^4$ | POC | POC | F | OH | $G^2$ | D | HHD | H | — | — | — | D | $NH_2$ |
| $P^4$ | POC | POC | F | OH | $G^2$ | D | HDD | H | — | — | — | D | $NH_2$ |
| $P^4$ | POC | POC | F | OH | $G^2$ | D | DDD | H | — | — | — | D | $NH_2$ |
| $P^4$ | POC | POC | F | OH | $G^2$ | D | HHH | D | — | — | — | D | $NH_2$ |
| $P^4$ | POC | POC | F | OH | $G^2$ | D | HHD | D | — | — | — | D | $NH_2$ |
| $P^4$ | POC | POC | F | OH | $G^2$ | D | HDD | D | — | — | — | D | $NH_2$ |
| $P^4$ | POC | POC | F | OH | $G^2$ | D | DDD | D | — | — | — | D | $NH_2$ |
| $P^4$ | POC | POC | F | F | $G^2$ | H | HHH | H | — | — | — | H | $OCH_2CH_3$ |
| $P^4$ | POC | POC | F | F | $G^2$ | H | HHD | H | — | — | — | H | $OCH_2CH_3$ |
| $P^4$ | POC | POC | F | F | $G^2$ | H | HDD | H | — | — | — | H | $OCH_2CH_3$ |
| $P^4$ | POC | POC | F | F | $G^2$ | H | DDD | H | — | — | — | H | $OCH_2CH_3$ |
| $P^4$ | POC | POC | F | F | $G^2$ | H | HHH | D | — | — | — | H | $OCH_2CH_3$ |
| $P^4$ | POC | POC | F | F | $G^2$ | H | HHD | D | — | — | — | H | $OCH_2CH_3$ |
| $P^4$ | POC | POC | F | F | $G^2$ | H | HDD | D | — | — | — | H | $OCH_2CH_3$ |
| $P^4$ | POC | POC | F | F | $G^2$ | H | DDD | D | — | — | — | H | $OCH_2CH_3$ |
| $P^4$ | POC | POC | F | F | $G^2$ | D | HHH | H | — | — | — | H | $OCH_2CH_3$ |
| $P^4$ | POC | POC | F | F | $G^2$ | D | HHD | H | — | — | — | H | $OCH_2CH_3$ |
| $P^4$ | POC | POC | F | F | $G^2$ | D | HDD | H | — | — | — | H | $OCH_2CH_3$ |
| $P^4$ | POC | POC | F | F | $G^2$ | D | DDD | H | — | — | — | H | $OCH_2CH_3$ |
| $P^4$ | POC | POC | F | F | $G^2$ | D | HHH | D | — | — | — | H | $OCH_2CH_3$ |
| $P^4$ | POC | POC | F | F | $G^2$ | D | HHD | D | — | — | — | H | $OCH_2CH_3$ |
| $P^4$ | POC | POC | F | F | $G^2$ | D | HDD | D | — | — | — | H | $OCH_2CH_3$ |
| $P^4$ | POC | POC | F | F | $G^2$ | D | DDD | D | — | — | — | H | $OCH_2CH_3$ |
| $P^4$ | POC | POC | F | F | $G^2$ | H | HHH | H | — | — | — | H | $NH_2$ |
| $P^4$ | POC | POC | F | F | $G^2$ | H | HHD | H | — | — | — | H | $NH_2$ |
| $P^4$ | POC | POC | F | F | $G^2$ | H | HDD | H | — | — | — | H | $NH_2$ |
| $P^4$ | POC | POC | F | F | $G^2$ | H | DDD | H | — | — | — | H | $NH_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,4}$ | $B^{2,4}$ | $B^{3,4}$ | $B^{4,4}$ | $B^{5,4}$ |
|---|---|---|---|---|---|---|---|---|---|---|---|---|---|
| $P^4$ | POC | POC | F | F | $G^2$ | H | HHH | D | — | — | — | H | $NH_2$ |
| $P^4$ | POC | POC | F | F | $G^2$ | H | HHD | D | — | — | — | H | $NH_2$ |
| $P^4$ | POC | POC | F | F | $G^2$ | H | HDD | D | — | — | — | H | $NH_2$ |
| $P^4$ | POC | POC | F | F | $G^2$ | H | DDD | D | — | — | — | H | $NH_2$ |
| $P^4$ | POC | POC | F | F | $G^2$ | D | HHH | H | — | — | — | H | $NH_2$ |
| $P^4$ | POC | POC | F | F | $G^2$ | D | HHD | H | — | — | — | H | $NH_2$ |
| $P^4$ | POC | POC | F | F | $G^2$ | D | HDD | H | — | — | — | H | $NH_2$ |
| $P^4$ | POC | POC | F | F | $G^2$ | D | DDD | H | — | — | — | H | $NH_2$ |
| $P^4$ | POC | POC | F | F | $G^2$ | D | HHH | D | — | — | — | H | $NH_2$ |
| $P^4$ | POC | POC | F | F | $G^2$ | D | HHD | D | — | — | — | H | $NH_2$ |
| $P^4$ | POC | POC | F | F | $G^2$ | D | HDD | D | — | — | — | H | $NH_2$ |
| $P^4$ | POC | POC | F | F | $G^2$ | D | DDD | D | — | — | — | H | $NH_2$ |
| $P^4$ | POC | POC | F | F | $G^2$ | H | HHH | H | — | — | — | D | $OCH_2CH_3$ |
| $P^4$ | POC | POC | F | F | $G^2$ | H | HHD | H | — | — | — | D | $OCH_2CH_3$ |
| $P^4$ | POC | POC | F | F | $G^2$ | H | HDD | H | — | — | — | D | $OCH_2CH_3$ |
| $P^4$ | POC | POC | F | F | $G^2$ | H | DDD | H | — | — | — | D | $OCH_2CH_3$ |
| $P^4$ | POC | POC | F | F | $G^2$ | H | HHH | D | — | — | — | D | $OCH_2CH_3$ |
| $P^4$ | POC | POC | F | F | $G^2$ | H | HHD | D | — | — | — | D | $OCH_2CH_3$ |
| $P^4$ | POC | POC | F | F | $G^2$ | H | HDD | D | — | — | — | D | $OCH_2CH_3$ |
| $P^4$ | POC | POC | F | F | $G^2$ | H | DDD | D | — | — | — | D | $OCH_2CH_3$ |
| $P^4$ | POC | POC | F | F | $G^2$ | D | HHH | H | — | — | — | D | $OCH_2CH_3$ |
| $P^4$ | POC | POC | F | F | $G^2$ | D | HHD | H | — | — | — | D | $OCH_2CH_3$ |
| $P^4$ | POC | POC | F | F | $G^2$ | D | HDD | H | — | — | — | D | $OCH_2CH_3$ |
| $P^4$ | POC | POC | F | F | $G^2$ | D | DDD | H | — | — | — | D | $OCH_2CH_3$ |
| $P^4$ | POC | POC | F | F | $G^2$ | D | HHH | D | — | — | — | D | $OCH_2CH_3$ |
| $P^4$ | POC | POC | F | F | $G^2$ | D | HHD | D | — | — | — | D | $OCH_2CH_3$ |
| $P^4$ | POC | POC | F | F | $G^2$ | D | HDD | D | — | — | — | D | $OCH_2CH_3$ |
| $P^4$ | POC | POC | F | F | $G^2$ | D | DDD | D | — | — | — | D | $OCH_2CH_3$ |
| $P^4$ | POC | POC | F | F | $G^2$ | H | HHH | H | — | — | — | D | $NH_2$ |
| $P^4$ | POC | POC | F | F | $G^2$ | H | HHD | H | — | — | — | D | $NH_2$ |
| $P^4$ | POC | POC | F | F | $G^2$ | H | HDD | H | — | — | — | D | $NH_2$ |
| $P^4$ | POC | POC | F | F | $G^2$ | H | DDD | H | — | — | — | D | $NH_2$ |
| $P^4$ | POC | POC | F | F | $G^2$ | H | HHH | D | — | — | — | D | $NH_2$ |
| $P^4$ | POC | POC | F | F | $G^2$ | H | HHD | D | — | — | — | D | $NH_2$ |
| $P^4$ | POC | POC | F | F | $G^2$ | H | HDD | D | — | — | — | D | $NH_2$ |
| $P^4$ | POC | POC | F | F | $G^2$ | H | DDD | D | — | — | — | D | $NH_2$ |
| $P^4$ | POC | POC | F | F | $G^2$ | D | HHH | H | — | — | — | D | $NH_2$ |
| $P^4$ | POC | POC | F | F | $G^2$ | D | HHD | H | — | — | — | D | $NH_2$ |
| $P^4$ | POC | POC | F | F | $G^2$ | D | HDD | H | — | — | — | D | $NH_2$ |
| $P^4$ | POC | POC | F | F | $G^2$ | D | DDD | H | — | — | — | D | $NH_2$ |
| $P^4$ | POC | POC | F | F | $G^2$ | D | HHH | D | — | — | — | D | $NH_2$ |
| $P^4$ | POC | POC | F | F | $G^2$ | D | HHD | D | — | — | — | D | $NH_2$ |
| $P^4$ | POC | POC | F | F | $G^2$ | D | HDD | D | — | — | — | D | $NH_2$ |
| $P^4$ | POC | POC | F | F | $G^2$ | D | DDD | D | — | — | — | D | $NH_2$ |
| $P^4$ | $P^1$ | $OH/O^-$ | OH | OH | $G^2$ | H | HHH | H | — | — | — | H | $OCH_2CH_3$ |
| $P^4$ | $P^1$ | $OH/O^-$ | OH | OH | $G^2$ | H | HHD | H | — | — | — | H | $OCH_2CH_3$ |
| $P^4$ | $P^1$ | $OH/O^-$ | OH | OH | $G^2$ | H | HDD | H | — | — | — | H | $OCH_2CH_3$ |
| $P^4$ | $P^1$ | $OH/O^-$ | OH | OH | $G^2$ | H | DDD | H | — | — | — | H | $OCH_2CH_3$ |
| $P^4$ | $P^1$ | $OH/O^-$ | OH | OH | $G^2$ | H | HHH | D | — | — | — | H | $OCH_2CH_3$ |
| $P^4$ | $P^1$ | $OH/O^-$ | OH | OH | $G^2$ | H | HHD | D | — | — | — | H | $OCH_2CH_3$ |
| $P^4$ | $P^1$ | $OH/O^-$ | OH | OH | $G^2$ | H | HDD | D | — | — | — | H | $OCH_2CH_3$ |
| $P^4$ | $P^1$ | $OH/O^-$ | OH | OH | $G^2$ | H | DDD | D | — | — | — | H | $OCH_2CH_3$ |
| $P^4$ | $P^1$ | $OH/O^-$ | OH | OH | $G^2$ | D | HHH | H | — | — | — | H | $OCH_2CH_3$ |
| $P^4$ | $P^1$ | $OH/O^-$ | OH | OH | $G^2$ | D | HHD | H | — | — | — | H | $OCH_2CH_3$ |
| $P^4$ | $P^1$ | $OH/O^-$ | OH | OH | $G^2$ | D | HDD | H | — | — | — | H | $OCH_2CH_3$ |
| $P^4$ | $P^1$ | $OH/O^-$ | OH | OH | $G^2$ | D | DDD | H | — | — | — | H | $OCH_2CH_3$ |
| $P^4$ | $P^1$ | $OH/O^-$ | OH | OH | $G^2$ | D | HHH | D | — | — | — | H | $OCH_2CH_3$ |
| $P^4$ | $P^1$ | $OH/O^-$ | OH | OH | $G^2$ | D | HHD | D | — | — | — | H | $OCH_2CH_3$ |
| $P^4$ | $P^1$ | $OH/O^-$ | OH | OH | $G^2$ | D | HDD | D | — | — | — | H | $OCH_2CH_3$ |
| $P^4$ | $P^1$ | $OH/O^-$ | OH | OH | $G^2$ | D | DDD | D | — | — | — | H | $OCH_2CH_3$ |
| $P^4$ | $P^1$ | $OH/O^-$ | OH | OH | $G^2$ | H | HHH | H | — | — | — | H | $NH_2$ |
| $P^4$ | $P^1$ | $OH/O^-$ | OH | OH | $G^2$ | H | HHD | H | — | — | — | H | $NH_2$ |
| $P^4$ | $P^1$ | $OH/O^-$ | OH | OH | $G^2$ | H | HDD | H | — | — | — | H | $NH_2$ |
| $P^4$ | $P^1$ | $OH/O^-$ | OH | OH | $G^2$ | H | DDD | H | — | — | — | H | $NH_2$ |
| $P^4$ | $P^1$ | $OH/O^-$ | OH | OH | $G^2$ | H | HHH | D | — | — | — | H | $NH_2$ |
| $P^4$ | $P^1$ | $OH/O^-$ | OH | OH | $G^2$ | H | HHD | D | — | — | — | H | $NH_2$ |
| $P^4$ | $P^1$ | $OH/O^-$ | OH | OH | $G^2$ | H | HDD | D | — | — | — | H | $NH_2$ |
| $P^4$ | $P^1$ | $OH/O^-$ | OH | OH | $G^2$ | H | DDD | D | — | — | — | H | $NH_2$ |
| $P^4$ | $P^1$ | $OH/O^-$ | OH | OH | $G^2$ | D | HHH | H | — | — | — | H | $NH_2$ |
| $P^4$ | $P^1$ | $OH/O^-$ | OH | OH | $G^2$ | D | HHD | H | — | — | — | H | $NH_2$ |
| $P^4$ | $P^1$ | $OH/O^-$ | OH | OH | $G^2$ | D | HDD | H | — | — | — | H | $NH_2$ |
| $P^4$ | $P^1$ | $OH/O^-$ | OH | OH | $G^2$ | D | DDD | H | — | — | — | H | $NH_2$ |
| $P^4$ | $P^1$ | $OH/O^-$ | OH | OH | $G^2$ | D | HHH | D | — | — | — | H | $NH_2$ |
| $P^4$ | $P^1$ | $OH/O^-$ | OH | OH | $G^2$ | D | HHD | D | — | — | — | H | $NH_2$ |
| $P^4$ | $P^1$ | $OH/O^-$ | OH | OH | $G^2$ | D | HDD | D | — | — | — | H | $NH_2$ |
| $P^4$ | $P^1$ | $OH/O^-$ | OH | OH | $G^2$ | D | DDD | D | — | — | — | H | $NH_2$ |
| $P^4$ | $P^1$ | $OH/O^-$ | OH | OH | $G^2$ | H | HHH | H | — | — | — | D | $OCH_2CH_3$ |
| $P^4$ | $P^1$ | $OH/O^-$ | OH | OH | $G^2$ | H | HHD | H | — | — | — | D | $OCH_2CH_3$ |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^4$ | $P^1$ | OH/O$^-$ | OH | OH | $G^2$ | H | HDD | H | — | — | — | D | OCH$_2$CH$_3$ |
| $P^4$ | $P^1$ | OH/O$^-$ | OH | OH | $G^2$ | H | DDD | H | — | — | — | D | OCH$_2$CH$_3$ |
| $P^4$ | $P^1$ | OH/O$^-$ | OH | OH | $G^2$ | H | HHH | D | — | — | — | D | OCH$_2$CH$_3$ |
| $P^4$ | $P^1$ | OH/O$^-$ | OH | OH | $G^2$ | H | HHD | D | — | — | — | D | OCH$_2$CH$_3$ |
| $P^4$ | $P^1$ | OH/O$^-$ | OH | OH | $G^2$ | H | HDD | D | — | — | — | D | OCH$_2$CH$_3$ |
| $P^4$ | $P^1$ | OH/O$^-$ | OH | OH | $G^2$ | H | DDD | D | — | — | — | D | OCH$_2$CH$_3$ |
| $P^4$ | $P^1$ | OH/O$^-$ | OH | OH | $G^2$ | D | HHH | H | — | — | — | D | OCH$_2$CH$_3$ |
| $P^4$ | $P^1$ | OH/O$^-$ | OH | OH | $G^2$ | D | HHD | H | — | — | — | D | OCH$_2$CH$_3$ |
| $P^4$ | $P^1$ | OH/O$^-$ | OH | OH | $G^2$ | D | HDD | H | — | — | — | D | OCH$_2$CH$_3$ |
| $P^4$ | $P^1$ | OH/O$^-$ | OH | OH | $G^2$ | D | DDD | H | — | — | — | D | OCH$_2$CH$_3$ |
| $P^4$ | $P^1$ | OH/O$^-$ | OH | OH | $G^2$ | D | HHH | D | — | — | — | D | OCH$_2$CH$_3$ |
| $P^4$ | $P^1$ | OH/O$^-$ | OH | OH | $G^2$ | D | HHD | D | — | — | — | D | OCH$_2$CH$_3$ |
| $P^4$ | $P^1$ | OH/O$^-$ | OH | OH | $G^2$ | D | HDD | D | — | — | — | D | OCH$_2$CH$_3$ |
| $P^4$ | $P^1$ | OH/O$^-$ | OH | OH | $G^2$ | D | DDD | D | — | — | — | D | OCH$_2$CH$_3$ |
| $P^4$ | $P^1$ | OH/O$^-$ | OH | OH | $G^2$ | H | HHH | H | — | — | — | D | NH$_2$ |
| $P^4$ | $P^1$ | OH/O$^-$ | OH | OH | $G^2$ | H | HHD | H | — | — | — | D | NH$_2$ |
| $P^4$ | $P^1$ | OH/O$^-$ | OH | OH | $G^2$ | H | HDD | H | — | — | — | D | NH$_2$ |
| $P^4$ | $P^1$ | OH/O$^-$ | OH | OH | $G^2$ | H | DDD | H | — | — | — | D | NH$_2$ |
| $P^4$ | $P^1$ | OH/O$^-$ | OH | OH | $G^2$ | H | HHD | D | — | — | — | D | NH$_2$ |
| $P^4$ | $P^1$ | OH/O$^-$ | OH | OH | $G^2$ | H | HDD | D | — | — | — | D | NH$_2$ |
| $P^4$ | $P^1$ | OH/O$^-$ | OH | OH | $G^2$ | H | DDD | D | — | — | — | D | NH$_2$ |
| $P^4$ | $P^1$ | OH/O$^-$ | OH | OH | $G^2$ | D | HHH | H | — | — | — | D | NH$_2$ |
| $P^4$ | $P^1$ | OH/O$^-$ | OH | OH | $G^2$ | D | HHD | H | — | — | — | D | NH$_2$ |
| $P^4$ | $P^1$ | OH/O$^-$ | OH | OH | $G^2$ | D | HDD | H | — | — | — | D | NH$_2$ |
| $P^4$ | $P^1$ | OH/O$^-$ | OH | OH | $G^2$ | D | DDD | H | — | — | — | D | NH$_2$ |
| $P^4$ | $P^1$ | OH/O$^-$ | OH | OH | $G^2$ | D | HHH | D | — | — | — | D | NH$_2$ |
| $P^4$ | $P^1$ | OH/O$^-$ | OH | OH | $G^2$ | D | HHD | D | — | — | — | D | NH$_2$ |
| $P^4$ | $P^1$ | OH/O$^-$ | OH | OH | $G^2$ | D | HDD | D | — | — | — | D | NH$_2$ |
| $P^4$ | $P^1$ | OH/O$^-$ | OH | OH | $G^2$ | D | DDD | D | — | — | — | D | NH$_2$ |
| $P^4$ | $P^1$ | OH/O$^-$ | OH | F | $G^2$ | H | HHH | H | — | — | — | H | OCH$_2$CH$_3$ |
| $P^4$ | $P^1$ | OH/O$^-$ | OH | F | $G^2$ | H | HHD | H | — | — | — | H | OCH$_2$CH$_3$ |
| $P^4$ | $P^1$ | OH/O$^-$ | OH | F | $G^2$ | H | HDD | H | — | — | — | H | OCH$_2$CH$_3$ |
| $P^4$ | $P^1$ | OH/O$^-$ | OH | F | $G^2$ | H | DDD | H | — | — | — | H | OCH$_2$CH$_3$ |
| $P^4$ | $P^1$ | OH/O$^-$ | OH | F | $G^2$ | H | HHH | D | — | — | — | H | OCH$_2$CH$_3$ |
| $P^4$ | $P^1$ | OH/O$^-$ | OH | F | $G^2$ | H | HHD | D | — | — | — | H | OCH$_2$CH$_3$ |
| $P^4$ | $P^1$ | OH/O$^-$ | OH | F | $G^2$ | H | HDD | D | — | — | — | H | OCH$_2$CH$_3$ |
| $P^4$ | $P^1$ | OH/O$^-$ | OH | F | $G^2$ | H | DDD | D | — | — | — | H | OCH$_2$CH$_3$ |
| $P^4$ | $P^1$ | OH/O$^-$ | OH | F | $G^2$ | D | HHH | H | — | — | — | H | OCH$_2$CH$_3$ |
| $P^4$ | $P^1$ | OH/O$^-$ | OH | F | $G^2$ | D | HHD | H | — | — | — | H | OCH$_2$CH$_3$ |
| $P^4$ | $P^1$ | OH/O$^-$ | OH | F | $G^2$ | D | HDD | H | — | — | — | H | OCH$_2$CH$_3$ |
| $P^4$ | $P^1$ | OH/O$^-$ | OH | F | $G^2$ | D | DDD | H | — | — | — | H | OCH$_2$CH$_3$ |
| $P^4$ | $P^1$ | OH/O$^-$ | OH | F | $G^2$ | D | HHH | D | — | — | — | H | OCH$_2$CH$_3$ |
| $P^4$ | $P^1$ | OH/O$^-$ | OH | F | $G^2$ | D | HHD | D | — | — | — | H | OCH$_2$CH$_3$ |
| $P^4$ | $P^1$ | OH/O$^-$ | OH | F | $G^2$ | D | HDD | D | — | — | — | H | OCH$_2$CH$_3$ |
| $P^4$ | $P^1$ | OH/O$^-$ | OH | F | $G^2$ | D | DDD | D | — | — | — | H | OCH$_2$CH$_3$ |
| $P^4$ | $P^1$ | OH/O$^-$ | OH | F | $G^2$ | H | HHH | H | — | — | — | H | NH$_2$ |
| $P^4$ | $P^1$ | OH/O$^-$ | OH | F | $G^2$ | H | HHD | H | — | — | — | H | NH$_2$ |
| $P^4$ | $P^1$ | OH/O$^-$ | OH | F | $G^2$ | H | HDD | H | — | — | — | H | NH$_2$ |
| $P^4$ | $P^1$ | OH/O$^-$ | OH | F | $G^2$ | H | DDD | H | — | — | — | H | NH$_2$ |
| $P^4$ | $P^1$ | OH/O$^-$ | OH | F | $G^2$ | H | HHH | D | — | — | — | H | NH$_2$ |
| $P^4$ | $P^1$ | OH/O$^-$ | OH | F | $G^2$ | H | HDD | D | — | — | — | H | NH$_2$ |
| $P^4$ | $P^1$ | OH/O$^-$ | OH | F | $G^2$ | H | DDD | D | — | — | — | H | NH$_2$ |
| $P^4$ | $P^1$ | OH/O$^-$ | OH | F | $G^2$ | D | HHH | H | — | — | — | H | NH$_2$ |
| $P^4$ | $P^1$ | OH/O$^-$ | OH | F | $G^2$ | D | HDD | H | — | — | — | H | NH$_2$ |
| $P^4$ | $P^1$ | OH/O$^-$ | OH | F | $G^2$ | D | DDD | H | — | — | — | H | NH$_2$ |
| $P^4$ | $P^1$ | OH/O$^-$ | OH | F | $G^2$ | D | HHH | D | — | — | — | H | NH$_2$ |
| $P^4$ | $P^1$ | OH/O$^-$ | OH | F | $G^2$ | D | HHD | D | — | — | — | H | NH$_2$ |
| $P^4$ | $P^1$ | OH/O$^-$ | OH | F | $G^2$ | D | HDD | D | — | — | — | H | NH$_2$ |
| $P^4$ | $P^1$ | OH/O$^-$ | OH | F | $G^2$ | D | DDD | D | — | — | — | H | NH$_2$ |
| $P^4$ | $P^1$ | OH/O$^-$ | OH | F | $G^2$ | H | HHH | H | — | — | — | D | OCH$_2$CH$_3$ |
| $P^4$ | $P^1$ | OH/O$^-$ | OH | F | $G^2$ | H | HHD | H | — | — | — | D | OCH$_2$CH$_3$ |
| $P^4$ | $P^1$ | OH/O$^-$ | OH | F | $G^2$ | H | HDD | H | — | — | — | D | OCH$_2$CH$_3$ |
| $P^4$ | $P^1$ | OH/O$^-$ | OH | F | $G^2$ | H | DDD | H | — | — | — | D | OCH$_2$CH$_3$ |
| $P^4$ | $P^1$ | OH/O$^-$ | OH | F | $G^2$ | H | HHH | D | — | — | — | D | OCH$_2$CH$_3$ |
| $P^4$ | $P^1$ | OH/O$^-$ | OH | F | $G^2$ | H | HHD | D | — | — | — | D | OCH$_2$CH$_3$ |
| $P^4$ | $P^1$ | OH/O$^-$ | OH | F | $G^2$ | H | HDD | D | — | — | — | D | OCH$_2$CH$_3$ |
| $P^4$ | $P^1$ | OH/O$^-$ | OH | F | $G^2$ | H | DDD | D | — | — | — | D | OCH$_2$CH$_3$ |
| $P^4$ | $P^1$ | OH/O$^-$ | OH | F | $G^2$ | D | HHH | H | — | — | — | D | OCH$_2$CH$_3$ |
| $P^4$ | $P^1$ | OH/O$^-$ | OH | F | $G^2$ | D | HHD | H | — | — | — | D | OCH$_2$CH$_3$ |
| $P^4$ | $P^1$ | OH/O$^-$ | OH | F | $G^2$ | D | HDD | H | — | — | — | D | OCH$_2$CH$_3$ |
| $P^4$ | $P^1$ | OH/O$^-$ | OH | F | $G^2$ | D | DDD | H | — | — | — | D | OCH$_2$CH$_3$ |
| $P^4$ | $P^1$ | OH/O$^-$ | OH | F | $G^2$ | D | HHH | D | — | — | — | D | OCH$_2$CH$_3$ |
| $P^4$ | $P^1$ | OH/O$^-$ | OH | F | $G^2$ | D | HHD | D | — | — | — | D | OCH$_2$CH$_3$ |
| $P^4$ | $P^1$ | OH/O$^-$ | OH | F | $G^2$ | D | HDD | D | — | — | — | D | OCH$_2$CH$_3$ |
| $P^4$ | $P^1$ | OH/O$^-$ | OH | F | $G^2$ | D | DDD | D | — | — | — | D | OCH$_2$CH$_3$ |

TABLE 3-continued

| R$^P$ | R$^1$ | R$^2$ | R$^4$ | R$^5$ | B$^1$ | R$^3$ | (R$^6$)$_3$ | R$^7$ | B$^{1A}$ | B$^{2A}$ | B$^{3A}$ | B$^{4A}$ | B$^{5A}$ |
|---|---|---|---|---|---|---|---|---|---|---|---|---|---|
| P$^4$ | P$^1$ | OH/O$^-$ | OH | F | G$^2$ | H | HHH | H | — | — | — | D | NH$_2$ |
| P$^4$ | P$^1$ | OH/O$^-$ | OH | F | G$^2$ | H | HHD | H | — | — | — | D | NH$_2$ |
| P$^4$ | P$^1$ | OH/O$^-$ | OH | F | G$^2$ | H | HDD | H | — | — | — | D | NH$_2$ |
| P$^4$ | P$^1$ | OH/O$^-$ | OH | F | G$^2$ | H | DDD | H | — | — | — | D | NH$_2$ |
| P$^4$ | P$^1$ | OH/O$^-$ | OH | F | G$^2$ | H | HHH | D | — | — | — | D | NH$_2$ |
| P$^4$ | P$^1$ | OH/O$^-$ | OH | F | G$^2$ | H | HHD | D | — | — | — | D | NH$_2$ |
| P$^4$ | P$^1$ | OH/O$^-$ | OH | F | G$^2$ | H | HDD | D | — | — | — | D | NH$_2$ |
| P$^4$ | P$^1$ | OH/O$^-$ | OH | F | G$^2$ | H | DDD | D | — | — | — | D | NH$_2$ |
| P$^4$ | P$^1$ | OH/O$^-$ | OH | F | G$^2$ | D | HHH | H | — | — | — | D | NH$_2$ |
| P$^4$ | P$^1$ | OH/O$^-$ | OH | F | G$^2$ | D | HHD | H | — | — | — | D | NH$_2$ |
| P$^4$ | P$^1$ | OH/O$^-$ | OH | F | G$^2$ | D | HDD | H | — | — | — | D | NH$_2$ |
| P$^4$ | P$^1$ | OH/O$^-$ | OH | F | G$^2$ | D | DDD | H | — | — | — | D | NH$_2$ |
| P$^4$ | P$^1$ | OH/O$^-$ | OH | F | G$^2$ | D | HHH | D | — | — | — | D | NH$_2$ |
| P$^4$ | P$^1$ | OH/O$^-$ | OH | F | G$^2$ | D | HHD | D | — | — | — | D | NH$_2$ |
| P$^4$ | P$^1$ | OH/O$^-$ | OH | F | G$^2$ | D | HDD | D | — | — | — | D | NH$_2$ |
| P$^4$ | P$^1$ | OH/O$^-$ | OH | F | G$^2$ | D | DDD | D | — | — | — | D | NH$_2$ |
| P$^4$ | P$^1$ | OH/O$^-$ | F | OH | G$^2$ | H | HHH | H | — | — | — | H | OCH$_2$CH$_3$ |
| P$^4$ | P$^1$ | OH/O$^-$ | F | OH | G$^2$ | H | HHD | H | — | — | — | H | OCH$_2$CH$_3$ |
| P$^4$ | P$^1$ | OH/O$^-$ | F | OH | G$^2$ | H | HDD | H | — | — | — | H | OCH$_2$CH$_3$ |
| P$^4$ | P$^1$ | OH/O$^-$ | F | OH | G$^2$ | H | DDD | H | — | — | — | H | OCH$_2$CH$_3$ |
| P$^4$ | P$^1$ | OH/O$^-$ | F | OH | G$^2$ | H | HHH | D | — | — | — | H | OCH$_2$CH$_3$ |
| P$^4$ | P$^1$ | OH/O$^-$ | F | OH | G$^2$ | H | HHD | D | — | — | — | H | OCH$_2$CH$_3$ |
| P$^4$ | P$^1$ | OH/O$^-$ | F | OH | G$^2$ | H | HDD | D | — | — | — | H | OCH$_2$CH$_3$ |
| P$^4$ | P$^1$ | OH/O$^-$ | F | OH | G$^2$ | H | DDD | D | — | — | — | H | OCH$_2$CH$_3$ |
| P$^4$ | P$^1$ | OH/O$^-$ | F | OH | G$^2$ | D | HHH | H | — | — | — | H | OCH$_2$CH$_3$ |
| P$^4$ | P$^1$ | OH/O$^-$ | F | OH | G$^2$ | D | HHD | H | — | — | — | H | OCH$_2$CH$_3$ |
| P$^4$ | P$^1$ | OH/O$^-$ | F | OH | G$^2$ | D | HDD | H | — | — | — | H | OCH$_2$CH$_3$ |
| P$^4$ | P$^1$ | OH/O$^-$ | F | OH | G$^2$ | D | DDD | H | — | — | — | H | OCH$_2$CH$_3$ |
| P$^4$ | P$^1$ | OH/O$^-$ | F | OH | G$^2$ | D | HHH | D | — | — | — | H | OCH$_2$CH$_3$ |
| P$^4$ | P$^1$ | OH/O$^-$ | F | OH | G$^2$ | D | HHD | D | — | — | — | H | OCH$_2$CH$_3$ |
| P$^4$ | P$^1$ | OH/O$^-$ | F | OH | G$^2$ | D | HDD | D | — | — | — | H | OCH$_2$CH$_3$ |
| P$^4$ | P$^1$ | OH/O$^-$ | F | OH | G$^2$ | D | DDD | D | — | — | — | H | OCH$_2$CH$_3$ |
| P$^4$ | P$^1$ | OH/O$^-$ | F | OH | G$^2$ | H | HHH | H | — | — | — | H | NH$_2$ |
| P$^4$ | P$^1$ | OH/O$^-$ | F | OH | G$^2$ | H | HHD | H | — | — | — | H | NH$_2$ |
| P$^4$ | P$^1$ | OH/O$^-$ | F | OH | G$^2$ | H | HDD | H | — | — | — | H | NH$_2$ |
| P$^4$ | P$^1$ | OH/O$^-$ | F | OH | G$^2$ | H | DDD | H | — | — | — | H | NH$_2$ |
| P$^4$ | P$^1$ | OH/O$^-$ | F | OH | G$^2$ | H | HHH | D | — | — | — | H | NH$_2$ |
| P$^4$ | P$^1$ | OH/O$^-$ | F | OH | G$^2$ | H | HHD | D | — | — | — | H | NH$_2$ |
| P$^4$ | P$^1$ | OH/O$^-$ | F | OH | G$^2$ | H | HDD | D | — | — | — | H | NH$_2$ |
| P$^4$ | P$^1$ | OH/O$^-$ | F | OH | G$^2$ | H | DDD | D | — | — | — | H | NH$_2$ |
| P$^4$ | P$^1$ | OH/O$^-$ | F | OH | G$^2$ | D | HHH | H | — | — | — | H | NH$_2$ |
| P$^4$ | P$^1$ | OH/O$^-$ | F | OH | G$^2$ | D | HHD | H | — | — | — | H | NH$_2$ |
| P$^4$ | P$^1$ | OH/O$^-$ | F | OH | G$^2$ | D | HDD | H | — | — | — | H | NH$_2$ |
| P$^4$ | P$^1$ | OH/O$^-$ | F | OH | G$^2$ | D | DDD | H | — | — | — | H | NH$_2$ |
| P$^4$ | P$^1$ | OH/O$^-$ | F | OH | G$^2$ | D | HHH | D | — | — | — | H | NH$_2$ |
| P$^4$ | P$^1$ | OH/O$^-$ | F | OH | G$^2$ | D | HHD | D | — | — | — | H | NH$_2$ |
| P$^4$ | P$^1$ | OH/O$^-$ | F | OH | G$^2$ | D | HDD | D | — | — | — | H | NH$_2$ |
| P$^4$ | P$^1$ | OH/O$^-$ | F | OH | G$^2$ | D | DDD | D | — | — | — | H | NH$_2$ |
| P$^4$ | P$^1$ | OH/O$^-$ | F | OH | G$^2$ | H | HHH | H | — | — | — | D | OCH$_2$CH$_3$ |
| P$^4$ | P$^1$ | OH/O$^-$ | F | OH | G$^2$ | H | HHD | H | — | — | — | D | OCH$_2$CH$_3$ |
| P$^4$ | P$^1$ | OH/O$^-$ | F | OH | G$^2$ | H | HDD | H | — | — | — | D | OCH$_2$CH$_3$ |
| P$^4$ | P$^1$ | OH/O$^-$ | F | OH | G$^2$ | H | DDD | H | — | — | — | D | OCH$_2$CH$_3$ |
| P$^4$ | P$^1$ | OH/O$^-$ | F | OH | G$^2$ | H | HHH | D | — | — | — | D | OCH$_2$CH$_3$ |
| P$^4$ | P$^1$ | OH/O$^-$ | F | OH | G$^2$ | H | HHD | D | — | — | — | D | OCH$_2$CH$_3$ |
| P$^4$ | P$^1$ | OH/O$^-$ | F | OH | G$^2$ | H | HDD | D | — | — | — | D | OCH$_2$CH$_3$ |
| P$^4$ | P$^1$ | OH/O$^-$ | F | OH | G$^2$ | H | DDD | D | — | — | — | D | OCH$_2$CH$_3$ |
| P$^4$ | P$^1$ | OH/O$^-$ | F | OH | G$^2$ | D | HHH | H | — | — | — | D | OCH$_2$CH$_3$ |
| P$^4$ | P$^1$ | OH/O$^-$ | F | OH | G$^2$ | D | HHD | H | — | — | — | D | OCH$_2$CH$_3$ |
| P$^4$ | P$^1$ | OH/O$^-$ | F | OH | G$^2$ | D | HDD | H | — | — | — | D | OCH$_2$CH$_3$ |
| P$^4$ | P$^1$ | OH/O$^-$ | F | OH | G$^2$ | D | DDD | H | — | — | — | D | OCH$_2$CH$_3$ |
| P$^4$ | P$^1$ | OH/O$^-$ | F | OH | G$^2$ | D | HHH | D | — | — | — | D | OCH$_2$CH$_3$ |
| P$^4$ | P$^1$ | OH/O$^-$ | F | OH | G$^2$ | D | HHD | D | — | — | — | D | OCH$_2$CH$_3$ |
| P$^4$ | P$^1$ | OH/O$^-$ | F | OH | G$^2$ | D | HDD | D | — | — | — | D | OCH$_2$CH$_3$ |
| P$^4$ | P$^1$ | OH/O$^-$ | F | OH | G$^2$ | D | DDD | D | — | — | — | D | OCH$_2$CH$_3$ |
| P$^4$ | P$^1$ | OH/O$^-$ | F | OH | G$^2$ | H | HHH | H | — | — | — | D | NH$_2$ |
| P$^4$ | P$^1$ | OH/O$^-$ | F | OH | G$^2$ | H | HHD | H | — | — | — | D | NH$_2$ |
| P$^4$ | P$^1$ | OH/O$^-$ | F | OH | G$^2$ | H | HDD | H | — | — | — | D | NH$_2$ |
| P$^4$ | P$^1$ | OH/O$^-$ | F | OH | G$^2$ | H | DDD | H | — | — | — | D | NH$_2$ |
| P$^4$ | P$^1$ | OH/O$^-$ | F | OH | G$^2$ | H | HHH | D | — | — | — | D | NH$_2$ |
| P$^4$ | P$^1$ | OH/O$^-$ | F | OH | G$^2$ | H | HHD | D | — | — | — | D | NH$_2$ |
| P$^4$ | P$^1$ | OH/O$^-$ | F | OH | G$^2$ | H | HDD | D | — | — | — | D | NH$_2$ |
| P$^4$ | P$^1$ | OH/O$^-$ | F | OH | G$^2$ | H | DDD | D | — | — | — | D | NH$_2$ |
| P$^4$ | P$^1$ | OH/O$^-$ | F | OH | G$^2$ | D | HHH | H | — | — | — | D | NH$_2$ |
| P$^4$ | P$^1$ | OH/O$^-$ | F | OH | G$^2$ | D | HHD | H | — | — | — | D | NH$_2$ |
| P$^4$ | P$^1$ | OH/O$^-$ | F | OH | G$^2$ | D | HDD | H | — | — | — | D | NH$_2$ |
| P$^4$ | P$^1$ | OH/O$^-$ | F | OH | G$^2$ | D | DDD | H | — | — | — | D | NH$_2$ |
| P$^4$ | P$^1$ | OH/O$^-$ | F | OH | G$^2$ | D | HHH | D | — | — | — | D | NH$_2$ |
| P$^4$ | P$^1$ | OH/O$^-$ | F | OH | G$^2$ | D | HHD | D | — | — | — | D | NH$_2$ |

TABLE 3-continued

| $R^P$ | $R^1$ | $R^2$ | $R^4$ | $R^5$ | $B^1$ | $R^3$ | $(R^6)_3$ | $R^7$ | $B^{1,A}$ | $B^{2,A}$ | $B^{3,A}$ | $B^{4,A}$ | $B^{5,A}$ |
|---|---|---|---|---|---|---|---|---|---|---|---|---|---|
| $P^A$ | $P^1$ | OH/O⁻ | F | OH | $G^2$ | D | HDD | D | — | — | — | D | $NH_2$ |
| $P^A$ | $P^1$ | OH/O⁻ | F | OH | $G^2$ | D | DDD | D | — | — | — | D | $NH_2$ |
| $P^A$ | $P^1$ | OH/O⁻ | F | F | $G^2$ | H | HHH | H | — | — | — | H | $OCH_2CH_3$ |
| $P^A$ | $P^1$ | OH/O⁻ | F | F | $G^2$ | H | HHD | H | — | — | — | H | $OCH_2CH_3$ |
| $P^A$ | $P^1$ | OH/O⁻ | F | F | $G^2$ | H | HDD | H | — | — | — | H | $OCH_2CH_3$ |
| $P^A$ | $P^1$ | OH/O⁻ | F | F | $G^2$ | H | DDD | H | — | — | — | H | $OCH_2CH_3$ |
| $P^A$ | $P^1$ | OH/O⁻ | F | F | $G^2$ | H | HHH | D | — | — | — | H | $OCH_2CH_3$ |
| $P^A$ | $P^1$ | OH/O⁻ | F | F | $G^2$ | H | HHD | D | — | — | — | H | $OCH_2CH_3$ |
| $P^A$ | $P^1$ | OH/O⁻ | F | F | $G^2$ | H | HDD | D | — | — | — | H | $OCH_2CH_3$ |
| $P^A$ | $P^1$ | OH/O⁻ | F | F | $G^2$ | H | DDD | D | — | — | — | H | $OCH_2CH_3$ |
| $P^A$ | $P^1$ | OH/O⁻ | F | F | $G^2$ | D | HHH | H | — | — | — | H | $OCH_2CH_3$ |
| $P^A$ | $P^1$ | OH/O⁻ | F | F | $G^2$ | D | HHD | H | — | — | — | H | $OCH_2CH_3$ |
| $P^A$ | $P^1$ | OH/O⁻ | F | F | $G^2$ | D | HDD | H | — | — | — | H | $OCH_2CH_3$ |
| $P^A$ | $P^1$ | OH/O⁻ | F | F | $G^2$ | D | DDD | H | — | — | — | H | $OCH_2CH_3$ |
| $P^A$ | $P^1$ | OH/O⁻ | F | F | $G^2$ | D | HHH | D | — | — | — | H | $OCH_2CH_3$ |
| $P^A$ | $P^1$ | OH/O⁻ | F | F | $G^2$ | D | HHD | D | — | — | — | H | $OCH_2CH_3$ |
| $P^A$ | $P^1$ | OH/O⁻ | F | F | $G^2$ | D | HDD | D | — | — | — | H | $OCH_2CH_3$ |
| $P^A$ | $P^1$ | OH/O⁻ | F | F | $G^2$ | D | DDD | D | — | — | — | H | $OCH_2CH_3$ |
| $P^A$ | $P^1$ | OH/O⁻ | F | F | $G^2$ | H | HHH | H | — | — | — | H | $NH_2$ |
| $P^A$ | $P^1$ | OH/O⁻ | F | F | $G^2$ | H | HHD | H | — | — | — | H | $NH_2$ |
| $P^A$ | $P^1$ | OH/O⁻ | F | F | $G^2$ | H | HDD | H | — | — | — | H | $NH_2$ |
| $P^A$ | $P^1$ | OH/O⁻ | F | F | $G^2$ | H | DDD | H | — | — | — | H | $NH_2$ |
| $P^A$ | $P^1$ | OH/O⁻ | F | F | $G^2$ | H | HHH | D | — | — | — | H | $NH_2$ |
| $P^A$ | $P^1$ | OH/O⁻ | F | F | $G^2$ | H | HHD | D | — | — | — | H | $NH_2$ |
| $P^A$ | $P^1$ | OH/O⁻ | F | F | $G^2$ | H | HDD | D | — | — | — | H | $NH_2$ |
| $P^A$ | $P^1$ | OH/O⁻ | F | F | $G^2$ | H | DDD | D | — | — | — | H | $NH_2$ |
| $P^A$ | $P^1$ | OH/O⁻ | F | F | $G^2$ | D | HHH | H | — | — | — | H | $NH_2$ |
| $P^A$ | $P^1$ | OH/O⁻ | F | F | $G^2$ | D | HHD | H | — | — | — | H | $NH_2$ |
| $P^A$ | $P^1$ | OH/O⁻ | F | F | $G^2$ | D | HDD | H | — | — | — | H | $NH_2$ |
| $P^A$ | $P^1$ | OH/O⁻ | F | F | $G^2$ | D | DDD | H | — | — | — | H | $NH_2$ |
| $P^A$ | $P^1$ | OH/O⁻ | F | F | $G^2$ | D | HHH | D | — | — | — | H | $NH_2$ |
| $P^A$ | $P^1$ | OH/O⁻ | F | F | $G^2$ | D | HHD | D | — | — | — | H | $NH_2$ |
| $P^A$ | $P^1$ | OH/O⁻ | F | F | $G^2$ | D | HDD | D | — | — | — | H | $NH_2$ |
| $P^A$ | $P^1$ | OH/O⁻ | F | F | $G^2$ | D | DDD | D | — | — | — | H | $NH_2$ |
| $P^A$ | $P^1$ | OH/O⁻ | F | F | $G^2$ | H | HHH | H | — | — | — | D | $OCH_2CH_3$ |
| $P^A$ | $P^1$ | OH/O⁻ | F | F | $G^2$ | H | HHD | H | — | — | — | D | $OCH_2CH_3$ |
| $P^A$ | $P^1$ | OH/O⁻ | F | F | $G^2$ | H | HDD | H | — | — | — | D | $OCH_2CH_3$ |
| $P^A$ | $P^1$ | OH/O⁻ | F | F | $G^2$ | H | DDD | H | — | — | — | D | $OCH_2CH_3$ |
| $P^A$ | $P^1$ | OH/O⁻ | F | F | $G^2$ | H | HHH | D | — | — | — | D | $OCH_2CH_3$ |
| $P^A$ | $P^1$ | OH/O⁻ | F | F | $G^2$ | H | HHD | D | — | — | — | D | $OCH_2CH_3$ |
| $P^A$ | $P^1$ | OH/O⁻ | F | F | $G^2$ | H | HDD | D | — | — | — | D | $OCH_2CH_3$ |
| $P^A$ | $P^1$ | OH/O⁻ | F | F | $G^2$ | H | DDD | D | — | — | — | D | $OCH_2CH_3$ |
| $P^A$ | $P^1$ | OH/O⁻ | F | F | $G^2$ | D | HHH | H | — | — | — | D | $OCH_2CH_3$ |
| $P^A$ | $P^1$ | OH/O⁻ | F | F | $G^2$ | D | HHD | H | — | — | — | D | $OCH_2CH_3$ |
| $P^A$ | $P^1$ | OH/O⁻ | F | F | $G^2$ | D | HDD | H | — | — | — | D | $OCH_2CH_3$ |
| $P^A$ | $P^1$ | OH/O⁻ | F | F | $G^2$ | D | DDD | H | — | — | — | D | $OCH_2CH_3$ |
| $P^A$ | $P^1$ | OH/O⁻ | F | F | $G^2$ | D | HHH | D | — | — | — | D | $OCH_2CH_3$ |
| $P^A$ | $P^1$ | OH/O⁻ | F | F | $G^2$ | D | HHD | D | — | — | — | D | $OCH_2CH_3$ |
| $P^A$ | $P^1$ | OH/O⁻ | F | F | $G^2$ | D | HDD | D | — | — | — | D | $OCH_2CH_3$ |
| $P^A$ | $P^1$ | OH/O⁻ | F | F | $G^2$ | D | DDD | D | — | — | — | D | $OCH_2CH_3$ |
| $P^A$ | $P^1$ | OH/O⁻ | F | F | $G^2$ | H | HHH | H | — | — | — | D | $NH_2$ |
| $P^A$ | $P^1$ | OH/O⁻ | F | F | $G^2$ | H | HHD | H | — | — | — | D | $NH_2$ |
| $P^A$ | $P^1$ | OH/O⁻ | F | F | $G^2$ | H | HDD | H | — | — | — | D | $NH_2$ |
| $P^A$ | $P^1$ | OH/O⁻ | F | F | $G^2$ | H | DDD | H | — | — | — | D | $NH_2$ |
| $P^A$ | $P^1$ | OH/O⁻ | F | F | $G^2$ | H | HHH | D | — | — | — | D | $NH_2$ |
| $P^A$ | $P^1$ | OH/O⁻ | F | F | $G^2$ | H | HHD | D | — | — | — | D | $NH_2$ |
| $P^A$ | $P^1$ | OH/O⁻ | F | F | $G^2$ | H | HDD | D | — | — | — | D | $NH_2$ |
| $P^A$ | $P^1$ | OH/O⁻ | F | F | $G^2$ | H | DDD | D | — | — | — | D | $NH_2$ |
| $P^A$ | $P^1$ | OH/O⁻ | F | F | $G^2$ | D | HHH | H | — | — | — | D | $NH_2$ |
| $P^A$ | $P^1$ | OH/O⁻ | F | F | $G^2$ | D | HHD | H | — | — | — | D | $NH_2$ |
| $P^A$ | $P^1$ | OH/O⁻ | F | F | $G^2$ | D | HDD | H | — | — | — | D | $NH_2$ |
| $P^A$ | $P^1$ | OH/O⁻ | F | F | $G^2$ | D | DDD | H | — | — | — | D | $NH_2$ |
| $P^A$ | $P^1$ | OH/O⁻ | F | F | $G^2$ | D | HHH | D | — | — | — | D | $NH_2$ |
| $P^A$ | $P^1$ | OH/O⁻ | F | F | $G^2$ | D | HHD | D | — | — | — | D | $NH_2$ |
| $P^A$ | $P^1$ | OH/O⁻ | F | F | $G^2$ | D | HDD | D | — | — | — | D | $NH_2$ |
| $P^A$ | $P^1$ | OH/O⁻ | F | F | $G^2$ | D | DDD | D | — | — | — | D | $NH_2$ |

$P^A$: -------- is absent and $R^P$ is

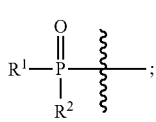

$P^1$: $R^1$ is

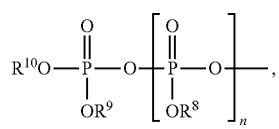

wherein $R^8$, $R^9$ and $R^{10}$ are independently absent or hydrogen, n is 0 or 1, and $R^2$ is —OH, or O⁻; or $R^1$ and $R^2$ are independently —OH or O⁻;

Ph: —O-optionally substituted phenyl;
Naph: —O-optionally substituted naphthyl;
POC:

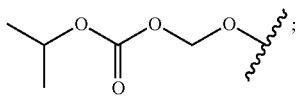

N-AA: N-linked amino acid or N-linked amino acid ester derivate;
$U^1$:

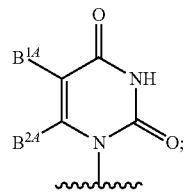

$G^1$:

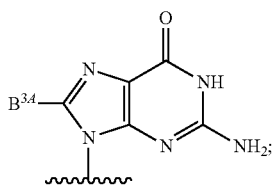

$G^2$:

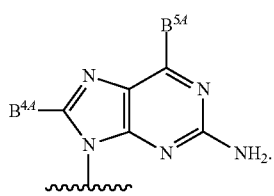

In some embodiments of the compounds of Table 3, $R^1$ can be an —O-optionally substituted phenyl or an —O-optionally substituted naphthyl, and $R^2$ can be

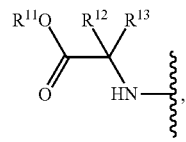

wherein $R^{11}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{12}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{13}$ can be hydrogen or an optionally substituted $C_{1-4}$-alkyl; or $R^{12}$ and $R^{13}$ are taken together to form an optionally substituted $C_{3-6}$ cycloalkyl. Examples of

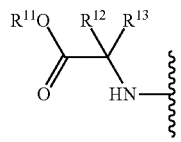

are described herein.

In some embodiment of the compounds of Table 3, $R^1$ and $R^2$ can both independently be —OH or O⁻, and form a monophosphate. In other embodiments of the compounds of Table 3, $R^1$ can be

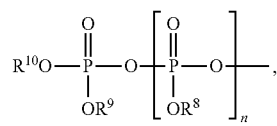

$R^9$ and $R^{10}$ can be independently absent or hydrogen, n can be 0, and $R^2$ can be —OH or O⁻, and form a diphosphate. In yet other embodiments of the compounds of Table 3, $R^1$ can be

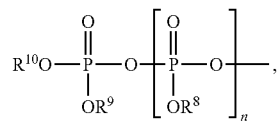

$R^8$, $R^9$ and $R^{10}$ can be independently absent or hydrogen, n can be 1, and $R^2$ can be —OH or O⁻, and form a triphosphate.

Examples of a compound of Formula (I), or a pharmaceutically acceptable salt thereof, include the following:

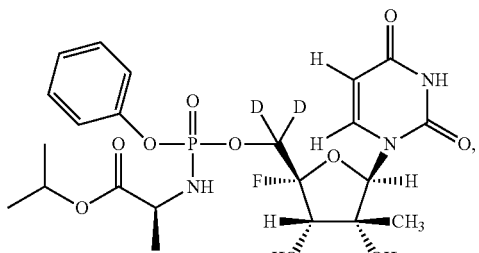

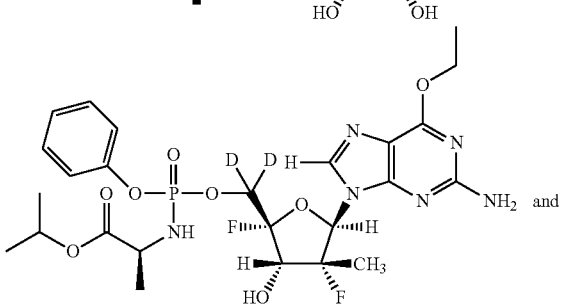 and

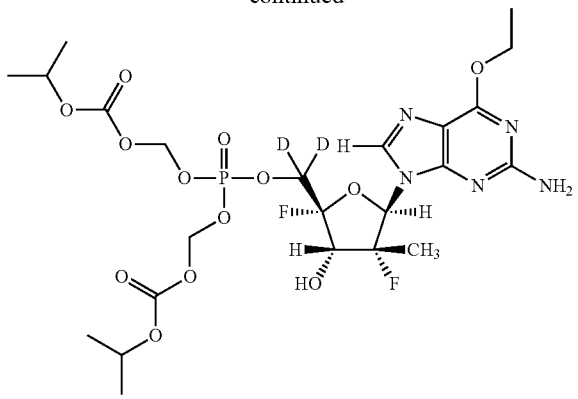

or a pharmaceutically acceptable salt of the foregoing.

Additional examples of a compound of Formula (I), or a pharmaceutically acceptable salt thereof, include the following:

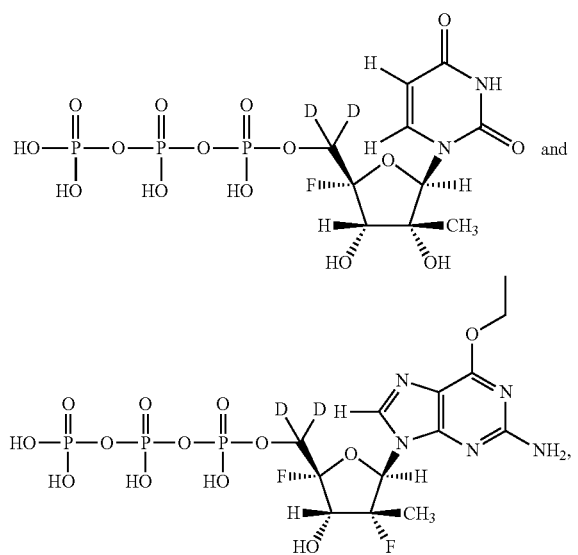

or a pharmaceutically acceptable salt of the foregoing.

By neutralizing the charge on the phosphate moiety of Formula (I), or a pharmaceutically acceptable salt thereof, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Furthermore, in some embodiments, varying the substituents on a compound described herein, such as a compound of Formula (I), or a pharmaceutically acceptable salt thereof, can help maintain the efficacy of the compound by reducing undesirable effects.

In some embodiments, varying the substituents on a compound described herein, such as a compound of Formula (I), or a pharmaceutically acceptable salt thereof, can result in the 5'-O-phosphorous being a chiral center. In some embodiments, the 5'-O-phosphorous can be in the (R)-configuration. In some embodiments, the 5'-O-phosphorous can be in the (S)-configuration. Examples of the two configurations are:

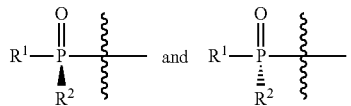

In some embodiments, a compound of Formula (I), or a pharmaceutically acceptable salt thereof, can be enriched in (R) or (S) configuration with respect to the 5'-O-phosphorous. For example, one of the (R) and (S) configuration with respect to the 5'-O-phosphorous atom can be present in an amount >50%, ≥75%, ≥90%, ≥95% or ≥99% compared to the amount of the other of the (R) or (S) configuration with respect to the 5'-O-phosphorous atom.

In some embodiments, a compound of Formula (I), or a pharmaceutically acceptable salt thereof, can act as a chain terminator of HCV replication. For example, compounds of Formula (I), or a pharmaceutically acceptable salt thereof, with a $-C(R^6)_3$ moiety at the 2'-carbon position can be incorporated into an RNA chain of HCV and then no further elongation is observed to occur.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having two hydrogens in place of the two deuteriums at the 5'-position. In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have a biological half-life greater than a compound that is identical in structure but for having two hydrogens in place of the two deuteriums at the 5'-position. In some embodiments, a compound of Formula (I), or a pharmaceutically acceptable salt thereof, can have more potent antiviral activity (for example, a lower $EC_{50}$ in an HCV replicon assay) as compared to the current standard of care. In some embodiments, a compound of Formula (I), or a pharmaceutically acceptable salt thereof, does not significantly inhibit mitochondrial function of the mitochondrial RNA polymerase. For example, a compound of Formula (I), or a pharmaceutically acceptable salt thereof, is incorporated in the human mitochondrial RNA polymerase less than 10% compared to the natural 5'-triphosphate nucleotide with the same $B^1$.

Additionally, in some embodiments, the presence of a phosphoramidate or bis(POC) in a compound of Formula (I) or a pharmaceutically acceptable salt thereof, can increase the stability of the compound by inhibiting its degradation. Also, in some embodiments, the presence of a phosphoramidate or bis(POC) can make the compound more resistant to cleavage in vivo and provide sustained, extended efficacy. In some embodiments, a phosphoramidate or bis(POC) can facilitate the penetration of the cell membrane by a compound of Formula (I) or a pharmaceutically acceptable salt thereof, by making the compound more lipophilic. In some embodiments, a phosphoramidate or bis(POC) can have improved oral bioavailability, improved aqueous stability and/or reduced risk of byproduct-related toxicity. In some embodiments, for comparison purposes, a compound of Formula (I) or a pharmaceutically acceptable salt thereof, can be compared to a compound that is identical in structure but for having two hydrogens in place of the two deuteriums at the 5'-position.

Synthesis

Compounds of Formula (I) or a pharmaceutically acceptable salt thereof, and those described herein may be prepared in various ways. General synthetic routes to the compound of Formula (I), or a pharmaceutically acceptable salt thereof, and some examples of starting materials used to synthesize the compounds of Formula (I) or a pharmaceutically acceptable salt thereof, are shown in Schemes 1 and 2, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) or a pharmaceutically acceptable salt thereof, can be prepared using various methods known to those skilled in the art. Examples of methods are shown in Schemes 1 and 2. Suitable phosphorus containing precursors can be commercially obtained or prepared by synthetic methods known to those skilled in the art. Examples of general structures of phosphorus containing precursors are shown in Schemes 1 and 2, and involve the use of phosphorochloridates. Suitable phosphorochloridates are commercially available and/or can be synthetically prepared.

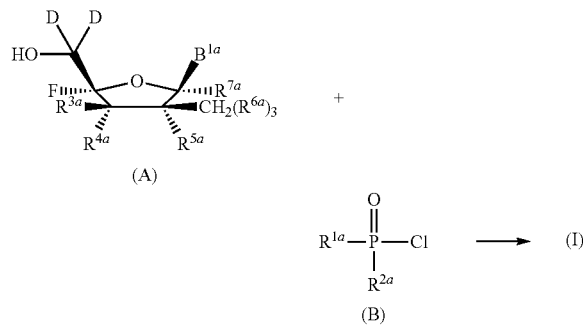

One method for forming a compound of Formula (I) or a pharmaceutically acceptable salt thereof, is shown in Scheme 1. In Scheme 1, $R^{1a}$, $R^{2a}$, $R^{3a}$, $R^{4a}$, $R^{5a}$, $R^{6a}$, $R^{7a}$ and $B^{1a}$ can be the same as $R^1$, $R^2$, $R^3$ $R^4$, $R^5$, $R^6$, $R^7$ and $B^1$ as described herein for Formula (I). In some embodiments, a compound of Formula (I) or a pharmaceutically acceptable salt thereof, can be generated from a compound of Formula (A) and a compound of Formula (B) using an organometallic reagent, such as a Grignard reagent. Suitable Grignard reagents are known to those skilled in the art and include, but are not limited to, alkylmagnesium chlorides and alkylmagnesium bromides. In other embodiments, an appropriate base can be used to form a compound of Formula (I). Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)).

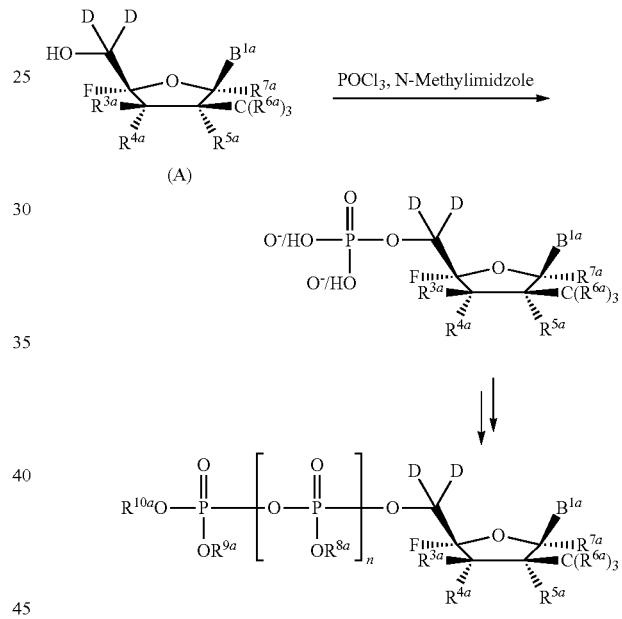

A phosphorus containing precursor can be coupled to the nucleoside, for example, a compound of Formula (A). Following the coupling of the phosphorus containing precursor, any leaving groups can be cleaved under suitable conditions, such as hydrolysis. In Scheme 2, $R^{1a}$, $R^{2a}$, $R^{3a}$, $R^{4a}$, $R^{5a}$, $R^{6a}$, $R^{7a}$, $R^{8a}$, $R^{9a}$, $R^{10a}$ and $B^{1a}$ can be the same as $R^1$, $R^2$, $R^3$, $R^4$, $R^5$, $R^6$, $R^7$, $R^8$, $R^9$, $R^{10}$ and $B^1$ as described herein for Formula (I). Further phosphorus containing groups can be added using methods known to those skilled in the art, for example using a pyrophosphate. If desired, one or more bases can be used during the addition of each phosphorus-containing group. Examples of suitable bases are described herein.

To reduce the formation of side products, one or more of the groups attached to the pentose ring can be protected with one or more suitable protecting groups. As an example, if $R^{4a}$ and/or $R^{5a}$ is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4"-trimethoxytrityl (TMTr), 4,4',4"-tris-(benzoyloxy) trityl (TBTr), 4,4',4"-tris(4,5-dichlorophthalimido) trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4"-tris-(tert-butylphenyl) methyl (TTTr) and 4,4'-di-3, 5-hexadienoxytrityl. Examples of suitable silyl groups are described herein and include trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Alternatively, $R^{4a}$ and/or $R^{5a}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy)propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject an effective amount of one or more compounds described herein, such as a compound of Formula (I), or a pharmaceutically acceptable salt thereof, or a pharmaceutical composition that includes a compound described herein, or a pharmaceutically acceptable salt thereof. Other embodiments disclosed herein relate to a method of treating and/or ameliorating a disease or condition that can include administering to a subject identified as suffering from the disease or condition an effective amount of one or more compounds described herein, such as a compound of Formula (I), or a pharmaceutically acceptable salt thereof, or a pharmaceutical composition that includes a compound described herein, or a pharmaceutically acceptable salt thereof.

Some embodiments disclosed herein relates to a method of ameliorating or treating a HCV infection that can include administering to a subject identified as suffering from a HCV infection an effective amount of one or more compounds described herein (for example, a compound of Formula (I)), or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HCV infection that can include administering to a subject identified as suffering from a HCV infection an effective amount of one or more compounds described herein. Still other embodiments described herein relate to one or more compounds described herein, or a pharmaceutically acceptable salt of a compound described herein, that can be used for ameliorating and/or treating a HCV infection by administering to a subject identified as suffering from a HCV infection an effective amount of one or more compounds described herein.

Some embodiments disclosed herein relate to methods of ameliorating and/or treating a HCV infection that can include contacting a cell infected with the hepatitis C virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HCV infection that can include contacting a cell infected with the hepatitis C virus with an effective amount of said compound(s). Still other embodiments described herein relate to one or more compounds described herein, or a pharmaceutically acceptable salt of a compound described herein, that can be used for ameliorating and/or treating a HCV infection by contacting a cell infected with the hepatitis C virus with an effective amount of said compound(s).

Some embodiments disclosed herein relate to methods of inhibiting replication of a hepatitis C virus that can include contacting a cell infected with the hepatitis C virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a hepatitis C virus that can include contacting a cell infected with the hepatitis C virus with an effective amount of said compound(s). Still other embodiments described herein relate to a compound described herein, or a pharmaceutically acceptable salt of a compound described herein, that can be used for inhibiting replication of a hepatitis C virus by contacting a cell infected with the hepatitis C virus with an effective amount of said compound(s).

In some embodiments, the compound can be a compound of Formula (I), wherein the compound of Formula (I) is a mono, di, or triphosphate, or a pharmaceutically acceptable salt of the foregoing. In other embodiments, the compound can be a compound of Formula (I), wherein the compound of Formula (I) is a phosphoramidate, or a pharmaceutically acceptable salt thereof. In still other embodiments, the compound can be a compound of Formula (I), wherein the compound of Formula (I) is a bis(POC), or a pharmaceutically acceptable salt thereof. In some embodiments, the compound of Formula (I), or a pharmaceutically acceptable salt thereof, that can be used for ameliorating and/or treating a viral infection (for example, a HCV infection) and/or inhibit replication of a virus (such as a HCV virus) can be any of the embodiments described in Tables 1, 2 and/or 3.

HCV is an enveloped positive strand RNA virus in the Flaviviridae family. There are various nonstructural proteins of HCV, such as NS2, NS3, NS4, NS4A, NS4B, NS5A and NS5B. NS5B is believed to be an RNA-dependent RNA polymerase involved in the replication of HCV RNA.

Some embodiments described herein relate to a method of inhibiting NS5B polymerase activity that can include contacting a cell infected with hepatitis C virus with an effective amount of a compound of Formula (I), or a pharmaceutically acceptable salt thereof. Some embodiments described herein relate to a method of inhibiting NS5B polymerase activity that can include administering to a subject infected with hepatitis C virus an effective amount of a compound of Formula (I), or a pharmaceutically acceptable salt thereof. In some embodiments, a compound of Formula (I), or a pharmaceutically acceptable salt thereof, can inhibit a RNA dependent RNA polymerase, and thus, inhibit the replication of HCV RNA. In some embodiments, a compound of Formula (I), or a pharmaceutically acceptable salt thereof, can inhibit a HCV polymerase (for example, NS5B polymerase).

Some embodiments described herein relate to a method of treating a condition selected from liver fibrosis, liver cirrhosis and liver cancer in a subject suffering from one or more of the aforementioned liver conditions that can include administering to the subject an effective amount of a compound or a pharmaceutical composition described herein (for example, a compound of Formula (I), or a pharmaceutically acceptable salt thereof), wherein the liver condition is caused by a HCV infection. Some embodiments described herein relate to a method of increasing liver function in a subject having a HCV infection that can include administering to the subject an effective amount of a compound or a pharmaceutical composition described herein (for example, a compound of Formula (I), or a pharmaceutically acceptable salt thereof). Also contemplated is a method for reducing or eliminating further virus-caused liver damage in a subject having an HCV infection by administering to the subject an effective amount of a compound or a pharmaceutical composition described herein (for example, a compound of Formula (I), or a pharmaceutically acceptable salt thereof). In some embodiments, this method can include slowing or halting the progression of liver disease. In other embodiments, the course of the disease can be reversed, and stasis or improvement in liver function is contemplated. In some embodiments, liver fibrosis, liver cirrhosis and/or liver cancer can be treated; liver function can be increased; virus-caused liver damage can be reduced or eliminated; progression of liver disease can be slowed or halted; the course of the liver disease can be reversed and/or liver function can be improved or maintained by contacting a cell infected with hepatitis C virus with an effective amount of a compound described herein (for example, a compound of Formula (I), or a pharmaceutically acceptable salt thereof.)

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of a compound of Formula (I), or a pharmaceutically acceptable salt thereof, or a pharmaceutical composition that includes an effective amount of a compound of Formula (I), or a pharmaceutically acceptable salt thereof, can be effective to treat at least one genotype of HCV. In some embodiments, a compound described herein (for example, a compound of Formula (I), or a pharmaceutically acceptable salt thereof) can be effective to treat all 11 genotypes of HCV. In some embodiments, a compound described herein (for example, a compound of Formula (I), or a pharmaceutically acceptable salt thereof) can be effective to treat 3 or more, 5 or more, 7 or more, or 9 or more genotypes of HCV. In some embodiments, a compound of Formula (I), or a pharmaceutically acceptable salt thereof can be more effective against a larger number of HCV genotypes than the standard of care. In some embodiments, a compound of Formula (I), or a pharmaceutically acceptable salt thereof, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase and/or other indicator of disease response. Similarly, successful therapy with an effective amount of a compound or a pharmaceutical composition described herein (for example, a compound of Formula (I), or a pharmaceutically acceptable salt thereof) can reduce the incidence of liver cancer in HCV infected subjects.

In some embodiments, an effective amount of a compound of Formula (I), or a pharmaceutically acceptable salt thereof, is an amount that is effective to reduce HCV viral titers to undetectable levels, for example, to about 100 to about 500, to about 50 to about 100, to about 10 to about 50, or to about 15 to about 25 international units/mL serum. In some embodiments, an effective amount of a compound of Formula (I), or a pharmaceutically acceptable salt thereof, is an amount that is effective to reduce HCV viral load compared to the HCV viral load before administration of the compound of Formula (I), or a pharmaceutically acceptable salt thereof. For example, wherein the HCV viral load is measured before administration of the compound of Formula (I), or a pharmaceutically acceptable salt thereof, and again after completion of the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce HCV viral load to lower than about 25 international units/mL serum. In some embodiments, an effective amount of a compound of Formula (I), or a pharmaceutically acceptable salt thereof, is an amount that is effective to achieve a reduction in HCV viral titer in the serum of the subject in the range of about 1.5-log to about a 2.5-log reduction, about a 3-log to about a 4-log reduction, or a greater than about 5-log reduction compared to the viral load before administration of the compound of Formula (I), or a pharmaceutically acceptable salt thereof. For example, the HCV viral load can be measured before administration of the compound of Formula (I), or a pharmaceutically acceptable salt thereof, and again after completion of the treatment regime with the compound of Formula (I), or a pharmaceutically acceptable salt thereof (for example, 1 month after completion).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of the hepatitis C virus relative to pre-treatment levels in a subject, as determined after completion of the treatment regime (for example, 1 month after completion). In some embodiments, a compound of Formula (I), or a pharmaceutically acceptable salt thereof, can result in a reduction of the replication of the hepatitis C virus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of the hepatitis C virus replication in the range of 1 to 1.5 log, 1.5 log to 2 log, 2 log to 2.5 log, 2.5 to 3 log, 3 log to 3.5 log or 3.5 to 4 log more reduction of the hepatitis C virus replication compared to the reduction of the hepatitis C virus reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formula (I), or a pharmaceutically acceptable salt thereof, is an amount that is effective to achieve a sustained viral response, for example, non-detectable or substantially non-detectable HCV RNA (e.g., less than about 500, less than about 200, less than about 100, less than about 25, or less than about 15 international units per milliliter serum) is found in the subject's serum for a period of at least about one month, at least about two months, at least about three months, at least about four months, at least about five months, or at least about six months following cessation of therapy.

In some embodiments, an effective amount of a compound of Formula (I), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formula (I), or a pharmaceutically acceptable salt thereof, can be an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formula (I), or a pharmaceutically acceptable salt thereof, can be administered to a treatment failure subject suffering from HCV. In some embodiments, a compound of Formula (I), or a pharmaceutically acceptable salt thereof, can be administered to a non-responder subject suffering from HCV. In some embodiments, a compound of Formula (I), or a pharmaceutically acceptable salt thereof, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an HCV strain that is resistant to one or more different anti-HCV agents (for example, an agent used in a conventional standard of care). In some embodiments, development of resistant HCV strains is delayed when a subject is treated with a compound of Formula (I), or a pharmaceutically acceptable salt thereof, compared to the development of HCV strains resistant to other HCV drugs (such as an agent used in a conventional standard of care).

In some embodiments, an effective amount of a compound of Formula (I), or a pharmaceutically acceptable salt thereof, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formula (I), or a pharmaceutically acceptable salt thereof, can be provided to a subject that is hypersensitive to interferon and/or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be administered to a subject experiencing viral load rebound, or can prevent such viral load rebound when used to treat the subject.

The standard of care for treating HCV has been associated with several side effects (adverse events). In some embodiments, a compound of Formula (I), or a pharmaceutically acceptable salt thereof, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HCV therapy because of one or more adverse effects or side effects associated with one or more other HCV agents (for example, an agent used in a conventional standard of care).

Table 4 provides some embodiments of the percentage improvement obtained using a compound of Formula (I), or a pharmaceutically acceptable salt thereof, as compared to the standard of care. Examples include the following: in some embodiments, a compound of Formula (I), or a pharmaceutically acceptable salt thereof, results in a percentage of non-responders that is 10% less than the percentage of non-responders receiving the standard of care. In some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 4

| Percentage of non-responders | Percentage of relapsers | Percentage of resistance | Percentage of viral load rebound | Number of side effects | Severity of side effects |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a HCV infection. In some embodiments, the total time of the treatment regime with a compound of Formula (I), or a pharmaceutically acceptable salt thereof, can be less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents currently used in a conventional standard of care for treating HCV, HCV protease inhibitors, HCV polymerase inhibitors, NS5A inhibitors, other antiviral compounds, compounds of Formula (AA), (including pharmaceutically acceptable salts and pharmaceutical compositions that can include a compound of Formula (AA), or a pharmaceutically acceptable salt thereof), compounds of Formula (BB) (including pharmaceutically acceptable salts and pharmaceutical compositions that can include a compound of Formula (BB), or a pharmaceutically acceptable salt thereof), compounds of Formula (CC) (including pharmaceutically acceptable salts and pharmaceutical compositions that can include a compound of Formula (CC), or a pharmaceutically acceptable salt thereof), compounds of Formula (DD) (including pharmaceutically acceptable salts and pharmaceutical compositions that can include a compound of Formula (DD), or a pharmaceutically acceptable salt thereof), and/or combinations thereof. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, Pegylated interferon-alpha-2b (brand name PEG-INTRON®) and ribavirin, Pegylated interferon-alpha-2a, Pegylated interferon-alpha-2b, or ribavirin.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HCV, a compound of Formula (I), or a pharmaceutically acceptable salt thereof, or a pharmaceutical composition that includes a compound of Formula (I), or a pharmaceutically acceptable salt thereof, can be used in place of ribavirin.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

Figure 1:
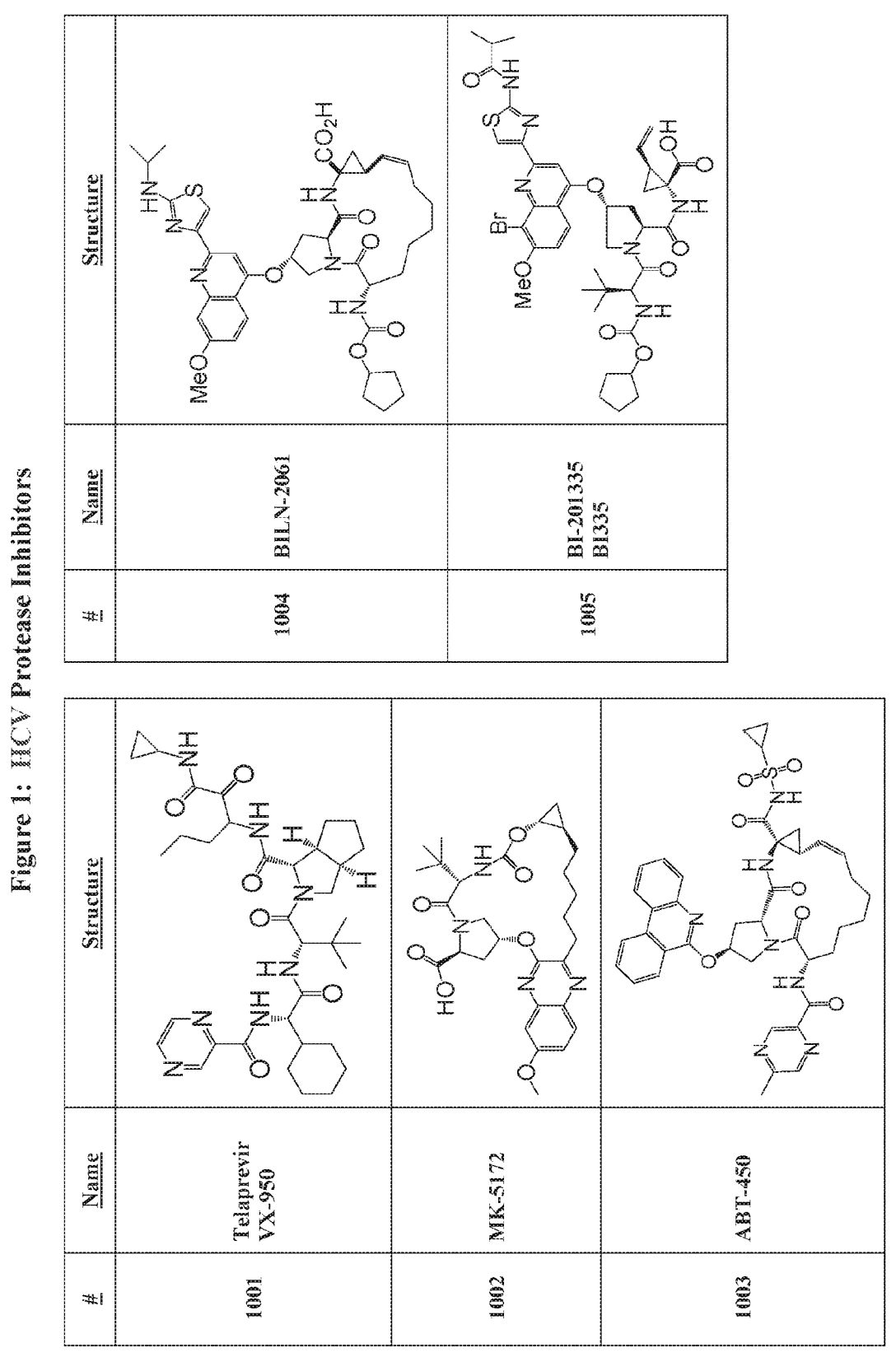

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435 (SIMEPREVIR®), ITMN-191 (DANOPREVIR®) and/or a combination thereof. A non-limiting list of example HCV protease inhibitors includes the compounds numbered 1001-1016 in FIG. 1.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-189, PSI-352938, PSI-661, 4'-azidouridine (including known prodrugs of 4'-azidouridine), GS-6620, IDX-184, and TMC649128 and/or combinations thereof. A non-limiting list of example nucleoside inhibitors includes compounds numbered 2001-2012 in FIG. 2. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3014 in FIG. 3. Further HCV polymerase inhibitors suitable for use in combination with a compound of Formula (I), or a pharmaceutically acceptable salt thereof, or a pharmaceutical composition that includes a compound of Formula (I), or a pharmaceutically acceptable salt thereof, include VX-500, VX-813, VBY-376, TMC-435350, EZ-058, EZ-063, GS-9132, ACH-1095, IDX-136, IDX-316, ITMN-8356, ITMN-8347, ITMN-8096, ITMN-7587, VX-985, VP-19744, PSI-879, VCH-759/VX-759, HCV-371, IDX-375, GL-60667, JTK-109, PSI-6130, R1479, R-1626, R-7128, MK-0608, INX-8014, INX-8018, A-848837, A-837093, BILB-1941, VCH-916, VCH-716, GSK-71185, GSK-625433, XTL-2125 and those disclosed in PCT Publication No. WO 2012/142085, which is hereby incorporated by reference for the limited purpose of its disclosure of HCV protease inhibitors, HCV polymerase inhibitors and NS5A inhibitors.

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. Examples of NS5A inhibitors include BMS-790052 (DACLASTASVIR®), PPI-461, ACH-2928, GS-5885, BMS-824393, ABT 267, ACH-3102, AZD-7295, IDX719, PPI-668, MK8742, GSK2336805 and/or combinations thereof. A non-limiting list of example NS5A inhibitors includes the compounds numbered 4001-4012 in FIG. 4. Additional NS5A inhibitors suitable for use in combination with a compound of Formula (I), or a pharmaceutically acceptable salt thereof, or a pharmaceutical composition that includes a compound of Formula (I), or a pharmaceutically acceptable salt thereof, include A-832, PPI-1301 and those disclosed in PCT Publication No. WO 2012/142085.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, Debio-025, MIR-122 inhibitor, cyclosporin A and/or combinations thereof. A non-limiting list of example other antiviral compounds includes the compounds numbered 5001-5011 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (AA), or a pharmaceutically acceptable salt thereof, or a pharmaceutical composition that includes a compound of Formula (AA), or a pharmaceutically acceptable salt thereof (see, U.S. Publication No. 2013/0164261, published Jun. 27, 2013, the contents of which are herein incorporated by reference in its entirety):

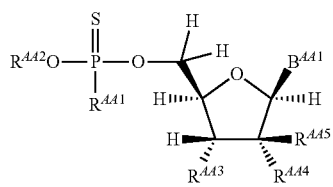

Formula (AA)

wherein: $B^{AA1}$ can be an optionally substituted heterocyclic base or an optionally substituted heterocyclic base with a protected amino group; $R^{AA1}$ can be selected from O⁻, OH, an optionally substituted N-linked amino acid and an optionally substituted N-linked amino acid ester derivative; $R^{AA2}$ can be absent or selected from hydrogen, an optionally substituted aryl, an optionally substituted heteroaryl, an optionally substituted heterocyclyl and

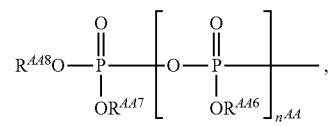

wherein $R^{AA6}$, $R^{AA7}$ and $R^{AA8}$ can be independently absent or hydrogen, and n can be 0 or 1; provided that when $R^{AA1}$ is O⁻ or OH, then $R^{AA2}$ is absent, hydrogen or

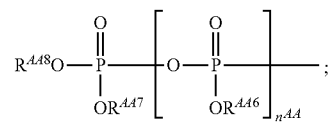

$R^{AA3}$ can be selected from hydrogen, halogen, —$OR^{AA9}$ and —OC(=O)$R^{AA10}$; $R^{AA4}$ can be selected from halogen, —$OR^{AA11}$ and —OC(=O)$R^{AA12}$; or $R^{AA3}$ and $R^{AA4}$ can be both an oxygen atom which are linked together by a carbonyl group; $R^{AA5}$ be selected from an optionally substituted $C_{2-6}$ alkyl, an optionally substituted $C_{2-6}$ alkenyl, an optionally substituted $C_{2-6}$ alkynyl and an optionally substituted $C_{3-6}$ cycloalkyl; or $R^{AA4}$ and $R^{AA5}$ together can form —($C_{1-6}$ alkyl)-O— or —O—($C_{1-6}$ alkyl)-; $R^{AA9}$ and $R^{AA11}$ can be independently hydrogen or an optionally substituted $C_{1-6}$ alkyl; and $R^{AA10}$ and $R^{AA12}$ can be independently an optionally substituted $C_{1-6}$ alkyl or an optionally substituted $C_{3-6}$ cycloalkyl. A non-limiting list of examples of compounds of Formula (AA) includes the compounds numbered 7000-7027 in FIG. 7.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (BB), or a pharmaceutically acceptable salt thereof, or a pharmaceutical composition that includes a compound of Formula (BB), or a pharmaceutically acceptable salt thereof (see, U.S. Publication No. 2012/0165286, published Jun. 28, 2012, the contents of which are herein incorporated by reference in their entireties):

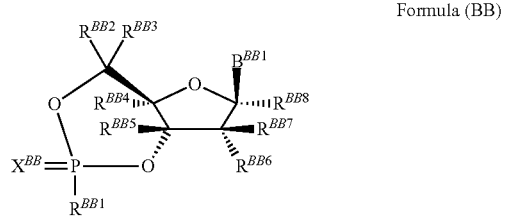

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from —$Z^{BB}$—$R^{BB9}$, an optionally substituted N-linked amino acid and an optionally substituted N-linked amino acid ester derivative; $Z^{BB}$ can be selected from O (oxygen), S (sulfur) and N($R^{BB10}$); $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted alkenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, —$OR^{BB11}$ and —$OC(=O)R^{BB12}$; $R^{BB7}$ can be selected from hydrogen, halogen, azido, cyano, an optionally substituted $C_{1-6}$ alkyl, —$OR^{BB13}$ and —$OC(=O)R^{BB14}$; $R^{BB8}$ can be selected from hydrogen, halogen, azido, cyano, an optionally substituted $C_{1-6}$ alkyl, —$OR^{BB15}$ and —$OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 8000-8016 in FIG. 8.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (CC), or a pharmaceutically acceptable salt thereof, or a pharmaceutical composition that includes a compound of Formula (CC), or a pharmaceutically acceptable salt thereof (see, U.S. Publication No. 2012/0071434, published Mar. 22, 2012, the contents of which are herein incorporated by reference in its entirety):

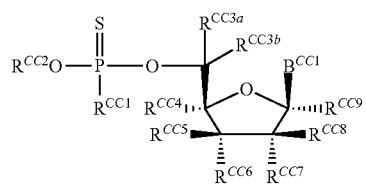

Formula (CC)

wherein $B^{CC1}$ can be an optionally substituted heterocyclic base or an optionally substituted heterocyclic base with a protected amino group; $R^{CC1}$ can be selected from O⁻, OH, an optionally substituted N-linked amino acid and an optionally substituted N-linked amino acid ester derivative; $R^{CC2}$ can be selected from an optionally substituted aryl, an optionally substituted heteroaryl, an optionally substituted heterocyclyl and

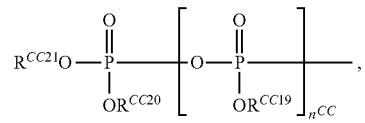

wherein $R^{CC19}$, $R^{CC20}$, and $R^{CC21}$ can be independently absent or hydrogen, and $n^{CC}$ can be 0 or 1; provided that when $R^{CC1}$ is O⁻ or OH, then $R^{CC2}$ is

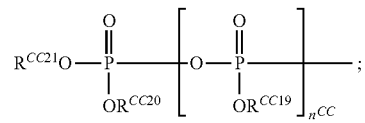

$R^{CC3a}$ and $R^{CC3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ can be taken together to form an optionally substituted $C_{3-6}$ cycloalkyl; $R^{CC4}$ can be selected from hydrogen, azido, an optionally substituted $C_{1-6}$ alkyl, an optionally substituted $C_{2-6}$ alkenyl and an optionally substituted $C_{2-6}$ alkynyl; $R^{CC5}$ can be selected from hydrogen, halogen, azido, cyano, an optionally substituted $C_{1-6}$ alkyl, —$OR^{CC10}$ and —$OC(=O)R^{CC11}$; $R^{CC6}$ can be selected from hydrogen, halogen, azido, cyano, an optionally substituted $C_{1-6}$ alkyl, —$OR^{CC12}$ and —$OC(=O)R^{CC13}$; $R^{CC7}$ can be selected from hydrogen, halogen, azido, cyano, an optionally substituted $C_{1-6}$ alkyl, —$OR^{CC14}$ and —$OC(=O)R^{CC15}$; or $R^{CC6}$ and $R^{CC7}$ can be both oxygen atoms and linked together by a carbonyl group; $R^{CC8}$ can be selected from hydrogen, halogen, azido, cyano, an optionally substituted $C_{1-6}$ alkyl, —$OR^{CC16}$ and —$OC(=O)R^{CC17}$; $R^{CC9}$ can be selected from hydrogen, azido, cyano, an optionally substituted $C_{1-6}$ alkyl and —$OR^{CC18}$; $R^{CC10}$, $R^{CC12}$, $R^{CC14}$, $R^{CC16}$ and $R^{CC18}$ can be independently selected from hydrogen and an optionally substituted $C_{1-6}$ alkyl; and $R^{CC11}$, $R^{CC13}$, $R^{CC15}$ and $R^{CC17}$ can be independently selected from an optionally substituted $C_{1-6}$ alkyl and an optionally substituted $C_{3-6}$ cycloalkyl. In some embodiments, when $R^{CC3a}$, $R^{CC3b}$, $R^{CC4}$, $R^{CC5}$, $R^{CC7}$, $R^{CC8}$ and $R^{CC9}$ are all hydrogen, then $R^{CC6}$ is not azido. In some embodiments, $R^{CC2}$ cannot be

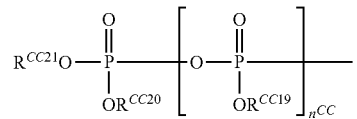

when $R^{CC3a}$ is hydrogen, $R^{CC3b}$ is hydrogen, $R^{CC4}$ is H $R^{CC5}$ is OH or H, $R^{CC6}$ is hydrogen, OH, or —$OC(=O)CH_3$, $R^{CC7}$ is hydrogen, OH, $OCH_3$ or —$OC(=O)CH_3$, $R^{CC8}$ is hydrogen, OH or $OCH_3$, $R^{CC9}$ is H and $B^{CC1}$ is an optionally substituted adenine, an optionally substituted guanine, an optionally substituted uracil or an optionally substituted hypoxanthine. In some embodiments, $R^{CC2}$ cannot be

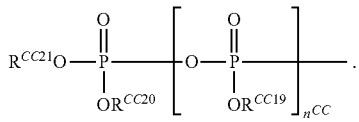

A non-limiting list of examples of compounds of Formula (CC) includes the compounds numbered 6000-6078 in FIG. 6.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (DD), or a pharmaceutically acceptable salt thereof, or a pharmaceutical composition that includes a compound of Formula (DD), or a pharmaceutically acceptable salt thereof (see, PCT Application No. WO 2014/100505 published Jun. 26, 2014, the contents of which are herein incorporated by reference in its entirety):

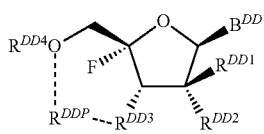

(DD)

wherein: $B^{DD}$ can be selected from an optionally substituted

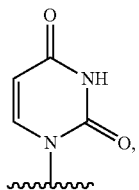 [SMILES: *n1ccc(=O)[nH]c1=O]

an optionally substituted

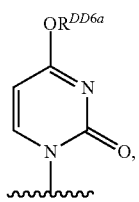

an optionally substituted

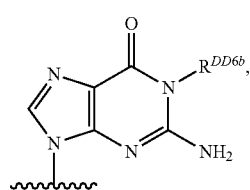

an optionally substituted

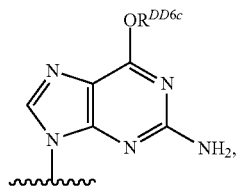

an optionally substituted

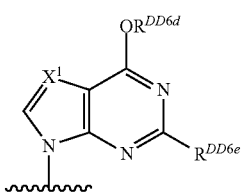

and an optionally substituted

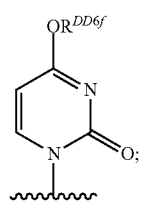

$R^{DD1}$ can be selected from an optionally substituted $C_{1-6}$ alkyl, an optionally substituted $C_{2-6}$ alkenyl, an optionally substituted $C_{2-6}$ alkynyl and an optionally substituted $C_{3-6}$ cycloalkyl; each -------- can be absent or a single bond, provided that both -------- are each absent or both -------- are each a single bond; when both ------ are each a single bond, then $R^{DD2}$ can be halo, $N_3$, —$OR^{DD7a}$ or —$N(R^{DD7b}R^{DD7c})$; $R^{DD4}$ can be absent; $R^{DD3}$ can be oxygen (O); and $R^{DDP}$ can be

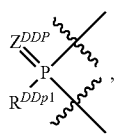

wherein $Z^{DDP}$ can be oxygen (O) or sulfur (S) and $R^{DDp1}$ can be selected from $O^-$, OH, an —O-optionally substituted $C_{1-6}$ alkyl,

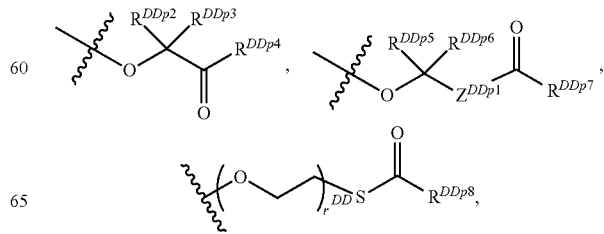

-continued

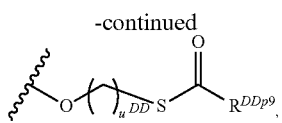

an optionally substituted N-linked amino acid and an optionally substituted N-linked amino acid ester derivative; when both ------ are each absent, then $R^{DDP}$ can be absent; $R^{DD2}$ can be halo, $N_3$, —$OR^{DD7a}$ or —$N(R^{DD7b}R^{DD7c})$; $R^{DD3}$ can be —OH or —$OC(=O)R^{DD8}$; or $R^{DD2}$ and $R^{DD3}$ can be each an oxygen atom which are linked together by a carbonyl group; and $R^{DD4}$ can be hydrogen or

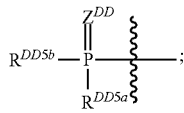

$R^{DD5a}$ can be selected from O⁻, OH, an optionally substituted N-linked amino acid, an optionally substituted N-linked amino acid ester derivative,

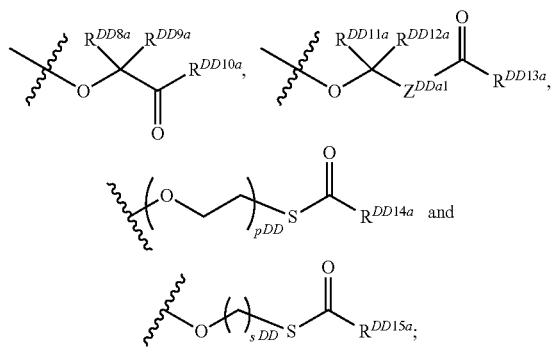

$R^{DD5b}$ can be selected from O⁻, OH, an —O-optionally substituted aryl, an —O-optionally substituted heteroaryl, an —O-optionally substituted heterocyclyl, an optionally substituted N-linked amino acid, an optionally substituted N-linked amino acid ester derivative,

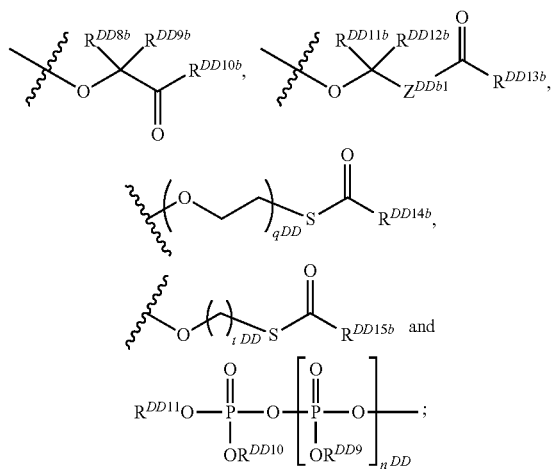

$R^{DD6a}$ can be an optionally substituted $C_{1-6}$ alkyl or an optionally substituted $C_{3-6}$ cycloalkyl; $R^{DD6b}$ and $R^{DD6c}$ can be independently selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl; $R^{DD6d}$ can be $NHR^{DD6g}$; $R^{DD6e}$ can be hydrogen, halogen or $NHR^{DD6h}$; $R^{DD6f}$ can be $NHR^{DD6i}$; $R^{DD6g}$ can be selected from hydrogen, an optionally substituted $C_{1-6}$ alkyl, an optionally substituted $C_{3-6}$ alkenyl, an optionally substituted $C_{3-6}$ cycloalkyl, —$C(=O)R^{DDa1}$ and —$C(=O)OR^{DDa2}$; $R^{DD6h}$ can be selected from hydrogen, an optionally substituted $C_{1-6}$ alkyl, an optionally substituted $C_{3-6}$ alkenyl, an optionally substituted $C_{3-6}$ cycloalkyl, $C(=O)R^{DDa3}$ and $C(=O)OR^{DDa4}$; $R^{DD6i}$ can be selected from hydrogen, an optionally substituted $C_{1-6}$ alkyl, an optionally substituted $C_{3-6}$ alkenyl, an optionally substituted $C_{3-6}$ cycloalkyl, —$C(=O)R^{DDa5}$ and —$C(=O)OR^{DDa6}$; $X^{DD}$ can be N (nitrogen) or —$CR^{DD6j}$, $R^{DD6j}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{DDa1}$, $R^{DDa2}$, $R^{DDa3}$, $R^{DDa4}$, $R^{DDa5}$ and $R^{DDa6}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_6$-10 aryl, heteroaryl, heterocyclyl, aryl($C_{1-6}$ alkyl), heteroaryl($C_{1-6}$ alkyl) and heterocyclyl($C_{1-6}$ alkyl); $R^{DD7a}$ can be hydrogen or —$C(=O)R^{DD12}$; $R^{DD7b}$ and $R^{DD7c}$ can be independently hydrogen or an optionally substituted $C_{1-6}$ alkyl; $R^{DD8}$ and $R^{DD12}$ can be independently an optionally substituted $C_{1-6}$ alkyl or an optionally substituted $C_{3-6}$ cycloalkyl; $R^{DD9}$, $R^{DD10}$ and $R^{DD11}$ can be independently absent or hydrogen; $R^{DD8a}$, $R^{DD9a}$, $R^{DD11a}$, $R^{DD12a}$, $R^{DD8b}$, $R^{DD9b}$, $R^{DD11b}$, $R^{DD12b}$, $R^{DDp2}$, $R^{DDp3}$, $R^{DDP5}$ and $R^{DDP6}$ can be independently selected from hydrogen, an optionally substituted $C_{1-24}$ alkyl and an optionally substituted aryl; $R^{DD10a}$, $R^{DD10b}$, $R^{DD13a}$, $R^{DD13b}$, $R^{DDp4}$ and $R^{DDp7}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; $R^{DD14a}$, $R^{DD14b}$, $R^{DD15a}$, $R^{DD15b}$, $R^{DDp8}$ and $R^{DDp9}$ can be independently selected from hydrogen, an optionally substituted $C_{1-24}$ alkyl and an optionally substituted aryl; $n^{DD}$ can be 0 or 1; and $p^{DD}$, $q^{DD}$, $r^{DD}$ can be independently 1 or 2; $s^{DD}$, $t^{DD}$ and $u^{DD}$ can be independently 3, 4 or 5; $Z^{DD}$, $Z^{DDa1}$, $Z^{DDb1}$ and $Z^{DDp1}$ can be independently O (oxygen) or S (sulfur); and provided that when $R^{DD4}$ is

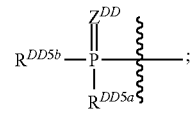

and $R^{DD5a}$ is O⁻ or OH, then $R^{DD5b}$ is O⁻, OH,

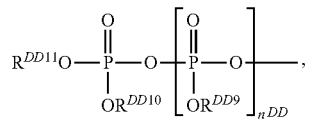

an optionally substituted N-linked amino acid or an optionally substituted N-linked amino acid ester derivative. A non-limiting list of example compounds of Formula (DD) includes the compounds numbered 9000-9105 in FIG. 9.

Some embodiments described herein relate to a method of ameliorating or treating a HCV infection that can include contacting a cell infected with the HCV infection with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) a compound of Formula (CC), and a compound of Formula (DD), or a pharmaceutically acceptable salt of any of the aforementioned compounds.

Some embodiments described herein relate to a method of ameliorating or treating a HCV infection that can include administering to a subject suffering from the HCV infection an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), a compound of Formula (CC) and a compound of Formula (DD), or a pharmaceutically acceptable salt of any of the aforementioned compounds.

Some embodiments described herein relate to a method of inhibiting the replication of a hepatitis C virus that can include contacting a cell infected with the hepatitis C virus with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), a compound of Formula (CC) and a compound of Formula (DD) or a pharmaceutically acceptable salt of any of the aforementioned compounds.

Some embodiments described herein relate to a method of inhibiting the replication of a hepatitis C virus that can include administering to a subject infected with the hepatitis C virus an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), a compound of Formula (CC) and a compound of Formula (DD), or a pharmaceutically acceptable salt of any of the aforementioned compounds.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt the thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 1-9 (including pharmaceutically acceptable salts and prodrugs thereof) can result in an additive effect. In some embodiments, the combination of a compound of Formula (I), or a pharmaceutically acceptable salt thereof, in combination with one or more additional agent(s) in FIGS. 1-9 (including pharmaceutically acceptable salts and prodrugs thereof) can result in a synergistic effect. In some embodiments, the combination of a compound of Formula (I), or a pharmaceutically acceptable salt thereof, in combination with one or more additional agent(s) in FIGS. 1-9 (including pharmaceutically acceptable salts and prodrugs thereof) can result in a strongly synergistic effect. In some embodiments, the combination of a compound of Formula (I), or a pharmaceutically acceptable salt thereof, in combination with one or more additional agent(s) in FIGS. 1-9 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 1-9 (including pharmaceutically acceptable salts thereof) may be a reduction in the required amount(s) of one or more compounds of FIGS. 1-9 (including pharmaceutically acceptable salts thereof) that is effective in treating a disease condition disclosed herein (for example, HCV), as compared to the amount required to achieve same therapeutic result when one or more compounds of FIGS. 1-9 (including pharmaceutically acceptable salts thereof) are administered without a compound of Formula (I), or a pharmaceutically acceptable salt thereof. For example, the amount of a compound in FIGS. 1-9 (including a pharmaceutically acceptable salt thereof), can be less compared to the amount of the compound in FIGS. 1-9 (including a pharmaceutically acceptable salt thereof), needed to achieve the same viral load reduction when administered as a monotherapy. Another potential advantage of utilizing a compound of Formula (I), or a pharmaceutically acceptable salt thereof, in combination with one or more additional agent(s) in FIGS. 1-9 (including pharmaceutically acceptable salts thereof) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 1-9 (including pharmaceutically acceptable salts thereof) may include little to no cross resistance between a compound of Formula (I), or a pharmaceutically acceptable salt thereof, and one or more additional agent(s) in FIGS. 1-9 (including pharmaceutically acceptable salts thereof) thereof; different routes for elimination of a compound of Formula (I), or a pharmaceutically acceptable salt thereof, and one or more additional agent(s) in FIGS. 1-9 (including pharmaceutically acceptable salts thereof); little to no overlapping toxicities between a compound of Formula (I), or a pharmaceutically acceptable salt thereof, and one or more additional agent(s) in FIGS. 1-9 (including pharmaceutically acceptable salts thereof); little to no significant effects on cytochrome P450; little to no pharmacokinetic interactions between a compound of Formula (I), or a pharmaceutically acceptable salt thereof, and one or more additional agent(s) in FIGS. 1-9 (including pharmaceutically acceptable salts thereof); greater percentage of subjects achieving a sustained viral response compared to when a compound is administered as monotherapy and/or a decrease in treatment time to achieve a sustained viral response compared to when a compound is administered as monotherapy.

EXAMPLES

Additional embodiments are disclosed in further detail in the following examples, which are not in any way intended to limit the scope of the claims.

Example 1

Compound 1

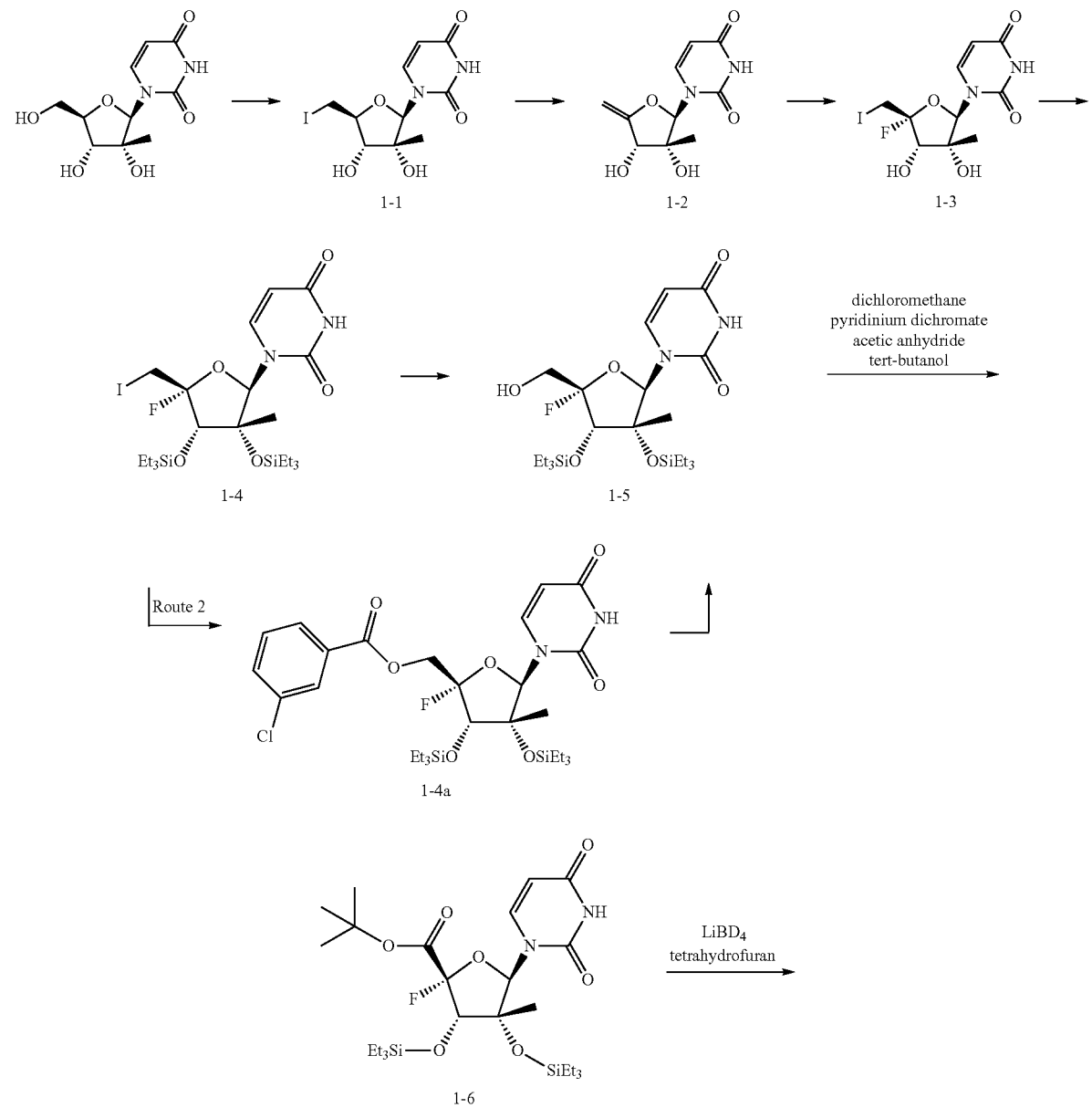

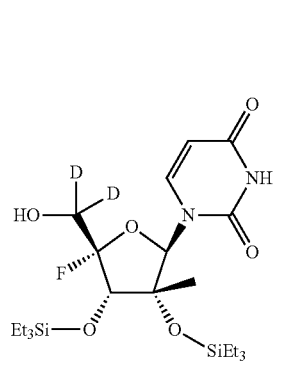
1-7

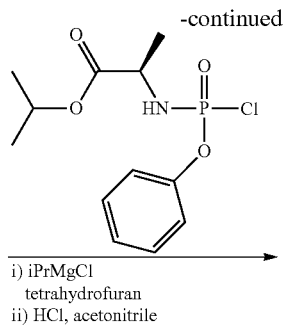
i) iPrMgCl
tetrahydrofuran
ii) HCl, acetonitrile

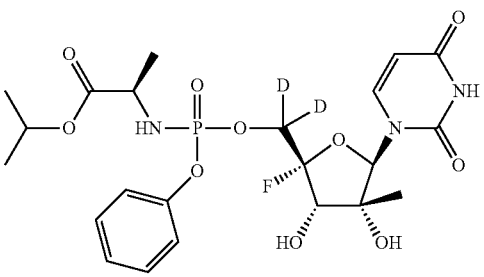
1

Compound 1 was prepared according to the scheme provide above. 3-Neck 3 L flask was charged with 2'-methyluridine (129 g, 500 mmol, 1.0 eq.), triphenylphosphine (196.5 g, 750 mmol, 1.5 eq.), imidazole (51 g, 750 mmol, 1.5 eq.) and anhydrous THF (750 mL). With stirring under an argon atmosphere, iodine (143.4 g, 565 mmol, 1.13 eq.) was added as a solution in THF (~300 mL), while maintaining the temperature below 25° C. The mixture was stirred overnight at room temperature (RT). THF was replaced by MeOH under reduced pressure. Compound 1-1 precipitated from methanol. The solid was aged overnight at 0° C., filtered off, washed with cold MeOH and dried under reduced pressure at 45-50° C. to yield 1-1 (114.6 g, 62%).

To a suspension of 1-1 (114.2 g, 310 mmol, 1 eq.) in MeOH (350 mL) was added sodium methoxide (176 mL 25% in MeOH, 775 mmol, 2.5 eq.). The mixture was heated at 60° C. for 3 h. HPLC showed complete conversion of 1-1 to 1-2. The mixture was cooled down to RT, and the excess of sodium methoxide was neutralized to pH ~5-7 with acetic acid (~30 mL) while maintaining the temperature below 25° C. Compound 1-2 precipitated during the addition of acetic acid. The solid was aged overnight at 0° C., isolated by filtration, washed with cold MeOH and dried under reduced pressure at 45° C. to yield 1-2 (60.9 g, 80.8%).

To a stirred at 0° C. slurry of 1-2 (28.8 g, 120 mmol, 1.0 eq.) in CH$_3$CN (240 mL) was added Et$_3$N.3HF (9.77 mL, 60 mmol, 0.5 eq., 1.5 eq. of HF) followed by addition of N-iodosuccinimide (35.1 g, 156 mmol, 1.3 eq.). Cooling was removed, and the mixture was stirred at RT for 2 h. Compound 1-3 precipitated. Compound 1-3 was filtered off, washed with DCM until the filtrate became colorless (3×) and dried under vacuum to give 1-3 (27.7 g, 59.8%) as a slightly yellow powder. The mother liquor (83% HPLC, 13% (β-isomer) was concentrated under reduced pressure to an oil. The oil was diluted with DCM (~100 mL). The solution was added to a stirred 10% aqueous solution of potassium bicarbonate (150 mL), followed by addition of sodium thiosulfate (~5 g as pentahydrate). A precipitate formed. The precipitate was isolated by filtration, washed with water followed by cold IPA and dried under reduced pressure to yield a second crop of compound C (8.0 g, 17%). The overall yield of 1-3 was (35.7 g, 76.8%).

Route 1: A solution of 1-3 (30.88 g, 80 mmol, 1.0 eq.) and imidazole (19.0 g, 280 mmol, 3.5 eq.) in DMF (140 mL) was treated with chlorotriethylsilane (33.5 mL, 200 mmol, 2.5 eq.) while maintaining the temperature below 25° C. After overnight stirring, the mixture was taken into water (250 mL) and IPAC (250 mL). The organic phase was separated, washed with water and concentrated under reduced pressure to a yellowish solid, ~59 g crude weight. A 3-neck 1-L flask was equipped with magnetic stirring bar, addition funnel and pH electrode. The flask was charged with tetrabutylammonium hydroxide (114 mL, 55% aqueous solution, 240 mmol, 3 eq.). With stirring, TFA (18.4 mL, 240 mmol, 3 eq.) was added slowly to pH 3.5 while maintaining the temperature below 20-25° C. Crude 1-4 was added to the flask as a solution in DCM (250 mL). The mixture was stirred vigorously. mCPBA (99 g as 70%, 400 mmol, 5 eq.) was added portion-wise over ~15 mins. The reaction temperature was maintained below 25° C. The mixture gradually became acidic (pH <1.5 in~1 h), and the pH was maintained between 1.8-2 by dropwise addition of 2N aqueous NaOH. After 6 h, the pH was brought to 3.5, and the mixture was stirred overnight (overall: 40 mL, 80 mmol, 1 eq. of NaOH).

The reaction was quenched by the addition of sodium thiosulphate (119 g as pentahydrate, 480 mmol, 1.2 eq. to mCPBA) while maintaining the temperature below 25° C. The mixture was subjected to reduced pressure to remove DCM. MTBE (~200 mL) was added. The mixture was stirred for ~10 mins. The mixture was then filtered, and the organic layer was separated. The aqueous phase was washed with MTBE (3×50 mL). The combined MTBE extracts were washed with 10% aqueous potassium bicarbonate (150 mL) followed by water. The organic solution was filtered through a silica gel plug (60 g, 15×95 mm), and additional MTBE (~150 mL) was used to elute the compound. The combined organic solution was concentrated to a thick slurry (~77 g, ~40 mL MTBE) which was diluted with hexane (325 mL). The resulted slurry was stirred for 15 mins at reflux, cooled to RT and left at 0° C. overnight. Compound 1-5 (24.4 g, 60.5%) was isolated by filtration, washed with cold hexane and dried under reduced pressure. The mother liquor (~20 g) was separated by column chromatography (350 g, step-wise gradient from 30 to 50% ethyl acetate-hexane). The desired fractions were concentrated, and 1-5 was isolated by crystallization from hexane (50 mL) to yield a second crop of 1-5 (3.3 g (8.2%).

Route 2: Compound 1-3 (9.65 g, 25 mmol, 1.0 eq.) was silylated as described for Route 1 to furnish the crude bis-triethylsilyl ether (20 g). A 3-neck 250 mL flask, equipped with magnetic stirring bar and pH meter electrode was charged with tetrabutylammonium hydrogensulfate (9.3 g, 27.5 mmol, 1.1 eq.), di-potassium hydrogenphosphate (9.6 g, 55 mmol, 2.2 eq.), 3-chlorobenzoic acid (4.3 g, 27.5 mmol, 1.1 eq.) and water (30 mL). The crude bis-triethylsilyl ether was added to the flask as a solution in DCM (60 mL). With stirring, mCPBA (27.7 g as 70%, 112.5 mmol, 4.5 eq.)

was added portionwise over ~5 mins. The reaction was stirred while maintaining the temperature below 25° C. The pH gradually decreased, and di-potassium hydrogenphosphate (4 g, 24 mmol, ~1 eq) was used to maintain the pH at approx. 3.5-4.5. The mixture was stirred overnight.

Sodium sulfite (17 g, 135 mmol, 1.2 eq. to mCPBA) was added while maintaining the temperature below 25° C. A solution of potassium carbonate (10 g) in water (~30 mL) was added to pH-8. A precipitate was filtered off and washed with DCM (~50 mL). The biphasic filtrate was transferred to a separating funnel. The organic layer was separated, the aqueous layer was washed with DCM (3×15 mL). The combined organic solution was concentrated to a semi-crystalline residue, which was partitioned between IPAC (60 mL) and 10% potassium bicarbonate (50 mL). The organic layer was separated, washed with water and concentrated under reduced pressure to give a crystalline residue (18 g).

The crude compound was dissolved in n-butylamine (20 mL) using rotovap agitation under cooling. The solution was concentrated under vacuum, and the residue was dissolved in MTBE (~50 mL). 2N Aqueous HCl was added to pH ~2 (~40 mL). The organic layer was separated, and washed sequentially with water, half-saturated sodium bicarbonate and water. MTBE was replaced with ACN under reduced pressure. The volume of the solution was adjusted to ~60 mL with ACN. The solution was seeded with 1-5 crystals. The precipitated 1-5 was aged overnight at 0° C., isolated by filtration, washed with a small amount of cold ACN and dried under vacuum to give compound D (7.09 g, 55%). The mother liquor was separated by column chromatography (100 g, step-wise gradient from 25 to 50% ethyl acetate-hexane). The desired fractions were concentrated, and 1-5 was isolated by crystallization from hexane (~30 mL) to yield a second crop of 1-5 (2.6 g, 20.6%).

Compound 1-5 was oxidized utilizing PCC to 1-6. The 5'-position was di-deuterated and reduced to provide 1-7. Compound 1 was obtained from the coupling of 1-7 and the shown phosphorochloridate using iPrMgCl and HCl/ACN. MS 546.1 [M-H]+.

Example 2

Compound 2

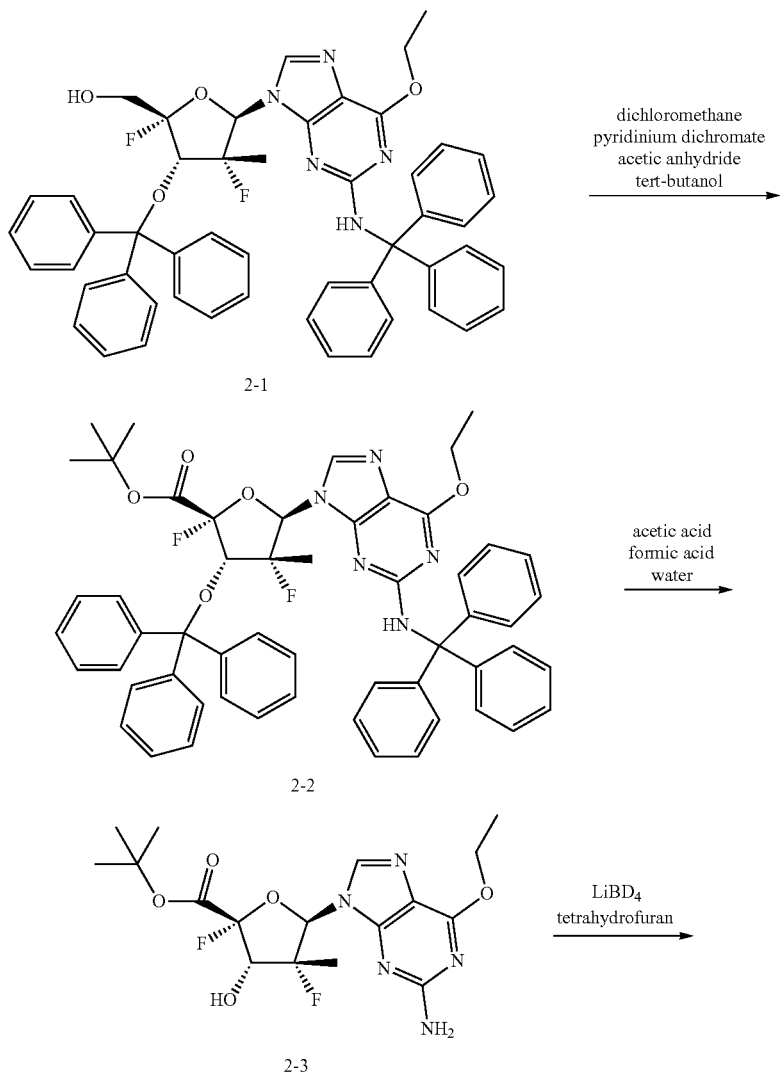

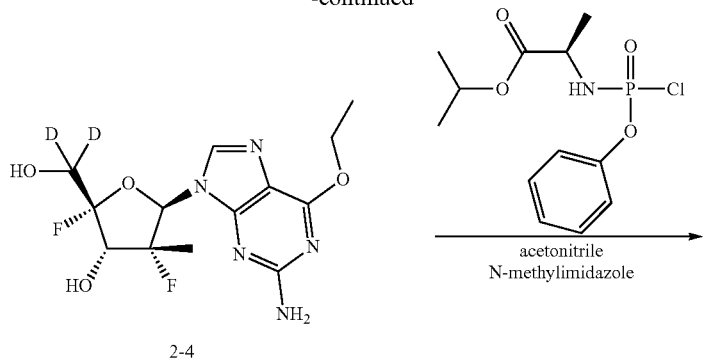

2-4

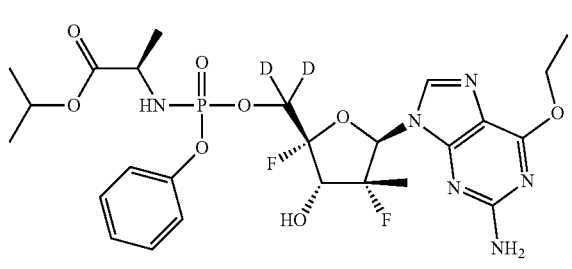

2

Compound 2 was prepared according to the scheme provide above. Compound 2-1 was oxidized utilizing PCC to 2-2. The protecting groups attached to the 3'-oxygen and base were removed using acid to give 2-3. The 5'-position was di-deuterated and reduced to provide 2-4. Compound 2 was obtained from the coupling of 2-4 and the shown phosphorochloridate. MS 617.2 [M-H]+.

Example 3

Triphosphates

Dry nucleoside (0.05 mmol) is dissolved in the mixture of PO(OMe)$_3$ (0.7 mL) and pyridine (0.3 mL). The mixture is evaporated in vacuum for 15 mins at bath temperature (42° C.), than cooled down to RT. N-Methylimidazole (0.009 mL, 0.11 mmol) is added followed by POCl$_3$ (9 µL, 0.11 mmol), and the mixture is kept at RT for 20-40 mins. The reaction is controlled by LCMS and monitored by the appearance of corresponding nucleoside 5'-monophosphate. After completion, tetrabutylammonium salt of pyrophosphate (150 mg) is added, followed by DMF (0.5 mL) to get a homogeneous solution. After 1.5 h at ambient temperature, the reaction is diluted with water (10 mL) and loaded on the column HiLoad 16/10 with Q Sepharose High Performance. Separation is done in a linear gradient of NaCl from 0 to 1N in 50 mM TRIS-buffer (pH 7.5). Triphosphate is eluted at 75-80% B. Corresponding fractions are concentrated. Desalting is achieved by RP HPLC on Synergy 4 micron Hydro-RP column (Phenominex). A linear gradient of methanol from 0 to 30% in 50 mM triethylammonium acetate buffer (pH 7.5) is used for elution. The corresponding fractions are combined, concentrated and lyophilized 3 times to remove excess of buffer.

| | Structure |
|---|---|
| 3 | 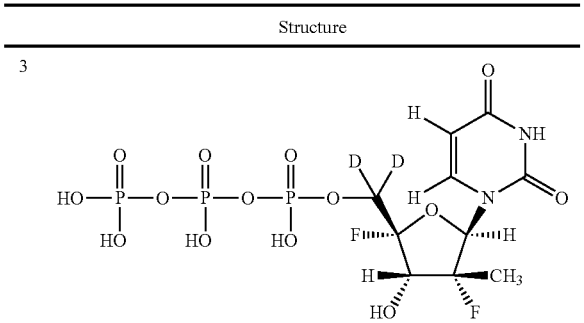 |
| 4 | 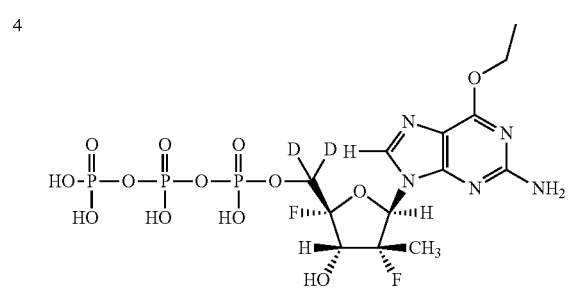 |

Example A

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of Anti-HCV Activity

Determination of 50% inhibitory concentration ($EC_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO were reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 h. At 72 h, cells were processed when the cells were still subconfluent. Compounds that reduced the LUC signal were determined by Bright-Glo Luciferase Assay (Promega, Madison, Wis.). % Inhibition was determined for each compound concentration in relation to the control cells (untreated HCV replicon) to calculate the $EC_{50}$. Compounds 1 and 2 both had an $EC_{50}$ of less than <1 µM.

Example B

NS5B Inhibition Assay

The enzyme activity of NS5B570-Con1 (Delta-21) is measured as an incorporation of tritiated NMP into acid-insoluble RNA products. The complementary IRES (cIRES) RNA sequence is used as a template, corresponding to 377 nucleotides from the 3'-end of HCV (−) strand RNA of the Con-1 strain, with a base content of 21% Ade, 23% Ura, 28% Cyt, and 28% Gua. The cIRES RNA is transcribed in vitro using a T7 transcription kit (Ambion, Inc.) and purified using the Qiagen RNeasy maxi kit. HCV polymerase reactions contain 50 nM NS5B570-Con1, 50 nM cIRES RNA, about 0.5 µCi tritiated NTP, 1 µm of competing cold NTP, 20 mM NaCl, 40 mM Tris-HCl (pH 8.0), 4 mM dithiothreitol, and 4 mM $MgCl_2$. Standard reactions are incubated for 2 h at 37° C., in the presence of increasing concentration of inhibitor. At the end of the reaction, RNA is precipitated with 10% TCA, and acid-insoluble RNA products are filtered on a size exclusion 96-well plate. After washing of the plate, scintillation liquid is added and radio labeled RNA products are detected according to standard procedures with a Trilux Topcount scintillation counter. The compound concentration at which the enzyme-catalyzed rate is reduced by 50% ($IC_{50}$) is calculated by fitting the data to a non-linear regression (sigmoidal).

Example C

Determination of Compound Half-life in Human Hepatocytes

Test compounds are dissolved in dimethylsulfoxide (DMSO) to form a 10-mM stock solution. Primary human hepatocytes are cultured in 6-well plates and maintained in Williams E. medium containing Life Tech's proprietary supplement cocktail. The cell concentration is approximately 1.5-2 million cells per well. The plated human hepatocytes in 3 mL of medium per well are acclimated overnight (>18 h) in a cell culture incubator at 37° C., 5% $CO_2$. An aliquot (15 µL) of test compound stock solution is added into each well to achieve a final concentration of 50 µM. After 24 hours of incubation at 37° C., 5% $CO_2$, the incubation medium containing the test compound is aspirated off and replaced with 3 mL of blank incubation medium. The cells are then placed back into the incubator after collection of the O-hour time point. The time points for the NTP stability assay are: 0, 3, 6, 10, 24, and 48 h. The cell number (1.5 or 2 million cells per well) is used to normalize the test compound concentration from micromolar to pmol/million cells.

At each designated timepoint, the plate is taken out of the incubator and the incubation medium is removed from the designated well. The cells are washed twice with 700 µL of cold 0.9% NaCl in water, and the washing buffer is aspirated off following wash. The cells are then lysed by adding 700 µL of methanol/water (70/30) into the well. The cells are harvested using a cell lifter to remove them from the plate. The cell lysate is transferred into an Eppendorf tube and stored at −20° C. for at least 3 h. After vortexing the Eppendorf tube for 1 minute and centrifuging at 14,000 rpm for 10 minutes, the supernatant is transferred into a clean Eppendorf tube and dried down in a Speed-Vac. The residue is reconstituted with 500 µL of 1 mM ammonium phosphate, vortexed for 1 minute, and centrifuged at 14,000 rpm for 10 mins. An internal standard (N6-benzoyl adenosine) is added to a 50 µL aliquot of the supernatant and transferred into an auto sampler vial and subjected to LC-MS/MS analysis. For NTP quantitation, NTP stock solutions at 3 mM in water are diluted with water to achieve a set of calibration spiking solutions. An aliquot of the spiking solutions is spiked into control cellular sample (from human hepatocytes incubated without test article and treated in the same manner as study samples) and the internal standard is added to form the NTP cellular calibration standards. The processed study samples and calibration standards are analyzed by LC-MS/MS to determine the NTP concentrations. Quantification of NTP from primary human hepatocytes is conducted using Analyst® software on a AB-Sciex® API 3200 tandem triple quadrupole mass spectrometer coupled to a Shimadzu® LC-20AD HPLC system with a Leap Technologies HTC PAL autosampler. The HPLC column is a Phenomenex Gemini C18 (3-µm particle size, 50×2 mm) column. Mobile Phase A consisted of 3 mM ammonium formate and 10 mM dimethyl hexylamine (DMHA) in water. Mobile Phase B consisted of 3 mM ammonium formate and 10 mM DMHA in 1:1 water/acetonitrile. The run time for each sample is 10 or 20 mins using a gradient LC separation coupled with negative ion MS/MS detection of NTP.

Example D

Combination of Compounds

Combination Testing

Two or more test compounds are tested in combination with each other using an HCV genotype 1b HCV replicon harbored in Huh7 cells with a stable luciferase (LUC) reporter. Cells are cultured under standard conditions in Dulbecco's modified Eagle's medium (DMEM; Mediatech Inc, Herndon, Va.) containing 10% heat-inactivated fetal bovine serum (FBS; Mediatech Inc, Herndon, Va.) 2 mM L-glutamine, and nonessential amino acids (JRH Biosciences). HCV replicon cells are plated in a 96-well plate at a density of $10^4$ cells per well in DMEM with 10% FBS. On the following day, the culture medium is replaced with DMEM containing either no compound as a control, the test compounds serially diluted in the presence of 2% FBS and 0.5% DMSO, or a combination of compound 18 with one or more test compounds serially diluted in the presence of 2% FBS and 0.5% DMSO. The cells are incubated with no compound as a control, with the test compounds, or the combination of compounds for 72 h. The direct effects of the combination of the test compounds are examined using a luciferase (LUC) based reporter as determined by the Bright-Glo Luciferase Assay (Promega, Madison, Wis.). Dose-response curves are determined for individual compounds and fixed ratio combinations of two or more test compounds.

The method utilized for evaluating combination effects uses a program called MacSynergy II. MacSynergy II software is kindly provided by Dr. M. Prichard (University of Michigan). The Prichard Model allows for a three-dimensional examination of drug interactions and a calculation of the synergy volume (units: $\mu M^2\%$) generated from running the replicon assay using a checkerboard combination of two or more inhibitors. The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

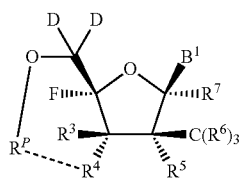

(I)

wherein:

$B^1$ is an optionally substituted

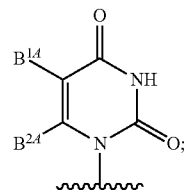

-------- is absent or a single bond;

when ------ is a single bond, then $R^P$ is

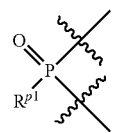

and $R^4$ is O;

when ------ is absent, then $R^P$ is hydrogen or

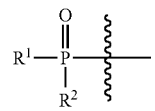

and $R^4$ is —OH or F;

$R^1$ is selected from the group consisting of an —O-optionally substituted aryl,

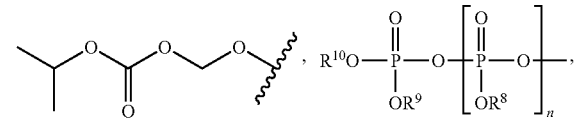

O⁻, and —OH;

$R^2$ is selected from the group consisting of O⁻, —OH, an optionally substituted N-linked amino acid, an optionally substituted N-linked amino acid ester derivative and

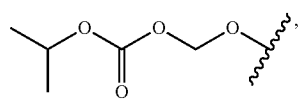 [SMILES: *OCOC(=O)OC(C)C]

provided that when $R^2$ is O⁻ or —OH, $R^1$ is selected from the group consisting of

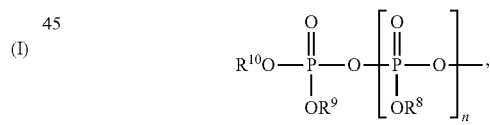

O⁻ and —OH;

$R^3$, each $R^6$ and $R^7$ are independently hydrogen or deuterium;

$R^5$ is —OH;

$R^8$, $R^9$ and $R^{10}$ are independently absent or hydrogen;

$B^{1A}$ and $B^{2A}$ are independently hydrogen or deuterium;

$R^{P1}$ is selected from the group consisting of O⁻, OH, an —O-optionally substituted $C_{1-6}$ alkyl, an —O-optionally substituted aryl,

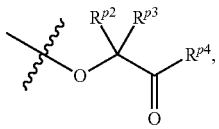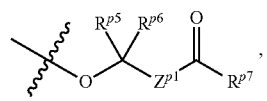

-continued

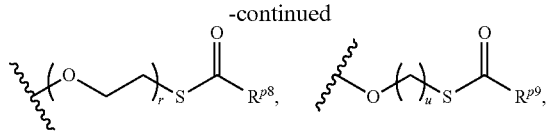

an optionally substituted N-linked amino acid and an optionally substituted N-linked amino acid ester derivative;
$R^{p2}$, $R^{p3}$, $R^{p5}$ and $R^{p6}$ are independently selected from the group consisting of hydrogen, an optionally substituted $C_{1-24}$ alkyl and an optionally substituted aryl;
$R^{p4}$ and $R^{p7}$ are independently selected from the group consisting of hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl;
$R^{p8}$ and $R^{p9}$ are independently selected from the group consisting of hydrogen, an optionally substituted $C_{1-24}$ alkyl and an optionally substituted aryl;
n is 0 or 1;
r is 1 or 2;
u is 3, 4, or 5; and
$Z^{p1}$ is O or S.

2. The compound of claim 1, wherein -------- is absent, $R^P$ is

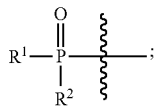

and $R^4$ is —OH or F.

3. The compound of claim 1, wherein $R^1$ is an —O-optionally substituted aryl.

4. The compound of claim 3, wherein $R^1$ is an —O-optionally substituted phenyl.

5. The compound of claim 3, wherein $R^2$ is an optionally substituted N-linked amino acid or is an optionally substituted N-linked amino acid ester derivative.

6. The compound of claim 2, wherein $R^2$ is

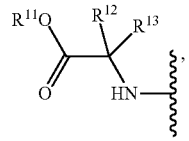

wherein:
$R^{11}$ is selected from the group consisting of hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl;
$R^{12}$ is selected from the group consisting of hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{13}$ is hydrogen or an optionally substituted $C_{1-4}$-alkyl;
or $R^{12}$ and $R^{13}$ are taken together to form an optionally substituted $C_{3-6}$ cycloalkyl.

7. The compound of claim 6, wherein

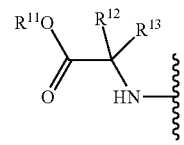

is selected from the group consisting of

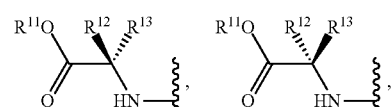

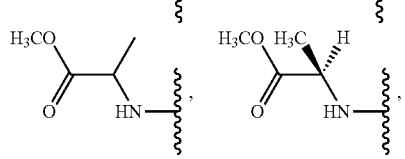

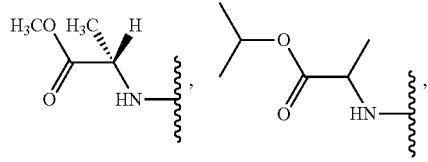

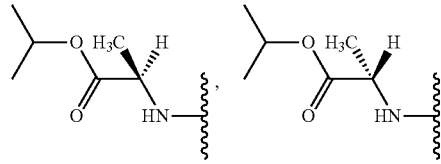

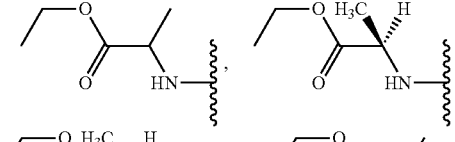

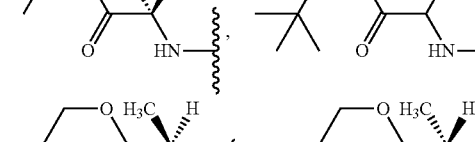

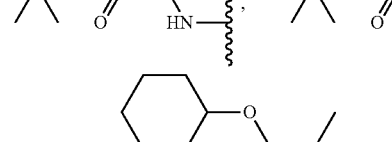

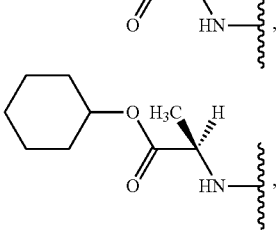

-continued

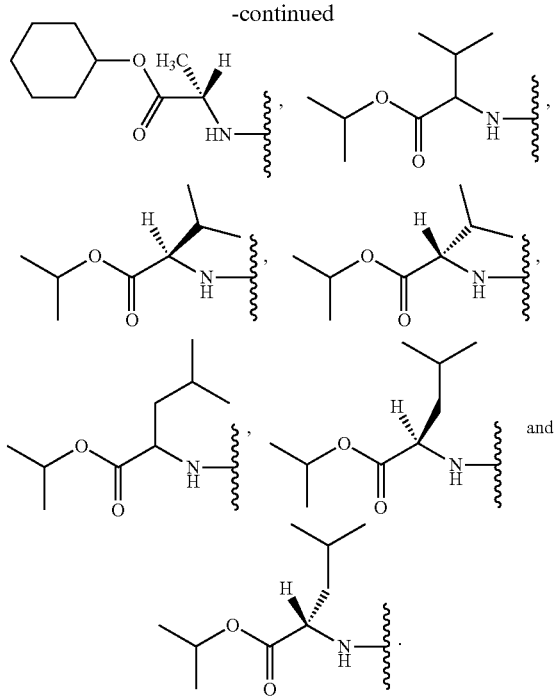

8. The compound of claim 1, wherein $R^2$ is $O^-$ or —OH; and $R^1$ is selected from the group consisting of

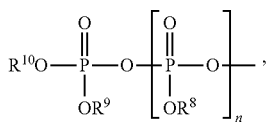

$O^-$ and —OH.

9. The compound of claim 8, wherein $R^1$ is $O^-$ or —OH.
10. The compound of claim 8 wherein $R^1$ is

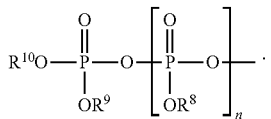

11. The compound of claim 10, wherein n is 0.
12. The compound of claim 10, wherein n is 1.
13. The compound of claim 1, wherein -------- is absent, $R^P$ is hydrogen; and $R^4$ is —OH or F.
14. The compound of claim 1, wherein $R^4$ is —OH.
15. The compound of claim 1, wherein $R^4$ is F.
16. The compound of claim 1, wherein ------ is a single bond, $R^P$ is

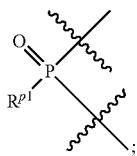

and $R^4$ is O.

17. The compound of claim 1, wherein each $R^6$ is hydrogen.
18. The compound of claim 1, wherein at least one $R^6$ is deuterium.
19. The compound of claim 1, wherein the compound is

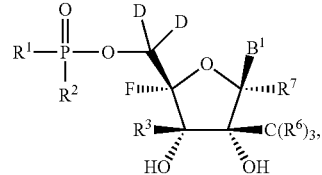

or a pharmaceutically acceptable salt thereof.

20. The compound of claim 1, wherein the compound is

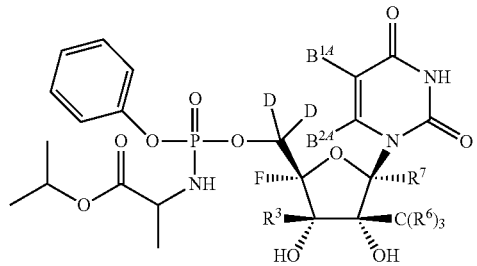

or a pharmaceutically acceptable salt thereof.

21. The compound of claim 1, wherein the compound is

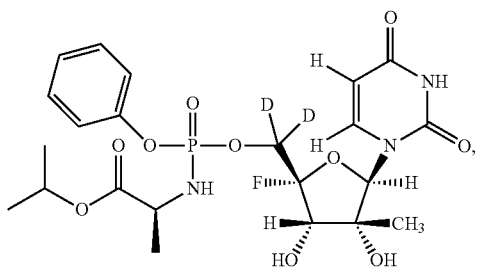 [SMILES: [2H]C([2H])(OP(=O)(N[C@@H](C)C(=O)OC(C)C)Oc1ccccc1)[C@@]1(F)O[C@@H](n2ccc(=O)[nH]c2=O)[C@](C)(O)[C@@H]1O]

or a pharmaceutically acceptable salt thereof.

22. The compound of claim 1, wherein the compound is

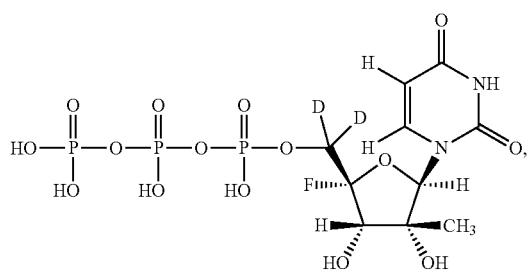 [SMILES: [2H]C([2H])(OP(=O)(O)OP(=O)(O)OP(=O)(O)O)[C@@]1(F)O[C@@H](n2ccc(=O)[nH]c2=O)[C@](C)(O)[C@@H]1O]

or a pharmaceutically acceptable salt thereof.

23. A pharmaceutical composition comprising an effective amount of a compound of claim 1, or a pharmaceutically acceptable salt thereof, and a pharmaceutically acceptable carrier, diluent, excipient or combination thereof.

24. A method for inhibiting NS5B polymerase activity of a hepatitis C virus comprising contacting a cell infected with the hepatitis C virus with an effective amount of a compound of claim 1, or a pharmaceutically acceptable salt thereof.

25. A method for inhibiting replication of a hepatitis C virus comprising contacting a cell infected with the hepatitis C virus with a compound of claim 1, or a pharmaceutically acceptable salt thereof.

26. A method for ameliorating or treating a HCV infection comprising contacting a cell infected with the hepatitis C virus with a compound of claim 1, or a pharmaceutically acceptable salt thereof.

27. The method of claim 26, further comprising contacting the cell with one or more agents selected from the group consisting of an interferon, ribavirin, a HCV protease inhibitor, a HCV polymerase inhibitor, a NS5A inhibitor, an antiviral compound, a compound of Formula (AA), a compound of Formula (BB), a compound of Formula (CC) and a compound of Formula (DD), or a pharmaceutically acceptable salt of any of the aforementioned compounds.

28. The method of claim 27, wherein the one or more agents are selected from the group consisting of Compounds 1001-1016, 2001-2012, 3001-3014, 4001-4012, 5001-5011, 6001-6078, 7000-7027, 8000-8016 and 9000-9105, or a pharmaceutically acceptable salt of any of the aforementioned compounds.

29. A compound of Formula (I), or a pharmaceutically acceptable salt thereof, having the structure:

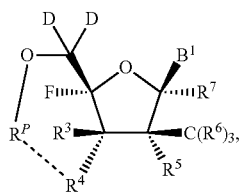

(I)

wherein:

$B^1$ is selected from the group consisting of an optionally substituted

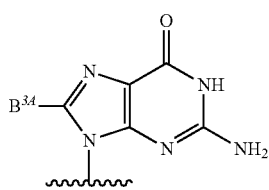

and an optionally substituted

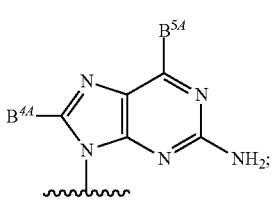

-------- is absent or a single bond;

when ------ is a single bond, then $R^P$ is

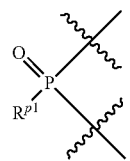

and $R^4$ is O;

when ------ is absent, then $R^P$ is hydrogen or

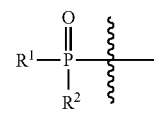

and $R^4$ is —OH or F;

$R^1$ is selected from the group consisting of an —O-optionally substituted aryl,

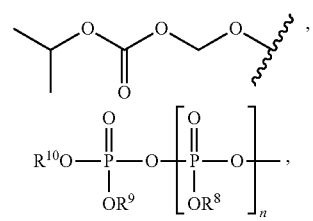

O⁻, and —OH;

$R^2$ is selected from the group consisting of O⁻, —OH, an optionally substituted N-linked amino acid, an optionally substituted N-linked amino acid ester derivative and

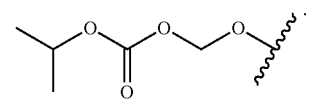 [SMILES: *OCOC(=O)OC(C)C]

provided that when $R^2$ is O⁻ or —OH, $R^1$ is selected from the group consisting of

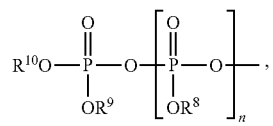

O⁻ and —OH;

$R^3$, each $R^6$ and $R^7$ are independently hydrogen or deuterium;

$R^5$ is F;

$R^8$, $R^9$ and $R^{10}$ are independently absent or hydrogen;

$B^{3A}$ and $B^{4A}$ are independently hydrogen or deuterium;

$B^{5A}$ is —O-optionally substituted $C_{1-6}$ alkyl or —NH$_2$;

$R^{P1}$ is selected from the group consisting of O⁻, OH, an —O-optionally substituted $C_{1-6}$ alkyl, an —O-optionally substituted aryl,

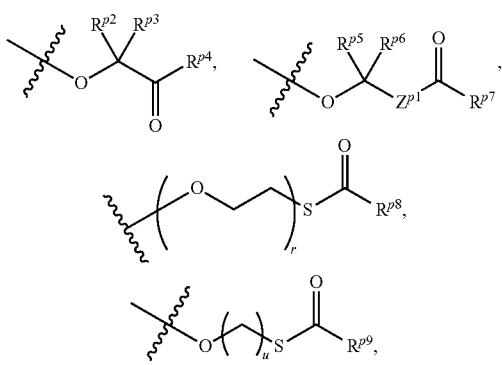

an optionally substituted N-linked amino acid and an optionally substituted N-linked amino acid ester derivative;

$R^{p2}$, $R^{p3}$, $R^{p5}$ and $R^{p6}$ are independently selected from the group consisting of hydrogen, an optionally substituted $C_{1-24}$ alkyl and an optionally substituted aryl;

$R^{p4}$ and $R^{p7}$ are independently selected from the group consisting of hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl;

$R^{p8}$ and $R^{p9}$ are independently selected from the group consisting of hydrogen, an optionally substituted $C_{1-24}$ alkyl and an optionally substituted aryl;

n is 0 or 1;

r is 1 or 2;

u is 3, 4, or 5; and $Z^{p1}$ is O or S.

30. The compound of claim 29, wherein -------- is absent, $R^P$ is

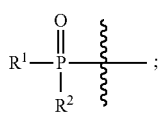

and $R^4$ is —OH or F.

31. The compound of claim 29, wherein $R^1$ and $R^2$ are each

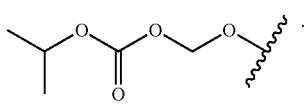 [SMILES: *OCOC(=O)OC(C)C]

32. The compound of claim 29, wherein $R^2$ is O⁻ or —OH; and $R^1$ is selected from the group consisting of

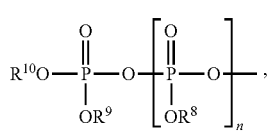

O⁻ and —OH.

33. The compound of claim 32, wherein $R^1$ is O⁻ or —OH.

34. The compound of claim 32 wherein $R^1$ is

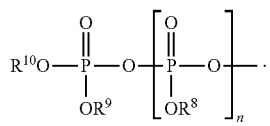

35. The compound of claim 34, wherein n is 0.

36. The compound of claim 34, wherein n is 1.

37. The compound of claim 29, wherein -------- is absent, $R^P$ is hydrogen; and $R^4$ is —OH or F.

38. The compound of claim 29, wherein $R^4$ is —OH.

39. The compound of claim 29, wherein $R^4$ is F.

40. The compound of claim 29, wherein ------ is a single bond, $R^P$ is

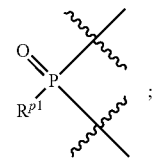

and $R^4$ is O.

41. The compound of claim 29, wherein each $R^6$ is hydrogen.

42. The compound of claim 29, wherein at least one $R^6$ is deuterium.

43. The compound of claim 29, wherein $B^1$ is an optionally substituted

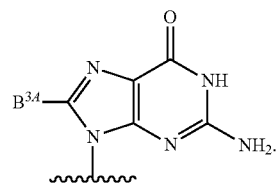

44. The compound of claim 29, wherein $B^1$ is an optionally substituted

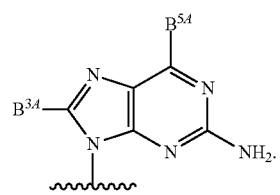

45. The compound of claim 29, wherein the compound is

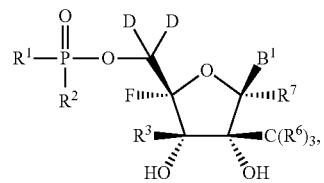

or a pharmaceutically acceptable salt thereof.

46. The compound of claim 29 selected from the group consisting of:

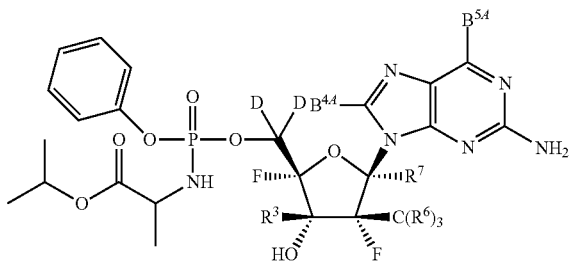

and

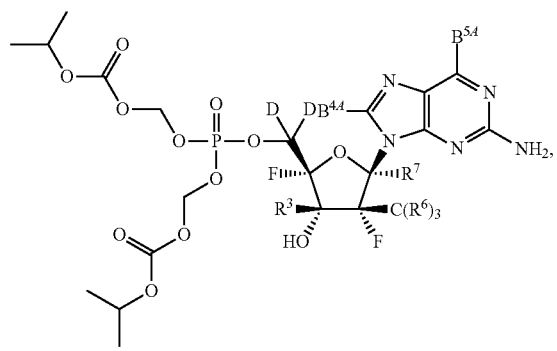

or a pharmaceutically acceptable salt of the foregoing.

47. The compound of claim 29 selected from the group consisting of:

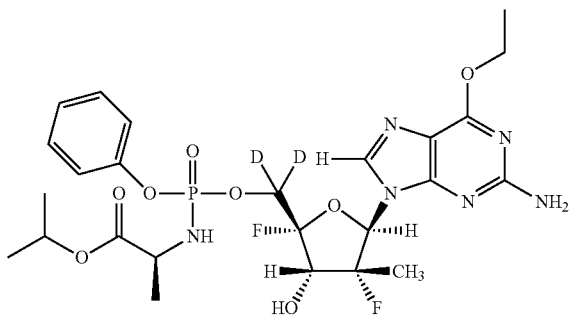

and

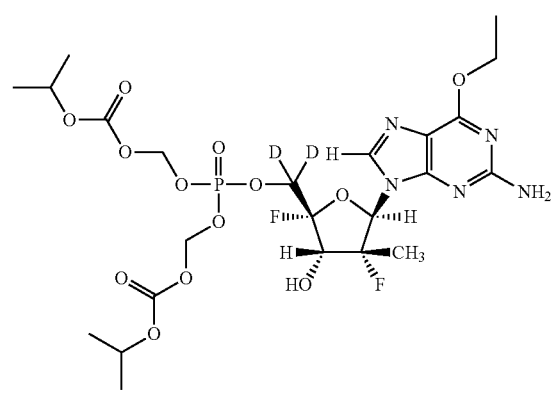

or a pharmaceutically acceptable salt of the foregoing.

48. The compound of claim 29, wherein the compound is

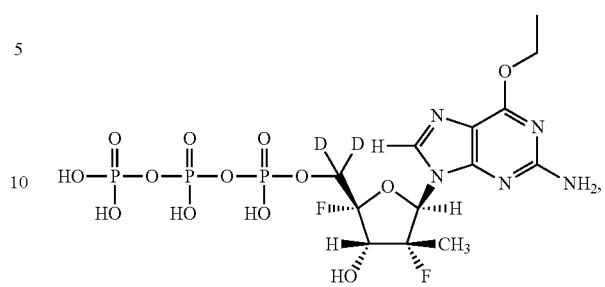

or a pharmaceutically acceptable salt thereof.

49. A pharmaceutical composition comprising an effective amount of a compound of claim 29, or a pharmaceutically acceptable salt thereof, and a pharmaceutically acceptable carrier, diluent, excipient or combination thereof.

50. A method for inhibiting NS5B polymerase activity of a hepatitis C virus comprising contacting a cell infected with the hepatitis C virus with an effective amount of a compound of claim 29, or a pharmaceutically acceptable salt thereof.

51. A method for inhibiting replication of a hepatitis C virus comprising contacting a cell infected with the hepatitis C virus with a compound of claim 29, or a pharmaceutically acceptable salt thereof.

52. A method for ameliorating or treating a HCV infection comprising contacting a cell infected with the hepatitis C virus with a compound of claim 29, or a pharmaceutically acceptable salt thereof.

53. The method of claim 52, further comprising contacting the cell with one or more agents selected from the group consisting of an interferon, ribavirin, a HCV protease inhibitor, a HCV polymerase inhibitor, a NS5A inhibitor, an antiviral compound, a compound of Formula (AA), a compound of Formula (BB), a compound of Formula (CC) and a compound of Formula (DD), or a pharmaceutically acceptable salt of any of the aforementioned compounds.

54. The method of claim 53, wherein the one or more agents are selected from the group consisting of Compounds 1001-1016, 2001-2012, 3001-3014, 4001-4012, 5001-5011, 6001-6078, 7000-7027, 8000-8016 and 9000-9105, or a pharmaceutically acceptable salt of any of the aforementioned compounds.

* * * * *